US008491890B2

(12) United States Patent
Gendelman et al.

(10) Patent No.: US 8,491,890 B2
(45) Date of Patent: Jul. 23, 2013

(54) METHODS AND COMPOSITIONS FOR INHIBITING DISEASES OF THE CENTRAL NERVOUS SYSTEM

(75) Inventors: Howard E. Gendelman, Omaha, NE (US); R. Lee Mosley, Omaha, NE (US); Ashley D. Reynolds, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 790 days.

(21) Appl. No.: 12/500,414

(22) Filed: Jul. 9, 2009

(65) Prior Publication Data
US 2010/0028320 A1 Feb. 4, 2010

Related U.S. Application Data

(60) Provisional application No. 61/134,350, filed on Jul. 9, 2008, provisional application No. 61/208,090, filed on Feb. 20, 2009.

(51) Int. Cl.
| *A61K 38/44* | (2006.01) |
| *A61K 38/00* | (2006.01) |
| *A61P 25/00* | (2006.01) |
| *C07K 14/47* | (2006.01) |
| *A61K 38/48* | (2006.01) |
| *A61K 39/00* | (2006.01) |
| *A61K 47/42* | (2006.01) |
| *C12Q 1/37* | (2006.01) |
| *C12N 9/00* | (2006.01) |
| *C12N 5/02* | (2006.01) |
| *G01N 33/15* | (2006.01) |
| *A61P 25/28* | (2006.01) |
| *A61P 25/16* | (2006.01) |

(52) U.S. Cl.
USPC .......... 424/94.4; 424/185.1; 424/94.6; 435/4; 435/183; 435/325; 435/375; 436/86; 436/89; 514/1.1; 514/17.7; 514/17.8; 514/17.9; 514/772; 514/773; 514/13.1

(58) Field of Classification Search
None
See application file for complete search history.

(56) References Cited

U.S. PATENT DOCUMENTS 5,620,708 A * 4/1997 Amkraut et al. ............... 424/491
2003/0086938 A1* 5/2003 Jensen et al. ............... 424/185.1

OTHER PUBLICATIONS

Cao,J-J;Li,K-S;Shen,Y-Q "Activated Immune Cells in Parkinson's Disease" J Neuroimmune Pharmacol,2011,6(3),pp. 323-329.*
Anderson, JK "Oxidative Stress in Neurodegeneration: Cause or Consequence?" Nature Reviews Neuroscience, 2004,5, S18-S25.*
Ischiropoulos, H and Beckman, J S "Oxidative Stress and Nitration in Neurodegeneration: Cause, Effect, or Association?" J. Clin. Invest. 2003,111(2), pp. 163-169.*
Hodara,R; Norris EH; Giasson, Bl; Mishizen-Eberz, AJ; Lynch, DR; Lee, VM-Y; Ischiropoulos, H "Functional Consequences of alpha-Synuclein Tyrosine Nitration" JBC, Nov. 12, 2004 (publised online Sep. 9, 2004), 279(46), pp. 47746-47753.*
Zidek, Z "Role of Cytokines in the Modulation of Nitric Oxide Production by Cyclic AMP" European Cytokine Network, Mar. 2001, 12(1), pp. 22-32.*
Sigma "Granulocyte-Macrophage Colony-Stimulating Factor (GM-CSF)" Sigma Cell Cuture Catalogue, 1995, p. 61.*
Sigma "Vasoactive Intestinal Peptide (VIP)" Sigma Peptides and Amino Acids Catalogue, 1995, p. 31.*
Campbell, Arezoo "Inflammation, Neurodegenerative Diseases, and Environmental Exposures" Ann. N.Y. Acad. Sci. 2004, 1035, pp. 117-132.*
Chung, CY; Seo, H; Sonntag, KC; Brooks, A; Lin, L; Isacson, O; et al "Cell Type-Specific Gene Expression of Midbrain Dopaminergic Neurons Reveals Molecules Involved in Their Vulnerability and Protection" Human Molecular Genetics, May 11, 2005, 14(13), pp. 1709-1725.*
Zhu, M and Fink, AL "The Association of α-Synuclein with Membranes Affects Bilayer Structure, Stability, and Fibril Formation" JBC, Oct. 10, 2003, 278(41), pp. 40186-40197.).*
Kipnis, J., et al. "Myelin specific Th1 cells are necessary for post-traumatic protective autoimmunity." J Neuroimmunol. Sep. 2002;130(1-2):78-85.
Klegeris, A., et al. "Therapeutic approaches to inflammation in neurodegenerative disease." Curr Opin Neurol. Jun. 2007;20(3):351-7.
Kohutnicka, M., et al. "Microglial and astrocytic involvement in a murine model of Parkinson's disease induced by 1-methyl-4-phenyl-1,2,3,6-tetrahydropyridine (MPTP)." Immunopharmacology. Jun. 1998;39(3):167-80.
Krishnan, S., et al. "Oxidative dimer formation is the critical rate-limiting step for Parkinson's disease alpha-synuclein fibrillogenesis." Biochemistry. Jan. 28, 2003;42(3):829-37.
Kruger, R., et al. "Ala30Pro mutation in the gene encoding alpha-synuclein in Parkinson's disease." Nat Genet. Feb. 1998;18(2):106-8.
Kurkowska-Jastrzebska, I., et al. "Dexamethasone protects against dopaminergic neurons damage in a mouse model of Parkinson's disease." Int. Immunopharmacol. Oct. 2004;4(10-11):1307-1318.
Laurie, C., et al. "CD4+ T cells from Copolymer-1 immunized mice protect dopaminergic neurons in the 1-methyl-4-phenyl-1,2,3,6-tetrahydropyridine model of Parkinson's disease." J Neuroimmunol. Feb. 2007;183(1-2):60-8. Epub Dec. 28, 2006.
Lee, H.J., et al. "Intravesicular localization and exocytosis of alpha-synuclein and its aggregates." J Neurosci. Jun. 22, 2005;25(25):6016-24.
Lee, H.J., et al. "Clearance and deposition of extracellular alpha-synuclein aggregates in microglia." Biochem Biophys Res Commun. Aug. 1, 2008;372(3):423-8. Epub May 19, 2008.
Hodaie, M., et al. "The dopaminergic nigrostriatal system and Parkinson's disease: molecular events in development, disease, and cell death, and new therapeutic strategies." Neurosurgery. Jan. 2007;60(1):17-28; discussion 28-30.
Ling, Z., et al. "Rotenone potentiates dopamine neuron loss in animals exposed to lipopolysaccharide prenatally." Exp Neurol. Dec. 2004;190(2):373-83.

(Continued)

*Primary Examiner* — Chris R Tate
*Assistant Examiner* — Aaron J Kosar
(74) *Attorney, Agent, or Firm* — Dann, Dorfman, Nerrell & Skillman; Robert C. Netter, Jr.

(57) ABSTRACT

Methods and compositions for treating central nervous system diseases and disorders are disclosed.

19 Claims, 115 Drawing Sheets

OTHER PUBLICATIONS

Lipton, S.A., et al. "Inflammatory mediators leading to protein misfolding and uncompetitive/fast off-rate drug therapy for neurodegenerative disorders." Int Rev Neurobiol. 2007;82:1-27.

Liu, B., et al. "Role of microglia in inflammation-mediated neurodegenerative diseases: mechanisms and strategies for therapeutic intervention." J Pharmacol Exp Ther. Jan. 2003;304(1):1-7.

Liu, J., et al. "T cell independent mechanism for copolymer-1-induced neuroprotection." Eur J Immunol. Nov. 2007;37(11):3143-54.

Liu, J., et al. "Identification of proteins involved in microglial endocytosis of alpha-synuclein." J Proteome Res. Sep. 2007;6(9):3614-27. Epub Aug. 3, 2007.

Luo, C., et al. "Alpha-synuclein and tyrosine hydroxylase expression in acute rotenone toxicity." Int J Mol Med. Mar. 2007;19(3):517-21.

Masliah, E., et al. "Effects of alpha-synuclein immunization in a mouse model of Parkinson's disease." Neuron. Jun. 16, 2005;46(6):857-68.

McGeer, P.L., et al. "Inflammation and neurodegeneration in Parkinson's disease." Parkinsonism Relat Disord. May 2004;10 Suppl 1:S3-7.

Mevorach, D., et al. "Systemic exposure to irradiated apoptotic cells induces autoantibody production." J Exp Med. Jul. 20, 1998;188(2):387-92.

Ohmori, H., et al. "Immunogenicity of an inflammation-associated product, tyrosine nitrated self-proteins." Autoimmun Rev. Apr. 2005;4(4):224-9. Epub Dec. 30, 2004.

Oswald-Richter, K., et al. "HIV infection of naturally occurring and genetically reprogrammed human regulatory T-cells." PLoS Biol. Jul. 2004;2(7):E198. Epub Jul. 13, 2004.

Paxinou, E., et al. "Induction of alpha-synuclein aggregation by intracellular nitrative insult." J Neurosci. Oct. 15, 2001;21(20):8053-61.

Polymeropoulos, M.H., et al. "Mutation in the alpha-synuclein gene identified in families with Parkinson's disease." Science. Jun. 27, 1997;276(5321):2045-7.

Reynolds, A., et al. "Oxidative stress and the pathogenesis of neurodegenerative disorders." Int Rev Neurobiol. 2007;82:297-325.

Reynolds, A.D., et al. "Neuroprotective activities of CD4+CD25+ regulatory T cells in an animal model of Parkinson's disease." J Leukoc Biol. Nov. 2007;82(5):1083-94. Epub Aug. 3, 2007.

Reynolds, A.D., et al. "Nitrated alpha-synuclein-activated microglial profiling for Parkinson's disease." J Neurochem. Mar. 2008;104(6):1504-25. Epub Nov. 22, 2007.

Reynolds, A.D., et al. "Nitrated alpha-synudein and microglial neuroregulatory activities." J Neuroimmune Pharmacol. Jun. 2008;3(2):59-74. Epub Jan. 17, 2008.

Reynolds, A.D., et al. "Nitrated {alpha}-synuclein-induced alterations in microglial immunity are regulated by CD4+ T cell subsets." J Immunol. Apr. 1, 2009;182(7):4137-49.

Sakaguchi, S. "Naturally arising CD4+ regulatory t cells for immunologic self-tolerance and negative control of immune responses." Annu Rev Immunol. 2004;22:531-62.

Scali, C., et al. "Neutrophils CD11 b and fibroblasts PGE(2) are elevated in Alzheimer's disease." Neurobiol Aging. Jul.-Aug. 2002;23(4):523-30.

Schori, H., et al. "T-cell-based immunity counteracts the potential toxicity of glutamate in the central nervous system." J Neuroimmunol. Oct. 1, 2001;119(2):199-204.

Sidhu, A., et al. "Does alpha-synuclein modulate dopaminergic synaptic content and tone at the synapse?" Faseb J. Apr. 2004;18(6):637-47.

Singleton, A.B., et al. "alpha-Synuclein locus triplication causes Parkinson's disease." Science. Oct. 31, 2003;302(5646):841.

Smith, M.A., et al. "Predicting the failure of amyloid-beta vaccine." Lancet. May 25, 2002;359(9320):1864-5.

Souza, J.M., et al. "Dityrosine cross-linking promotes formation of stable alpha-synuclein polymers. Implication of nitrative and oxidative stress in the pathogenesis of neurodegenerative synucleinopathies." J Biol Chem. Jun. 16, 2000;275(24):18344-9.

Spillantini, M.G., et al. "Alpha-synuclein in Lewy bodies." Nature. Aug. 28, 1997;388(6645):839-40.

Spira, P.J., et al. "Clinical and pathological features of a Parkinsonian syndrome in a family with an Ala53Thr alpha-synuclein mutation." Ann Neurol. Mar. 2001;49(3):313-9.

Sugama, S., et al. "Age-related microglial activation in 1-methyl-4-phenyl-1,2,3,6-tetrahydropyridine (MPTP)-induced dopaminergic neurodegeneration in C57BL/6 mice." Brain Res. Feb. 28, 2003;964(2):288-94.

Teismann, P., et al. "Inhibition of the cyclooxygenase isoenzymes COX-1 and COX-2 provide neuroprotection in the MPTP-mouse model of Parkinson's disease." Synapse. Feb. 2001;39(2):167-74.

Teismann, P., et al. "Cyclooxygenase-2 is instrumental in Parkinson's disease neurodegeneration." Proc Natl Acad Sci U S A. Apr. 29, 2003;100(9):5473-8. Epub Apr. 17, 2003.

Theodore, S., et al. "Targeted overexpression of human alpha-synuclein triggers microglial activation and an adaptive immune response in a mouse model of Parkinson disease." J Neuropathol Exp Neurol. Dec. 2008;67(12):1149-58.

Thomas, M.P., et al. "Ion channel blockade attenuates aggregated alpha synuclein induction of microglial reactive oxygen species: relevance for the pathogenesis of Parkinson's disease." J Neurochem. Jan. 2007;100(2):503-19.

Thornton, A.M., et al. "Suppressor effector function of CD4+CD25+ immunoregulatory T cells is antigen nonspecific." J Immunol. Jan. 1, 2000;164(1):183-90.

Tiemessen, M.M., et al. "CD4+CD25+Foxp3+ regulatory T cells induce alternative activation of human monocytes/macrophages." Proc Natl Acad Sci U S A. Dec. 4, 2007;104(49):19446-51. Epub Nov. 27, 2007.

Utz, P.J., et al. "Posttranslational protein modifications, apoptosis, and the bypass of tolerance to autoantigens." Arthritis Rheum. Jul. 1998;41(7):1152-60.

Uversky, V.N., et al. "Why are "natively unfolded" proteins unstructured under physiologic conditions?" Proteins. Nov. 15, 2000;41(3):415-27.

Uversky, V.N., et al. "Evidence for a partially folded intermediate in alpha-synuclein fibril formation." J Biol Chem. Apr. 6, 2001;276(14):10737-44. Epub Jan. 10, 2001.

Uversky, V.N., et al. "Effects of nitration on the structure and aggregation of alpha-synuclein." Brain Res Mol Brain Res. Mar. 24, 2005;134(1):84-102.

Vijitruth, R., et al. "Cyclooxygenase-2 mediates microglial activation and secondary dopaminergic cell death in the mouse MPTP model of Parkinson's disease." J Neuroinflammation. Mar. 27, 2006;3:6.

Wang, H.Y., et al. "Tumor-specific human CD4+ regulatory T cells and their ligands: implications for immunotherapy." Immunity. Jan. 2004;20(1):107-18.

Weinreb, P.H., et al. "NACP, a protein implicated in Alzheimer's disease and learning, is natively unfolded." Biochemistry. Oct. 29, 1996;35(43):13709-15.

Wersinger, C., et al. "An inflammatory pathomechanism for Parkinson's disease?" Curr Med Chem. 2006;13(5):591-602.

Wu, D.C., et al. "Blockade of microglial activation is neuroprotective in the 1-methyl-4-phenyl-1,2,3,6-tetrahydropyridine mouse model of Parkinson disease." J Neurosci. Mar. 1, 2002;22(5):1763-71.

Yamin, G., et al. "Nitration inhibits fibrillation of human alpha-synuclein in vitro by formation of soluble oligomers." FEBS Lett. May 8, 2003;542(1-3):147-52.

Zarranz, J.J., et al. "The new mutation, E46K, of alpha-synuclein causes Parkinson and Lewy body dementia." Ann Neurol. Feb. 2004;55(2):164-73.

Zhang, W., et al. "Aggregated alpha-synuclein activates microglia: a process leading to disease progression in Parkinson's disease." Faseb J. Apr. 2005;19(6):533-42.

Zhang, R., et al. "Evidence for systemic immune system alterations in sporadic amyotrophic lateral sclerosis (sALS)." J Neuroimmunol. Feb. 2005;159(1-2):215-24. Epub Nov. 26, 2004.

Zhang, R., et al. "MCP-1 chemokine receptor CCR2 is decreased on circulating monocytes in sporadic amyotrophic lateral sclerosis (sALS)." J Neuroimmunol. Oct. 2006; 179(10-11):87-93.

Zhao, W., et al. "Protective effects of an anti-inflammatory cytokine, interleukin-4, on motoneuron toxicity induced by activated microglia." J Neurochem. Nov. 2006;99(4):1176-87. Epub Oct. 2, 2006.

Delgado, M., et al. "Vasoactive intestinal peptide and pituitary adenylate cyclase-activating polypeptide stimulate the induction of Th2 responses by up-regulating B7.2 expression." J Immunol. Oct. 1, 1999;163(7):3629-35.

Delgado, M., et al. "Vasoactive intestinal peptide and pituitary adenylate cyclase-activating polypeptide inhibit interleukin-12 transcription by regulating nuclear factor kappaB and Ets activation." J Biol Chem. Nov. 5, 1999;274(45):31930-40.

Delgado, M., et al. "Neuroprotective effect of vasoactive intestinal peptide (VIP) in a mouse model of Parkinson's disease by blocking microglial activation." Faseb J. May 2003;17(8):944-6. Epub Mar. 5, 2003.

Delgado, M., et al. "Vasoactive intestinal peptide and pituitary adenylate cyclase-activating polypeptide promote in vivo generation of memory Th2 cells." Faseb J. Nov. 2002;16(13):1844-6. Epub Sep. 5, 2002.

Delgado, M., et al. "Vasoactive intestinal peptide prevents activated microglia-induced neurodegeneration under inflammatory conditions: potential therapeutic role in brain trauma." Faseb J. Oct. 2003;17(13):1922-4. Epub Aug. 15, 2003.

Aharoni, R., et al. "The immunomodulator glatiramer acetate augments the expression of neurotrophic factors in brains of experimental autoimmune encephalomyelitis mice." Proc Natl Acad Sci U S A. Dec. 27, 2005;102(52):19045-50. Epub Dec. 19, 2005.

Alexinau, M.E., et al. "Immune reactivity in a mouse model of familial ALS correlates with disease progression." Neurology. Oct. 9, 2001;57(7):1282-9.

Amoura, Z., et al. "The key role of nucleosomes in lupus." Arthritis Rheum. May 1999;42(5):833-43.

Angelov, D.N., et al. "Therapeutic vaccine for acute and chronic motor neuron diseases: implications for amyotrophic lateral sclerosis." Proc Natl Acad Sci U S A. Apr. 15, 2003;100(8):4790-5. Epub Mar. 31, 2003.

Avidan, H., et al. "Vaccination with autoantigen protects against aggregated beta-amyloid and glutamate toxicity by controlling microglia: effect of CD4+CD25+ T cells." Eur J Immunol. Dec. 2004;34(12):3434-45.

Bakalash, S., et al. "T-cell-based vaccination for morphological and functional neuroprotection in a rat model of chronically elevated intraocular pressure." J Mol Med. Nov. 2005;83(11):904-16. Epub Aug. 12, 2005.

Bal-Price, A., et al. "Inflammatory neurodegeneration mediated by nitric oxide from activated glia-inhibiting neuronal respiration, causing glutamate release and excitotoxicity." J Neurosci. Sep. 1, 2001;21(17):6480-91.

Banerjee, R., et al. "Adaptive immune neuroprotection in G93A-SOD1 amyotrophic lateral sclerosis mice." PLoS One. Jul. 23, 2008;3(7):e2740.

Bar-Or, A., et al. "Analyses of all matrix metalloproteinase members in leukocytes emphasize monocytes as major inflammatory mediators in multiple sclerosis." Brain. Dec. 2003;126(Pt 12):2738-49. Epub Sep. 23, 2003.

Bas, J., et al. "Lymphocyte populations in Parkinson's disease and in rat models of parkinsonism." J Neuroimmunol. Feb. 1, 2001;113(1):146-52.

Benner, E.J., et al. "Therapeutic immunization protects dopaminergic neurons in a mouse model of Parkinson's disease." Proc Natl Aced Sci U S A. Jun. 22, 2004;101(25):9435-40. Epub Jun. 14, 2004.

Benner, E.J., et al. "Nitrated alpha-synuclein immunity accelerates degeneration of nigral dopaminergic neurons." PLoS One. Jan. 2, 2008;3(1):e1376.

Brochard, V., et al. "Infiltration of CD4+ lymphocytes into the brain contributes to neurodegeneration in a mouse model of Parkinson disease." J Clin Invest. Jan. 2009;119(1):182-92. doi: 10.1172/JCI36470. Epub Dec. 22, 2008.

Burkhardt, H., et al. "Chicken and egg in autoimmunity and joint inflammation." Trends Immunol. Jun. 2001;22(6):291-3.

Butovsky, O., et al. "Glatiramer acetate fights against Alzheimer's disease by inducing dendritic-like microglia expressing insulin-like growth factor 1." Proc Natl Acad Sci U S A. Aug. 1, 2006;103(31):11784-9. Epub Jul. 24, 2006.

Casal, J.A., et al. "Serum markers of monocyte/macrophage activation in patients with Alzheimer's disease and other types of dementia." Clin Biochem. Oct. 2003;36(7):553-6.

Casciola-Rosen, L., et al. "Scleroderma autoantigens are uniquely fragmented by metal-catalyzed oxidation reactions: implications for pathogenesis." J Exp Med. Jan. 6, 1997;185(1):71-9.

Cederbom, L., et al. "CD4+CD25+ regulatory T cells down-regulate co-stimulatory molecules on antigen-presenting cells." Eur J Immunol. Jun. 2000;30(6):1538-43.

Chartier-Harlin, M.C., et al. "Alpha-synuclein locus duplication as a cause of familial Parkinson's disease." Lancet. Sep. 25-Oct. 1, 2004;364(9440):1167-9.

Cho, B.P., et al. "Microglial phagocytosis of dopamine neurons at early phases of apoptosis." Cell Mol Neurobiol. Oct. 2003;23(4-5):551-60.

Choi, D.K., et al. "Ablation of the inflammatory enzyme myeloperoxidase mitigates features of Parkinson's disease in mice." J Neurosci. Jul. 13, 2005;25(28):6594-600.

Birnboim, H.C., et al. "Cutting edge: MHC class II-restricted peptides containing the inflammation-associated marker 3-nitrotyrosine evade central tolerance and elicit a robust cell-mediated immune response." J Immunol. Jul. 15, 2003;171(2):528-32.

Croisier, E., et al. "Microglial inflammation in the parkinsonian substantia nigra: relationship to alpha-synuclein deposition." J Neuroinflammation. Jun. 3, 2005;2:14.

Curiel, T.J., et al. "Specific recruitment of regulatory T cells in ovarian carcinoma fosters immune privilege and predicts reduced survival." Nat Med. Sep. 2004;10(9):942-9. Epub Aug. 22, 2004.

Delgado, M., et al. "Vasoactive intestinal peptide generates CD4+CD25+ regulatory T cells in vivo." J Leukoc Biol. Dec. 2005;78(6):1327-38. Epub Oct. 4, 2005.

Doyle, H.A., et al. "Post-translational protein modifications in antigen recognition and autoimmunity." Trends Immunol. Aug. 2001;22(8):443-9.

Du, Y., et al. "Minocycline prevents nigrostriatal dopaminergic neurodegeneration in the MPTP model of Parkinson's disease." Proc Natl Acad Sci U S A. Dec. 4, 2001;98(25):14669-74. Epub Nov. 27, 2001.

Dufty, B.M., et al. "Calpain-cleavage of alpha-synuclein: connecting proteolytic processing to disease-linked aggregation." Am J Pathol. May 2007;170(5):1725-38.

Eggena, M.P., et al. "Depletion of regulatory T cells in HIV infection is associated with immune activation." J Immunol. Apr. 1, 2005;174(7):4407-14.

El-Agnaf, O.M., et al. "Alpha-synuclein implicated in Parkinson's disease is present in extracellular biological fluids, including human plasma." Faseb J. Oct. 2003;17(13):1945-7. Epub Aug. 15, 2003.

Eliezer, D., et al. "Conformational properties of alpha-synuclein in its free and lipid-associated states."J Mol Biol. Apr. 6, 2001;307(4):1061-73.

Filion, L.G., et al. "Monocyte-derived cytokines in multiple sclerosis." Clin Exp Immunol. Feb. 2003;131(2):324-34.

Garg, S.K., et al. "Neuroprotective immunity: T cell-derived glutamate endows astrocytes with a neuroprotective phenotype." J Immunol. Mar. 15, 2008;180(6):3866-73.

Gendelman, H.E., et al. "Neural immunity: Friend or foe?" J Neurovirol. Dec. 2002;8(6):474-9.

Giasson, B.I., et al. "Oxidative damage linked to neurodegeneration by selective alpha-synuclein nitration in synucleinopathy lesions." Science. Nov. 3, 2000;290(5493):985-9.

Goedert, M. "Filamentous nerve cell inclusions in neurodegenerative diseases: tauopathies and alpha-synucleinopathies." Philos Trans R Soc Lond B Biol Sci. Jun. 29, 1999;354(1386)1101-18.

Gonzalez-Rey, E., et al. "Vasoactive intestinal peptide generates human tolerogenic dendritic cells that induce CD4 and CD8 regulatory T cells." Blood. May 1, 2006;107(9):3632-8. Epub Jan. 5, 2006.

Gorantla, S., et al. "Modulation of innate immunity by copolymer-1 leads to neuroprotection in murine HIV-1 encephalitis." Glia. Jan. 15, 2008;56(2):223-32.

Graves, M.C., et al. "Inflammation in amyotrophic lateral sclerosis spinal cord and brain is mediated by activated macrophages, mast cells and T cells." Amyotroph Lateral Scler Other Motor Neuron Disord. Dec. 2004;5(4):213-9.

Habisch, H.J., et al. "Limited effects of glatiramer acetate in the high-copy No. hSOD1-G93A mouse model of ALS." Exp Neurol. Aug. 2007;206(2):288-95. Epub May 18, 2007.

Haenggeli, C., et al. "Therapeutic immunization with a glatiramer acetate derivative does not alter survival in G93A and G37R SOD1 mouse models of familial ALS." Neurobiol Dis. Apr. 2007;26(1):146-52. Epub Dec. 30, 2006.

Hasegawa, M., et al. "Phosphorylated alpha-synudein is ubiquitinated in alpha-synudeinopathy lesions." J Biol Chem. Dec. 13, 2002;277(50):49071-6. Epub Oct. 10, 2002.

Henkel, J.S., et al. "Presence of dendritic cells, MCP-1, and activated microglia/macrophages in amyotrophic lateral sclerosis spinal cord tissue." Ann Neurol. Feb. 2004;55(2):221-35.

Henkel, J.S., et al. "The chemokine MCP-1 and the dendritic and myeloid cells it attracts are increased in the mSOD1 mouse model of ALS." Mol Cell Neurosci. Mar. 2006;31(3):427-37. Epub Dec. 5, 2005.

Hermanowicz, N. "Drug therapy for Parkinson's disease." Semin Neurol. Apr. 2007;27(2):97-105.

Hodara, R., et al. "Functional consequences of alpha-synuclein tyrosine nitration: diminished binding to lipid vesicles and increased fibril formation." J Biol Chem. Nov. 12, 2004;279(46):47746-53. Epub Sep. 9, 2004.

Jin, J., et al. "Prostaglandin E2 receptor subtype 2 (EP2) regulates microglial activation and associated neurotoxicity induced by aggregated alpha-synuclein." J Neuroinflammation. Jan. 4, 2007;4:2.

Kakimura, J., et al. "Release and aggregation of cytochrome c and alpha-synuclein are inhibited by the antiparkinsonian drugs, talipexole and pramipexole." Eur J Pharmacol. Apr. 6, 2001;417(1-2):59-67.

Kinter, A.L., et al. "CD25(+)CD4(+) regulatory T cells from the peripheral blood of asymptomatic HIV-infected individuals regulate CD4(+) and CD8(+) HIV-specific T cell immune responses in vitro and are associated with favorable clinical markers of disease status." J Exp Med. Aug. 2, 2004;200(3):331-43. Epub Jul. 26, 2004.

Kipnis, J., et al. "T cell immunity to copolymer 1 confers neuroprotection on the damaged optic nerve: possible therapy for optic neuropathies." Proc Natl Acad Sci U S A. Jun. 20, 2000;97(13):7446-51.

\* cited by examiner

| Protein ID by LC/MS/MS* | SwissProt† | IPI‡ | M.wt.§ (DA) | pI‖ | Subcellular Location¶ | Function# | Peptide** # | DIGE†† Index | P-value‡‡ |
|---|---|---|---|---|---|---|---|---|---|
| Heterogeneous nuclear ribonucleoprotein A2/B1 isoform 2 | O88569 | IPI00622847 | 37403 | 8.97 | Nucleus | transcription | 2 | -1.69 | |
| Guanine nucleotide-binding protein | P62880 | IPI00162780 | 37331 | 5.60 | Cytoplasm | GTPase activity | 2 | -1.5 | 0.004 |
| Guanine nucleotide-binding protein | Q61011 | IPI00116938 | 37240 | 5.41 | Cytoplasm | GTPase activity | 2 | -1.5 | 0.004 |
| Interleukin-6 receptor subunit beta | Q00560 | IPI00120155 | 102452 | 5.32 | Membrane | signal transduction | 3 | -1.84 | 0.05 |
| Ubiquitin A-52 residue ribosomal protein fusion | B0LAC2 | IPI00138892 | 8038.2 | 6.89 | Ribosome | protein modification | 2 | -1.51 | 0.05 |
| Alpha tubulin | P68369 | IPI00110753 | 50136 | 4.94 | Cytoskeleton | cell motility | 2 | -2.21 | |
| Beta actin | P60710 | IPI00110850 | 269833 | 5.82 | Cytoskeleton | cell motility | 3 | -1.5 | 0.046 |
| Dynein cytoplasmic 1 intermediate chain 2 | O88487 | IPI00131086 | 68394 | 5.16 | Cytoskeleton | cell motility | 2 | -2.21 | |
| Galectin 3 | P16110 | IPI00131259 | 27515 | 8.47 | Cytoplasm/nucleus | protein binding, phagocytosis | 4 | -2.96 | |
| L-plastin | Q61233 | IPI00118892 | 70149 | 5.2 | Cytoskeleton | phagocytosis | 2 | -1.95 | |
| RuvB-like protein 1 | P60122 | IPI00133985 | 50214 | 6.02 | Nucleus | proliferation | 5 | -1.5 | |
| Voltage-dependent anion channel 2 | Q60930 | IPI00122547 | 31733 | 7.44 | Mitochondria | ion transport | 6 | -1.71 | |

Figure 22A

| Protein ID by LC/MS/MS* | SwissProt† | IPI‡ | M.wt§ (DA) | pI∥ | Subcellular Location¶ | Function# | Peptide** # | DIGE†† Index | P-value‡‡ |
|---|---|---|---|---|---|---|---|---|---|
| Voltage-dependent anion channel 3 | Q60931 | IPI00876341 | 30753 | 8.96 | Mitochondria | ion transport | 19 | -1.94 | |
| Vacuolar H+ATPase B2 | P62814 | IPI00119113 | 56551 | 5.57 | Membrane | ion transport | 6 | -1.82 | 0.04 |
| Voltage-dependent anion-selective channel protein 1 (VDAC-1) | Q60932 | IPI00230540 | 32351 | 8.55 | Membrane/ Mitochondria | ion transport | 3 | -1.94 | |
| G-protein beta subunit | Q61621 | IPI00120716 | 13533 | 5.50 | Membrane | G-protein signaling | 4 | -1.5 | 0.004 |
| Lamin A isoform C2 | P48678 | IPI00230435 | 74238 | 6.54 | Nucleus | membrane stabilization | 22 | -1.67 | 0.017 |
| Cofilin 1 | P18760 | IPI00890117 | 18559 | 8.22 | Cytoskeleton | actin polymerization | 3 | -2.15 | 0.02 |
| Cofilin 2 | P45591 | IPI00266188 | 18710 | 7.66 | Cytoskeleton | actin polymerization | 2 | -2.15 | 0.02 |
| Vimentin | P20152 | IPI00227299 | 53688 | 5.06 | Cytoskeleton | stabilize cytoskeleton | 5 | -2.35 | 0.05 |
| Peripherin | P15331 | IPI00129527 | 54268 | 5.40 | Cytoskeleton | cytoskeleton organization | 2 | -2.35 | 0.05 |
| Desmin | P31001 | IPI00130102 | 53498 | 5.21 | Cytoskeleton | stabilize cytoskeleton | 2 | -2.35 | 0.05 |
| Adenylyl cyclase-associated protein 1 (CAP 1) | P40124 | IPI00137331 | 51575 | 7.16 | Cytoskeleton | cytoskeleton organization | 3 | -2.39 | 0.05 |
| Fascin | Q61553 | IPI00353563 | 54508 | 6.44 | Filopodium | actin binding | 3 | -1.63 | |

Figure 22B

| Protein ID by LC/MS/MS* | SwissProt† | IPI‡ | M.wt§ (DA) | pI¶ | Subcellular Location¶ | Function# | Peptide** # | DIGE†† Index | P-value‡‡ |
|---|---|---|---|---|---|---|---|---|---|
| Annexin A2 | P07356 | IPI00468203 | 38676 | 7.55 | Secreted | matrix | 2 | -1.5 | |
| Annexin A10 | Q9QZ10 | IPI00136659 | 37301 | 5.40 | Mitochondria | matrix | 2 | -1.63 | 0.05 |
| Inner membrane protein, mitochondria | Q8CAQ8 | IPI00228150 | 83900 | 6.18 | Mitochondria | matrix | 7 | -1.58 | |
| Gelsolin | A2AL35 | IPI00117167 | 85942 | 5.83 | Cytoskeleton | apoptosis and inflammation, vesicle transport | 8 | 1.53 | 0.05 |
| Annexin A1 | P10107 | IPI00230395 | 38734 | 6.97 | Cytoplasm | membrane fusion and exocytosis | 2 | -1.5 | |
| Palmitoyl-protein thioesterase 1 | B1B0P8 | IPI00881289 | 19550 | 8.09 | Membrane/ Lysosome | endocytosis/ protein transport | 2 | -1.5 | |
| Rho GDP dissociation inhibitor (GDI) alpha | Q99PT1 | IPI00322312 | 23407 | 5.12 | Cytoplasm/ membrane | protein binding | 9 | -2.08 | |
| Cryptochrome 2 | Q9R194 | IPI00128234 | 66850 | 8.66 | Cytoplasm/nucleus | protein transport | 3 | -1.5 | 0.039 |
| 14-3-3 zeta | P63101 | IPI00116498 | 27111 | 4.73 | Mitochondria | protein targeting | 5 | -2.39 | 0.05 |
| Ferritin light chain 1 | P29391 | IPI00762203 | 20802 | 5.66 | Cytoplasm | iron homeostasis | 5 | -1.75 | 0.05 |
| Ferritin heavy chain 1 | P09528 | IPI00230145 | 21067 | 5.53 | Cytoplasm | iron homeostasis | 3 | -1.61 | 0.02 |
| Acetyl-Coenzyme A acetyltransferase 1 | A8XUS5 | IPI00228253 | 41298 | 7.16 | Cytoplasm | metabolism | 4 | -1.52 | |
| Acetyl-Coenzyme A acyltransferase 2 | A8XUT1 | IPI00881591 | 38147 | 7.63 | Cytoplasm | metabolism | 2 | -1.52 | |

Figure 22C

| Protein ID by LC/MS/MS* | SwissProt† | IPI‡ | M.wt.§ (DA) | pI^a | Subcellular Location¶ | Function^# | Peptide** # | DIGE†† Index | P-value‡‡ |
|---|---|---|---|---|---|---|---|---|---|
| Aldehyde dehydrogenase, mitochondrial | P47738 | IPI00111218 | 56538 | 7.53 | Mitochondria | metabolism | 23 | -2.79 | |
| Hexosaminidase B | P20060 | IPI00115530 | 61116 | 8.28 | Lysosome | metabolism | 4 | -2.79 | |
| Ugp2 protein | Q8R0M2 | IPI00279474 | 55498 | 6.92 | Cytoplasm | metabolism | 6 | -1.5 | 0.028 |
| Pyrophosphatase | Q9D819 | IPI00110684 | 32667 | 5.37 | Cytoplasm | metabolism | 7 | -1.73 | |
| Aldo-keto reductase family 1, member B8 | Q3UJW9 | IPI00466128 | 36615 | 6.90 | Cytoplasm/ membrane | catabolism | 4 | 1.6 | |
| Catechol O-methyltransferase | O88587 | IPI00759876 | 29496 | 5.52 | Cytoplasm | catabolism | 3 | 1.51 | 0.05 |
| Glutamate oxaloacetate transaminase 2, mitochondrial | P05202 | IPI00117312 | 47411 | 9.13 | Mitochondria | catabolism | 6 | -1.5 | 0.046 |
| Fatty acid-binding protein | P05201 | IPI00230204 | 46232 | 6.68 | Cytoplasm | catabolism | 4 | -3.57 | 0.02 |
| Cathepsin B | P10605 | IPI00113517 | 37280 | 5.57 | Lysosome | thiol protease | 4 | 2.86 | 0.005 |
| Cathepsin D | P18242 | IPI00111013 | 44954 | 6.71 | Lysosome | acid protease | 4 | 1.62 | 0.036 |
| Calreticulin | P14211 | IPI00123639 | 47995 | 4.33 | Membrane/ ER | chaperone | 6 | -4.6 | |
| Calreticulin 3 isoform 1 | Q9D9Q6 | IPI00113023 | 44198 | 5.99 | ER | chaperone | 2 | -2.75 | |
| Chaperonin subunit 6a zeta | Q52KG9 | IPI00116281 | 58076 | 6.46 | Cytoplasm | chaperone | 3 | -1.67 | 0.017 |
| HSP 10 | Q64433 | IPI00263863 | 10963 | 7.91 | Mitochondria | chaperone | 2 | -3.29 | |

Figure 22D

| Protein ID by LC/MS/MS* | SwissProt† | IPI‡ | M.wt§ (DA) | pI‖ | Subcellular Location¶ | Function# | Peptide** # | DIGE†† Index | P-value‡‡ |
|---|---|---|---|---|---|---|---|---|---|
| HSP 60 | P63038 | IPI00308885 | 60955 | 5.91 | Mitochondria | chaperone | 17 | -2.35 | 0.05 |
| HSP 70 | P63017 | IPI00323357 | 70871 | 5.37 | Cytoplasm | chaperone | 17 | -2.35 | 0.05 |
| Proteasome subunit, alpha type 2 | P49722 | IPI00890001 | 25926 | 8.39 | Cytoplasm | Ubiquitin-Proteasome system | 2 | -1.53 | 0.05 |
| Proteasome subunit, alpha type 3 | O70435 | IPI00331644 | 28405 | 5.29 | Cytoplasm/nucleus | Ubiquitin-Proteasome system | 6 | -2.39 | 0.05 |
| Proteasome subunit, alpha type 6 | Q9QUM9 | IPI00131845 | 27372 | 6.35 | Cytoplasm/nucleus | Ubiquitin-Proteasome system | 4 | -1.54 | |
| Proteasome subunit, alpha type 7 | Q9Z2U0 | IPI00131406 | 27855 | 8.59 | Cytoplasm/nucleus | Ubiquitin-Proteasome system | 3 | -1.69 | 0.027 |
| 20S proteasome subunit C2 | Q9JHS5 | IPI00283862 | 4581.4 | 8.07 | Cytoplasm | Ubiquitin-Proteasome system | 2 | -1.54 | 0.05 |
| Ubiquitin-conjugating enzyme E2-25K | P61087 | IPI00322440 | 22407 | 5.33 | Cytoplasm | Ubiquitin-Proteasome system | 8 | -1.51 | 0.05 |
| Superoxide dismutase 1, soluble | P08228 | IPI00130589 | 15943 | 6.02 | Cytoplasm/mitochondria | redox | 9 | -1.54 | 0.05 |
| Thioredoxin reductase 2 | Q9JLT4 | IPI00124699 | 56453 | 8.72 | Mitochondria | redox | 2 | -1.5 | 0.028 |
| Biliverdin reductase B (NADPH) | Q923D2 | IPI00113996 | 22197 | 6.49 | Cytoplasm | redox | 9 | -1.53 | 0.05 |
| Peroxiredoxin 1 | P35700 | IPI00121788 | 22177 | 8.26 | Cytoplasm | redox | 2 | -1.54 | 0.05 |
| Peroxiredoxin 4 | O08807 | IPI00116254 | 31053 | 6.67 | Cytoplasm | redox | 2 | -1.69 | 0.05 |
| Peroxiredoxin 6 | O08709 | IPI00555059 | 24871 | 5.71 | Cytoplasm/lysosome | redox | 6 | -1.59 | 0.05 |

Figure 22E

| Protein ID by LC/MS/MS* | SwissProt† | IPI‡ | M.wt§ (DA) | pI‖ | Subcellular Location¶ | Function# | Peptide** # | DIGE†† Index | P-value‡‡ |
|---|---|---|---|---|---|---|---|---|---|
| Isocitrate dehydrogenase [NADP] cytoplasmic | O88844 | IPI00135231 | 46660 | 6.48 | Cytoplasm | redox | 4 | -4.43 | |
| Glutaredoxin 1 | Q9QUH0 | IPI00331528 | 11871 | 8.68 | Cytoplasm | redox | 4 | -1.72 | |
| Glutathione reductase 1 precursor | P47791 | IPI00111359 | 53663 | 8.19 | Cytoplasm/mitochondria | redox | 2 | -1.5 | 0.028 |
| Alpha enolase | P17182 | IPI00462072 | 47141 | 6.37 | Cytoplasm/ membrane | glycolysis | 3 | -2.08 | |
| Enolase 3, beta | P21550 | IPI00228548 | 47025 | 6.73 | Cytoplasm | glycolysis | 2 | 1.56 | |
| Lactate dehydrogenase A | P06151 | IPI00319994 | 36499 | 7.61 | Cytoplasm | glycolysis | 12 | 1.63 | |
| Pyruvate dehydrogenase (lipoamide) beta | Q9D051 | IPI00132042 | 38937 | 6.41 | Mitochondria | glycolysis | 8 | -1.5 | 0.004 |
| Pyruvate dehydrogenase E1 alpha 1 | P35486 | IPI00337893 | 43232 | 8.49 | Mitochondria | glycolysis | 2 | -2.66 | |
| Pyruvate kinase M | P52480 | IPI00407130 | 57845 | 7.17 | Mitochondria | glycolysis | 2 | -2.08 | |
| Triosephosphate isomerase 1 | P17751 | IPI00467833 | 26713 | 6.90 | Cytoplasm | glycolysis | 2 | -1.53 | 0.05 |
| Malate dehydrogenase | P14152 | IPI00336324 | 36511 | 6.16 | Cytoplasm | TCA cycle | 2 | -1.94 | |
| Dihydrolipoamide dehydrogenase | O08749 | IPI0087445 | 54272 | 7.99 | Mitochondria | oxidoreductase | 2 | -1.63 | |
| Nucleoside-diphosphate kinase | Q5NC82 | IPI00127417 | 17363 | 6.97 | Mitochondria | cell survival/apoptosis | 4 | -5.68 | |

Figure 22F

| Protein ID by LC/MS/MS* | SwissProt† | IPI‡ | M.wt§ (DA) | pI‖ | Subcellular Location¶ | Function# | Peptide** # | DIGE†† Index | P-value‡‡ |
|---|---|---|---|---|---|---|---|---|---|
| ATP synthase, H+ transporting mitochondrial F1 complex, delta subunit | Q4FK74 | IPI00453777 | 17600 | 5.03 | Mitochondria (Complex V) | oxidative phosphorylation | 3 | -1.84 | 0.05 |
| ATP synthase, H+ transporting, mitochondrial F0 complex, subunit d | B1ASE1 | IPI00230507 | 18749 | 5.52 | Mitochondria (Complex V) | oxidative phosphorylation | 2 | -1.51 | |
| ATP synthase, H+ transporting, mitochondrial F0 complex, subunit b | Q5IOW0 | IPI00341282 | 28949 | 9.11 | Mitochondria (Complex V) | oxidative phosphorylation | 3 | -2.66 | |
| ATP synthase, H+ transporting, mitochondrial F1F0 complex, subunit e | Q5EBI8 | IPI00111770 | 8236.5 | 7.99 | Mitochondria (Complex V) | oxidative phosphorylation | 20 | -1.88 | 0.011 |
| Electron transferring flavoprotein, alpha polypeptide | B1B1B4 | IPI00116753 | 35009 | 8.62 | Mitochondria | electron transport | 2 | -1.71 | |

Figure 22G

| LC/MS* Protein ID by | SwissProt† | IPI‡ | M.wt.§ (DA) | pI" | Subcellular Location¶ | Function# | Peptide#** | DIGE†† Index | P-value‡‡ |
|---|---|---|---|---|---|---|---|---|---|
| VIP-receptor-gene repressor protein | O88461 | IPI00209665 | 72972 | 9.57 | Nucleus | transcription | 2 | 1.5 | 0.0011 |
| TAR DNA binding protein | Q921F2 | IPI00121758 | 44548 | 6.26 | Nucleus | transcription | 2 | 1.52 | 0.003 |
| MRG-binding protein | Q9DAT2 | IPI00119018 | 23888 | 4.87 | Nucleus | transcription | 2 | -3.79 | <0.0001 |
| Ubiquitin conjugating enzyme E2N | P61089 | IPI00165854 | 17138 | 6.13 | Nucleus | transcription | 3 | 2.15 | 0.0076 |
| Eukaryotic translation initiation factor 3, subunit H | Q91WK2 | IPI00128202 | 39832 | 6.19 | Nucleus | translation | 2 | -1.52 | 0.0037 |
| Laminin B2 | Q61292 | IPI00119065 | 196352 | 6.28 | Secreted | cell motility | 2 | -1.51 | 0.0038 |
| Beta actin | P60710 | IPI00110850 | 269833 | 5.82 | Cytoskeleton | cell motility | 5 | -2.09 | 0.0008 |
| Alpha-tubulin | P68369 | IPI00110753 | 50136 | 4.94 | Cytoskeleton | cell motility | 2 | -1.51 | 0.0038 |
| Microtubule-associated protein, RP/EB family, member 1 | Q7TN34 | IPI00117896 | 29885 | 5.12 | Cytoskeleton | cell motility | 9 | 1.5 | 0.0011 |
| Chloride intracellular channel 1 | Q9Z1Q5 | IPI00130344 | 27013 | 5.09 | Cytoplasm | ion channel | 6 | 1.55 | 0.003 |
| Voltage-dependent anion channel 2 | Q60930 | IPI00122547 | 31733 | 7.44 | Mitochondria | ion channel | 3 | 1.53 | 0.005 |
| Voltage-dependent anion channel 1 | Q60932 | IPI00122549 | 32351 | 8.55 | Mitochondria | ion channel | 5 | 1.88 | <0.0001 |

Figure 22H

| LC/MS/MS Protein ID | SwissProt† | IPI‡ | M.wt.§ (DA) | pI" | Subcellular Location¶ | Function# | Peptide #** | DIGE†† Index | P-value‡‡ |
|---|---|---|---|---|---|---|---|---|---|
| Vimentin | P20152 | IPI00227299 | 53688 | 5.06 | Cytoskeleton | stabilize cytoskeleton | 6 | -1.63 | 0.0002 |
| Cofilin 1 | P18760 | IPI00890117 | 18559 | 8.22 | Cytoskeleton | actin polymerization | 3 | -1.61 | 0.0022 |
| Cofilin 2 | P45591 | IPI00266188 | 18710 | 7.66 | Cytoskeleton | actin polymerization | 2 | -1.5 | 0.05 |
| Macrophage capping protein (CAPG) | P24452 | IPI00136906 | 39240 | 6.73 | Cytoplasm | inhibits actin polymerization | 9 | 1.82 | 0.036 |
| Guanine nucleotide exchange factor GEFT | Q9CWR0 | IPI00109434 | 68262 | 5.19 | Cytoplasm | actin reorganization | 4 | 2.7 | <0.0001 |
| Gelsolin | A2AL35 | IPI00117167 | 85942 | 5.83 | Cytoskeleton | apoptosis and inflammation, vesicle transport | 5 | -2.48 | 0.0002 |
| Galectin 3 | P16110 | IPI00131259 | 27515 | 8.47 | Cytoplasm/nucleus | protein binding, phagocytosis | 26 | -1.68 | 0.0016 |
| Early endosome antigen 1 | Q8BL66 | IPI00453776 | 160915 | 5.99 | Cytoplasm | endosomal trafficking | 8 | -2.41 | <0.0001 |
| Annexin A1 | P10107 | IPI00230395 | 38734 | 6.97 | Cytoplasm | membrane fusion and exocytosis | 3 | 1.53 | 0.0047 |
| Annexin A4 | P97429 | IPI00353727 | 35990 | 5.43 | Cytoplasm | membrane fusion and exocytosis | 18 | 1.5 | 0.0011 |
| Nestin | Q6P5H2 | IPI00453692 | 207124 | 4.3 | Cytoplasm | protein trafficking | 2 | 1.51 | 0.023 |
| cAMP-dependent protein kinase | P05132 | IPI00227900 | 40571 | 8.84 | Cytoplasm | protein trafficking | 5 | -1.59 | 0.05 |
| Non-specific lipid transfer protein | P32020 | IPI00134131 | 59126 | 7.16 | Cytoplasm | lipid protein transfer | 3 | 4.42 | <0.0001 |

Figure 22I

| LC/MS/MS* Protein ID | SwissProt† | IPI‡ | M.wt§ (DA) | pI‖ | Subcellular Location¶ | Function# | Peptide #** | DIGE†† Index | P-value‡‡ |
|---|---|---|---|---|---|---|---|---|---|
| Glycolipid transfer protein | Q9JL62 | IPI00229718 | 23690 | 6.9 | Cytoplasm | lipid protein transfer | 2 | 1.55 | 0.003 |
| Peptide chain release factor 1 | Q8BWY3 | IPI00312468 | 49031 | 5.51 | Cytoplasm | termination of peptide synthesis | 3 | 1.71 | 0.034 |
| L-Plastin | Q61233 | IPI00118892 | 70149 | 5.2 | Cytoskeleton | phagocytosis | 25 | 2.1 | 0.0029 |
| Ferritin light chain 1 | P29391 | IPI00762203 | 20802 | 5.66 | Cytoplasm | iron homeostasis | 2 | 1.51 | 0.023 |
| Ferritin heavy chain | P09528 | IPI00230145 | 21067 | 5.53 | Cytoplasm | iron homeostasis | 8 | -1.54 | 0.0033 |
| Transaldolase 1 | Q93092 | IPI00124692 | 37387 | 6.57 | Cytoplasm | metabolism | 7 | 1.71 | 0.034 |
| Hypoxanthine guanine phosphoribosyl transferase 1 | P00493 | IPI00284806 | 24570 | 6.21 | Cytoplasm | metabolism | 4 | 2.33 | <0.0001 |
| Sterol carrier protein 2 | A2APS3 | IPI00134131 | 59126 | 7.16 | Mitochondria | metabolism | 9 | 4.42 | <0.0001 |
| Aconitate hydratase | Q99KI0 | IPI00116074 | 85464 | 8.08 | Mitochondria | enzyme | 2 | 1.51 | 0.023 |
| Lysosomal alpha-mannosidase precursor | O09159 | IPI00381303 | 114604 | 8.3 | Lysosome | catabolism | 3 | 2.59 | <0.0001 |
| Contrapsin | P07759 | IPI00131830 | 46880 | 5.05 | Secreted | protease inhibitor | 3 | 6.56 | <0.0001 |
| Calpastatin | P51125 | IPI00409176 | 84922 | 5.37 | Cytoplasm | protease inhibitor | 2 | -1.86 | 0.0004 |
| Cathepsin B | P10605 | IPI00113517 | 37280 | 5.57 | Lysosome | thiol protease | 15 | -3.34 | <0.0001 |
| Cathepsin D | P18242 | IPI00111013 | 44954 | 6.71 | Lysosome | acid protease | 5 | -2.09 | 0.0008 |
| Cathepsin Z | Q9R1T3 | IPI00207663 | 34194 | 6.74 | Cytoplasm/Secreted | peptidase | 2 | 1.5 | 0.0011 |
| SDF2 like protein 1 | Q9ESP1 | IPI00227657 | 23648.34 | 6.92 | ER | stress response | 3 | 2.59 | 0.0067 |
| Calreticulin | P14211 | IPI00123639 | 47995 | 4.33 | Membrane/ER | chaperone | 20 | 2.32 | <0.0001 |

Figure 22J

| LC/MS/MS Protein ID | SwissProt[†] | IPI[‡] | M.wt.[§] (DA) | pI[∥] | Subcellular Location[¶] | Function[#] | Peptide[**] # | DIGE[††] Index | P-value[‡‡] |
|---|---|---|---|---|---|---|---|---|---|
| HSP 10 | Q64433 | IPI00263863 | 109627 | 7.91 | Mitochondria | chaperone | 5 | 1.52 | 0.0025 |
| HSP 70 | P63017 | IPI00323357 | 70871 | 5.37 | Cytoplasm | chaperone | 3 | 1.59 | 0.0097 |
| HSP 90 | Q80Y52 | IPI00330804 | 84788 | 4.93 | Cytoplasm | chaperone | 2 | 2.09 | 0.0004 |
| Proteasome subunit beta type-2 | Q9R1P3 | IPI00128945 | 22906 | 6.52 | Cytoplasm | Ubiquitin-Proteasome system | 4 | 2.59 | <0.0001 |
| Proteasome (prosome, macropain) subunit, alpha type 2 | P49722 | IPI00890001 | 25926 | 8.39 | Cytoplasm | Ubiquitin-Proteasome system | 7 | 6.56 | <0.0001 |
| Ubiquitin specific protease 19 | Q3UJD6 | IPI00420483 | 150549 | 5.99 | Cytoplasm | Ubiquitin-Proteasome system | 2 | 4.42 | <0.0001 |
| Ubiquitin fusion degradation | P70362 | IPI00656165 | 34484 | 6.97 | Cytoplasm/ ER | Ubiquitin-Proteasome system | 2 | 1.52 | 0.0037 |
| Immune costimulatory protein B7-H4 | Q7TSP5 | IPI00169522 | 30875 | 5.69 | Membrane | immune response | 2 | -1.59 | 0.05 |
| Interferon-alpha/beta receptor alpha chain precursor | P33896 | IPI00115420 | 65777 | 5.37 | Membrane | immune response | 2 | 3.29 | <0.0001 |
| Interferon-induced GTP-binding protein | Q01514 | IPI00124675 | 67712 | 5.41 | Membrane | immune response | 2 | -1.83 | 0.0011 |
| Peroxiredoxin 1 | P35700 | IPI00121788 | 22177 | 8.26 | Cytoplasm | redox | 7 | 2.59 | <0.0001 |
| Peroxiredoxin 3 | Q9Z0V6 | IPI00208215 | 28295 | 7.14 | Mitochondria | redox | 7 | 2.7 | <0.0001 |
| Peroxiredoxin 4 | O08807 | IPI00116254 | 31053 | 6.67 | Cytoplasm | redox | 8 | 2.33 | <0.0001 |
| Peroxiredoxin 5 | P99029 | IPI00129517 | 21897 | 9.1 | Mitochondria | redox | 3 | 2.43 | <0.0001 |
| Peroxiredoxin 6 | O08709 | IPI00555059 | 24871 | 5.71 | Cytoplasm/lysosome | redox | 4 | 1.7 | 0.05 |

Figure 22K

| LC/MS/MS* Protein ID | SwissProt† | IPI‡ | M.wt.§ (DA) | pI" | Subcellular Location¶ | Function# | Peptide#** | DIGE†† Index | P-value‡‡ |
|---|---|---|---|---|---|---|---|---|---|
| Superoxide dismutase 1 [Cu-Zn] | P08228 | IPI00130589 | 15943 | 6.02 | Cytoplasm/mitochondria | redox | 2 | 1.6 | 0.05 |
| Superoxide dismutase 2 [Mn] | P09671 | IPI00109109 | 24603 | 8.8 | Mitochondria | redox | 2 | 1.71 | <0.0001 |
| Glutaredoxin 1 | Q9QUH0 | IPI00331528 | 11871 | 8.68 | Cytoplasm | redox | 2 | 1.82 | <0.0001 |
| Biliverdin reductase B (NADPH) | Q923D2 | IPI00113996 | 22197 | 6.49 | Cytoplasm | redox | 13 | 6.56 | <0.0001 |
| Oxidation resistance 1 | Q4KMM3 | IPI00277552 | 83016 | 4.9 | Mitochondria | redox | 2 | 1.51 | 0.05 |
| Thioredoxin 1 | P10639 | IPI00226993 | 11675 | 4.8 | Mitochondria | redox | 3 | 3.36 | <0.0001 |
| Catalase | P24270 | IPI00312058 | 59765 | 7.72 | Mitochondria | redox | 2 | 2.13 | 0.014 |
| Prohibitin | P67778 | IPI00133440 | 29820 | 5.57 | Mitochondria | respiration activity | 2 | 2.7 | <0.0001 |
| NADH dehydrogenase (ubiquinone) Fe-S protein-2 | Q923F9 | IPI00229008 | 18518 | 9.9 | Mitochondria (Complex I) | oxidative phosphorylation | 3 | 2.94 | 0.0012 |
| Mitochondrial ATP synthase, O subunit | Q9DB20 | IPI00118986 | 23364 | 10 | Mitochondria (Complex V) | oxidative phosphorylation | 3 | 2.59 | 0.0067 |
| H(+)-ATP synthase subunit e | P56382 | IPI00230241 | 5838 | 10.01 | Mitochondria (Complex V) | oxidative phosphorylation | 2 | 1.52 | 0.0025 |
| ATP synthase, H+ transporting, mitochondrial F1F0 complex, subunit e | Q5EBI8 | IPI00111770 | 8237 | 7.99 | Mitochondria (Complex V) | oxidative phosphorylation | 4 | 1.52 | 0.0025 |
| ATP synthase, H+ transporting, mitochondrial F0 complex, subunit d | B1ASE1 | IPI00230507 | 18749 | 5.52 | Mitochondria (Complex V) | oxidative phosphorylation | 21 | -1.83 | 0.0011 |

Figure 22L

| LC/MS/MS* Protein ID | SwissProt† | IPI‡ | M.wt.§ (DA) | pI∥ | Subcellular Location¶ | Function# | Peptide#** | DIGE†† Index | P-value‡‡ |
|---|---|---|---|---|---|---|---|---|---|
| Cytochrome c oxidase, subunit Va | P12787 | IPI00120719 | 16101 | 6.08 | Mitochondria (Complex IV) | oxidative phosphorylation | 4 | 2.65 | 0.014 |
| Cytochrome c oxidase, subunit VIb polypeptide 1 | P56391 | IPI00225390 | 10071 | 8.96 | Mitochondria (Complex IV) | oxidative phosphorylation | 2 | 2 | 0.0012 |

Figure 22M

| LC/MS/MS* Protein ID by | SwissProt† | IPI‡ | M.wt.§ (DA) | pI" | Subcellular Location¶ | Function# | Peptide#** | DIGE†† Index | P-value‡‡ |
|---|---|---|---|---|---|---|---|---|---|
| Histone H4 | P62806 | IPI00407339 | 11367 | 11.21 | Nucleus | nucleosome component | 3 | -1.56 | 0.021 |
| Histone H2B | Q64475 | IPI00554853 | 13592 | 10.31 | Nucleus | nucleosome component | 2 | -2.28 | |
| Heterogeneous nuclear ribonucleoprotein A3 (hnRNP A3) | Q8BG05 | IPI00269661 | 39652 | 8.46 | Nucleus | cytoplasmic trafficking of RNA | 5 | -1.62 | |
| GTP-binding nuclear protein Ran | P62827 | IPI00134621 | 24423 | 7.19 | Nucleus/Cytoplasm | GTPase activity | 5 | 1.35 | 0.033 |
| Rho GTPase-activating protein 1 | Q5FWK3 | IPI00404970 | 50411 | 5.97 | Membrane | GTPase activity | 2 | -1.75 | 0.05 |
| Rho GDP-dissociation inhibitor | Q99PT1 | IPI00322312 | 23407 | 5.12 | Cytoplasm | GTPase activity | 2 | 1.48 | 0.046 |
| Guanine nucleotide-binding protein subunit beta-2 | P62880 | IPI00162780 | 37331 | 7.06 | Membrane | signaling | 14 | 1.32 | 0.018 |
| Stathmin | P54227 | IPI00551236 | 17274 | 5.77 | Cytoplasm | cell motility | 3 | 1.52 | 0.0024 |
| Beta-actin | P60710 | IPI00110850 | 41737 | 5.78 | Cytoplasm | cell motility | 7 | 1.53 | 0.015 |
| Gamma-actin | P63260 | IPI00874482 | 41793 | 5.56 | Cytoplasm/Cytoskeleton | cell motility | 9 | 1.54 | |
| Cofilin-1 | P18760 | IPI00890117 | 18560 | 8.22 | Cytoplasm | actin polymerization | 2 | 1.63 | 0.0065 |
| Brain acid soluble protein 1 | Q91XV3 | IPI00129519 | 22087 | 4.5 | Membrane | nurite outgrowth | 9 | 1.55 | |

Figure 22N

| LC/MS/MS* Protein ID | SwissProt† | IPI‡ | M.wt§ (DA) | pI" | Subcellular Location¶ | Function# | Peptide#** | DIGE†† Index | P-value‡‡ |
|---|---|---|---|---|---|---|---|---|---|
| Gelsolin | A2AL35 | IPI00117167 | 85942 | 5.83 | Cytoskeleton | apoptosis and inflammation, vesicle transport | 7 | 1.73 | 0.004 |
| Galectin-3 | P16110 | IPI00131259 | 27515 | 8.5 | Nucleus | protein binding, phagocytosis | 7 | 1.65 | 0.067 |
| Cyclophilin A | P17742 | IPI00554989 | 17971 | 7.74 | Cytoplasm | protein folding | 6 | 1.48 | 0.05 |
| Protein disulfide isomerase | Q8BXZ1 | IPI00453798 | 51848 | 5.02 | ER | protein folding | 18 | -1.53 | 0.0072 |
| L-Plastin | Q61233 | IPI00118892 | 70149 | 5.21 | Cytoplasm | Phagocytosis | 17 | -1.53 | 0.0072 |
| Ferritin heavy chain | P09528 | IPI00230145 | 21067 | 5.53 | Cytoplasm | iron homeostasis | 2 | 1.50 | 0.0072 |
| Ferritin Light Chain 1 | P29391 | IPI00762203 | 20802 | 5.66 | Cytoplasm | iron homeostasis | 2 | 1.5 | 0.0072 |
| Leupaxin | Q8R355 | IPI00387515 | 43460 | 5.88 | Cytoplasm | zinc ion binding | 2 | 1.4 | 0.0021 |
| Aldolase I | P05064 | IPI00221402 | 39356 | 8.31 | Cytoplasm | metabolism | 4 | -2.16 | 0.0089 |
| Aldehyde dehydrogenase 2 | Q3TVM2 | IPI00111218 | 56596 | 7.03 | Mitochondria | metabolism | 4 | -1.75 | 0.05 |
| Phosphoglycerate mutase 1 | Q9DBJ1 | IPI00457898 | 28832 | 6.75 | Cytoplasm | metabolism | 8 | 1.37 | 0.044 |
| Transmembrane glycoprotein NMB (Dendritic cell-associated transmembrane protein) | Q99P91 | IPI00311808 | 63675 | 7.88 | Membrane | enzyme | 2 | -3.50 | 0.0089 |
| Alpha-enolase | P17182 | IPI00462072 | 47141 | 6.36 | Cytoplasm | enzyme | 9 | 1.40 | 0.0021 |
| Beta enolase | P21550 | IPI00228548 | 47025 | 6.73 | Cytoplasm | enzyme | 3 | 1.4 | 0.0021 |
| S-formylglutathione hydrolase | Q9R0P3 | IPI00109142 | 31320 | 6.70 | Cytoplasm | enzyme | 5 | 1.49 | 0.0068 |

Figure 22O

| LC/MS/MS* Protein ID | SwissProt† | IPI‡ | M.wt.§ (DA) | pI" | Subcellular Location¶ | Function* | Peptide#** | DIGE†† Index | P-value‡‡ |
|---|---|---|---|---|---|---|---|---|---|
| Peptidylprolyl isomerase A | Q8CEC6 | IPI00229025 | 73431 | 6.58 | Cytoplasm | enzyme | 6 | 1.48 | 0.05 |
| Malate dehydrogenase, cytosolic | P14152 | IPI00336324 | 36511 | 6.16 | Cytoplasm | enzyme | 2 | 1.49 | 0.0068 |
| Nucleoside diphosphate kinase | Q9WV84 | IPI00125448 | 20549 | 9.21 | Mitochondria | enzyme | 5 | 1.48 | 0.05 |
| Phosphoglycerate kinase 1 | P09411 | IPI00555069 | 44540 | 8.02 | Cytoplasm | enzyme | 3 | 1.63 | 0.0065 |
| Adenylosuccinate synthase | P28650 | IPI00123190 | 50254 | 8.57 | Cytoplasm/Membrane | enzyme | 2 | -1.74 | |
| Cathepsin B precursor | P10605 | IPI00113517 | 37280 | 5.57 | Lysosome | thiol protease | 7 | 1.6 | 0.022 |
| Cathepsin D precursor | P18242 | IPI00111013 | 44954 | 6.71 | Lysosome | acid protease | 2 | 1.63 | 0.0065 |
| Vacuolar proton pump subunit E1 | P50518 | IPI00119115 | 26157 | 8.44 | Cytoplasm | proton pump for acidification of intracellular compartments | 8 | -2.08 | |
| Beta-N-acetylhexosaminidase | P29416 | IPI00125522 | 60599 | 6.09 | Lysosome | protein degradation | 2 | -1.75 | 0.05 |
| Peroxiredoxin-1 | P35700 | IPI00121788 | 22176 | 8.26 | Cytoplasm | redox | 6 | 1.38 | 0.022 |
| Peroxiredoxin-5 | P99029 | IPI00129517 | 21897 | 9.1 | Mitochondria/Cytoplasm | redox | 6 | 1.46 | 0.003 |
| Superoxide dismutase [Cu-Zn] | P08228 | IPI00130589 | 15943 | 6.03 | Cytoplasm | redox | 4 | 1.51 | 0.048 |
| Vat1 | Q62465 | IPI00126072 | 43097 | 5.95 | Membrane | redox | 15 | 1.4 | 0.0021 |
| H+ transporting two-sector ATPase alpha chain | Q03265 | IPI00130280 | 59753 | 9.22 | Mitochondria (Complex V) | oxidative phosphorylation | 18 | -1.75 | 0.048 |

Figure 22P

| LC/MS/MS* Protein ID | SwissProt† | IPI‡ | M.wt.§ (DA) | pI∥ | Subcellular Location¶ | Function# | Peptides#** | DIGE†† Index | P-value‡‡ |
|---|---|---|---|---|---|---|---|---|---|
| ATP synthase D chain, mitochondrial | Q9DCX2 | IPI00230507 | 18250 | 5.52 | Mitochondria (Complex V) | oxidative phosphorylation | 2 | 1.5 | 0.0072 |
| Translation elongation factor 1 | Q9D1M4 | IPI00133928 | 19859 | 8.6 | Nucleus/Cytoplasm | DNA damage response | 2 | -1.74 | |
| Apoptosis-associated speck-like protein containing a CARD | Q9EPB4 | IPI00109709 | 21459 | 5.03 | Cytoplasm | caspase-mediated apoptosis | 5 | 1.51 | |

Figure 22Q

A. Extracellular Metabolites

B. Intracellular Metabolites

SEQUENCE LISTING

```
<160> NUMBER OF SEQ ID NOS: 13

<210> SEQ ID NO 1
<211> LENGTH: 140
<212> TYPE: PRT
<213> ORGANISM: Mus musculus

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
```

```
              35                  40                  45
Val His Gly Val Thr Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Asn Ile Ala Ala Ala Thr Gly Phe Val Lys
                 85                  90                  95

Lys Asp Gln Met Gly Lys Gly Glu Glu Gly Tyr Pro Gln Glu Gly Ile
            100                 105                 110

Leu Glu Asp Met Pro Val Asp Pro Ser Ser Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 61
<212> TYPE: PRT
<213> ORGANISM: Artificial Sequence
<220> FEATURE:
<223> OTHER INFORMATION: Synthetic sequence

<400> SEQUENCE: 2

Met Gly Ser Ser His His His His His His Ser Ser Gly Leu Val Pro
 1               5                  10                  15

Arg Gly Ser His Met Gly Lys Gly Glu Glu Gly Tyr Pro Gln Glu Gly
             20                  25                  30

Ile Leu Glu Asp Met Pro Val Asp Pro Gly Ser Glu Ala Tyr Glu Met
         35                  40                  45

Pro Ser Glu Glu Gly Tyr Gln Asp Tyr Glu Pro Glu Ala
     50                  55                  60

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3 cccaagaag gaatgggtcc                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggttgtggaa aaggtagtgg                                             20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gttcctttgt ggcacttggt                                             20

<210> SEQ ID NO 6
```

```
<211> LENGTH: 24
<212> TYPE: DNA
<213> ORGANISM: Artificial Sequence
<220> FEATURE:
<223> OTHER INFORMATION: Primer

<400> SEQUENCE: 6
ctatgctgcc tgctcttact gact                                              24

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cagttattgt ctttcccggct gta                                               23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ctatgctgcc tgctcttact gact                                              24

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
tttgaggtca acaacaaccc aca                                                23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cgcaatcaca gtcttggcta                                                    20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggcagcctgt gagacctttg                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
```

```
gaagcgtttc gggatctgaa                                              20

<210> SEQ ID NO 13
<211> LENGTH: 140
<212> TYPE: PRT
<213> ORGANISM: Homo sapiens

<400> SEQUENCE: 13

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

METHODS AND COMPOSITIONS FOR INHIBITING DISEASES OF THE CENTRAL NERVOUS SYSTEM

This application claims priority under 35 U.S.C. §119(e) to U.S. Provisional Patent Application No. 61/134,350, filed on Jul. 9, 2008 and to U.S. Provisional Patent Application No. 61/208,090, filed on Feb. 20, 2009. The foregoing applications are incorporated by reference herein.

This invention was made with government support under 5R01NS034239-14 and P01 NS43986-06 awarded by the National Institutes of Nuerological Disorders and Stroke, National Institutes of Health. The government has certain rights in the invention.

FIELD OF THE INVENTION

The present invention relates to the fields of central nervous system disorders. More specifically, the invention provides compositions and methods for the treatment of central nervous disorders, particularly Parkinson's Disease.

BACKGROUND OF THE INVENTION

Several publications and patent documents are cited throughout the specification in order to describe the state of the art to which this invention pertains. Each of these citations is incorporated herein by reference as though set forth in full.

Parkinson's disease (PD) is a common progressive neurodegenerative disease clinically characterized by resting tremor, muscle rigidity, bradykinesia, and postural instability (Dauer et al. (2003) Neuron 39:889-909). PD is sporadic and of unknown cause although host genetics, environmental cues, aging, impaired energy metabolism and oxidative stress are linked to disease onset and progression (Klockgether, T. (2004) Cell Tissue Res., 318:115-120). Pathologically, PD is characterized by degeneration of dopaminergic cell bodies in the substantia nigra pars compacta (SNpc) and their associated caudate projections (Dauer et al. (2003) Neuron 39:889-909). Nonetheless, the pathological hallmark of PD is cytoplasmic inclusions of fibrillar, misfolded proteins called Lewy bodies composed principally of α-synuclein (α-Syn) (Spillantini et al. (1997) Nature, 388: 839-840).

α-Syn is a 140-amino acid (aa), natively unfolded, soluble protein that is localized in the pre-synaptic terminals of neurons of the central nervous system (CNS), where it interacts with and may regulate synaptic vesicles (Spillantini et al. (1997) Nature 388: 839-840; Sidhu et al. (2004) FASEB J., 18:637-647; Paxinou et al. (2001) J. Neurosci., 21:8053-8061; Weinreb et al. (1996) Biochemistry 35:13709-13715; Eliezer et al. (2001) J. Mol. Biol., 307:1061-1073; Uversky et al. (2000) Proteins 41:415-427). Three missense mutations (A53T, A30P and E46K) in the gene encoding α-Syn are linked to dominantly inherited PD (Kruger et al. (1998) Nat. Genet., 18:106-108; Polymeropoulos, et al. (1997) Science, 276:2045-2047; Zarranz et al. (2004) Ann. Neurol., 55:164-173). Moreover, multiplication of the wild-type (WT) gene has also been linked to PD, suggesting that the level of α-Syn is an important pathogenic factor (Chartier-Harlin et al. (2004) Lancet 364:1167-1169; Singleton et al. (2003) Science 302:841). Such familial cases are rare and in sporadic PD, there is no genetic aberration of α-Syn. However, it has been proposed that post-translational modifications such as nitration enhances WT α-Syn propensity to aggregate (Hodara et al. (2004) J. Biol. Chem., 279:47746-47753; Uversky et al. (2001) J. Biol. Chem., 276:10737-10744; Uversky et al. (2005) Brain Res. Mol. Brain. Res., 134:84-102; Yamin et al. (2003) FEBS Lett., 542:147-152). Oxidized and aggregated α-Syn, when released from dying neurons, may stimulate scavenger receptors on microglia resulting in their sustained activation and dopaminergic neurodegeneration (Wersinger et al. (2006) Curr. Med. Chem., 13: 591-602; Zhang et al. (2005) FASEB J., 19:533-542; Croisier et al. (2005) J. Neuroinflammation 2:14). Moreover, activated microglia generate nitric oxide and superoxide that rapidly react to form peroxynitrite which can then traverse cell membranes resulting in 3-nitrotyrosine (NT) formation, DNA damage, mitochondrial inhibition, or lipid peroxidation (Dringen, R. (2005) Antioxid. Redox. Signal 7:1223-1233; Ischiropoulos, et al. (2003) J. Clin. Invest., 111:163-169).

SUMMARY OF THE INVENTION

In accordance with the instant invention methods of treating a central nervous system disease or disorder in a patient in need thereof are provided. In a particular embodiment, the central nervous system disease or disorder is characterized by the presence of at least one abnormal protein. In yet another embodiment, the methods comprise administering to the patient a) at least one immunogen capable of inducing a humoral immune response against the abnormal protein, and b) at least one adjuvant that stimulates regulatory T cells.

In accordance with another aspect, compositions are provided for performing the methods of the instant invention. In a particular embodiment, the composition comprises a) at least one immunogen capable of inducing a humoral immune response against at least one abnormal protein of a central nervous system disease or disorder, and b) at least one adjuvant that stimulates regulatory T cells. In one embodiment, the composition further comprises at least one pharmaceutically acceptable carrier.

BRIEF DESCRIPTION OF THE DRAWINGS

FIG. 1A provides a Western blot of tissue homogenates from VMB and CLN of mice 20 hours following treatment with PBS or MPTP, probed with antibodies to α-Syn. FIG. 1B provides results of an N-α/β Syn IP with (clone nSyn12 antibodies) against CLN homogenates from PBS or MPTP-treated mice. Immunoprecipitates were fractionated on a 16% polyacrylamide gel and the gel stained with SYPRO® Red or blotted. The Western blot was probed with anti-α-Syn. Proteins recovered from in-gel digestion of 12-18 kD fragments from anti-N-α/β Syn of CLN immunoprecipitates were identified by LC-MS/MS. The sequence coverage by peptides identified by LC-MS/MS from the CLN of MPTP-treated mice is highlighted in yellow within the primary amino acid (aa) sequence of full-length mouse α-Syn (FIG. 1C; SEQ ID NO: 1). FIG. 1D provides Western blots of lymph node homogenates (Cervical, Axillary, and Inquinal) from mice treated with PBS or MPTP. Blots were probed with antibodies to nitrotyrosine (NT) or anti-myelin basic protein (MBP). FIG. 1E provides results from a flow cytometric analysis of CD11b and I-Ab expression in cells from CLN, show an increased number of CD11b$^+$ I-A$^+$ cells 24 hours after MPTP treatment compared to PBS administered animals (n=3 mice/group). FIG. 1F demonstrates antibodies against α-Syn and N-α-Syn in sera of B6 WT mice on day 21 following MPTP intoxication (n=8) or PBS control treatment (n=5) as determined by anti-α-Syn specific ELISA. Sera from MPTP treated group contained significantly higher IgG antibodies directed against 4YSyn (p=0.021) and N-4YSyn (p=0.016) compared to PBS treated control sera. Comparisons of mean IgG concentrations±SEM was by Student's t test.

FIG. 2A provides photomicrographs of TH-immunostained SN (left panels) and CD3-immunostained spleen sections (right panels) from B6 (WT), SCID, and reconstituted SCID (RCS-SCID) mice treated with PBS or MPTP and obtained on day 21 post-MPTP intoxication. Immunostaining for expression of CD3 in spleens show normal distributions of CD3+ T cells in B6 WT and RCS-SCID mice treated with PBS or MPTP. Note the absence of CD3+ T cells in spleens from SCID MPTP mice. FIG. 2B provides the quantification of TH+ neurons in the SN of B6 WT, SCID, or reconstituted (RCS) SCID mice treated with PBS or MPTP. Values represent mean number of TH+ neurons±SEM for 5-9 mice per group. $^{abcdefg}$pair-wise comparisons by Bonferroni post-hoc test: $^{acd}$p<0.0001, $^{bef}$p<0.001, $^{g}$p<0.05. FIG. 2C provides coronal VMB sections of MPTP intoxicated B6 mice reacted with antibodies against CD3, CD4 and CD8 show positive immunostaining of cells with small, round lymphocytic morphology (magnification=400×).

FIG. 3A provides the primary aa sequence of His-tagged 4YSyn peptide (SEQ ID NO: 2). The His-Tag sequence is highlighted. The sequence of 4YSyn (Syn100-140) is shown underlined with 4 Tyr residues highlighted as potent sites for nitration. Trypsin cleavage sites at Arg (arrowhead) and Lys (arrow) are shown. FIG. 3B shows purified 4YSyn (lane 1) and N-4YSyn following nitration with peroxynitrite (lane 2) fractionated on a 10-20% polyacrylamide gel and visualized using silver stain. Covalently cross-linked oligomers are indicated by arrowheads. FIG. 3C provides Western blot confirmation of purified 4YSyn and its associated NT modifications following peroxynitrite treatment. FIG. 3D provides MALDI-TOF spectra of purified 4YSyn (top panel), N-4YSyn (middle panel), and 4YSyn after tryptic digest (lower panel).

In FIG. 4A, B10.BR (H-2K) mice were immunized with PBS, 50 μg 4YSyn, or 50 μg N-4YSyn emulsified in CFA. Mice were boosted 14 days later with PBS or their respective antigens in IFA. After 5 days, donor mice were sacrificed and single cell suspensions were prepared from the draining inguinal lymph nodes and spleen, and T cells were enriched by negative selection. Twelve hours after the final MPTP injection, 5×10⁷ donor immune SPC or 2.5×10⁷ T cells were adoptively transferred to MPTP-treated recipient mice. SPC were evaluated for antigen specificity prior to adoptive transfer by lymphocyte proliferation assays. SN of recipients were evaluated after 28 days of MPTP treatment for migration of T cells, survival of dopaminergic neurons, and reactive microglia. In FIG. 4B, SPC were tested for antigen specific proliferation by culturing in the presence of media alone or media containing 3 μg/ml of immunizing antigens for 5 days and using standard 3H-thymidine incorporation assays.

FIG. 5A demonstrates the frequency of CD3+ T cells and CD19+ B cells before and after enrichment of T cells. Population of enriched T-cells was 94% CD3+ prior to adoptive transfer to B10.BR mice. FIG. 5B demonstrates that sections throughout the SNpc were immunostained for CD3 and counterstained with thionin. Clusters of CD3+ cells are observed within the SNpc (arrowheads) as seen at 100× magnification (left). Magnification (600×) of boxed area (left panel) is shown (right panel). CD3+ cells are small and round exhibiting lymphocyte morphology.

FIG. 7B provides the counts of nigral Nissl+(left bars), TH+(center bars), and TH- (right bars) neurons on day 28 after MPTP treatment as determined by stereological analysis. Control groups included mice treated with PBS alone (n=4), MPTP alone (n=8), and PBS animals that received immune effector SPC from N-4YSyn immunized donor mice PBS/N-4YSyn/SPC (n=6). Experimental groups included MPTP/PBS/SPC (n=6), MPTP/4YSyn/SPC (n=8), MPTP/N-4YSyn/SPC (n=9), and MPTP mice which received purified T cells from N-4YSyn vaccinated donors. Values are means±SEM. P<0.01 compared to the following treatment groups: $^{a}$PBS, $^{b}$MPTP, $^{c}$MPTP/4YSyn/SPC.

FIG. 9B provides the counts of nigral TH+ and TH2 neurons on day 7 after MPTP treatment. Experimental groups included mice treated with PBS alone (n=7), MPTP alone (n=7), MPTP/4YSyn (n=7), MPTP/N-4YSyn/CFA (n=6) and MPTP/N-4YSyn (n=6). Values are means±SEM. Analysis by ANOVA with Bonferroni post-hoc tests indicated. [a]p<0.0001 compared to PBS control; [b]p<0.001 compared to MPTP group; [c]p<0.001 compared to MPTP/4YSyn group; and [d]p<0.03 compared to MPTP/4YSynCFA SPC.

FIG. 12A provides photomicrographs of immunofluorescent detection for NF-κB p65 in stimulated microglia (scale bar: 25 μm) and analysis for MFI per cell. Arrows indicate areas where colocalization of NF-κB p65 and nuclei appears to have occurred. FIG. 12B provides Western blot analysis of nuclear fractions from stimulated microglia with Abs to the NF-κB subunits p50/RELA (top panel), p65/NFκB1 (middle panel), or a control Gapdh Ab (bottom panel). Mean OD was normalized to Gapdh expression. In addition, cDNA prepared from RNA isolated from duplicate samples was assessed by qPCR for expression of NF-κB-related genes Tnfa, Tnfrs1a, Rela, and Nos2 (FIG. 12C) and neurotrophins Bdnf and Gdnf (FIG. 12D). Mean expression levels shown were normalized to Gapdh expression. For FIGS. 12B and 12C, error bars represent SEM. Value of p<0.05 compared with media alone (CON; a), N-α-syn (b), or N-α-syn/Teff (c).

FIG. 13A shows cytokine/chemokine levels in microglial culture supernatants treated with media alone, or N-α-syn without or with pretreatment or post-treatment with CD3-activated Treg or Teff were measured by cytometric bead array. Microglia were also assessed by flow cytometry for surface expression of CD206 (FIG. 13B) and MHC class II (FIG. 13C). Alternatively, FITC-conjugated latex beads were added to the microglia cultures 30 minutes before flow cell analysis to evaluate phagocytosis by the MFI of microglia that phagocytized beads (FIG. 13D). Value of p<0.05 compared with microglia cultured with media alone (a), N-α-syn (b), or N-α-syn/Teff (c; FIGS. 13A-13D). Microglia were cultured without or with Treg either in direct contact or separated by Transwells™. Neutralizing Abs to IL-10, TGF-β, and CTLA-4 were added to tandem direct contact cultures of microglia without and with Treg. Cytokine/chemokine concentrations (IFN-γ, TNF-α, IL-12, IL-6, MCP-1, and IL-10) in culture supernatants were determined by cytometric bead array (FIG. 13E) or ELISArray (IL-1α and IL-1β; FIG. 13F). Value of p<0.01 compared with microglia cultured with N-α-syn (a) or with N-α-syn/Treg (b) in direct contact (FIGS. 13E and 13F). Error bars represent SEM.

FIG. 14A provides fluorescence 2D DIGE and Decyder analysis of N-α-syn-stimulated microglial cell lysates compared with unstimulated microglia. To assess phenotypic change following interaction with Treg, representative 2D gels and Decyder analysis were performed on microglial cell lysates assessing microglia cocultured with CD3-activated Treg before stimulation with N-α-syn (FIG. 14B, pretreatment) or added in tandem 12 hours following the addition of N-α-syn to the cultures (FIG. 14C, posttreatment). FIG. 14D provides Western blot analyses and volumetric and area intensity plot analyses by BVA for select proteins identified by LC-MS/MS are shown for cell lysates of unstimulated or N-α-syn stimulated without or with pretreatment with Treg or Teff and posttreatment with Treg or Teff: L-plastin (spot: 23), ferritin L chain (spot: 28), peroxiredoxin 1 (spot: 65), and cathepsin D (spot: 13).

FIG. 15A provides confocal photomicrographs of intracellular ROS production in microglia after 90 minutes of stimulation with media (CON) or N-α-syn without and with T cell pretreatment (scale bar: 25 μm). FIG. 15B provides the MFI of ROS production per cell. FIG. 15C shows microglial intracellular GSH concentration following 24 hour of exposure to N-α-syn without and with T cell pretreatment. Value of p<0.01 compared with microglia cultured with media alone (CON; a), N-α-syn (b), or N-α-syn/Teff (c; FIGS. 15B and 15C). Western blot analyses of select redoxactive proteins identified by LC-MS/MS, including THX 1 (spot: 49; FIG. 15D), BVR B (spot: 34; FIG. 15E), HSP 70 (spot: 3; FIG. 15F), and GLU 1 (spot: 64; FIG. 15G). CB activity in microglia after stimulation with N-α-syn for 24 hour is demonstrated by fluorescence photomicrographs (scale bar: 25 μm; FIG. 15H) and MFI analysis (FIG. 15I). Value of $p<0.05$ compared with microglia cultured to media alone (CON; a), N-α-syn (b), or N-α-syn/Teff (c). FIG. 15J provides representative Western blot analysis of microglial lysates and culture supernatants for CB [spot: 27] expression and reprobed with Ab against β-actin following pretreatment with Treg or Teff and stimulation for 24 hours with N-α-syn. Error bars represent SEM.

FIG. 16A provides Western blot analysis for caspase-3 (procaspase-3 and cleaved) expression in microglial cell lysates from unstimulated (lane 1) and N-α-syn stimulated alone (lane 2), pretreated with Treg or Teff (lanes 3 and 4), or post-treated with Treg or Teff (lanes 5 and 6). FIG. 16B provides flow cell analysis for MFI of active caspase-3 expression by microglia. Value of $p<0.05$ compared with media alone (a) and N-α-syn stimulation (b). FIG. 16C provides confocal photomicrographs and MFI for active caspase-3 on a per cell basis (scale bar: 25 μm). Value of $p<0.01$ compared with microglia cultured in media alone (CON; a), N-α-syn stimulation alone (b), or N-α-syn/Teff (c). FIG. 16D provides flow cell analysis for FasL expression by Treg or Teff immediately following isolation (naive T cells), following CD3 activation (anti-CD3 T cells), and after coculture with N-α-syn-stimulated microglia for 24 hours (post-coculture). Mean percentages of FasL+CD4+ T cells shown [value of $p<0.05$ compared with naive T cells (a) and αCD3 T cells (b)]. FIG. 16E provides flow cell analysis of Fas expression by microglia treated for 24 hours without and with N-α-syn stimulation and T cell post-treatment. Percentages of Fas+ cells are shown [value of $p<0.05$ compared with media alone (a) and N-α-syn stimulation alone (b)]. FIG. 16F provides an MTT assay to assess microglial susceptibility to spontaneous- and anti-CD95-induced apoptosis after culture for 24 hours in media alone and N-α-syn without or with T cell pretreatment. Value of $p<0.05$ compared with media alone (a), N-α-syn stimulation alone (b), N-α-syn/Teff (c), media alone with anti-CD95 stimulation (d), and N-α-syn with anti-CD95 stimulation (e). FIG. 16G provides a TUNEL assay of microglia treated with media (CON) and N-α-syn without and with post-treatment with Treg or Teff in the absence or presence of anti-FasL. Photomicrographs (scale bar: 25 μm) and MFI of TUNEL+ cells normalized to the number of DAPI-stained nuclei. FasL dependence in Treg-induced apoptosis of stimulated microglia was also assessed by MTT assay (H) and caspase 3/7 activity assays (FIG. 16I). Values shown as a percentage of unstimulated controls (MTT) or MFI (caspase-3/7 activity). Value of $p<0.05$ compared with media alone (a), N-α-syn stimulation alone (b), N-α-syn/Teff (c), and post-treatment without anti-FasL (d; FIGS. 16G-16I). Error bars represent SEM.

FIG. 17A provide Western blot analysis for CB and Gapdh expression in microglial cell lysates following treatment with media (CON) or N-α-syn without and with Treg or Teff after N-α-syn stimulation (post-treatment). FIG. 17B provides confocal photomicrographs (scale bar: 25 μm) and MFI per cell of active caspase-3 expression in N-α-syn-stimulated microglia in the presence or absence of Treg or Teff in the absence or presence of a cell-permeable CB inhibitor (CA-074 Me). The MTT assay (FIG. 17C) and caspase 3/7 activity assay (FIG. 17D) of microglia also revealed that inhibition of CB significantly diminished stimulation-induced apoptosis. Values shown are means (±SEM) of absorbance as a percentage of unstimulated controls (MTT) or MFI (caspase-3/7 activity). Value of $p<0.05$ compared with media alone (a), N-α-syn stimulation alone (b), N-α-syn/Teff (c), post-treatment without CA-074Me (d), and N-α-syn with CA-074Me (e).

FIGS. 20A-20F provide the classification of proteins modulated by N-α-syn stimulation and Treg treatment. Pie-chart diagrams represent the proportion (%) of proteins within specific categories based on classification and function identified by mass spectrometry. FIG. 20A provides classification of proteins differentially expressed by microglia in response to N-α-syn stimulation alone (clockwise from 17% segment: redox-active, proteases, chaperones, UPS, glycolysis, transcription, cell motility, structural, apoptosis, metabolism, ox. phospho.). FIG. 20B provides relative expression of proteins in response to N-α-syn stimulation compared to unstimulated controls. Several proteins within each category showing both increased and decreased proteins were identified including those for apoptosis (*gelsolin increased; nucleoside-diphosphate kinase decreased) and glycolysis ($enolase 3 and lactate dehydrogenase increased; alpha enolase, pyruvated dehydrogenase, pyruvate kinase, and triosphosphate isomerase 1 decreased). FIG. 20C provides proportion of microglial proteins differentially expressed in response to N-α-syn following Treg pre-treatment and the relative expression trends shown in FIG. 20D. Categories associated with transcription (*VIP-receptor gene repressor protein, TAR DNA binding protein, and Ubiquitin conjugating enzyme E2N increased; MRG-binding protein decreased), cell motility ($microtubule associated protein increased; laminin B2, beta actin, and alpha tubulin decreased), structural ([#]Capg and guanine nucleotide exchange factor increased; vimentin, cofilin 1 and 2 decreased), and oxidative phosphorylation ([†]NADH dehydrogenase Fe—S, ATP synthase O subunit, H+-ATP synthase e subunit, and cytochrome c oxidase increased; ATP synthase F0 complex decreased) consisted of both increased and decreased expression of proteins.

FIG. 21A provides photomicrographs (20× magnification) of Prx1 expression in microglia treated with media alone (CON), N-α-syn, or cultured with CD4+ T cell subsets following pre- and post-treatment. Values shown are the mean fluorescence intensity (MFI) per field±SEM. FIG. 21B provides Western blot analysis for α-tubulin, galectin 3 and gelsolin in response to treatment normalized to Gapdh expression within the same blot for comparisons. FIG. 21C provides photomicrographs (20× magnification) of actin expression or Hsp70 in microglia treated with media alone (CON), N-α-syn, or cultured with CD4+ T cell subsets following pre- and post-treatment. Values shown are the MFI per field±SEM. FIG. 21D demonstrates the survival of MES23.5 cells after co-culture with N-α-syn stimulated microglia with and without Treg or Teff or after culture with condition media (supernatants) of N-α-syn stimulated microglia treated with either Treg or Teff. Values SEM (P<0.01 vs. [a]CON, [b]N-α-syn alone, [c]N-α-syn/Teff).

FIGS. 22A-22G provide the N-α-syn stimulated proteome. FIGS. 22H-22M provide the modulation of the N-α-syn microglial proteome by Treg pretreatment. FIGS. 22N-22Q provide the modulation of the N-α-syn microglial proteome by Treg post-treatment *The CID spectra were compared against those of the EMBL nonredundant protein database by using SEQUEST (ThermoElectron, San Jose, Calif.). After filtering the results based on cross correlation ([†]Xcorr (cutoffs of 2.0 for [M+H]1+, 2.5 for [M+2H]2+, and 3.0 for [M+3H]3+), peptides with scores greater than 3000 and meeting delta cross-correlation scores (·Cn)>0.3, and fragment ion numbers >60% were deemed valid by these SEQUEST criteria thresholds, which have been determined to afford greater than 95% confidence level in peptide identification. [§§]SwissProt accession number (accessible at ca.expasy.org/sprot/). [‡]International Protein Index (IPI) (accessible at www.ebi.ac.uk/IPI/). §Theoretical molecular mass for the primary translation product calculated from protein DNA sequences. [⁂]Theoretical isoelectric point. ¶Postulated subcellular location (accessible at locate.imb.ug.edu.au). [#]Postulated cellular function (accessible at ca.expasy.org/sprot/). **Number of different peptides identified for each protein. [††](FIGS. 22A-22G) Fold changes of proteins in N-α-syn stimulated microglial lysates versus unstimulated microglial lysates. Negative DIGE index indicates decreased expression in N-α-syn stimulated microglia relative to controls. [††] (FIGS. 22H-22M) Fold changes of proteins in Treg pre-treated microglia versus N-α-syn alone stimulated microglial lysates. [††] (FIGS. 22N-22Q) Fold changes of proteins in Treg-post-treated microglia versus N-α-syn alone stimulated microglial lysates. [‡‡]P-values as determined by Biological Variation Analysis by one-way ANOVA for pair-wise comparison between treatments.

FIGS. 23A-23E demonstrate α-Syn nitration, aggregation, and microglial activation. FIG. 23A is a Coomassie stain of anti-N-α/β-synuclein immunoprecipitation from SN from control and PD brains. Arrowhead reflects the area excised from gel and submitted for LC-MS/MS analysis. Equal concentrations of proteins from control and experimental brain tissues served as loading controls. Peptides obtained by LC-MS/MS that matched human α-syn are highlighted within the full-length sequence (SEQ ID NO: 13). FIG. 23B is a western blot analyses of recombinant mouse α-syn and derivatives. Lane 1 is a nitrotyrosine modified protein provided by the manufacturer. Lanes 1-3 were blotted and probed with anti-nitrotyrosine, and lanes 4-6 were probed with anti-synuclein. FIG. 23C are AFM images are shown for unaggregated (0.4× 0.4 mm) and aggregated N-α-syn (1.6×1.6 mm). Arrow indicates location of inset photomicrograph. Scale bar corresponds to height of aggregates on the interface. FIG. 23D shows microglial morphology after exposure of microglia to media alone (control, left) or 100 nmol/L N-α-syn (center), and N-α-syn stimulated microglia in co-culture with MES23.5 cells (right; scale bar: 25 μm). Cells were stained with calcein AM to detect viable cells.

FIG. 24A is representative photomicrographs of Live/Dead assays of unstimulated or N-a-syn stimulated microglia co-cultured with MES23.5 cells for 24 hours (scale bars: 25 μm). FIGS. 24B and C are graphs of N-α-syn-induced microglial inhibition of cell survival. A time-course for cell survival is shown for MES23.5 cells and microglia co-cultured in the presence of media alone (Con, box), 100 nmol/L unmodified a-synuclein (α-syn, triangle), or 100 nmol/L N-α-synuclein (N-α-syn, circle). Cell viability was quantified using the Live/Dead assay by (FIG. 24B) cell count (n=9 fields, p<0.01 compared with a 0 hour and ball treatment groups at corresponding time point), and by (FIG. 24C) fluorometric analysis (n=9 fields, p<0.01 compared with [a]0 hour and [b]all treatment groups at corresponding time point). FIG. 24D provides cell survival of MES23.5 cells in co-culture with microglia after 72 hours of stimulation with either α-syn or N-α-syn (n=9, p<0.01 compared with [a]all treatment groups and [b]α-syn stimulated microglia). FIG. 24E shows the influence of secretory factors from microglia stimulated with either α-syn or N-α-syn for 24 hours on MES23.5 cells was determined. Cell survival was assessed following incubation with supernatants or in Transwell™ format for 24 hours (n=3, p<0.01 compared with [a]all treatment groups and [b]α-syn-stimulated microglia).

FIG. 27A provides general pathway-focused microarray revealed involvement of NF-κB signaling pathways. FIG. 27B provides focused arrays were utilized for regulation of NF-κB associated genes for microglia that were unstimulated (0 hour Control) or stimulated with 100 nmol/L N-a-syn or 100 ng/mL LPS for 1 hour and 4 hours, respectively. Boxes indicate genes that were induced by stimulation at 1 and 4 hours. FIG. 27C provides graphs of the qPCR of mRNA from samples confirmed representative inductions for genes (rank and file position in microarray) Ccl2 (F2), Il1b (H5), Tnfrsf1a (D13), Stat1 (11E), Rela (10F), Tnf (A13), and Nos2. Gene expression for the neurotrophins Bdnf and Gdnf were also assessed by qPCR from the same mRNA/cDNA samples [n=3, p<0.01 compared with $^a$0 hour control (C) and $^b$LPS at corresponding time point]. FIGS. 27D and 27E provide N-α-syn- and LPS-stimulated microglial transcriptome. Values represent fold-change versus unstimulated controls. $^b$NCBI Entrez GeneID. FIGS. 27F-27H provide N-α-syn-stimulated microglial proteome. $^a$The CID spectra were compared against those of the EMBL non-redundant protein database by using SEQUEST (ThermoElectron, San Jose, Calif.). After filtering the results based on cross-correlation Xcorr (cutoffs of 2.0 for [M+H] 1+, 2.5 for [M+2H]2+, and 3.0 for [M+3H]3+), peptides with scores greater than 3000 and meeting delta cross-correlation scores (DCn)>0.3, and fragment ion numbers >60% were deemed valid by these SEQUEST criteria thresholds, which have been determined to afford greater than 95% confidence level in peptide identification; $^b$Theoretical molecular mass; $^c$Isoelectric point; $^d$Accession numbers for UniProt (accessible at www.ipr.uniprot.org/search/textSearch.shtml); $^e$Hours following stimulation with N-α-syn; $^f$Number of peptides identified for each protein selected based on the above mentioned criteria; $^g$Volume ratio indicates fold-change versus control.

FIGS. 35A-35C provide photomicrographs (scale bar 25 μm) and enumeration of Mac-1+, FJ-C+, and TH+ cells, respectively, in the SNpc of mice treated with PBS, MPTP, or MPTP and N-4YSyn SPCs. FIG. 35A shows Mac-1+ reactive microglia per mm$^2$. FIG. 35B provides total numbers of FJ-C+ neurons. FIG. 35C shows dopaminergic neurons in the SNpc identified as TH+Niss1+ neurons (black bars), while non-dopaminergic neurons were identified as TH-Niss1+ neurons (gray bars). Differences in means (±SEM) were determined where P<0.05 compared with groups treated with $^a$PBS or $^b$MPTP. FIG. 35D provides images demonstrating that MPTP-intoxicated recipients of N-4YSyn SPC had increased infiltration of CD4+ cells within the SNpc following adoptive transfers, whereas MPTP-intoxication alone showed limited infiltrates at 48 hours-post intoxication and no CD4+ cells were identified in PBS-treated controls. FIG. 35E is a graph demonstrating that T cells isolated from N-4YSyn donors stimulated in vitro with anti-CD3 for 24 hours produced greater concentrations of IL-17a and TNF-α relative to naïve T cells. FIG. 35F is a graph demonstrating that N-4YSyn antigenic stimulation of CD4+ effector T cells isolated from immunized mice induced the production of certain cytokines. FIG. 35G is a graph of the capacity of Treg isolated from immunized FoxP3-GFP mice to inhibit effector T cell proliferation to anti-CD3 stimulation following immunization with N-4YSyn (20%) as compared to Treg isolated from naïve donors (80%) at a ratio of 1:1.

FIG. 37A provides photomicrographs (scale bar 25 μm) of midbrain immunostained for Mac-1 (top panel) or FJ-C to identify dead or dying neurons (bottom panel). FIG. 37B provides the mean numbers of Mac-1+ microglia and FIG. 37C provides FJ-C+ neurons within the SNpc. Differences in means (±SEM) were determined where P<0.05 compared to groups treated with $^a$PBS, $^b$MPTP, $^c$MPTP+N-4YSyn SPC, or $^d$MPTP+VIP SPC.

FIG. 38A shows midbrain sections (scale bar 25 μm) (top panel) and striatum (bottom panel) immunostained for TH. Dopaminergic neurons in the SNpc were identified as TH+Niss1+ neurons (left bars), while non-dopaminergic neurons were identified as TH-Niss1+ neurons (right bars) (FIG. 38B). Mean densities of striatal dopaminergic termini were determined by digital image analysis (FIG. 38C). Differences in means (±SEM) were determined where P<0.05 compared to groups treated with $^a$PBS, $^b$MPTP, $^c$MPTP+VIP SPC, $^d$MPTP+N-4YSyn SPC. Dopaminergic neuronal survival following adoptive transfer of 5×10$^7$ N-4YSyn SPC with 1×10$^6$ Treg (FIG. 38D). FIG. 38E shows density of striatal dopaminergic termini. Differences in means (±SEM) were determined where P<0.05 compared to groups treated with $^a$PBS, $^b$MPTP, $^c$MPTP+N-4YSyn SPC, $^d$MPTP+N-4YSyn+naive SPC, or $^e$MPTP+N-4YSyn+naïve Treg.

FIG. 39A shows immunization with N-4YSyn or treatment with VIP altered the frequencies of splenic CD3+, CD19+, CD4+, and CD4+ CD25+ cells. FIG. 39B is a graph showing the ability of CD4+ CD25+CD62L$^{low}$ Treg isolated from naïve, N-4YSyn-immunized, and VIP-treated mice to inhibit CD3-mediated proliferation of CD4+ CD25-naïve T cells. FIG. 39C is a table of relative fold-differences in expression of CD4+ T cell related genes from T cells isolated from N-4YSyn immunized, VIP-treated, and pooled T cells compared with T cells from naïve mice. FIG. 39D is a graph of the cytokine production assayed from T cell supernatants, normalized to absorbance obtained from supernatants of naïve T cells. FIG. 39E is a graph of T cell proliferation to no antigen [media], 4YSyn, or N-4YSyn. FIG. 39F is a dose response of N-4YSyn on T cell proliferation. FIG. 39G is graph of the fold difference to gene expression of N-4YSyn T cells.

FIG. 41A shows a flow cytometric analysis of Treg and Teff subsets from naïve C57BL/6 mice showing percentage distribution of the following CD4+ T cell phenotypes: CD4+ CD25+, CD4+ CD25−, CD4+ FoxP3+, or CD4+ FoxP3−. FIG. 41B provides a quantitative PCR analysis of mRNA encoding FoxP3, TGF-β, IL-10, IL-2, and IFN-γ from CD3-activated Treg (top bars) and Teff (bottom bars). Mean±SEM of mRNA levels was determined for triplicate cell samples and normalized to GAPDH. Significant differences in relative expression of mRNA from Treg compared with Teff were determined by Student's t test, *, $p<0.05$. FIG. 41C shows Treg inhibition of anti-CD3-mediated proliferation of $1\times10^4$ Teff. Cells were cocultured for 72 hours and pulsed with [$^3$H]thymidine for the final 18 hours of culture, harvested onto filters, and counted by beta scintillation spectrometry. FIG. 41E provides digital image quantification of fluorescence intensity in the stained area was analyzed under ×400 magnification using NIH Image J software. Eight fields in four sections in each experiment were subjected to quantitative analysis. Bar graphs represent mean of area stained positive intensities in a field of view (open bars, PBS; gray bars, HIV-1/VSV; speckled bars, HIV-1/VSV/Teff; or black bars, HIV-1/VSV/Treg). FIG. 41F shows representative Western blot analysis of Iba1, GFAP, TNF-α and β-actin levels from brains of mice treated with PBS, HIV-1/VSV, HIV-1/VSV/Teff (Teff), or HIV-1/VSV/Treg (Treg). FIG. 41G shows densitometric quantification of Western blots for Iba1, GFAP, and TNF-α levels in mice treated with PBS (open bars), HIV-1/VSV (gray bars), HIV-1/VSV/Teff (speckled bars), or HIV-1/VSV/Treg (black bars). Levels were normalized to β-actin levels and mean densities±SEM were determined from four mice per group. FIGS. 41E and 41G, compared with PBS: *, $p<0.05$; , $p<0.01$; *, $p<0.001$; and compared with HIV/VSV group: #, $p<0.05$; and ###, $p<0.001$.

FIG. 42A shows serial sections of brains from PBS control, HIV-1/VSV, HIV-1/VSV/Teff, and HIV-1/VSV/Treg were stained for MAP2, NeuN, BDNF and GDNF and visualized by confocal laser-scanning microscopy. Images are shown at ×400 original magnification and the scale bars equal 50 μm. FIG. 42B shows stained sections from mice (eight fields in four sections in each mouse) treated with PBS (open bars), HIV-1/VSV (gray bars), HIV-1/VSV/Teff (speckled bars), or HIV-1/VSV/Treg (black bars) which were digitally analyzed using NIH Image J software. Bar graphs showed mean of fluorescence intensity per field of view. FIGS. 42C and 42D show Western blot analysis of BDNF expression (FIG. 42C) and densitometric quantification of BDNF Western blots (FIG. 42D) from lysates of brain tissues from mice treated with PBS, HIV-1/VSV, HIV-1/VSV/Teff, or HIV-1/VSV/Treg. BDNF levels were normalized to β-actin expression. Values are expressed as mean±SEM for four mice per group and were significant compared with the PBS group: *, $p<0.001$; , $p<0.01$; *, $p<0.001$, and compared with HIV/VSV group: ##, $p<0.01$; and ###, $p<0.001$.

In FIG. 43A, after 3 days, cell viabilities were determined by MTT assay. For FIG. 43B, cell survival/cytotoxicity was assayed by LIVE/DEAD cytotoxicity immunostaining (Invitrogen) and visualized by fluorescent microscopy at ×400 original magnification. Scale bar equals 50 μm. Mean percentages of cells±SEM were determined for three cultures/group and significant differences in means were determined by Student's t test compared with uninfected control group: *, $p<0.05$; **, $p<0.001$; and compared with HIV-1/VSV group: #, $p<0.001$. For FIG. 43C, HIV-1/VSV-infected BMM were stereotactically injected i.c. into the basal ganglia of syngeneic C57BL/6J mice. Treg or Teff ($1\times10^6$) were adoptively transferred into HIVE mice 1 day postinfection. Serial sections of brain tissue that comprise the injection area were obtained on day 7 postinfection and analyzed by immunohistochemistry for TUNEL and nuclei by DAPI stain. Scale bars: 50 μm; original magnification: ×400.

FIG. 44A shows supernatants from cultures of uninfected BMM (Control; closed triangles), HIV-1/VSV-infected BMM (closed squares), HIV-1/VSV/Teff (open circles), and HIV-1/VSV/Treg (open diamonds) which were collected from day 1 to day 6 after the addition of T cells and assessed for reverse transcriptase (RT) activity. For FIG. 44B, virally infected BMM cultured in the absence or presence Teff or Treg or uninfected BMM (Control) were harvested at the end of day 6 and stained for expression of HIV-1 p24 and visualized by light microscopy at ×400 original magnification. Scale bars equal 50 μm. For FIG. 44C, HIV-1 p24-positive BMM were counted and percentages of HIV-p24-positive BMM were determined. For FIGS. 44A and 44C, means±SEM were determined from three independent experiments. Compared with HIV-1/VSV BMM group by Student's test: #, $p<0.01$; ##, $p<0.001$.

FIG. 47A shows a Kaplan-Meier analysis of the proportion of surviving SOD1 Tg mice as a function of age. Cox's F-test comparison showed groups treated with PBS vs COP-1 q1wk (p=0.0413) or COP-1 q2wk (p=0.1151), and COP-1 q1wk vs COP-1 q2wk (p=0.1673). FIG. 47B shows a log-normal analysis of mortality probability at 10 day intervals for mice treated with PBS, COP-1 q1wk, COP-1q2wk. FIG. 47C provides a Kaplan-Meier plot of the proportion of surviving female SOD1 Tg mice (left panel) or male SOD1 Tg mice (right panel) as a function of age showing the gender effect. Cox's F-test comparison showed female mice groups treated with PBS vs COP-1 q1wk (p=0.0434) or COP-1 q2wk (p=0.2449), and COP-1 q1wk vs COP-1 q2wk (p=0.0846) and male mice groups treated with PBS vs COP-1 q1wk (p=0.4240) or COP-1 q2wk (p=0.1615), and COP-1 q1wk vs COP-1 q2wk (p=0.1430). FIG. 47D provides the mean age of survival±SEM for 7-10 female or 5-6 male SOD1 Tg mice/ group treated with PBS, COP-1 q1wk, or COP-1 q2wk. [a]P<0.05 compared to PBS treated mice with Bonferroni post-hoc tests. Spleen cells from B6 Tg mice treated with PBS, COP-1 q1wk, or COP-1 q2wk were stimulated with (FIG. 47E) Cop-1 (5 μg/ml), (FIG. 47F) ConA (2 μg/ml) or cultured in media alone. Cells were pulsed with [$^3$H]-TdR for the final 18 hours of culture, harvested onto glass fiber filters and counted by b-scintillation spectrometry. Counts were normalized as a ratio of those obtained from culture in media alone to generate a stimulation index for spleen cell proliferation from each animal. A stimulation index of 1 is defined by spleen cells cultured in media alone (dashed line). Means of stimulation indices (6SEM) were determined from 4-5 mice/group for (FIG. 47E) antigen-specific proliferation elicited by Cop-1 and (FIG. 47F) polyclonal T cell proliferation induced by the T cell mitogen, Con A. [a]P<0.05, above media control (stimulation index=1, dashed line); and [b]P<0.05 compared to weeks 4 or 8 within each treatment group.

FIG. 48A shows the morphology and size of spleens from B6SJL SOD1 Tg mice and Wt littermates at 14 weeks of age (left panel) and 20 weeks of age (right panel). FIG. 48B shows mean spleen weights were compared between B6SJLWt littermates and B6SJL SOD1 Tg mice at 7, 16 and 19 weeks age and between B6 Wt and B6 SOD1 Tg mice at 22 weeks age (n=5-9 mice/group). FIG. 48C shows total spleen cell numbers were compared between Wt littermates and B6SJL SOD1 Tg mice at 14 and 22 weeks of age. Values are means±SEM for 3-9 mice per group.

FIG. 51A shows representative dot plot for FCM analysis of CD4+ gated naive (CD44$^{lo}$CD62L$^{hi}$) and memory (CD44$^{hi}$CD62$^{lo}$) T cells from Wt (left) and SOD1 Tg (right) mice at 14 weeks of age. For FIG. 50B, mean percentages (±SEM) of CD4+ naive and memory T cells (left panel) and ratios of naive/memory CD4+ T cells (right panel) were determined for 5 Wt and 5 B6SJL SOD1 Tg mice. For FIG. 50C, percentages of annexin-V+7ADD+ (necrotic) and annexin-V+7ADD2 (apoptotic) Thy-1+T cells or CD45RB220+B cells amongst splenic lymphocytes were assessed in Wt and B6SJL SOD1 Tg mice at 14 weeks of age. For FIG. 50D, lymphoproliferative responses of Wt littermates and B6SJL SOD1 Tg mice at 14 weeks of age were evaluated after in vitro stimulation for 3 days with anti-CD3 (1 µg/ml), anti-IgM (20 µg/ml), or media alone. Stimulation indices for [$^3$H]-TdR uptake by splenocytes from each animal were determined from quadruplicate cultures and values represent the mean±SEM for 5 mice per group.

FIG. 52A provides Kaplan-Meier analysis of the proportion of surviving SOD1 Tg mice as a function of age. P=0.2035 by Cox's F-test for comparison of PBS and RCS groups. FIG. 52B provides mean age of survival±SEM for 20 mice/group treated with PBS (black bar, 149.3±7.5 days) or reconstituted with naive lymphocytes (RCS) (white bar, 151.5±7.5 days). Comparison of treatment groups indicated p=0.315 by ANOVA. FIG. 52C provides mean clinical scores (±SEM) of PBS- or RCS-treated SOD1 Tg mice as a function of age in weeks. *P<0.05 compared to PBS treated group by factorial ANOVA and Fisher's LSD post-hoc tests of treatment and age. FIG. 52D provides Kaplan-Meier analysis of age and cumulative proportion of SOD1 Tg mice reaching onset of disease (clinical score=3). P=0.0012 by Cox's F-test comparison of reconstituted mice to those treated with PBS. FIG. 52E provides Kaplan-Meier analysis of age and proportion of SOD1 Tg reaching late disease stage (clinical score=1). P=0.0191 by Cox's F-test comparison of reconstituted mice to those treated with PBS. FIG. 52F provides Kaplan-Meier analysis of the cumulative proportion of SOD1 Tg mice surviving after the time of disease onset (clinical score=3). P=0.2021 by Cox's F test comparison of RCS and those mice treated with PBS.

FIG. 53A provides Kaplan-Meier analysis of the proportion of surviving SOD1 Tg mice as a function of age. Cox's F-test comparison of groups treated with PBS vs Treg (p=0.0054) or Teff (p=0.0002), and Treg vs Teff (p=0.2505). FIG. 53B provides clinical scores of SOD1 Tg mice as a function of age in weeks. *P<0.05 compared to PBS treated group at each time point by factorial ANOVA and Fisher's LSD post-hoc tests. FIG. 53C provides Kaplan-Meier analysis for age and proportion of SOD1 Tg reaching late disease stage (clinical score=1). Cox's F-test comparison of groups treated with PBS vs Treg (p=0.006) or Teff (p=0.0003), and Treg vs Teff (p=0.1883). FIG. 53D provides Kaplan-Meier analysis of age and cumulative proportion of SOD1 Tg mice reaching onset of disease (clinical score=3). Cox's F test comparison of groups treated with PBS vs Treg (p=0.002) or Teff (p=0.4215), and Treg vs Teff (p=0.0014). FIG. 53E provides Kaplan-Meier analysis of the cumulative proportion of SOD1 Tg mice and the time after disease onset (clinical score=3) to reach late stage (clinical score=1). Cox's F test comparison of groups treated with PBS vs Treg (p=0.2716) or Teff (p=0.0098), and Treg vs Teff (p=0.0055). FIG. 53F provides Kaplan-Meier analysis of the age and the cumulative proportion of SOD1 Tg mice that exhibited a reduction of maximum body weight ≧10%. Cox's F-test comparison of groups treated with PBS vs Treg (p=0.2131) or Teff (p=0.003), and Treg vs Teff (p=0.0807).

FIG. 54A provides mean age of survival±SEM for 14-15 SOD1 Tg mice/group treated with PBS (152.7±2.0 days), Treg (165.8±5.0 days), or Teff (170.1±3.4 days). $^a$P<0.04 compared to PBS-treated mice by ANOVA and Bonferroni post-hoc tests. FIG. 54B provides mean age±SEM for SOD1Tg mice reaching late stage (clinical score=1) after treatment with PBS (136.9±3.1 days), Treg (153.5±5.8 days), or Teff (160.1±4.3 days). $^a$P<0.04 compared to PBS control group by ANOVA and Bonferroni post-hoc tests. FIG. 54C provides mean age±SEM for SOD1 Tg mice at disease onset (clinical score=3) after treatment with PBS (77.7±1.3 days), Treg (89.8±2.7 days), or Teff (75.7±1.9 days). $^a$P=0.0003 compared to PBS control group by ANOVA and Bonferroni post-hoc tests. FIG. 54D provides mean age±SEM for SOD1 Tg mice that exhibit a reduction of maximum body weight ≧10% after treatment with PBS (147.2±2.5 days), Treg (152.8±3.7 days), or Teff (159.7±4.0 days). $^a$P<0.04 compared to PBS control group by ANOVA and Bonferroni post-hoc tests.

FIG. 55A provides Kaplan-Meier analysis of the age and the cumulative proportion of SOD1 Tg mice that exhibited a ≧75% reduction of overall rotarod performance (ORP). Cox's F-test comparison of groups treated with PBS vs Treg (p=0.0377) or Teff (p=0.0084), and Tregs vs Teffs (p=0.27). FIG. 55B provides mean age±SEM for 14-15 SOD1 Tg mice/group at which mice exhibited a $75% reduction in ORP after treatment with PBS (142.1±2.8 days), Treg (154.0±5.6 days), or Teff (157.5±4.4 days). $^a$P<0.05 compared to PBS treated mice by ANOVA and Bonferroni post-hoc tests. FIG. 55C provides Kaplan-Meier analysis of ages and cumulative proportion of SOD1 Tg mice that exhibited ≧25% reduction in ORP. Cox's F-test comparison of groups treated with PBS vs Treg (p=0.0054) or Teff (p=0.0020), and Treg vs Teff (p=0.20). FIG. 55D provides mean age±SEM for 14-15 SOD1 Tg mice/group at which mice exhibited ≧25% reduction in ORP after treatment with PBS (117.7±3.5 days), Treg (136.5±6.2 days), or Teff (143.7±6.1 days). $^a$P<0.0025 compared to PBS treated mice by ANOVA and Bonferroni post-hoc tests. FIG. 55E provides Kaplan-Meier analysis for age and proportion of SOD1 Tg mice that exhibited ≧75% reduction of maximum Paw Grip Endurance (PaGE) after treatment with PBS, Treg, or Teff. Cox's F test comparison of groups treated with PBS vs Treg (p=0.001) or Teff (p=0.0003), and Treg vs Teff (p=0.14). FIG. 55F provides mean age±SEM for SOD1Tg mice that exhibited ≧75% reduction of maximum PaGE after treatment with PBS (94.5±5.6 days), Treg (131.1±4.2 days), or Teff (137.2±4.5 days). $^a$P<0.0001 compared to PBS control group by ANOVA and Bonferroni post-hoc tests. FIG. 55G provides Kaplan-Meier analysis for age (days) and proportion of SOD1 Tg mice that exhibited $25% reduction of maximum PaGE after treatment with PBS, Treg, or Teff. Cox's F test comparison of groups treated with PBS vs Treg (p<0.0001) or Teff (p=0.0033), and Treg vs Teff (p=0.42). FIG. 55G provides mean age±SEM at which SOD1 Tg mice exhibited at least 25% reduction of maximum PaGE after treatment with PBS (68.5±3.6 days), Treg (119.1±7.2 days), or Teff (108.7±11.3 days). $^a$P<0.002 compared to PBS control group by ANOVA and Dunnett's post-hoc tests.

DETAILED DESCRIPTION OF THE INVENTION

Figure 1:
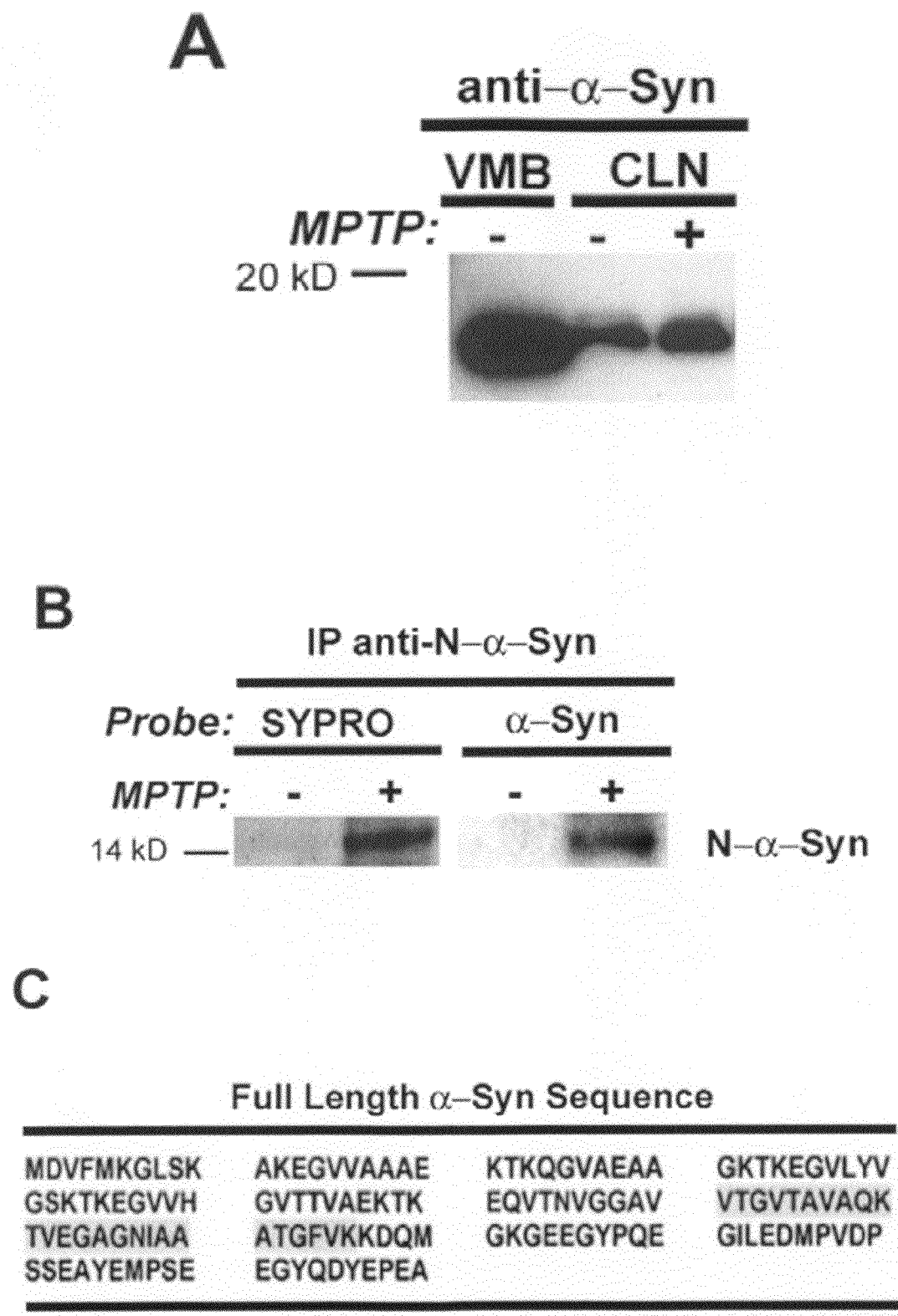
FIGS. 1A-1F demonstrate drainage of N-α-Syn and MBP to CLN with macrophage activation and production of α-Syn serum antibodies after MPTP intoxication.
Figure 1:
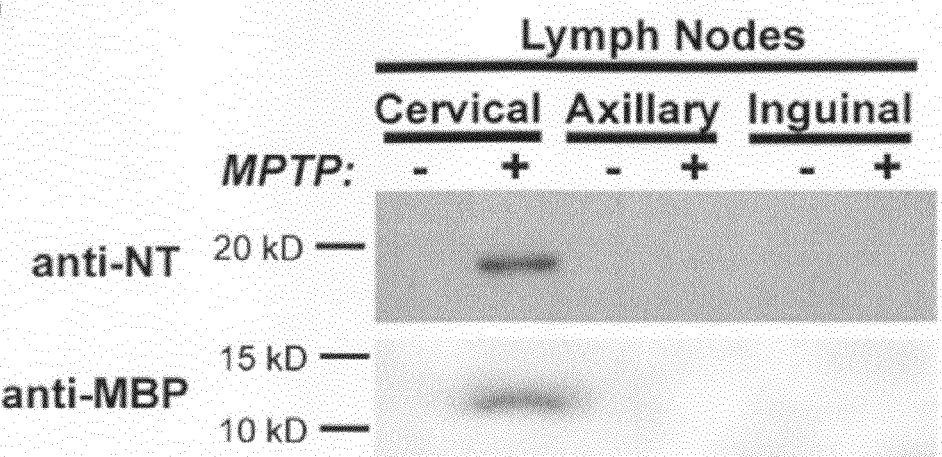
Figure 1:
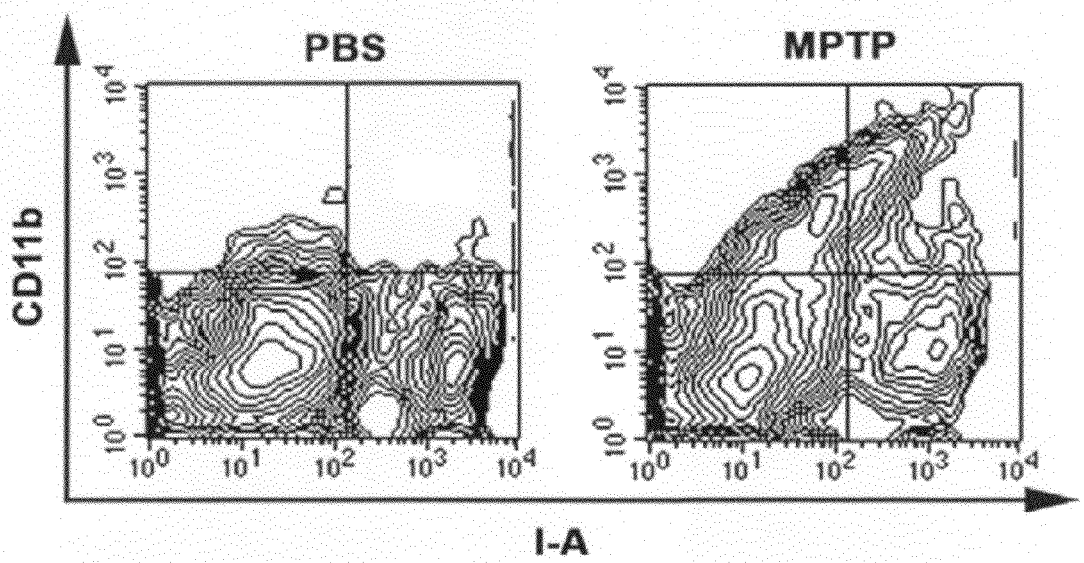
Figure 1:
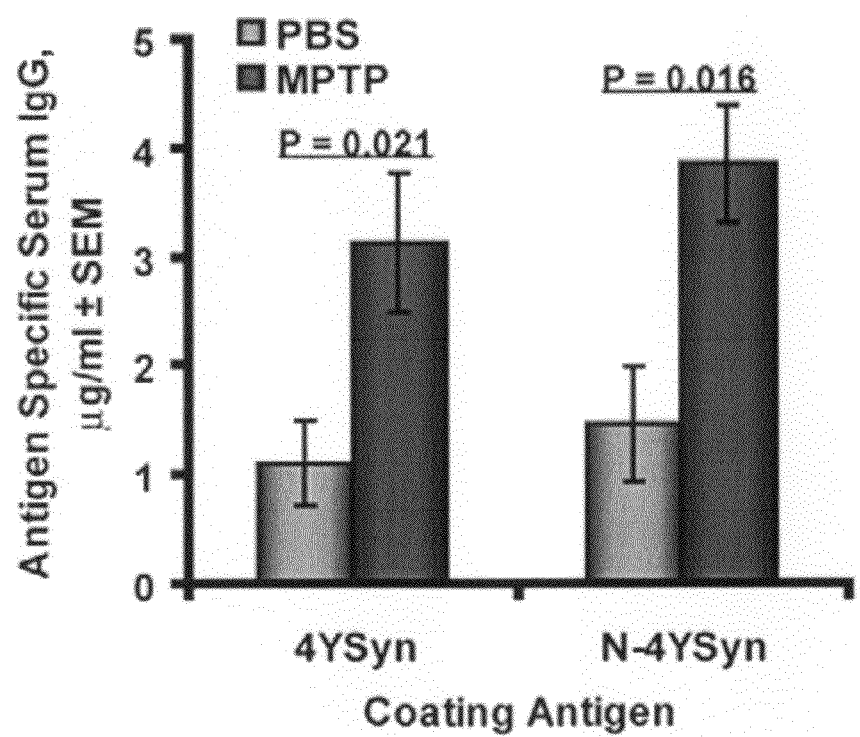

Direct evidence is provided herein that the adaptive immune system can exacerbate dopaminergic neuronal loss in animal models of Parkinson's disease. Nitrated proteins that drain from the CNS into lymphatics induce macrophage activation and T cell responses. Moreover, it is shown that these T cell responses to N-α-Syn elicit profound neurodegeneration. Cell damage resulting from N-α-Syn is not limited to brain cells as it affects both T cell function and numbers and can affect regulatory T cell subsets. The data, taken together, indicates that an exacerbated immune response induced by N-α-Syn plays a role in PD pathogenesis.

It is proposed herein that modified "self" epitopes as neoepitopes, including 3-nitrotyrosine (NT) modifications within α-Syn, can bypass or break immunological tolerance (Ohmori et al. (2005) Autoimmun. Rev., 4: 224-229; Mevorach et al. (1998) J. Exp. Med., 188:387-392; Casciola-Rosen et al. (1997) J. Exp. Med., 185:71-79; Amoura et al. (1999) Arthritis Rheum., 42:833-843; Burkhardt et al. (2001) Trends Immunol., 22:291-293; Utz et al. (1998) Arthritis Rheum., 41:1152-1160; Doyle et al. (2001) Trends Immunol., 22: 443-449) and activate peripheral leukocytes in draining lymphoid tissue. In keeping with this, NT-modifications incorporated into self-peptides were sufficient to evade immunological tolerance as was previously reported (Bimboim et al. (2003) J. Immunol., 171:528-532). The recruitment of activated T cells, specific for disease-associated protein modifications in α-Syn, can promote a toxic microglial phenotype. The role of the adaptive immune system is becoming increasingly important in "non-autoimmune" diseases of the CNS (Gendelman, H. E. (2002) J. Neurovirol., 8:474-479). Research in traumatic and neurodegenerative models have suggested a neuroprotective role for T and B cells within the CNS and that manipulation of the peripheral immune system can affect neurodegeneration (Kipnis et al. (2002) J. Neuroimmunol., 130:78-85). Other studies demonstrated that immunization of mice with glatiramer acetate generate T cells that recognize myelin basic protein ($T_{MBP}$), secrete interleukin (IL)-10, IL-4, and transforming growth factor (TGF)-β, and confer protection against 1-methyl-4-phenyl-1,2,3,6-tetrahydropyridine (MPTP)-induced neurodegeneration presumably by suppression of microglial activation (Benner, et al. (2004) Proc. Natl. Acad. Sci., 101:9435-9440). Antibodies generated through active immunization of human α-Syn transgenic mice with purified human α-Syn protein reduced α-Syn aggregation in cell bodies and terminals, and was associated with protection of dopaminergic nerve terminals (Masliah et al. (2005) Neuron, 46:857-868). The conclusions were that anti-α-Syn antibodies target the aggregated protein to lysosomal pathways for degradation and that the strategy could be applied for treatment of human disease. That work was conducted however in an animal model of PD that lacks a neuroinflammatory component. As such, the study did not address the cellular arm of the immune system, which likely requires cytokine and chemokine gradients for efficient cell entry into diseased regions. Nevertheless, other work supports the potential importance for adaptive immunity and for immune-based strategies for the treatment of PD (Masliah et al. (2005) Neuron, 46:857-868).

Herein, it is reported that NT-modified CNS antigens drain to the deep cervical lymph nodes (CLN) of mice following exposure to MPTP. Moreover, antigen-presenting cells (APC) within CLN increase surface expression of major histocompatibility complex (MHC) class II, initiating the molecular machinery necessary for efficient antigen presentation. The differential outcome on the susceptibility to MPTP-induced dopaminergic neurodegeneration amongst WT and severe combined immunodeficient (SCID) mice suggest a functional link of the adaptive immune system to MPTP-induced neurotoxicity. It is further demonstrated in mice of two disparate haplotypes, that adoptive transfer of T cells from syngeneic WT donors immunized with nitrated α-Syn (N-α-Syn) prolongs MPTP-induced dopaminergic neuronal loss and hence warrants caution against the use of N-α-Syn or self-proteins that are prone to nitrate modifications for vaccine-based PD therapies.

It is also shown herein that N-α-syn immunization elicits adaptive immune responses, to novel antigenic epitopes, that exacerbate nigrostriatal degeneration in the 1-methyl-4-phenyl-1,2,3,6-tetrahydropyridine (MPTP) mouse model of Parkinson's disease (PD). Such neuroimmune degenerative activities, in most significant measure, are Th17 mediated and accelerated through numbers of dysfunctional CD4+ CD25+ regulatory T cells (Treg). These are contained within N-α-syn T cell mixtures. Significantly, Treg reconstitution by vasoactive intestinal peptide (VIP) reverses neurodegeneration by induction of a robust neuroprotective T cell response. These attenuate nigrostriatal destruction by N-α-syn T cells. Combinations of adoptively transferred N-α-syn and VIP immunocytes to MPTP mice produce nigrostriatal protection associated with reduced microglial inflammatory responses. Taken together, these results demonstrate that Treg halts N-α-syn neurodestructive immunity providing a sound rationale for PD immunization strategies.

In accordance with one aspect of the instant invention, methods of treating a central nervous system disease or disorder are provided. In a preferred embodiment, the central nervous system disease or disorder is characterized by the presence of an abnormal protein(s) (e.g., a mutant protein and/or over-expressed protein (including inappropriate expression at a particular site)). In a particular embodiment, the methods comprise administering to a subject in need thereof: 1) at least one immunogen capable of inducing a humoral immune response against the abnormal protein(s) and 2) at least one adjuvant that stimulates functional regulatory T cells. In a preferred embodiment, the humoral immune response causes the abnormal protein to be substantially cleared and eliminated from the site where it is located within the central nervous system. The immunogen and adjuvant may be contained in the same composition or in separate compositions. When the compositions are administered separately, the compositions may be administered simultaneously or sequentially (e.g., the adjuvant may be administered first and then the immunogen, the immunogen may be administered first and then the adjuvant, or multiple administrations of each component may be used in any order).

While the above methods are described as treating a central nervous system diseases or disorders, the methods of the instant invention also encompass the prevention of a central nervous system disease or disorder. In a particular embodiment, the methods of the instant invention delay or inhibit the onset of the central nervous system disease or disorder and/or symptoms associated therewith. For example, the compositions of the instant invention may be administered to a healthy individual, particularly one at risk for a central nervous disease or disorder.

The methods of the instant invention may further comprise administering other therapies which are beneficial to the treatment of the particular central nervous system disease or disorder. The methods of the instant invention may also further comprise the step of monitoring the subject for the central nervous system disease or disorder after the administration of the compositions of the instant invention. For example, the subject may be monitored at least once, at least twice, at least three times or more after treatment. The monitoring may be performed over the course of weeks, months, and/or years. The central nervous system disease or disorder may be monitored through, for example, biological (clinical) diagnosis and/or monitoring of the symptoms associated with the central nervous system disease or disorder.

In accordance with another aspect of the instant invention, compositions for the treatment/prevention of a central nervous system disease or disorder are provided. In one embodiment, the composition comprises 1) at least one immunogen capable of inducing a humoral immune response against an abnormal protein(s) and 2) at least one adjuvant that stimulates the production of regulatory T cells. In a particular embodiment, the instant invention encompasses a kit comprising at least two compositions: wherein at least one composition comprises the at least immunogen and, optionally, at least one pharmaceutically acceptable carrier; and at least one other composition comprises the at least one adjuvant and, optionally, at least one pharmaceutically acceptable carrier.

The central nervous disease or disorder of the instant invention can be any central nervous system disease or disorder. In a preferred embodiment, the central nervous system disease or disorder to characterized by at least one disease specific protein against which an immune response is desirable. Examples of central nervous system diseases and disorders include, without limitation, multi-infarct dementia, stroke, Pick's Disease, frontal lobe degeneration, corticobasal degeneration, multiple system atrophy, progressive supranuclear palsy, Creutzfeldt-Jakob disease, lewy body disease, neuroinflammatory disease, Parkinson's Disease, Alzheimer's Disease, amyotrophic lateral sclerosis, neuroAIDS, Chron's Disease, and Huntington's Disease. In a particular embodiment of the instant invention, the central nervous system disease is selected from a group consisting of Parkinson's Disease, Alzheimer's Disease, amyotrophic lateral sclerosis, neuroAIDS, Chron's Disease, and Huntington's Disease.

In a particular embodiment, the adjuvant induces a T cell phenotypic switch from pro-inflammatory (TH1 and TH17) to anti-inflammatory and regulatory (TH2, Treg, and Tr1). In one embodiment, the adjuvant of the methods and compositions of the instant invention is selected from the group consisting of glatiramer acetate (Cop-1, Copaxone®), vasoactive intestinal peptide, vitamin D (1 alpha, 25-dihydroxyvitamin D3), granulocyte macrophages colony stimulating factor, and transforming growth factor beta. In a particular embodiment, the adjuvant is vasoactive intestinal peptide (particularly human, but the instant invention encompasses VIP from other species).

As stated hereinabove, the immune response (e.g., humoral immune response) induced by the administration of a composition of the instant invention to a subject causes the abnormal protein (including polypeptides and peptides) which characterizes the central nervous disease or disorder to be substantially reduced (preferably eliminated) from the site of abnormal expression (e.g., within the central nervous system). In a particular embodiment, the immunogen comprises at least one antigenic epitope of the abnormal protein. In yet another embodiment, the immunogen is the abnormal protein. Immunogens include, without limitation, alpha synuclein (preferably nitrated alpha synuclein), amyloid beta (particularly the amyloid beta associated with Alzheimer's (e.g., amyloid beta 42)), and superoxide dismutase (preferably, superoxide dismutase 1). In a particular embodiment, the immunogen is alpha synuclein when the central nervous disease is Parkinson's Disease; the immunogen is amyloid beta when the central nervous disease is Alzheimer's Disease; the immunogen is superoxide dismutase when the central nervous system disease is amyotrophic lateral sclerosis; and the immunogen is HIV (e.g., attenuated/dead) and/or envelope glycoprotein (e.g., gp120) when the central nervous system disease is neuroAIDS.

The alpha synuclein is preferably nitrated. The alpha synuclein may be from any species, particularly human. An example of an amino acid sequence of alpha synuclein is SEQ ID NO: 13 (see also GenBank Accession No. P37840). An alpha synuclein amino acid sequence may have 75%, 80%, 85%, 90%, 95%, 97%, or 99% homology with any of the alpha synuclein sequences provided herein. In a particular embodiment, a fragment of alpha synuclein is used. In a particular embodiment, the fragment is the C-terminal 40 amino acids of alpha synuclein (e.g., amino acids 101-140 of SEQ ID NO: 13). In another embodiment, the fragment is a peptide consisting of anywhere from the C-terminal 20 amino acids to the C-terminal 70 amino acids, particularly the from the C-terminal 30 amino acids to the C-terminal 50 amino acids. In a particular embodiment, the fragment is the C-terminal 40 amino acids plus or minus 1, 2, 3, 4, or 5, amino acids. The fragments may optionally have an N-terminal methionine added. The fragments may have 75%, 80%, 85%, 90%, 95%, 97%, or 99% homology with the above alpha synuclein sequences. As stated hereinabove, the alpha synuclein is preferably nitrated. The alpha synuclein of fragment thereof may comprise at least one, at least two, at least three, at least four, at least five or all of the tyrosines nitrated into nitrotyrosines.

The compositions described herein will generally be administered to a patient as a pharmaceutical preparation. The term "patient" or "subject", as used herein, refers to human or animal subjects. The compositions of the instant invention may be employed therapeutically, under the guidance of a physician.

The compositions of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the active agents in the chosen medium may be varied and the medium may be chosen based on the desired route of administration of the pharmaceutical preparation. Except insofar as any conventional media or agent is incompatible with the polymer-therapeutic agent complexes to be administered, its use in the pharmaceutical preparation is contemplated.

The dose and dosage regimen of the compositions according to the invention that are suitable for administration to a particular patient may be determined by a physician considering the patient's age, sex, weight, general medical condition, and the specific condition for which the polymer-therapeutic agent complex is being administered and the severity thereof. The physician may also take into account the route of administration, the pharmaceutical carrier, and the particular agent's biological activity. Selection of a suitable pharmaceutical preparation will also depend upon the mode of administration chosen. For example, the compositions of the invention may be administered by direct injection to a desired site. In this instance, a pharmaceutical preparation comprises the active agents of the instant invention dispersed in a medium that is compatible with the site of injection. The compositions of the instant invention may be administered by any method. For example, the compositions can be administered, without limitation parenterally, subcutaneously, orally, topically, pulmonarily, rectally, vaginally, ocularly, intravenously, intraperitoneally, intracranial, intrathecally, intracerbrally, epidurally, intramuscularly, intradermally, or intracarotidly. In a particular embodiment, the compositions are administered intravenously, subcutaneously, or orally or by direct injection. Pharmaceutical preparations for injection are known in the art. If injection is selected as a method for administering the compositions, steps must be taken to ensure that sufficient amounts of the molecules reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of the composition may be determined by evaluating the toxicity of the molecules or cells in animal models. Various concentrations of active agents in pharmaceutical preparations may be administered to mice or other animal models, and the minimal and maximal dosages may be determined based on the beneficial results and side effects observed as a result of the treatment. Appropriate dosage unit may also be determined by assessing the efficacy of the treatment in combination with other standard drugs. The dosage units of the compositions of the instant invention may be determined individually or in combination with each treatment according to the effect detected.

The pharmaceutical preparation of the instant invention may be administered at appropriate intervals (e.g., at least one booster), for example, once every 2-4 days, once a week, or once every 2-6 of weeks until the pathological symptoms are reduced or alleviated, after which the dosage may be reduced to a maintenance level or eliminated. The appropriate interval in a particular case would normally depend on the condition of the patient. In a particular embodiment, the composition is administered to the body in an isotonic solution at physiological pH 7.4. However, the complexes can be prepared before administration at a pH below or above pH 7.4.

Definitions

The term "treat" as used herein refers to any type of treatment that imparts a benefit to a patient afflicted with a disease, including improvement in the condition of the patient (e.g., in one or more symptoms), delay in the progression of the condition, etc.

A "therapeutically effective amount" of a compound or a pharmaceutical composition refers to an amount effective to prevent, inhibit, treat, or lessen the symptoms of a particular disorder or disease. The treatment of a central nervous disease or disorder herein may refer to curing, relieving, and/or preventing the central nervous system disease or disorder, a symptom(s) of it, or the predisposition towards it.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

The term "neuroAIDS" (also referred to as HIV-associated neurocognitive disorders), as used herein, encompasses those novel neurologic disorders which are a primary consequence of damage to the central nervous system by HIV. The clinical syndromes identified include sensory neuropathy, myelopathy, HIV dementia, and cognitive/motor disorder.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

An "immunogen" refers to a compound comprising a peptide, polypeptide or protein which is "immunogenic," i.e., capable of eliciting, augmenting or boosting an immune response (e.g., cellular and/or humoral). The immunogen can be recombinantly produced. An immunogen comprises at least one antigenic determinant or epitope.

As used herein, "regulatory T cells" are CD4+CD25+ cells that exhibit immunoinhibitory properties.

The following examples are provided to illustrate certain embodiments of the invention. They are not intended to limit the invention in any way.

EXAMPLE 1

Materials and Methods

Animals

Male 6-7 week old, WT C57BL/6J (stock 000664, denoted as B6) (H-2$^b$), B6.CB17-Prkdc$^{scid}$/SzJ (stock 001913, herein denoted as SCID) (H-2$^b$) and B10.BR-H2k H2-T18$^a$/SgSnJ (stock 000465, herein denoted as B10.BR) (H-2$^k$) mice were purchased from Jackson Laboratories (Bar Harbor, Me.). All animal procedures were in accordance with National Institutes of Health (NIH) guidelines and approved by the Institutional Animal Care and Use Committee (IACUC) of the University of Nebraska Medical Center (UNMC).

MPTP Intoxication

For chronic intoxication, B6 mice received 5 intraperitoneal (i.p.) injections at 24 hour intervals for 5 days of either vehicle (PBS, 10 ml/kg) or MPTP-HCl (30 mg/kg of free base in PBS) (Sigma-Aldrich, St. Louis, Mo.). For acute intoxication, mice received 4 i.p. injections, one every 2 hours, of either vehicle (PBS, 10 ml/kg) or MPTP-HCl (18 mg/kg of free base in PBS for B10.BR mice, 14 or 18 mg/kg for B6 mice). At selected time points following MPTP intoxication, mice were sacrificed and brains processed for subsequent analyses. MPTP handling and safety measures were in accordance with published guidelines (Przedborski et al. (2001) J. Neurochem., 76:1265-1274).

Immunohistochemistry

At the time points indicated following MPTP intoxication, mice were transcardially perfused with 4% paraformaldehyde (PFA) in 0.1 M PBS using 0.9% saline as vascular rinse. Brains were post-fixed in 4% PFA overnight, kept in 30% sucrose for 2 days, snap frozen, embedded in OCT compound, and 30 mm sections cut on a cryostat (CM1900, Leica, Bannockburn, Ill.). The sections were collected in PBS and processed free-floating. Primary antibodies used for immunohistochemistry includes rabbit anti-TH antibody (1:2000; Calbiochem/EMD Biosciences, Inc., San Diego, Calif.), rat anti-mouse CD11b or Mac-1 (1:1,000; Serotec, Raleigh, N.C.), rat anti-CD3 (1:800; BD Pharmingen, San Diego, Calif.,) rat anti-CD4 (BD Pharmingen), and rat anti-CD8 (BD Pharmingen). Immunostaining was visualized using diaminobenzidine (Sigma-Aldrich) as the chromogen and mounted on slides. TH, CD3-, CD4- and CD8-immunostained brain sections were counterstained with thionin (Sigma-Aldrich) as previously described (Benner et al. (2004) Proc. Natl. Acad. Sci., 101:9435-9440; Wu et al. (2003) Proc. Natl. Acad. Sci., 100:6145-6150). Fluoro-Jade C (Chemicon International, Inc., Temecula, Calif.) was used to stain degenerating neurons (Schmued et al. (2005) Brain Res., 1035:24-31) and was detected as green fluorescence by fluorescence microscopy with FITC filter (Eclipse E800, Nikon, Inc., Melville, N.Y.).

Stereology of TH-Positive Neurons

Total numbers of Nissl- and TH-stained neurons throughout the entire SNpc were counted stereologically in a blinded fashion with Stereo Investigator software (MicroBrightfield, Williston, Vt.) using the Optical Fractionator probe module as previously described (Benner et al. (2004) Proc. Natl. Acad. Sci., 101:9435-9440).

Cloning α-Syn and 4YSyn

Total RNA from adult C57BL/6 mouse brain was extracted using TRIzol® reagent (Invitrogen, Carlsbad, Calif.) according to the manufacturer's instructions. The full-length mouse α-Syn gene (504 bp) and 120 bp length encoding the C-terminal portion (4YSyn) was amplified by reverse transcriptase-polymerase chain reaction (RT-PCR) using Platinum® Taq DNA Polymerase High Fidelity (Invitrogen). The 5' primer was designed to introduce a Nde1 site at position 1. This fragment was blunt cloned into the pZero-1 (Invitrogen) Eco RV site using standard cloning procedures. Transformed cells were plated on low salt agar containing Zeocyn and 3 mM IPTG. Colonies were screened using colony PCR with α-Syn primers. Colonies containing the full-length mouse α-Syn gene or the 39 fragment encoding 4YSyn were grown overnight and plasmid DNA was isolated using standard mini-prep (Invitrogen). The gene was digested out of pZero with Nde1 and Xho1 and subcloned into the Nde 1 and Xho1 sites in the pET-28a prokaryotic expression vector using DH5-α cells. Colonies were screened using colony PCR. Purified plasmids were submitted to the UNMC core facility for sequence confirmation. Plasmids containing the complete sequence were transformed into BL-21 E. coli cells for expression. Frozen glycerol stocks were maintained at −80° C.

4YSyn Expression

Glycerol stocks were streaked on Luria-Bertani (LB) agar plate containing 30 µg/ml kanamycin. A single colony was inoculated into LB broth containing 30 µg/ml kanamycin, grown for 8 hours, and stored at 4° C. until the following day. The starter culture was diluted 1:100 into fresh liquid medium containing 30 µg/ml kanamycin and allowed to grow to an $OD_{600}$=0.6. Expression of recombinant protein was induced by the addition of 3 mM IPTG with continued incubation for 3 hours at 37° C. Following induction, cells were centrifuged, weighed, and stored at −80° C. until purification protocol was resumed. >90% of detectable 4YSyn was found in the soluble fraction.

Protein Purification and Nitration

Cell lysis was performed with BugBuster® reagent (Novagen/EMD Biosciences, Inc., San Diego, Calif.) at 5 ml/g cells with addition of EDTA-free protease inhibitor cocktail (Calbiochem). Benzonase nuclease (Novagen) was added to reduce viscosity during lysis following manufacturer's instructions. Insoluble cell debris was removed by centrifugation at 16,000×g for 20 minutes at 4° C. The soluble fraction was directly subjected to column affinity chromatography and was carried out in the following steps: His-tagged protein was bound to Ni-NTA His-Bind Resin (Novagen) in Bug Buster reagent with the addition of imidazole (10 mM). The column was washed first with 50 mM $NaH_2PO_4$/300 mM NaCl/20 mM imidazole, pH 8.0 and then with 50 mM $NaH_2PO_4$/300 mM NaCl/35 mM imidazole, pH 8.0. Elution was carried out 50 mM $NaH_2PO_4$/300 mM NaCl/250 mM imidazole pH 8.0. Samples were separated by SDS-PAGE and stained with Brilliant Blue G-Colloidal Coomassie stain (Invitrogen) to confirm purity of the eluted fraction. Full-length α-Syn and 4YSyn were visualized by silver stain (Silver Xpress, Invitrogen). Purified full-length α-Syn was dialyzed in 50 mM $NaH_2PO_4$ buffer. Thrombin cleavage was carried out using biotinylated thrombin cleavage capture kit (Novagen) following manufacturer's instructions. Cleaved His-tags were removed with Ni-NTA resin. His-tag free full-length α-Syn and His-tagged 4YSyn (unable to remove the His-tag) were dialyzed against water for 24-48 hours with multiple water changes, lyophilized, and weighed. Endotoxin was removed by polymyxin B agarose beads following manufacturer's instructions (Sigma-Aldrich) and tested for residual endotoxin by Limulus amebocyte lysate (LAL) assay (E-Toxate, Sigma-Aldrich). Recombinant α-Syn-derived proteins were endotoxin-free as all batches of purified proteins utilized tested below the limit of detection for endotoxin by LAL (<0.05 endotoxin units, EU).

Lyophilized protein was resuspended (2 mg protein/ml) in 50 mM $NaH_2PO_4$ buffer containing 5 mM $FeCl_3$ as a Lewis acid. Peroxynitrite (Upstate Biotechnology, Inc. Lake Placid, N.Y.) was added dropwise to protein to achieve a 5 M excess while vigorously mixing the reaction mixture. Nitrated protein was dialyzed against water for 48 hours using multiple water exchanges, lyophilized, and stored at −80° C.

MALDI-TOF Mass Spectrometry

MALDI-TOF mass spectrometric analysis was performed using a Voyager DE Pro mass analyzer (Applied Biosystems, Framingham, Mass.), which was externally calibrated prior to each assay. Data acquisition was performed using 500 laser shots. The MS scan range was set from 500 to 20,000 m/z. Saturated cyanohydroxycinnamic acid (Sigma-Aldrich) was used as matrix in these assays and samples were manually spotted onto MALDI targets.

Enzyme-Linked immunosorbant Assay (ELISA)

Individual wells of Immunolon II ELISA plates (Thermo Electron Corp., Waltham, Mass.) were coated with 100 μl/well of native 4YSyn or N-4YSyn at 1 μg/ml PBS, pH 8.5. Plates were incubated for 2 hours at 37° C. and washed with 0.5% Tween20/PBS, pH 7.2 (PBS-T). Nonspecific binding was blocked by the addition of 1% bovine serum albumin in PBS, pH 7.2 (PBS-BSA) and incubation at 37° C. for 1 hour. Plates were washed with PBS-T, 100 μl of 2-fold serial dilutions (from an initial 1:50 dilution in PBS-BSA) of serum samples from MPTP- or PBS-treated mice were added to each well, and incubated at 37° C. for 1 hour. Plates were washed with PBS-T and 100 μl/well of a 1:5000 dilution of horseradish peroxidase (HRP)-conjugated anti-mouse IgG (SouthernBiotech, Birmingham, Ala.) was added. Plates were incubated at 37° C. for 1 hour, washed with PBS-T, and reacted with 0.012% $H_2O_2$ and 2.2 mM o-phenylenediamine dihydrochloride (Sigma-Aldrich) in 100 μl of 0.1 M phosphate-citrate buffer, pH 5.0. The reaction was stopped with the addition of 2 N $H_2SO_4$, read at 490 nm on a microplate reader (Vmax® Kinetic Microplate Reader, Molecular Devices Corporation, Sunnyvale, Calif.), and acquired data analyzed with interfacing SoftMax® Pro software (Molecular Devices). Serum IgG concentrations were quantified from a standard curve prepared from known concentrations of mouse IgG (SouthernBiotech).

Immunization and Immune Cell Adoptive Transfers

B10.BR(H-$2^K$) mice were immunized with PBS, 50 μg of 4YSyn or N-4YSyn emulsified in an equal volume of CFA containing 1 mg/ml *Mycobacterium tuberculosis* (Sigma-Aldrich). B6 (H-2b) mice were immunized with PBS, 10 μg of 4YSyn or N-4YSyn with or without CFA. While immunization with adjuvant were administered subcutaneous (s.c.) on either side of the tail base, s.c. injections without adjuvant were given at 5 different sites. Fourteen days after primary immunization, mice were boosted with their respective antigens. CFA recipient mice were boosted with their respective antigens emulsified in IFA (Sigma-Aldrich). Five days following their final immunizations, donor mice were sacrificed and single cell suspensions were prepared from the spleen and draining lymph nodes after lysing red blood cells with ammonium chloride-potassium (ACK) lysis buffer (0.15M NH4Cl, 10 mM KHCO3, 0.1 mM Na2EDTA, pH 7.2). T cells were enriched by using the PAN T cell isolation kit (Miltenyi Biotec, Auburn, Calif.) and by depletion of magnetically labeled cells employing AutoMACS (Miltenyi Biotec). Twelve hours post-MPTP intoxication, both B10.BR and B6 mice received intravenous (i.v.) injections of 5×10$^7$ spleen cells (SPC) in 0.25 ml of Hanks' balanced salt solution (HBSS). B10.BR mice also received 2.5×10$^7$ purified T cells. SCID mice were reconstituted with i.v. injections of 8×10$^7$ unfractionated SPC populations from WT B6 mice. RCS-SCID mice were rested for 4 wks prior to MPTP intoxication.

$^3$H-Thymidine in vitro Proliferation Assays

Samples of pooled immunized donor cells used for adoptive transfer were tested for their proliferative capacity by $^3$H-thymidine incorporation after stimulation with either immunizing or irrelevant antigen. Donor SPC were plated at a density of 2×10$^6$ cells/ml complete RPMI tissue culture media [RPMI 1640 supplemented with 10% fetal bovine serum (FBS), 2 mM L-glutamine, 10 mM HEPES, 1 mM sodium pyruvate, 1× nonessential aa, 55 μM 2-mercaptoethanol, 100 U/ml penicillin, and 100 μg/ml streptomycin (Mediatech Inc., Herndon, Va.)]. SPC from PBS, 4YSyn, and N-4YSyn immunized mice were stimulated with 0, 1, 10, 50 μg/ml of immunizing antigen, 4YSyn or N-4YSyn, and cultured at 37° C. for 5 days. Cells were pulsed with 1 mCi $^3$H-thymidine/well for the final 18 hours of culture, harvested onto glass fiber plates, and counted by β-scintillation spectrometry (TopCount, Packard-PerkinElmer Instruments, Wellesley, Mass.).

Western Blot Analysis

Ventral midbrain (VMB) and lymphoid organ protein extracts (80 μg/lane) were separated by 16% SDS-PAGE (Invitrogen) and transferred for 45 minutes onto 0.2 mm PVDF membranes (Millipore, Bedford, Mass.). Membranes were probed with rabbit antibodies to NT (1:2000; Chemicon) or monoclonal rat antibodies to myelin basic protein (MBP, 1:1000, Chemicon) or guinea pig antibodies to α-Syn (1:1000; Ab-1, Oncogene/EMD Biosciences). Appropriate HRP-conjugated secondary antibodies (Santa Cruz Biotechnology, Santa Cruz, Calif.) were used to visualize blots using SuperSignal® West Pico Chemiluminescent substrate and CCL-XPosure film (Pierce Biotechnology, Inc., Rockford, Ill.). Immunoblots were stripped and reprobed with antibodies to α-actin (1:5000; Chemicon,) as an internal control.

Identification of α-Syn in MPTP-CLN

Anti-N-α/β-syn (clone nSyn12, mouse ascites, Upstate) that specifically recognizes N-α-Syn (14.5 kD) and N-β-Syn (17 kD) but not non-nitrated α/β-Syn was used for immunoprecipitation (IP). VMB and CLN from PBS or MPTP treated mice were dissected out, homogenized in ice-cold RIPA buffer, pH 7.4 and centrifuged at 10,000×g for 10 minutes at 4° C. to remove cellular debris. Protein A/G PLUS-Agarose beads (Santa Cruz Biotechnology) were added to 2 mg total cellular protein, incubated for 1 hour at 4° C. Beads were centrifuged at 1,000×g for 5 minutes at 4° C. The supernatant was incubated with 40 ml anti-N-α-Syn overnight at 4° C. on a rotating device, and then with Protein A/G PLUS Agarose beads for 1 hour on a rotating device at 4° C. Immunoprecipitates were collected after centrifugation at 1,000×g for 5 minutes at 4° C., washed once with RIPA buffer and twice with PBS, resuspended in 40 ml of 1× electrophoresis sample buffer.

N-α-Syn IP samples were fractionated by large format 16% Tricine SDS-PAGE (Jule Inc., Milford, Conn.; BIORAD Laboratories, Inc, Los Angeles, Calif.) at constant voltage for 8-10 hours. The gel was stained with highly sensitive SYPRO Ruby stain (Invitrogen) and scanned at excitation (400 nm) and emission (630 nm) wavelengths using Typhoon scanner (Amersham Biosciences, Piscataway, N.J.) to visualize the protein bands. Small gel fragments (3-4 mm) corresponding to molecular weight (12-18 kD) were excised from each lane of the same gel stained with Coomassie. In brief, gel pieces were destained for 1 hour at room temperature using 100 ml of 50% ACN/50 mM NH4CO3. Gel pieces were dried and incubated with trypsin in 10 mM NH4CO3 (Promega, Madison, Wis.) overnight at 37° C. Peptides were extracted by washing gel pieces twice with 0.1% TFA and 60% ACN. Dried samples were resuspended in 12 ml of 0.1% formic acid in water for automated injection. All samples were purified using ZipTip® (Millipore) prior to MS analysis. In-gel trypsin digested proteins were fractionated on microcapillary RP-C18 (Ciborowski et al. (2004) J. Neuroimmunol., 157: 11-16). The resulting peptides were sequenced using Electrospray Ionization (ESI)-LC MS/MS (ProteomeX System with LCQDecaPlus mass spectrometer, thermoElectron, Inc., San Jose, Calif.) with a nanospray configuration. The spectra obtained from LC-MS/MS analysis were searched against the NCBI.fasta rodent protein database using SEQUEST search engine (BioWorks 3.2 SR software from ThermoElectron, Inc, San Jose, Calif.). Criteria for high confidence protein identification were used as previously published (Ciborowski et al. (2004) J. Neuroimmunol., 157:11-16; Enose et al. (2005) Glia 51:161-172; Ricardo-Dukelow et al. (2007) J. Neuroimmunol., 185:37-46; Ciborowski et al. (2007) Virology 363:198-209; Glanzer et al. (2007) J. Neurochem., 102: 627-45; Kadiu et al. (2007) J. Immunol., 178:6404-6415).

Flow Cytometry

Single cell suspensions were prepared from deep CLN from C57BL/6 mice 20-24 hours post PBS or MPTP (18 mg/kg) intoxication. Cell suspensions were analyzed for cell surface expression of CD11c, CD11b, and MHC class II (I-A$^b$). Also, prior to adoptive transfers, cell populations from immunized donors were stained for T cells using PE conjugated anti-mouse CD3ε (BD Pharmingen) and B cells with FITC conjugated anti-mouse CD19 (BD Pharmingen). Analysis was performed with a FACSCalibur™ flow cytometer interfaced with CellQuest™ software (BD-Biosciences, Immunocytometry Systems, San Jose, Calif.).

Determination of N-4YSyn-mediated Toxicity In Vitro

For proliferation analyses, purified T cells from naive B6 mice were plated with SPC irradiated at 3000 rad (1:3) at $2 \times 10^6$ cells/ml in complete RPMI tissue culture media and activated with anti-CD3 (0.5 µg/ml, 145-2C11; BD Pharmingen) in U-bottom 96-well tissue culture plates. Graded concentrations of 4YSyn or N-4YSyn were added to quadruplicate wells. After activation for 3 days, $^3$H-thymidine incorporation was performed as described previously.

To assess α-Syn-mediated cytotoxicity, purified T cells were stimulated with anti-CD3 and cultured at a density of $1 \times 10^6$ cells/ml for 24 hours in media alone or in the presence of 4YSyn or N-4YSyn at concentrations of 1, 3, 10, or 30 µg/ml. Cells were stained with PI, washed and the percentages of PI$^+$ dead cells and MFI were analyzed by flow cytometry.

Macrophage and MES 23.5 Cultures

BMM were prepared from C57BL/6 adult male (6-12 weeks old) mice. The animals were sacrificed by CO2 asphyxiation. Single cell suspensions of bone marrow cells were obtained from femur bone marrow cavities after flushing with HBSS, and red blood cells lysed with ACK buffer. The bone marrow cells were cultured in complete DMEM medium (Dulbecco's Modified Eagles Media supplemented with 10% FBS, 2 mM L-glutamine, and 1% penicillin/streptomycin) containing 2 µg/ml macrophage colony stimulating factor (MCSF), a generous gift from Wyeth Pharmaceuticals (Cambridge, Mass.) in a 5% $CO_2/37°$ C. incubator. Nonadherent cells were removed from flasks at 1, 4, and 7 days by successive DMEM washes. Adherent BMM were harvested and replated for experiments following 7-14 days of culture. Cells from the MES 23.5 dopaminergic cell line were cultured in 75-cm$^2$ flasks in DMEM/F12 with 15 mM HEPES (Invitrogen) containing N2 supplement (Invitrogen), 100 U/ml of penicillin, 100 µg/ml streptomycin, and 5% FBS. Cells were grown to 80% confluence then co-cultured with BMM in serum free MEM/F12 at a density of $1 \times 10^5$ cells (1:1) on sterile glass coverslips.

N-α-Syn SPC-Induced Microglia Cytotoxicity

SPC isolated from N-4YSyn (10 µg) immunized B6 mice were cultured in RPMI media and activated in vitro for 4 days with N-4YSyn (1 µg/ml). MES 23.5 cells or macrophages alone or MES 23.5 and macrophage co-cultures were stimulated with aggregated N-α-Syn (1.45 µg/ml) alone and in combination with either activated SPC or supernatants obtained from activated SPC for 24 hours. Unstimulated cultures served as controls. Assays for viable and dead cells were performed with Live/Dead Viability/Cytotoxicity kit (Invitrogen) according to the manufacturer's protocol and viewed under a fluorescence microscope (Nikon Eclipse E800, Buffalo Grove, Ill.). Images were captured at 100× magnification and quantification of live (green) and dead (red) counts was performed from 4-8 different fields.

Cytokine Array

Triplicate co-cultures of antigen presenting cells (APC) and T cells from PBS, 4YSyn- and N-4YSyn-immunized mice were stimulated with 4YSyn or N-4YSyn. After 24 hours of culture, 50 µl samples were collected, centrifuged, and supernatants frozen at −80° C. until utilized. Frozen supernatants were thawed only once and analyzed using the BD Cytometric Bead Array Mouse Th1/Th2 Kit (BD Biosciences, San Jose, Calif.) according to the manufacturer's instructions.

Statistical Analysis

All values are expressed as mean±SEM. Differences among normally distributed means were evaluated by Student's t test for two group comparisons or one-way ANOVA followed by Bonferroni post-hoc tests for pairwise comparisons amongst multiple data sets (Statistica v7, Statsoft, Tulsa, Okla., and SPSS v13, SPSS, Inc., Chicago, Ill.) and were considered significant at $p \leq 0.05$ unless otherwise indicated. Kolmogorov-Smirnov (K-S) analysis was performed for flow cytometric data analysis.

Results

CNS Antigens Drain to CLN Following MPTP Intoxication

To determine if CNS antigens drain to CLN during established neurodegeneration of the nigrostriatal pathway, their presence in ventral midbrain (VMB), cervical, axillary, inguinal, mesenteric lymph nodes and spleens were determined 24 hours after MPTP-intoxication in C57BL6 mice. The presence of unmodified α-Syn was demonstrated in VMB and CLN (FIG. 1A) as well as other lymph nodes and in the spleen from phosphate-buffered (PBS)— or MPTP-treated mice in anti-α-Syn-probed immunoblots. These findings also confirmed the expression of unmodified α-Syn amongst cells of hematopoietic lineage (Shin et al. (2000) Mol. Cells, 10:65-70). N-α-Syn IP showed that N-α-Syn was present in the CLN of MPTP-treated, but not PBS-treated mice as similar molecular weight bands were observed from gels probed with SYPRO® Red and Western blots performed with α-Syn antibodies (FIG. 1B). To validate the presence of NT-modified α-Syn after MPTP treatment, N-α-Syn immunoprecipitates were obtained after in-gel tryptic digestion of 12-18 kD fragments acquired from the VMB and CLN and sequenced by LC-MS/MS. This regions was chosen as it represents the molecular mass ranges of oxidized α-Syn (Weinreb et al. (1996) Biochemistry 35:13709-3715; Hodara et al. (2004) J. Biol. Chem., 279:47746-47753; Dufty et al. (2007) Am. J. Pathol., 170:1725-1738; Hasegawa et al. (2002) J. Biol. Chem., 277: 49071-49076; El-Agnaf et al. (2003) Faseb J., 17: 1945-194). Sequence analysis demonstrated α-Syn peptides (yellow highlighted sequences, FIG. 1C) in the VMB from both PBS- and MPTP-treated mice but exclusively in the CLN of MPTP-intoxicated mice (Table 1). α-Syn peptides were identified at >99.999% confidence (Table 1). Western blot analysis of lymphoid tissue homogenates using rabbit NT antibodies detected a single band with a molecular mass of ~16-18 kD, which is comparable to that of α-Syn, in CLN from MPTP-intoxicated animals, but not in other lymph nodes or spleen (FIG. 1D). These results were confirmatory for the presence of N-α-Syn in the draining CLN. Another CNS antigen, MBP was also detected only in the CLN of MPTP intoxicated animals (FIG. 1D). NT-modified proteins and MBP were absent in lymph nodes and spleens of control (PBS-injected) mice. These data suggest that brain proteins released as a consequence of nigrostriatal injury, drain to the deep CLN, placing them in organs associated with efficient presentation of antigen. To demonstrate the functional significance of these observations, single cell suspensions were prepared from CLN isolated from MPTP animals and controls, and analyzed by flow cytometry for MHC class II expression on CD11b$^+$ APC (FIG. 1E). Increased frequencies of CD11b+/MHC class II$^+$ in MPTP-treated mice compared to PBS controls was taken as evidence of leukocyte activation in the deep CLN following MPTP-induced nigrostriatal injury. Supporting the induction of a α-Syn specific immune response, sera from WT B6 mice 21 days after chronic MPTP intoxication were analyzed for anti-α-Syn IgG and compared to animals that received PBS. Serum levels of α-Syn antibodies in mice exposed to MPTP were significantly increased (FIG. 1F). Together, these results demonstrate that NT-modified α-Syn draining into the deep CLN is capable of eliciting a peripheral immune response.

Adaptive Immunity Participates in MPTP-Nigral Degeneration

Figure 2:
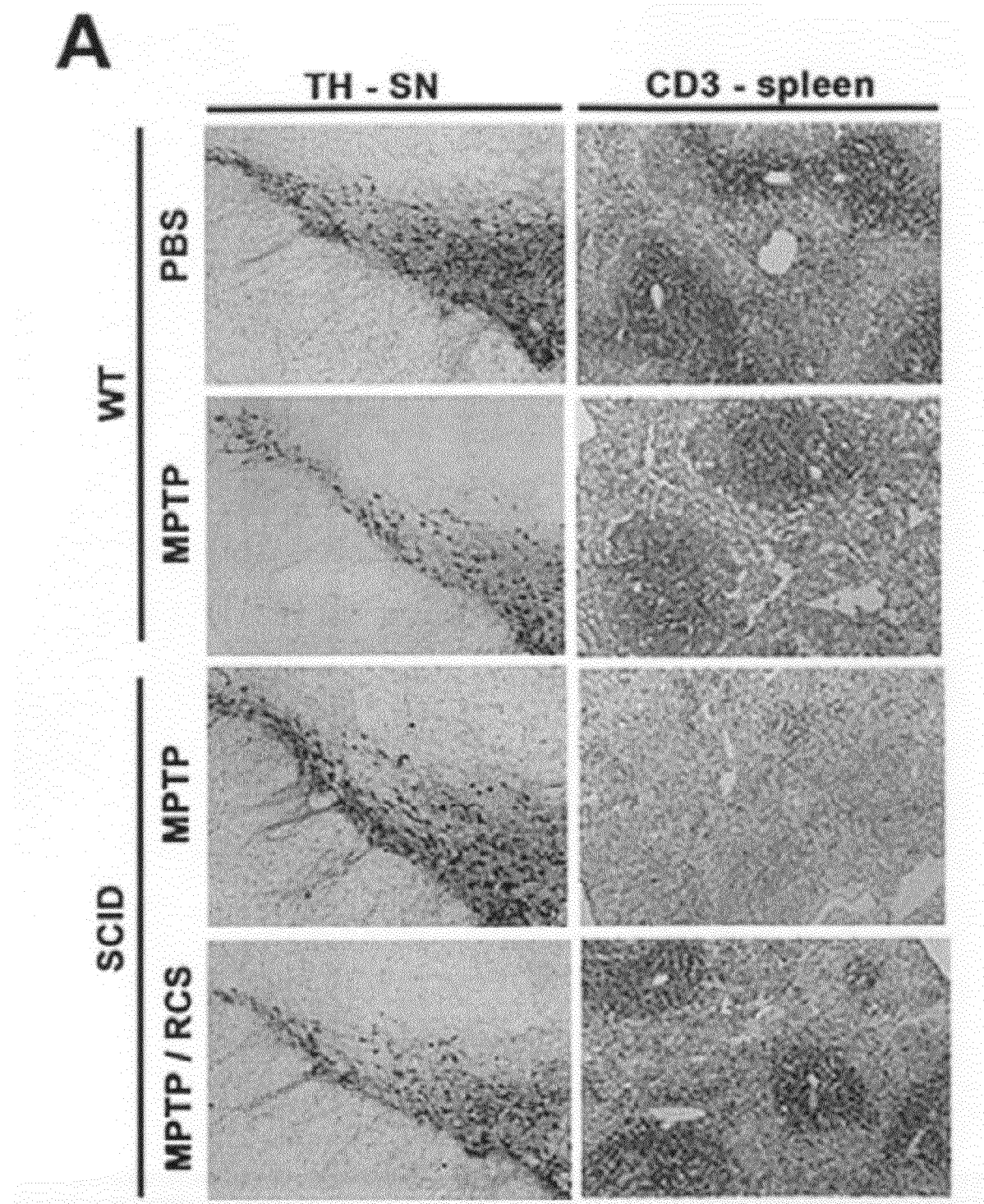
FIGS. 2A-2C demonstrate nigral degeneration following MPTP-intoxication in B6 SCID mice before and after lymphoid cell reconstitution.
Figure 2:
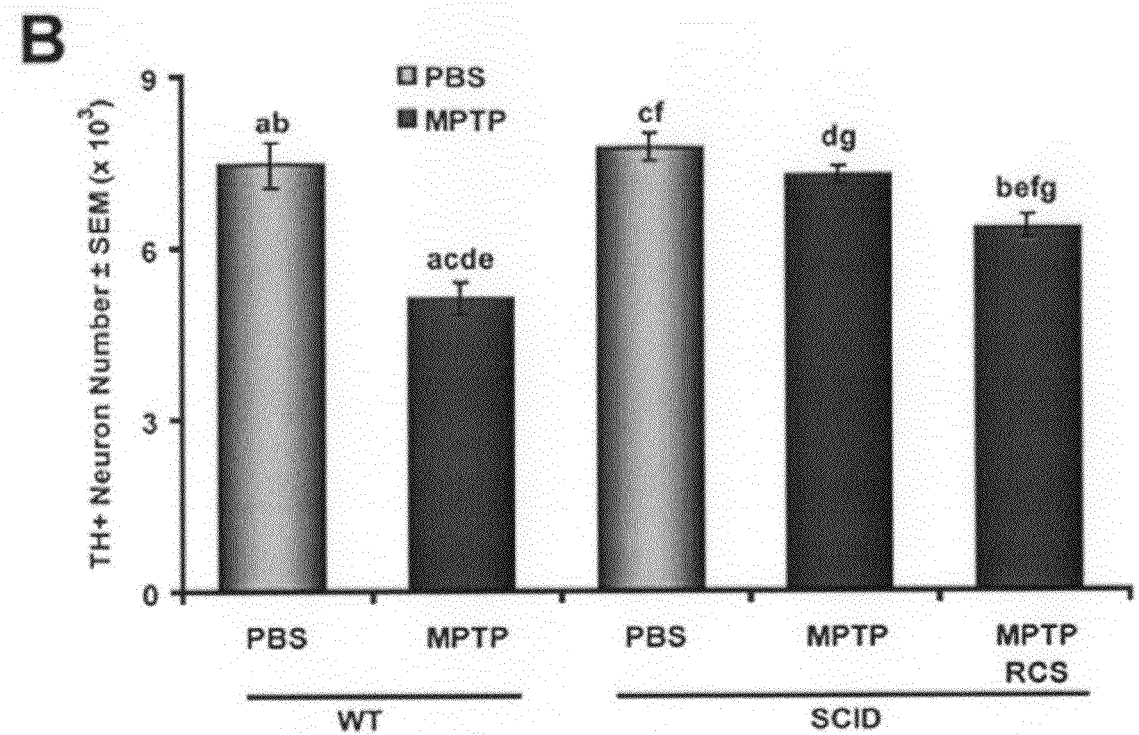
Figure 2:
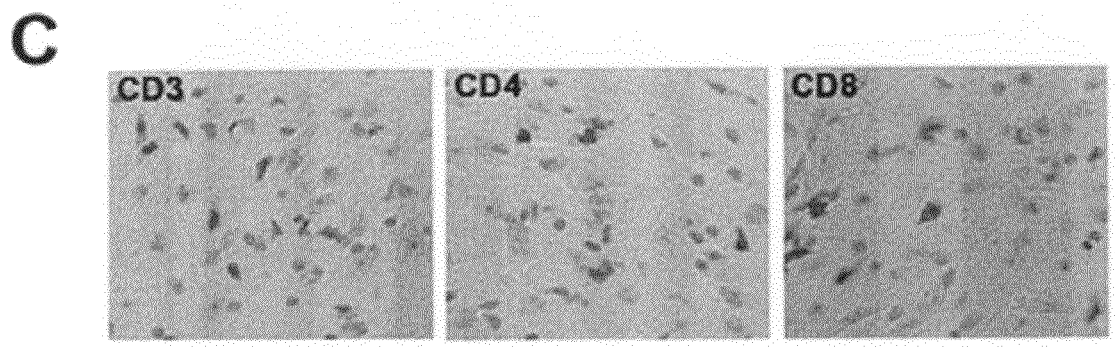

The presence of NT modifications of α-Syn in draining lymphatic tissue following MPTP-induced nigrostriatal injury, along with evidence of lymphoid-associated APC activation provided support for antigen presentation to T cells and subsequent immune responsiveness. To substantiate this, it was explored whether an endogenous adaptive immune system was required for MPTP-induced nigrostriatal degeneration. B6 WT mice, B6 SCID mice, and B6 SCID mice reconstituted with 10$^8$ B6 WT splenocytes (SPC) (RCS-SCID) were treated with PBS or a chronic MPTP regimen. Mice were sacrificed at 21 days after the last MPTP injection, and VMB sections immunostained for tyrosine hydroxylase (TH), the rate-limiting enzyme in dopamine synthesis (FIG. 2A, left panels). The numbers of TH$^+$ neurons in the SN showed a 33% reduction in WT B6 animals that received MPTP compared to those that received PBS (FIG. 2B). No significant difference in the numbers of TH$^+$ neurons was observed in MPTP-treated SCID mice compared to SCID mice that received PBS (FIG. 2B). In contrast, immune reconstituted SCID mice (RCS-SCID) treated with MPTP showed significantly fewer TH$^+$ neurons compared to the SCID MPTP group (FIGS. 2A and 2B). To validate the reconstitu-

TABLE 1

Probabilities (p values) of protein sequence matches within 12-18 kD bands from anti-N-α/β-synuclein immunoprecipitation and LC MS-MS analyses of VMB and CLN from PBS- or MPTP-treated mice.

| | P value for protein matches from | | | |
|---|---|---|---|---|
| | VMB | | MPTP | |
| Protein Match | PBS | MPTP | PBS | MPTP |
| α-synuclein | $5.9 \times 10^{-7}$ | $7.7 \times 10^{-6}$ | | $1.0 \times 10^{-6}$ |
| β-synuclein | $4.3 \times 10^{-7}$ | $3.8 \times 10^{-9}$ | | |
| myelin basic protein | | $3.4 \times 10^{-5}$ | | |
| MHC class I antigen | | | | $4.0 \times 10^{-3}$ |
| immunoglobulin heavy chain variable region | | $5.8 \times 10^{-5}$ | | |
| chemokine-like factor super family five variant 4 | $3.8 \times 10^{-4}$ | | | |
| ribosomal protein S14 | | | $5.6 \times 10^{-6}$ | |
| Tesp4 protein | | | $1.8 \times 10^{-5}$ | |
| A chain A, complex of the second kunitz domain of tissue factor pathway inhibitor | | $2.0 \times 10^{-4}$ | | $8.7 \times 10^{-5}$ |
| structural constituent of ribosome | | | | $6.3 \times 10^{-5}$ |
| parotid secretory protein | | $2.6 \times 10^{-4}$ | | |
| ribosomal protein S14 | | | | $4.9 \times 10^{-4}$ |
| Similar to NADH dehydrogenase (ubiquinone) 1 beta subcomple | $5.9 \times 10^{-4}$ | | | |
| mediator of RNA polymerase II transcription, subunit 8 homolog isoform | | | | $9.9 \times 10^{-4}$ |
| cAMP-dependent protein kinase, alpha-catalytic subunit (PKA C-alpha) | | | $1.3 \times 10^{-3}$ | |
| step II splicing factor SLU7 | | | $2.4 \times 10^{-3}$ | |
| parotid secretory protein | | | | $3.5 \times 10^{-3}$ |
| Similar to protease, serine, 3 | $1.2 \times 10^{-5}$ | | | |
| hypothetical protein LOC320696 | | | $4.5 \times 10^{-3}$ | |
| Unknown (protein for MGC: 116262) | | | | $2.9 \times 10^{-6}$ |
| unnamed protein product (16288 kD) | | | | $1.6 \times 10^{-4}$ |
| unnamed protein product (25311 kD) | | | $1.1 \times 10^{-5}$ | |
| unnamed protein product (27163 kD) | | $2.4 \times 10^{-4}$ | | |
| unnamed protein product (58621 kD) | $1.2 \times 10^{-5}$ | | | $8.2 \times 10^{-5}$ |
| unnamed protein product (65626 kD) | $2.7 \times 10^{-6}$ | $1.4 \times 10^{-5}$ | | $2.5 \times 10^{-5}$ |
| pancreatic trypsin 1 | $3.7 \times 10^{-5}$ | $2.7 \times 10^{-6}$ | $1.5 \times 10^{-6}$ | $1.3 \times 10^{-4}$ |
| trypsin 10 | $2.9 \times 10^{-3}$ | $1.8 \times 10^{-4}$ | $5.1 \times 10^{-5}$ | $8.6 \times 10^{-5}$ |
| trypsinogen 7 | | $2.2 \times 10^{-5}$ | | $2.6 \times 10^{-6}$ | tion of RCS-SCID mice, spleens were immunostained for CD3+ T cell distribution (FIG. 2A, right panels). T cell repopulation was confirmed by the presence of CD3+ T cells in the periarteriolar lymphoid sheath of RCS-SCID mouse spleens (FIG. 2A), VMB and cerebellum control sections of WT, SCID, and RCS-SCID mice treated with MPTP were immunostained for T cells using antibodies against CD3, CD4, and CD8. CD3 immunostaining of MPTP-treated B6 mice demonstrated CD3+ cells in the VMB beginning at day 0, present at day 4 after MPTP intoxication (FIG. 2C) that persisted to day 14. Both CD4+ and CD8+ subpopulations were also present in VMB of only MPTP-treated animals at 4 and 14 days (FIG. 2C). No T cell accumulation was observed in PBS or MPTP-treated SCID mice at any time point, whereas CD3+ T cell accumulations in VMB of RCS-SCID mice after MPTP-treatment were identified. Cerebellar tissue of MPTP animals had $\leq 1$ CD3+ T cell per high power field examined present suggesting specific cell entry into affected regions. Taken together, these data support the occurrence of an adaptive immune response triggered by modified CNS antigens that modulates the vulnerability of the dopaminergic neurons to MPTP through the migration of T cells into the CNS.

Prediction of Mouse N-α-Syn Specific T Cell Epitopes

To test the probability of N-α-Syn induced adaptive immune responses, the numbers of predicted α-Syn specific T cell epitopes were compared with the propensity to bind class I MHC grooves (Peters et al. (2006) PLoS Comput. Biol., 2:e65) for the murine MHC haplotypes, H-$2^k$ and H-$2^b$ (see Table 2). However, since the last 40 aa of the mouse α-Syn contains 4 Tyr residues available for nitration, the analysis focused on this C-terminal α-Syn fragment. Table 2 shows that H-$2K^k$ epitopes have a superior ability to bind with high and intermediate affinity α-Syn-derived 8-11-meric peptide fragments derived from the whole α-Syn molecule or from its C-terminal 38-meric fragment. These data demonstrate significant T cell induction potential. In fact, α-Syn has 100 potential T cell epitopes, 73 of which contain Tyr that were predicted to bind H-$2K^k$ molecules, while only 8 and 15 potential epitopes may bind H-2 $D^b$ and H-2 $K^b$ molecules, respectively. This was also for nitrated epitopes containing Tyr residue including those with a Tyr residue within the central region of the epitope that presents prominently to the T cell receptor. These epitopes do not contain anchor aa that mediate binding to the MHC groove. Dramatic difference in the number of Tyr-containing T cell epitopes from C-terminal segment of α-Syn predicted to bind H-$2K^k$ but not any of H-$2^b$ molecules (Table 2, data in brackets) suggests a potential preference for H-$2K^k$ versus H-$2^b$ mice to induce T cell responses to nitrated C-terminal fragments of α-Syn. These fragments, if facing T cell receptors, have greater chances of inducing MHC class I-restricted CD8+ T cells due to lack of negative selection against N-α-Syn epitopes in the embryonic thymus. Further epitope prediction analysis revealed a number of 15-meric epitopes, including Tyr-containing peptides from C-terminal, that can bind with increased affinity class II MHC groove, thus increasing the propensity of inducing MHC class II-restricted CD4+ T cells specific for Tyr-containing α-Syn C-terminal fragments. Therefore, mice expressing MHC class I and II molecules of H-2k haplotypes are capable of generating immune responses to NT-modified α-Syn. Interestingly, that α-Syn C-terminal fragment contains several Tyr-containing peptides with predicted significant binding affinity for IA$^k$ and IA$^b$ MHC molecules (18 and 14 epitopes, respectively) suggests a significant potential for CD4+ T cells of mice expressing IA$^k$ or IA$^b$ to respond to nitrated epitopes from α-Syn C-terminal.

TABLE 2

Numbers of putative α-Syn epitopes for presentation to T cell receptors predicted from the binding potential of MHC class I and II molecules for the aa sequence of α-Syn. Number of predicted T-cell epitopes from the 38-mer C-terminal fragment of α-Syn are in brackets.

| Predicted binding of epitopes | [a]MHC class I | | | [b]MHC class II | | |
|---|---|---|---|---|---|---|
| | $K^k$ | $D^b$ | $K^b$ | IA$^k$ | IE$^k$ | IA$^b$ |
| All | 143 (100) | 72 (1) | 73 (13) | 116 (32) | 59 (8) | 129 (32) |
| High | 29 (26) | 1 (0) | 1 (1) | 19 (12) | 0 (0) | 2 (2) |
| Intermediate | 71 (58) | 7 (0) | 14 (6) | 55 (13) | 6 (1) | 70 (16) |
| Low | 43 (16) | 64 (1) | 58 (6) | 42 (7) | 53 (8) | 57 (14) |
| Containing Tyr | 101 (77) | 50 (1) | 48 (8) | 34 (23) | 8 (5) | 33 (24) |
| High | 24 (21) | 1 (0) | 1 (1) | 9 (10) | 0 (0) | 2 (2) |
| Intermediate | 49 (43) | 7 (0) | 12 (4) | 19 (8) | 0 (0) | 16 (12) |
| Low | 28 (13) | 42 (1) | 35 (3) | 6 (5) | 8 (5) | 15 (10) |

[a]For class I MHC binders three following grades for scoring included: low immunogenic epitopes, scores <−3; mild immunogenic epitopes, scores >−3 but <−2; high immunogenic, scores >−2; all computations were done using the Immune Epitope Database and Analysis Resource (IEDB) (immuneepitope.org) and integrative epitope prediction tool [proteasomes cleavage, Transporter associated with Antigen Processing (TAP) binding, processing and MHC binding].
[b]For class II MHC binders, scoring grades were based on predicted IC$_{50}$ values and were: low (1000 nM-5000 nM), intermediate (200-1000 nM) and high (<200 nM) for groove binding prediction by MHCPred. This prediction algorithm considers peptides with predicted IC$_{50}$ > 5000 nM as non-binders (Guan et al. (2003) Appl. Bioinformatics 2: 63-66; Guan et al. (2003) Nucleic Acids Res., 31: 3621-3624).

Purification and Nitration of Recombinant α-Syn

Figure 3:
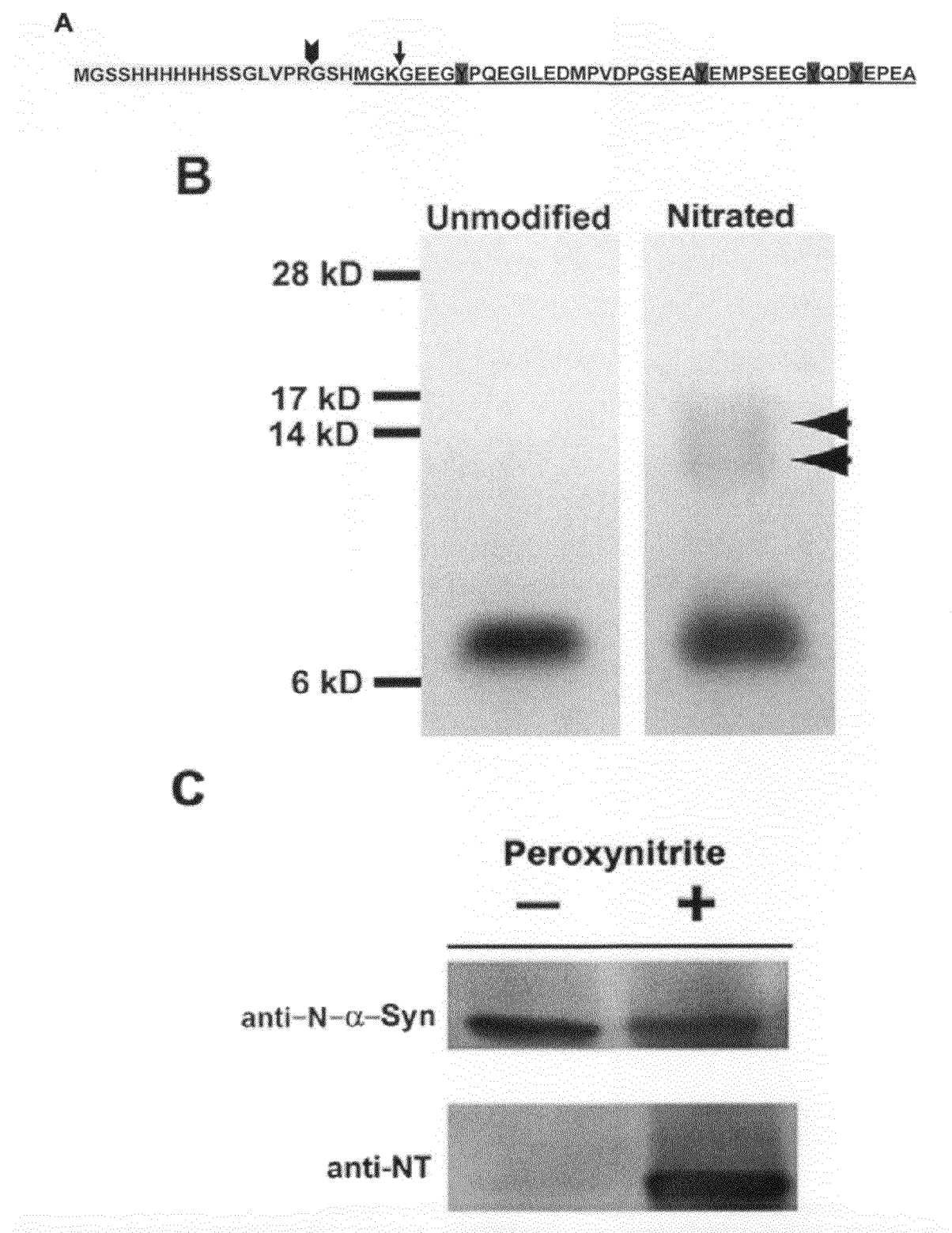
FIGS. 3A-3D provide the characterization of purified and nitrated recombinant 4YSyn.
Figure 3:
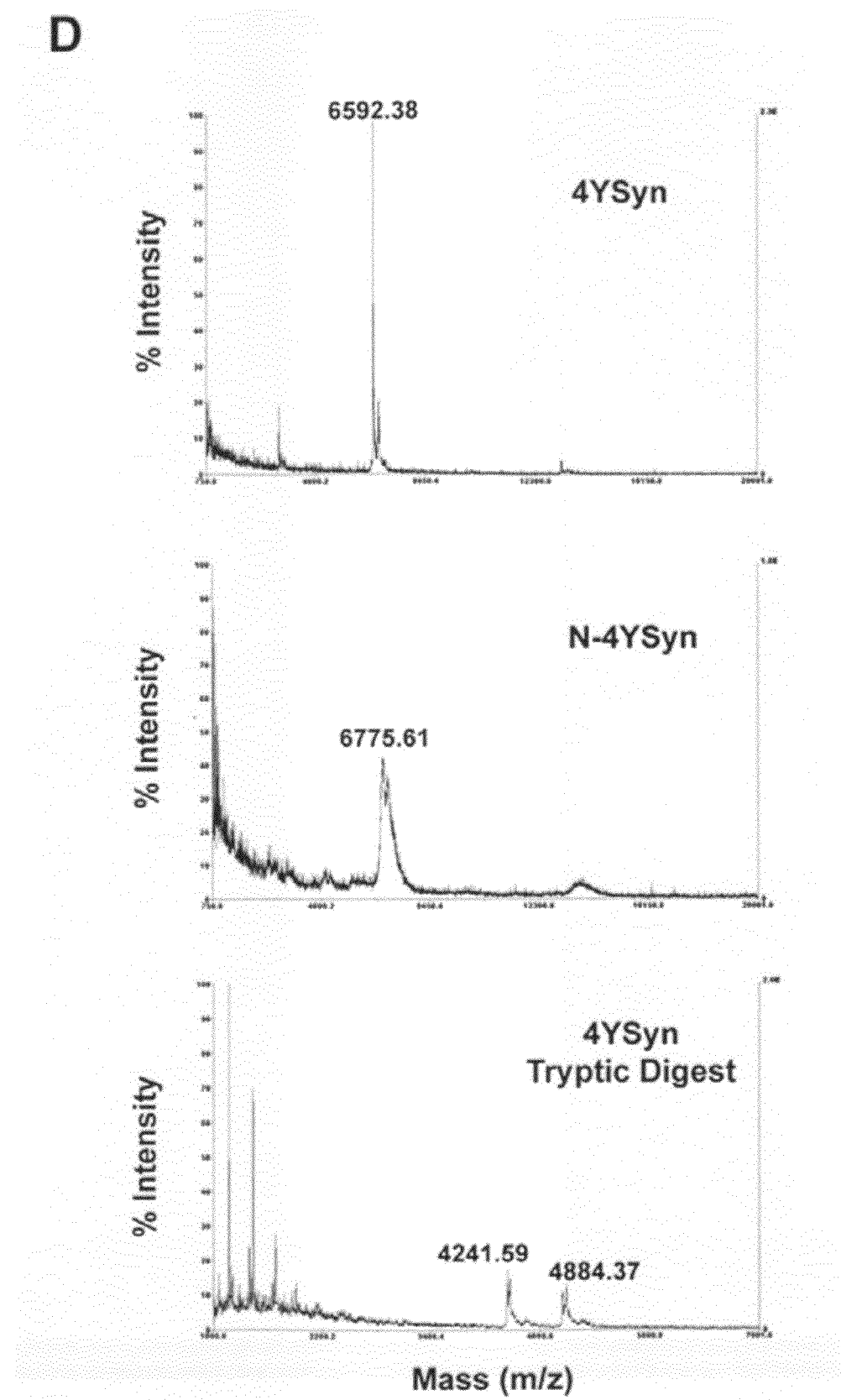

Based on the above findings, it was hypothesized that in PD, NT modifications of a-Syn could be a key step converting the endogenous protein to an immunogen. Here, the C-terminal 40 aa α-Syn fragment (4YSyn) was used as it contains all four tyrosine residues that are nitrated, thus limiting the possible specificities of epitopes capable of generating an immune response. For this, the mouse cDNA encoding the final 40 aa was cloned into the bacterial pET-28a His-tag expression vector and recombinant protein expressed in BL21 E. coli following isopropyl-β-D-thiogalactopyranoside (IPTG) induction. Expression of the recombinant protein exhibited no apparent toxicity to the bacterial expression system. Affinity-purified 4YSyn peptide from E. coli lysates was detected as a prominent single band using silver staining on 12% polyacrylamide gel (FIG. 3B) and by Western blot using a polyclonal antibody raised against aa 120-140 of α-Syn (FIG. 3C). Reverse-phase high performance liquid chromatography (RP-HPLC) analysis of isolated 4YSyn products demonstrated purities equal to or in excess of 97%. NT modifications of 4YSyn peptide (N-4YSyn) after peroxynitrite nitration was confirmed by Western blot using mouse monoclonal anti-NT antibody (FIG. 3C).

Homogeneity of purified 4YSyn and its modified forms (aggregated and nitrated) was assessed based on: 1D SDS-PAGE (FIG. 3B), Western blot (FIG. 3C), and matrix-assisted laser desorption ionization-time of flight (MALDI-TOF) mass spectrometry (FIG. 3D). The predominant peak for 4YSyn by MALDI-TOF analysis was 6592 m/z, which corresponded to the 6718 expected mass of purified recombinant α-Syn within <2% mass accuracy (FIG. 3D and Table 3). To provide proof that the mass discrepancy originated from recombination errors within the His-tag region obtained during protein purification, but not within the biologically active portion of the molecule, the recombinant 4YSyn protein was digested with trypsin and measured masses of resulting fragments using MALDI-TOF. The observed masses of the generated fragments were Arg-cleaved 4YSyn and Lys-cleaved 4YSyn. These corresponded to the expected masses with 0.07% of mass accuracy. Next, the mass of native 4YSyn was compared to N-4YSyn. The oxidized peptide or its trypsin cleaved fragments revealed a 184 D mass increase that is analogous to the expected mass of 4 nitro groups corresponding to 4 NT-residues (FIGS. 3A and 3D). Based on these observations, it was concluded that reaction of 4YSyn with peroxynitrite, under the conditions used in this study, efficiently nitrated all four available Tyr residues in 4YSyn.

TABLE 3

Theoretical and observed masses of 4YSyn, N-4YSyn and tryptic digest fragments.

| Peptide | Theoretical Mass (D) | Observed Mass (D) |
| --- | --- | --- |
| His-Tagged 4YSyn | 6718 | 6592 |
| His-Tagged N-4YSyn | 6902 | 6775 |
| Arg Cleaved 4YSyn | 4836 | 4833 |
| Lys Cleaved 4YSyn (K) | 4238 | 4241 |
| Arg Cleaved N-4YSyn | 5020 | 5073 |
| Lys Cleaved N-4YSyn | 4422 | |

N-4YSyn Induces Specific Immune Responses in B10.BR Mice

Figure 4A:
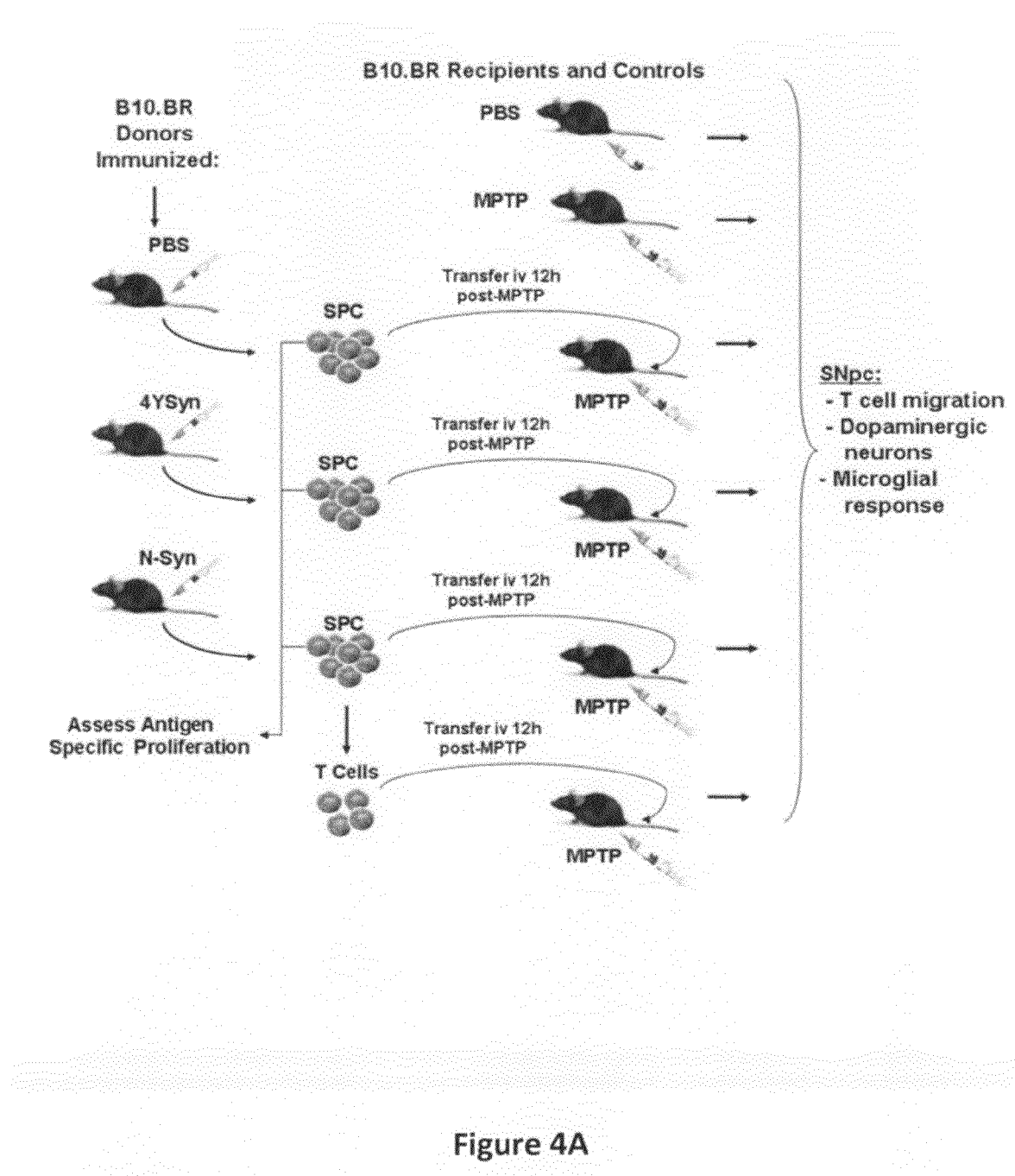
FIGS. 4A-4B provide the experimental protocol for adoptive transfer and lymphocyte proliferation assessment of donor SPC in B10.BR mice.
Figure 4:
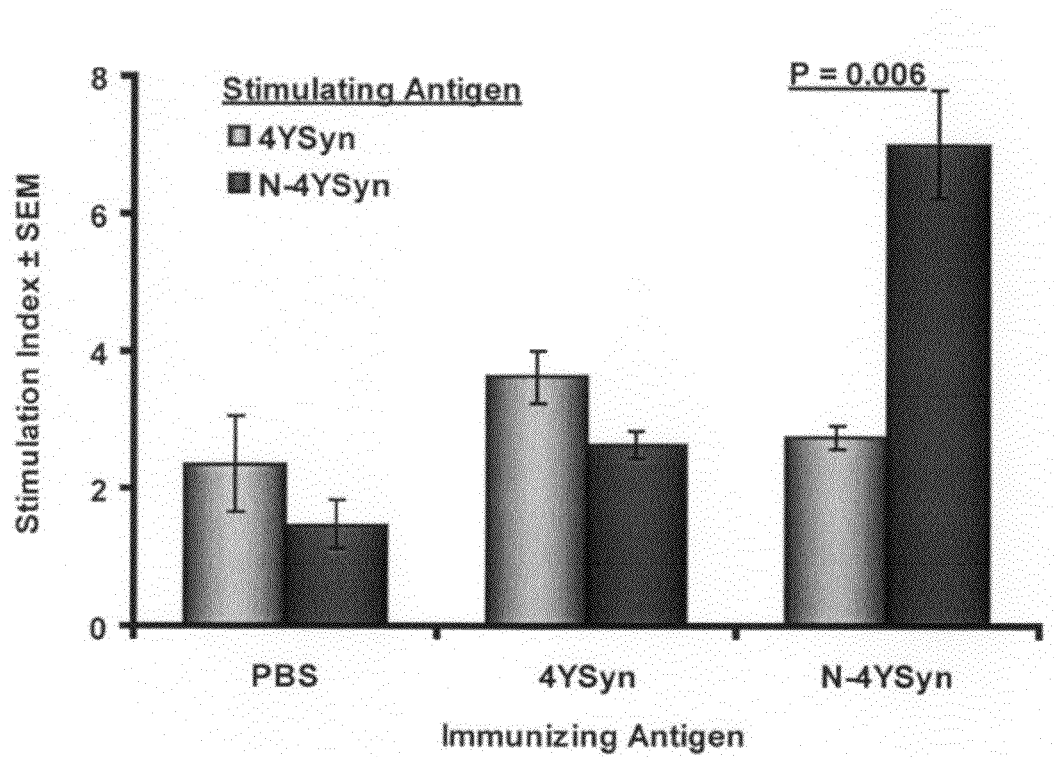

To test the predictions of immune responses to N-α-Syn, B10.BR (H-$2^k$) mice were immunized with N-4YSyn, 4YSyn, or PBS each emulsified in complete Freund's adjuvant (CFA) (FIG. 4A). Fourteen days following the initial immunization, mice were boosted with their respective immunogens emulsified in incomplete Freund's adjuvant (IFA). Five days later, mice were sacrificed and SPC were tested for antigen-specific T cell proliferative responses to N-4YSyn or 4YSyn. Stimulation with 4YSyn yielded no significant immune responses regardless of whether mice were immunized with adjuvant containing PBS, 4YSyn or N-4YSyn (FIG. 4B). In contrast, significant proliferative responses were afforded from SPC of mice immunized with N-4YSyn and challenged in vitro with N-4YSyn, but not 4YSyn. Moreover, N-4YSyn stimulated SPC from mice immunized with adjuvant containing 4YSyn or PBS failed to induce significant proliferative responses. These data indicate that immunization with N-4YSyn, but not 4YSyn is capable of inducing antigen specific immune responses to NT-modified CNS antigens.

Figure 5:
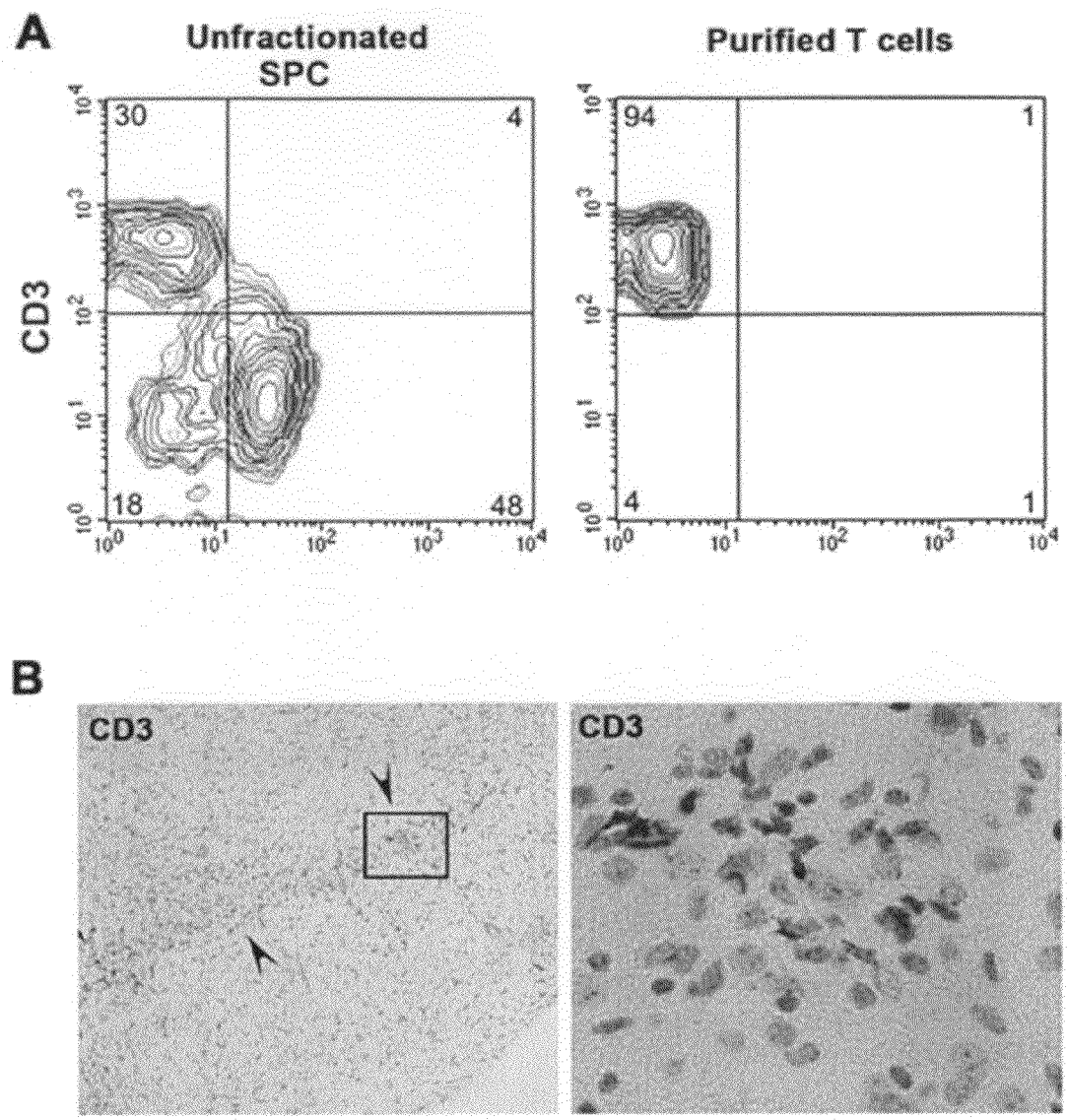
FIGS. 5A and 5B demonstrate that adoptive transfer of SPC and purified T cells from N-4YSyn vaccinated B10.BR donors leads to infiltration of T cells in the SNpc of MPTP mice on day 2.

Adoptive Transfer of N-4YSyn SPC and T Cells Exacerbates MPTP-induced Microglial Activation and Dopaminergic Neuronal Death In light of the fact that modified α-Syn is capable of evading tolerance and inducing reactive T cells, it was tested whether modified α-Syn-activated T cells could exacerbate MPTP-induced dopaminergic neurodegeneration. The experimental scheme for adoptive transfer of SPC or purified T cells from immunized animals is outlined in FIG. 4A. For these studies, B10.BR (H-$2^k$) donor mice were immunized and boosted with N-4YSyn or 4YSyn, and SPC were adoptively transferred to MPTP-treated syngeneic recipients. To delineate effects due specifically to T cells, CD3+ T cells were enriched by negative selection and transferred to an additional group of MPTP-treated animals. Flow cytometric analysis showed that the enriched population from N-4YSyn mice was 94% CD3+ T cells (FIG. 5A). Adoptive transfer of purified T cells from N-4YSyn immunized donors to MPTP intoxicated mice revealed $CD3^+$ T cell infiltrates in the SNpc on day 2 after MPTP treatment (FIG. 5B).

Figure 6:
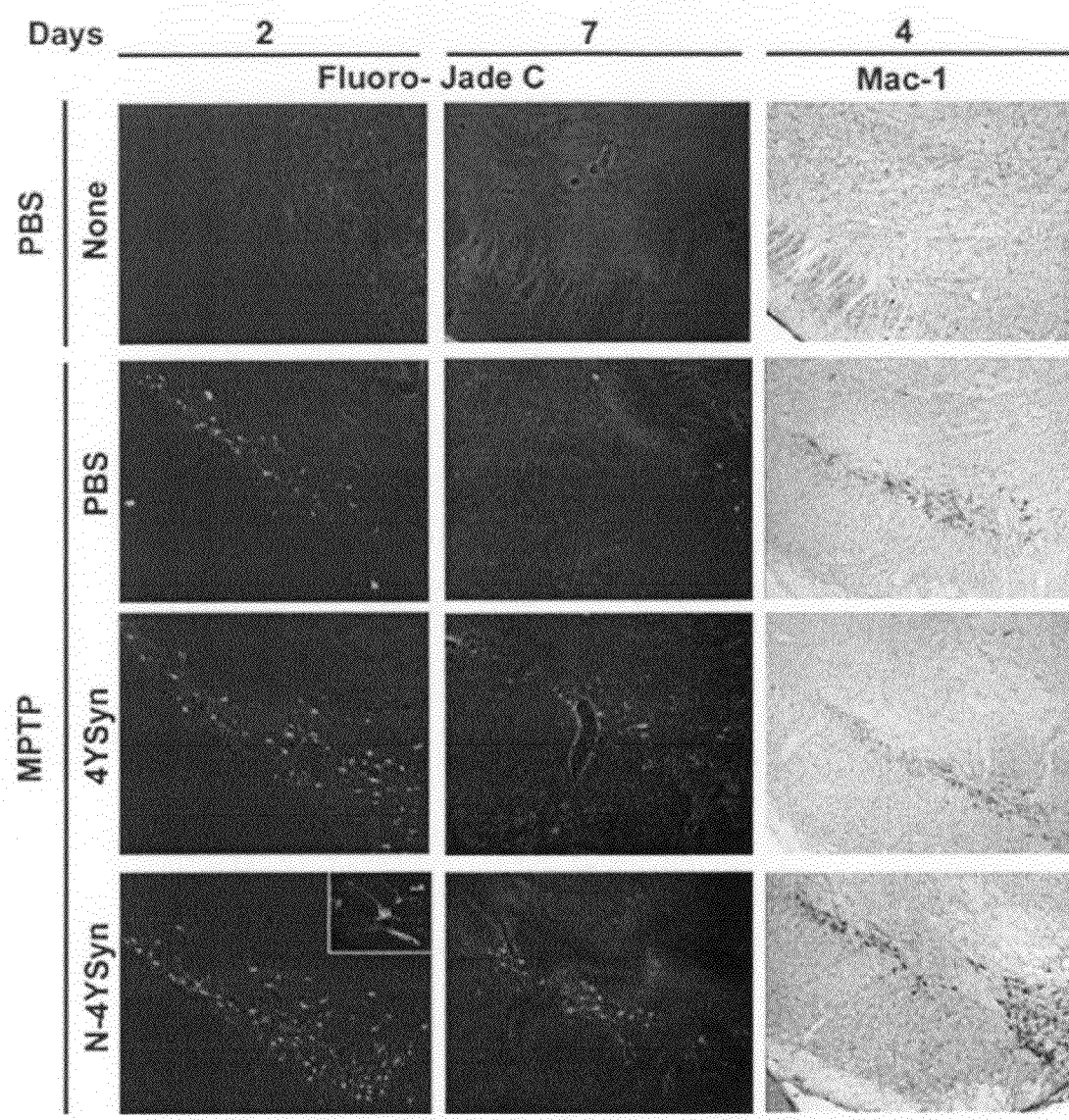
FIG. 6 demonstrates that SPC from N-4YSyn immunized B10.BR mice exacerbate MPTP-induced dopaminergic neurodegeneration and induce microglial responses in the SNpc. Photomicrographs from VMB sections stained with Fluoro-Jade C (left and middle panels) and Mac-1 antibody (right panels). PBS controls (PBS/none) exhibit an absence of Fluoro-Jade C stained dead neurons on days 2 and 7, and only faint Mac-1 immunoreactivity on day 4 post-treatment. In MPTP-treated mice that received SPC from PBS/adjuvant treated donors (MPTP/PBS), Fluoro-Jade C stained neurons are evident at day 2, but not detectable by day 7. MPTP-treated mice that received SPC from 4YSyn immunized donors (MPTP/4YSyn), also exhibits dead fluorescent neurons by day 2 comparable to the MPTP/PBS control group, and only rare degenerating neurons are visible by day 7. Mac-1 immunoreactivity in those mice is comparably resolved to levels seen in MPTP/PBS control group. SPC transfers from N-4YSyn immunized donors to MPTP-treated mice (MPTP/N-4YSyn) induced a robust and prolonged microglial response, conspicuously enhanced when compared to MPTP/PBS-treated controls, with concomitant neuronal death still evident by Fluoro-Jade C staining at day 7.

MPTP treated mice showed fluorescent neurons within the SN using the degenerating cell marker Fluoro-Jade C by day 2, but not by day 7 (FIG. 6, left and middle panels) confirming previous kinetic data regarding MPTP-induced nigral neuronal death obtained by silver staining techniques (Jackson-Lewis et al. (1995) Neurodegeneration 4:257-269). MPTP treated mice that received immune cells from N-4YSyn immune mice showed more Fluoro-Jade C stained neurons within the SN by day 2 than MPTP-intoxication alone, and, in contrast to the latter, Fluoro-Jade C stained neurons within the SN by day 7 as well. In the PBS control group, no Fluoro-Jade C stained neurons were observed at any time point. Following MPTP administration, microgliosis is striking and immediate. The initial time course studies are in line with these findings and show that the microgliosis and dopaminergic neurodegeneration in B10.BR mice are virtually resolved respectively by days 4 and 7 post-MPTP injection (FIG. 6, right and middle panels, respectively). However, adoptive transfer of SPC from B10.BR mice, regardless of immunization protocol, was associated with a persistent microglial response, as evidenced by quantitative morphology with Mac-1 immunostaining (FIG. 6, right panel). Counts of Mac-1+ microglia were greatest (p<0.0001) in MPTP mice treated with SPC from N-4YSyn immunized mice [84.1±7.0/mm$^2$ (mean±SEM)] compared to those from mice treated with MPTP and SPC from 4YSyn immunized mice (26.9±3.5/mm$^2$), MPTP alone (27.7±3.2/mm$^2$), or PBS (0.7±0.3/mm$^2$). These data indicate that the adaptive immune components of H-$2^k$ mice following MPTP administration contribute to the neuroinflammatory phenotype seen in these animals.

Figure 7:
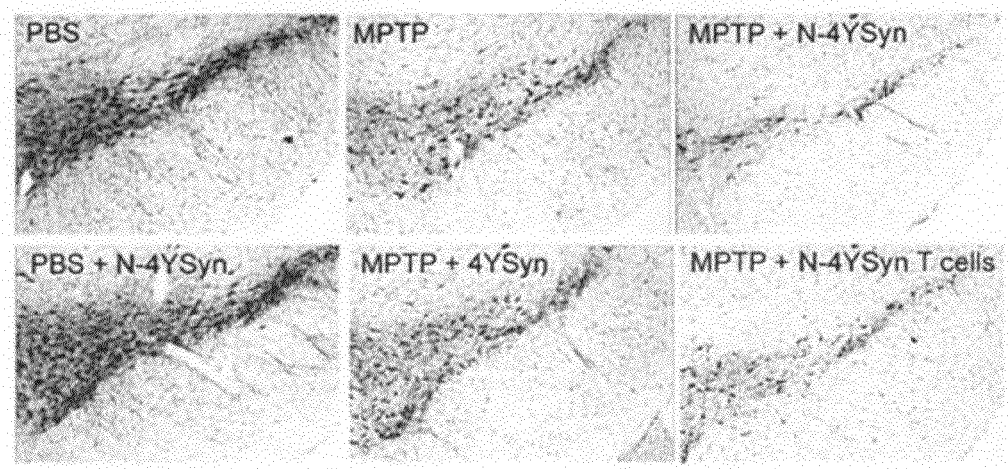
FIGS. 7A and 7B show N-4YSyn immunization with adjuvant exacerbates dopaminergic neuronal cell loss in B10.BR mice. All panels of FIG. 7A show TH-positive neurons in the SN from mice treated with: [top row, L to R] PBS or MPTP alone, MPTP and SPC from N-4YSyn immunized donors (MPTP+N-4YSyn), [bottom row, L to R] PBS and SPC from N-4YSyn immunized donors (PBS+N-4YSyn), MPTP and SPC from 4YSyn immunized donors (MPTP+4YSyn), and MPTP and T cells from N-4YSyn immunized donors (MPTP+N-4YSyn T Cells). Tissues collected 28 days post-MPTP treatment.
Figure 7:
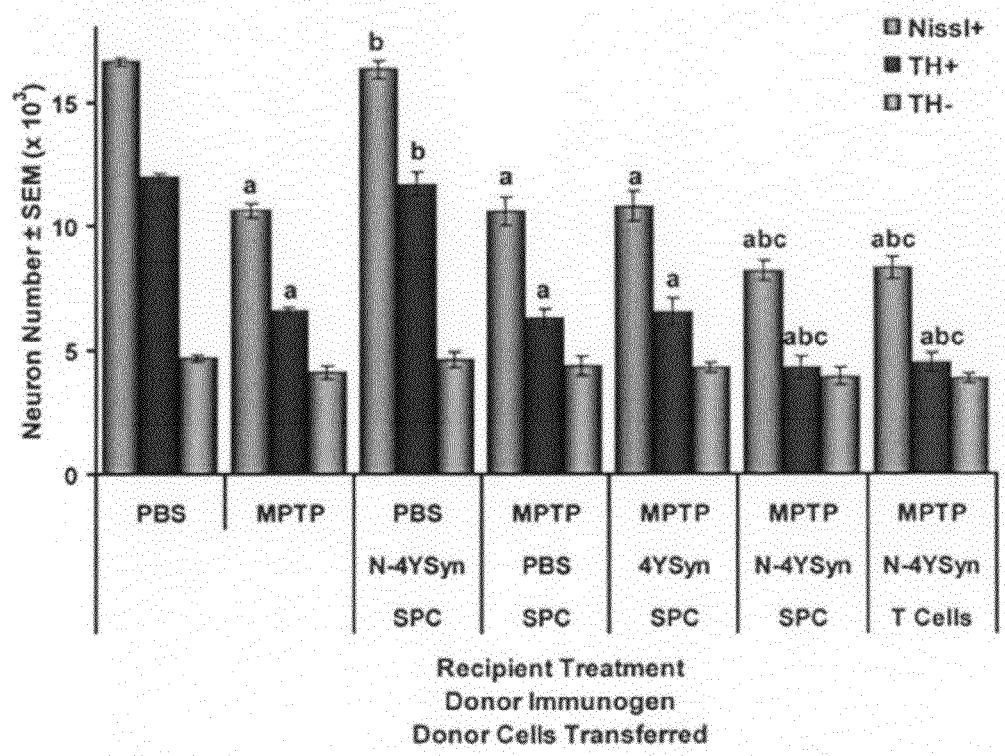

Based on these findings, it was investigated whether the immune response mediated by N-α-Syn affects degeneration of dopaminergic cell bodies in the SNpc. To test this, MPTP-intoxicated B10.BR mice received 5×10$^7$ donor SPC from mice immunized with PBS, 4YSyn, or N-4YSyn, or 2.5×10$^7$ enriched T cells from 4YSyn-immunized donors. PBS- and MPTP-treated mice that did not receive cells served as controls for no neuronal loss and loss attributable to MPTP treatment alone, respectively. PBS-treated mice that received N-4YSyn immunized donor SPC served as additional controls. VMB sections were obtained from mice at 2, 7, and 28 days following MPTP treatment and immunostained for TH (FIG. 7A). Stereological analysis showed that MPTP induced a 45% reduction of SN TH$^+$ neurons compared to PBS controls (FIG. 7B). Similar results were observed in MPTP-injected mice that received SPC from PBS or 4YSyn immune donors (MPTP/PBS/SPC and MPTP/4YSyn/SPC, respectively). In contrast, recipients that received immune N-4YSyn SPC (MPTP/N-4YSyn/SPC) or N-4YSyn T cells (MPTP/N-4YSyn/T Cells) exhibited significantly greater reductions of SNpc TH+ neurons (64 and 63%, respectively) compared to all other MPTP-treated animals (FIG. 7B). PBS-treated mice that received immune SPC from N-4YSyn immunized donors showed no change in TH+ neuron numbers, demonstrating the necessity for an initiating neuronal insult. Significant effects from any treatment were not observed among the numbers of non-dopaminergic neurons (Niss1+TH−). Correlation analysis of total Niss1+ neurons compared to TH+ and TH− neurons demonstrated that the number of total neurons strongly correlated with numbers of TH+ neurons (r=0.981, p<0.0001) compared to numbers of TH− neurons (r=0.522, p=0.004). This confirmed that differences in TH+ neuron counts are due to differences in numbers of structurally intact neurons and eliminates the possibility that differences resulted from the down-regulation of TH itself. Thus, these data demonstrate that adaptive immune responses against the nitrated form of α-Syn exacerbated MPTP-induced nigrostriatal degeneration.

Figure 8:
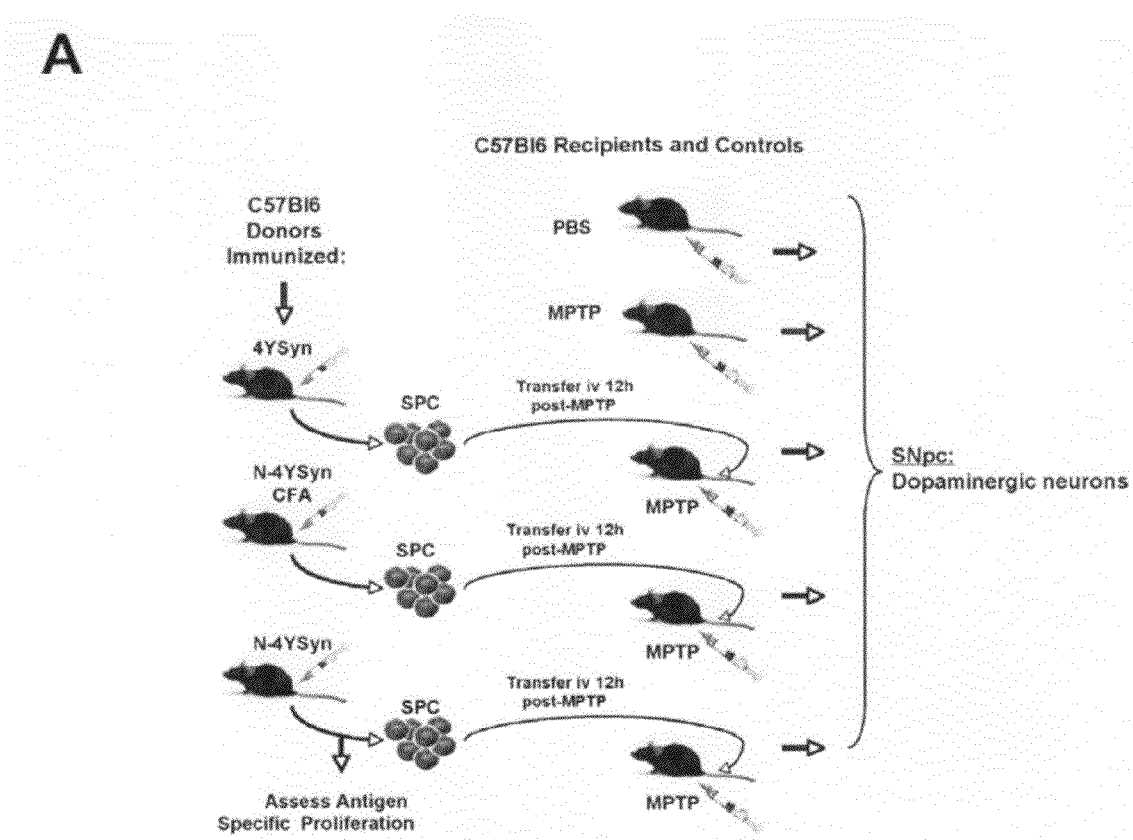
FIG. 8A provides a scheme for immunization, lymphocyte proliferation assessment, and adoptive transfer of donor SPC in B6 mice. B6 (H-2b) mice were immunized with 10 μg 4YSyn in PBS, 50 μg N-4YSyn in CFA, 10 μg N-4YSyn in PBS or PBS in CFA. Mice were boosted 14 days later with their respective antigens as formulated previously with or without IFA. After 5 days, single lymphoid cell suspensions were prepared and assessed for antigen-specific responses in standard lymphocyte proliferation assays. Single cell suspensions were pooled and adoptively transferred to MPTP-treated syngeneic recipients 12 hours after the final MPTP injection. 5×10⁷ donor immune SPC were adoptively transferred to MPTP-treated recipient mice. Survival of dopaminergic neurons in the SN of recipient mice were evaluated after 7 days.
FIG. 8B demonstrates antigen specific proliferation of SPC from B6 (H-2b) mice (n=5/group) immunized with PBS/CFA or N-4YSyn/CFA, and cultured for 5 days in media alone (left bars) or in the presence 1 μg/ml of 4YSyn (center bars) or N-4YSyn (right bars). Cultures were pulsed for 18 hours, cells harvested and $^3$H-thymidine incorporation counted by β-scintillation spectrometry. Values represent mean stimulation indices6SEM and analyzed by ANOVA and Bonferroni post-hoc tests. [a]p=0.0478.
Figure 8:
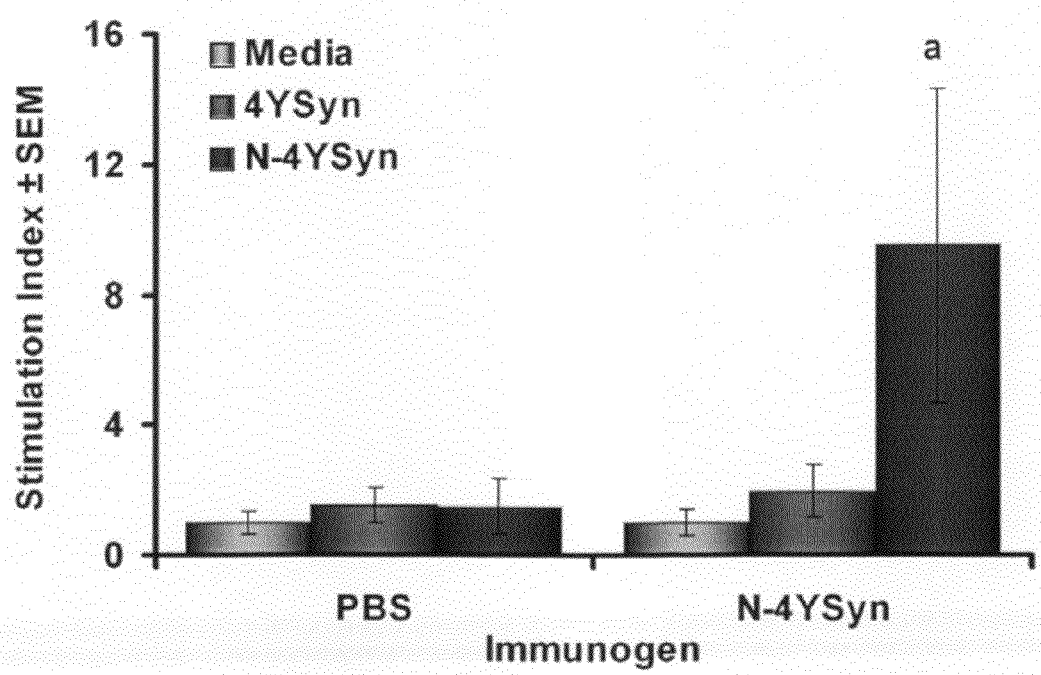

Based on MHC binding affinity algorithms, mice expressing $H-2^b$ were predicted to respond poorly to α-Syn epitopes; yet 21 days after chronic MPTP-intoxication, B6 mice that express the $H-2^b$ haplotype yielded significant antibody responses to N-α-Syn. This suggested that mice expressing $H-2^b$ have the potential to develop immune responses to N-α-Syn that may affect disease progression. To assess that possibility, B6 (H-2b) mice were immunized and boosted with 4YSyn or N-4YSyn either in PBS or emulsified in adjuvant (FIG. 8A). Five days after the final boost SPC were harvested, assessed for antigen specific lymphocyte proliferation, and adoptively transferred to MPTP-intoxicated recipients. Stimulation of SPC from PBS-treated controls indicated that neither 4YSyn nor N-4YSyn induced significant proliferation above medium background levels (FIG. 8B). In contrast, stimulation of SPC from N-4YSyn/PBS immunized mice with N-4YSyn induced a significant lymphocyte proliferative response indicating that immunization with N-4YSyn/PBS in the absence of adjuvant is capable of inducing an antigen specific adaptive immunity.

Figure 9:
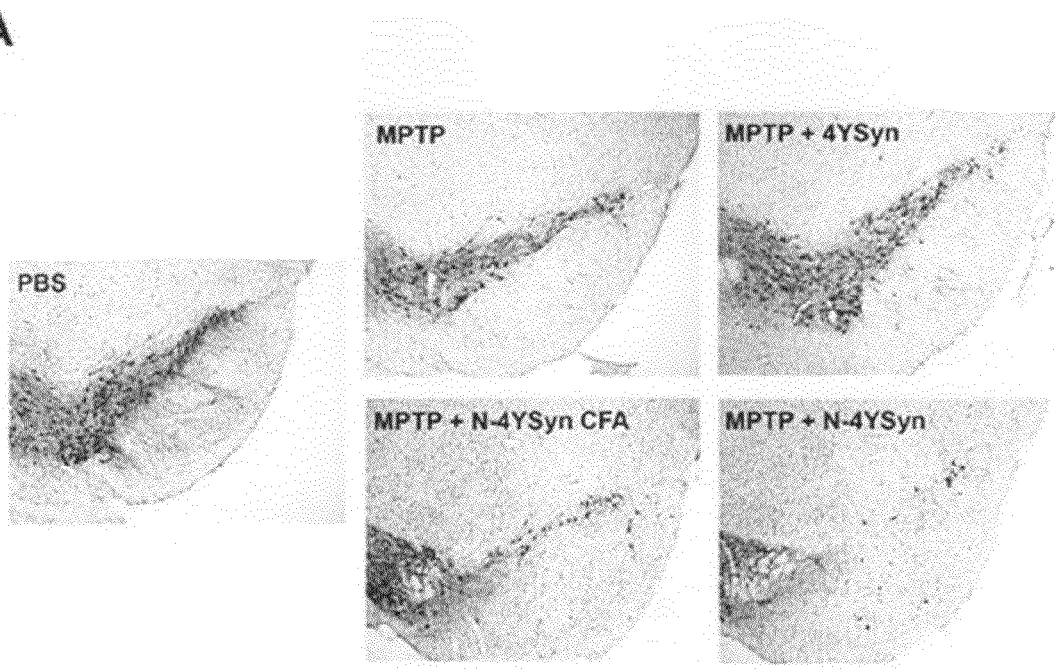
FIGS. 9A and 9B demonstrate that lymphocytes from N-4YSyn immunization exacerbate nigral dopaminergic neuronal loss in B6 mice. All panels of FIG. 9A show TH+ neurons in the SN from mice treated with PBS or MPTP alone, MPTP and SPC from 4YSyn immunized donors (MPTP+4YSyn), MPTP and SPC from N-4YSyn immunized donors (MPTP+N-4YSyn) and lastly, MPTP and SPC from N-4YSyn+CFA immunized donors (MPTP+N-4YSyn CFA).
Figure 9:
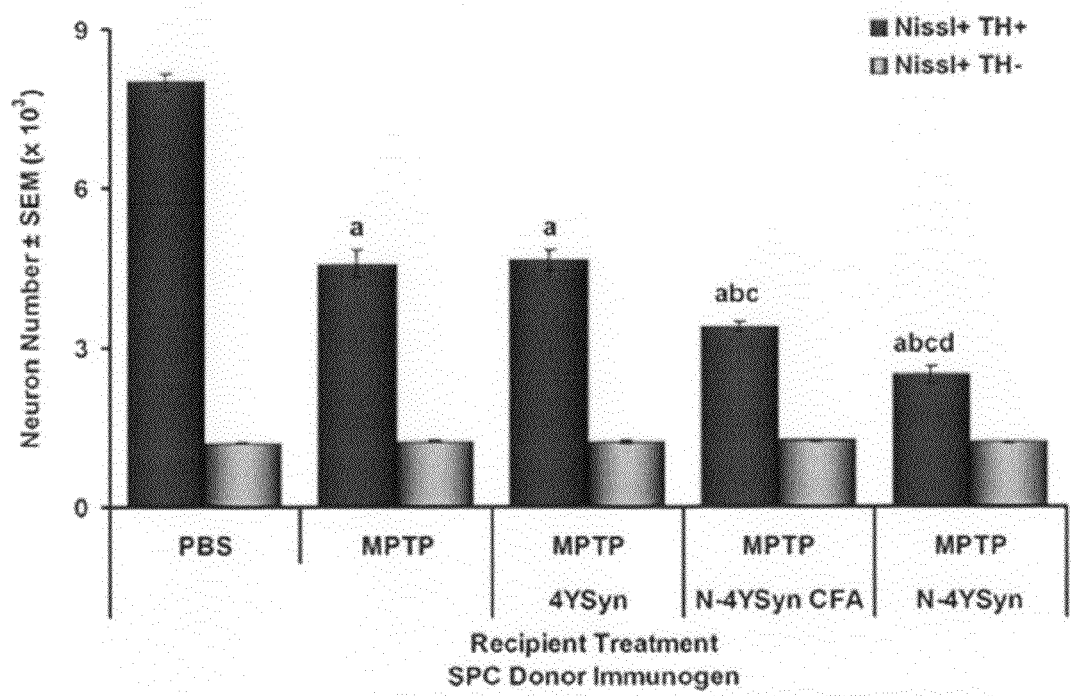

TH stained sections of VMB from MPTP-intoxicated mice that received SPC from donors immunized with N-4YSyn either in PBS excipient or adjuvant showed significant dopaminergic neuronal losses compared to MPTP-treated mice or those that received SPC from 4YSyn immunized mice (FIG. 9A), suggesting 4YSyn immunization increased the MPTP-induced lesion. Next, the sections were assessed by stereological analysis to obtain estimates of dopaminergic neuronal survival and loss after treatment compared to PBS-treated mice. MPTP-intoxication of B6 mice induced 43% loss of TH+ nigral neurons compared to PBS-treated controls (FIG. 9B). Numbers of dopaminergic neurons from MPTP mice treated with SPC from 4YSyn immunized mice were not significantly different compared to MPTP-treated mice and showed a similar 42% loss of neurons. However, adoptive transfer of SPC from N-4YSyn/Adjuvant immune donors significantly increased MPTP-induced dopaminergic neuron loss to 58%. Interestingly, SPC from mice immunized with N-4YSyn without adjuvant induced a 69% loss of nigral TH+ neurons after MPTP intoxication, which was significantly greater than losses due to SPC from 4YSyn- or N-4YSyn/Adjuvant immunized donors. Neither MPTP treatment nor adoptive transfer of immune SPC significantly affected numbers of non-dopaminergic neurons. Thus, taken together these data demonstrate that N-α-Syn, but not unmodified α-Syn, has the capacity to induce specific immune responses by which exacerbates neuronal loss in the context of dopaminergic neurodegeneration. Moreover, these results in $H-2^b$ mice, predicted to provide poor immune response, suggests that epitopes modified by inflammatory processes may function unlike their tolerated unmodified self-analogues to induce immune responses to levels sufficient to alter disease progression.

Nitrated α-Syn Inhibits Proliferation of Anti-CD3 Activated T Cells

Figure 10:
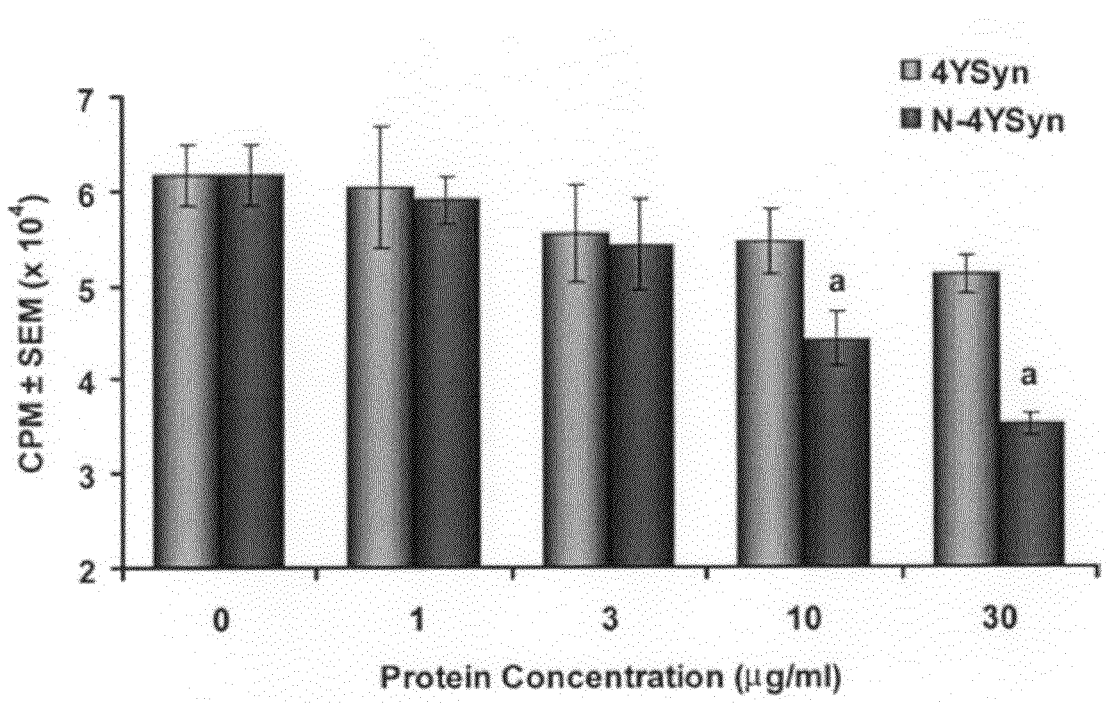
FIG. 10 demonstrates N-4YSyn-mediated inhibition of T cell proliferation. Proliferative responses of anti-CD3 stimulated T cells from naive B6 mice in presence of graded concentrations of 4YSyn or N-4YSyn (1, 3, 10, 30 μg/ml) or in media alone (0 μg/ml). T cells were cultured for 72 hours and pulsed with $^3$H-thymidine for the final 18 hours of culture. Harvested cells were counted for $^3$H-thymidine uptake by β-scintillation spectrometry and proliferation was expressed as mean counts per min (CPM)±SEM for quadruplicate samples and evaluated by ANOVA with Bonferroni post-hoc tests. [a]p<0.01 compared with T cells stimulated with anti-CD3 and cultured in media alone.

It was observed that antigen specific proliferative responses were inhibited by N-4YSyn in a dose dependent manner ($r^2=0.96$, p=0.002). Significant inhibition was not seen by 4YSyn ($r^2=0.53$, p=0.273). To rule out an antigen specific suppressive effect, purified T cells obtained from naive mice were stimulated with anti-CD3 for 24 hours in media or in the presence of 4YSyn or N-4YSyn at concentrations of 1, 3, 10 and 30 μg/ml. N-4YSyn inhibited proliferation of anti-CD3 stimulated T cells in a dose dependent fashion ($r^2=0.6803$, p<0.0001). A significant inhibition of 31 and 47% was observed when stimulated T cells were co-cultured at N-4YSyn concentrations of 10 and 30 mg/ml (FIG. 10). In contrast, proliferation of anti-CD3 stimulated T cells was not inhibited by 4YSyn (p=0.435) or by increasing 4YSyn concentration ($r^2=0.1554$, p=0.0854). Moreover, the inverse effect on anti-CD3 activated T cells with increasing N-4YSyn concentration was greater (p=0.016) compared to that induced by 4YSyn. Second, to assess whether this effect was due to a cytotoxic mechanism, anti-CD3 stimulated T cells were stained for the membrane impermeant DNA dye, propidium iodide (PI) that is excluded from intact, living cells, and analyzed by flow cytometry. T cells cultured in the presence of N-4YSyn exhibited a dose-dependent increase in the mean fluorescent intensity (MFI) of PI ($r^2=0.9261$, p=0.0008) and in the percentage of PI+ dead T cells ($r^2=0.9743$, p=0.0018) (Table 4). In comparison, percentages of PI stained dead T cells cultured with 4YSyn and the PI MFI were not different from the basal level in absence of either of the peptides and did not change with increasing 4YSyn concentration ($r^2=0.5983$, p=0.1249, and $r^2=0.5016$, p=0.1807, respectively). Taken together, increasing N-4YSyn concentrations strongly correlated with inhibition of T cell proliferation, percent PI+ T cells, and increased MFI for PI (r>0.945, p<0.0154 for all comparisons combined). In contrast, no significant correlations were associated with increasing 4YSyn concentrations. Thus, cytotoxic interference of immune response induction by N-α-Syn may affect disease progression as these processes are shared by both effector and regulatory T cells.

TABLE 4

N-4YSyn-induced cytotoxicity of stimulated T cells.

| [a]T cell Treatment | Conc. μg/ml | [b]% PI+ T cells | [c]MFI | [d]D | [e]Index of Similarity |
|---|---|---|---|---|---|
| Medium | | 5.7 | 33.0 | * | 0 |
| 4YSyn | 1 | 4.9 | 32.3 | 0.08 | 3.8 |
| | 3 | 6 | 34.1 | 0.08 | 4.2 |
| | 10 | 4.7 | 25.2 | 0.1 | 5.1 |
| | 30 | 4.2 | 26.8 | 0.16 | 8.1 |
| N-4YSyn | 1 | 15.9 | 42.8 | 0.31 | 15.7 |
| | 3 | 17.9 | 58.7 | 0.33 | 15.6 |

TABLE 4-continued

N-4YSyn-induced cytotoxicity of stimulated T cells.

| [a]T cell Treatment | Conc. µg/ml | [b]% PI+ T cells | [c]MFI | [d]D | [e]Index of Similarity |
|---|---|---|---|---|---|
| | 10 | 47.8 | 71.6 | 0.64 | 30.9 |
| | 30 | 91.3 | 106.1 | 0.87 | 43.4 |

[a]Anti-CD3 stimulated T cells were cultured for 24 hours in media alone or in the presence of different concentrations of 4YSyn or N-4YSyn, stained with 2 µg/ml of the vital dye, PI, washed, and assessed by flow cytometric analysis for uptake of PI.
[b]Percentage of T cells susceptible to PI permeation as determined by flow cytometric analysis.
[c]Mean fluorescence intensity of PI-stained T cells.
[d]D statistic at $\alpha = 0.001$ of Kolmogorov-Smirnov (K-S) analysis for fluorescence intensities of PI-stained T cells as the sigmoidal function of the accumulated cell frequency curve and fluorescence intensity (channel number) compared to the curve of PI-stained T cells from the medium control (asterisk) as computed by Cellquest software (BD Biosciences) (Young, I. T. (1977) J. Histochem. Cytochem., 25: 935-941).
[e]Index of similarity = $D/[(n_c + n_t)/(n_c \cdot n_t)]^{1/2}$, where $n_c$ and $n_t$ are the number of events in cell frequency curves for medium control (c) and test substance (t), respectively (BD Biosciences) (Young, I. T. (1977) J. Histochem. Cytochem., 25: 935-941). An index of similarity = 0 indicates the curves are identical.

N-4YSyn-Stimulated Immune SPC Enhance Dopaminergic Cell Death

Figure 11:
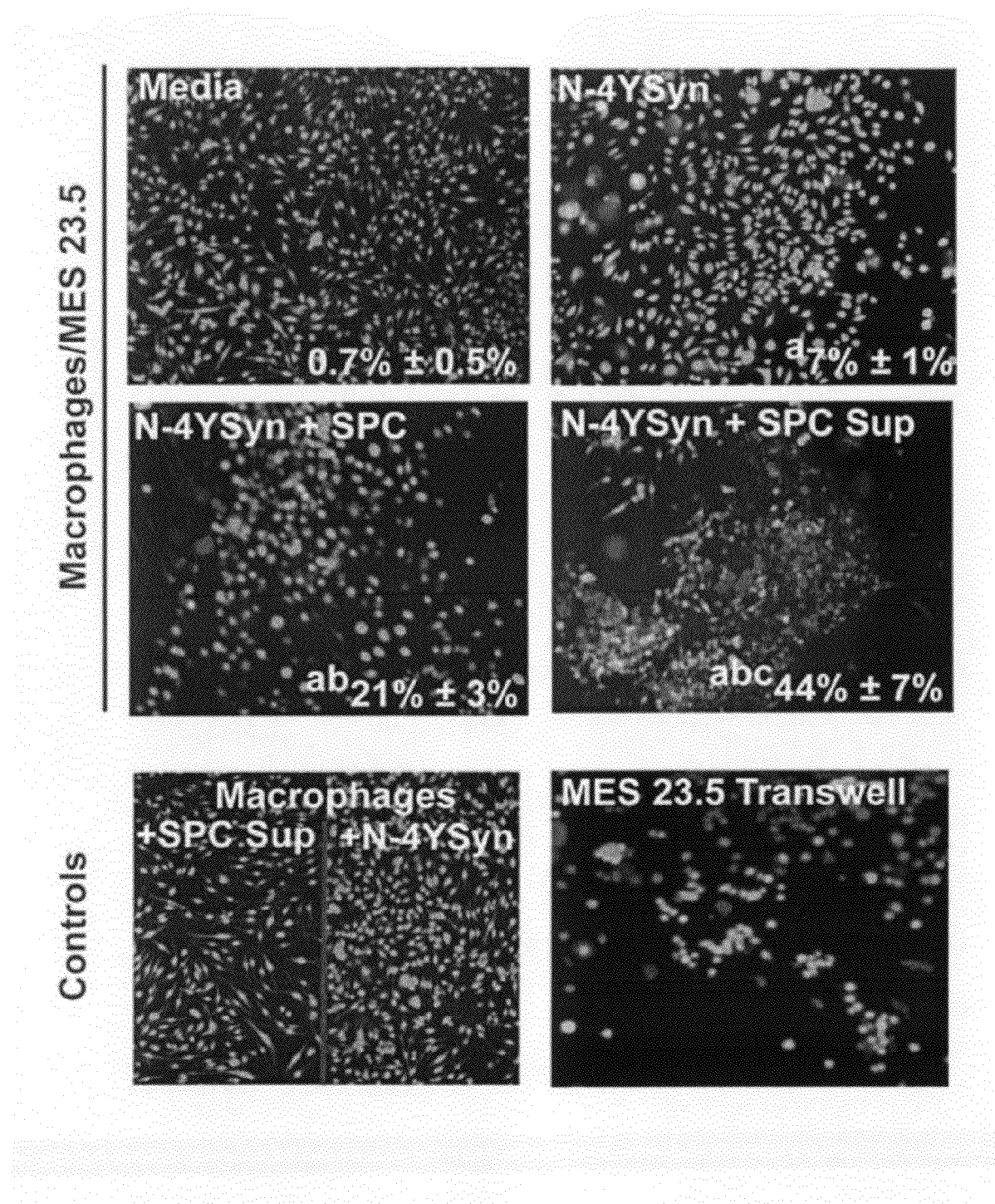
FIG. 11 demonstrates N-4YSyn activated immune SPC induces macrophage-mediated dopaminergic cell death. Representative fluorescence photomicrographs are shown of live and dead cells from 24 hour macrophage/MES 23.5 co-cultures in the presence of media alone, N-4YSyn, N-4YSyn and antigen-stimulated SPC of N-4YSyn-immunized mice (N-4YSyn+SPC), or N-4YSyn and the supernatants from antigen-stimulated SPC of N-4YSyn-immunized mice (N-4YSyn+SPC Sup). Antigen-stimulated SPC from N-4YSyn immune were induced in vitro with N-4YSyn, and cells and supernatants for use in the assay were harvested after 5 days of culture. Controls included macrophages cultured in the presence of SPC supernatants from antigen-stimulated SPC of N-4YSyn-immunized mice (Macrophages+SPC Sup); macrophages cultured in the presence of N-4YSyn alone (Macrophages+N4YSyn); and Transwell™ cultures of plated MES 23.5 cells and macrophages in the Transwell™ stimulated with N-4YSyn. Frequencies (±SEM) of dead cells for 4-8 fields/assay are provided in the lower right corner of each panel. Differences in the mean frequencies of dead cells were evaluated by ANOVA and Bonferroni post-hoc tests. p<0.01 compared to cultures treated with [a]Media, [b]N-4YSyn, or [c]N-4YSyn+SPC.

To directly test the neurotoxic capacity of the N-4YSyn immune response, proliferating T cells or supernatants from N-4YSyn stimulated SPC of N-4YSyn immunized mice were assessed in live/dead assays with co-cultures of N-α-Syn activated bone marrow-derived macrophages (BMM) and MES 23.5 cells. Minimal cytotoxicity was afforded from co-cultures of unstimulated BMM/MES 23.5 co-cultures with virtual 100% MES 23.5 cell survival, whereas activation with aggregated N-α-Syn resulted in 7% cell death after 24 hours (FIG. 11). Activated and proliferating T cells from 5 day cultures of antigen-specific stimulation of N-4YSyn immune SPC when added to activated BMM/MES 23.5 cultures induced 21% cell death (N-4YSyn+SPC), while supernatants (Sup) from those SPC cultures resulted in 44% cell death (N-4YSyn+SPC Sup), and no cytotoxicity to activated BMM cultured in the absence of MES 23.5 cells (Macrophages+SPC Sup). In Transwell™ studies wherein N-4YSyn-stimulated BMM was separated from MES 23.5 targets, virtually all cytotoxicity was concentrated among the MES 23.5 cell population (MES 23.5 Transwell™) with no cytotoxicity attributed to BMM. T cells isolated from N-4YSyn-immunized donors and restimulated in vitro with N-4Ysyn, but not 4YSyn, showed TNF-α levels (26.0±1.2 pg/ml) that were increased (p<0.008) compared to levels from T cells of either PBS or 4YSyn immunized mice which were below the limits of detection.

EXAMPLE 2

Parkinson's disease (PD) is characterized by progressive nigrostriatal degeneration and deficits in dopamine transmission. A pathological hallmark of PD are Lewy bodies (LB) that present as intracellular inclusions of aggregated proteins and lipids in dopaminergic (DA) neurons (Duda et al. (2000) Am. J. Pathol., 157:1439-1445; Hurtig et al. (2000) Neurology 54:1916-1921). A major constituent of LB is α-synuclein (α-syn; Giasson et al. (2000) Science 290:985-989), characterized by self-aggregation and covalently bonded protein dimers modified by oxidative stress and protein nitration (Krishnan et al. (2003) Biochemistry 42:829-837; Paxinou et al. (2001) J. Neurosci. 21:8053-8061; Souza et al. (2000) J. Biol. Chem., 275: 18344-18349).

Linkages between DA neurodegeneration and microglial neuroinflammatory activities are well-known and demonstrated by large numbers of immune-competent microglia within the substantia nigra of postmortem PD brains appearing as phagocytic cells engulfing damaged DA neurons (McGeer et al. (1988) Neurology 38:1285-1291; Cho et al. (2003) Cell. Mol. Neurobiol., 23:551-560). In transgenic mutant α-syn mice and in mice treated with 1-methyl-4-phenyl-1,2,3,6-tetrahydropyridine (MPTP) and rotenone (Cho et al. (2003) Cell. Mol. Neurobiol., 23:551-560; Kohutnicka et al. (1998) Immunopharmacology 39:167-180; Sugama et al. (2003) Brain Res., 964:288-294), similar microglial responses are operative. Importantly, such microglial activation is associated with α-syn deposition (Jin et al. (2007) J. Neuroinflammation 4:2; Ling et al. (2004) Exp. Neurol., 190: 373-383; Luo et al. (2007) Int. J. Mol. Med., 19:517-521) and internalization (Liu et al. (2007) J. Proteome Res., 6:3614-3627). This occurs throughout disease, suggesting linkages to oxidative damage, α-syn nitration and aggregation, and PD-associated neurodegeneration (McGeer et al. (2004) Parkinsonism Relat. Disord., 10: S3-S7; Teismann et al. (2003) Proc. Natl. Acad. Sci., 100:5473-5478). Indeed, microglial activation is strongly associated with neurotoxic responses and collateral neuronal damage (Gao et al. (2008) Environ. Health Perspect., 116: 593-598; Huang et al. (2008) Neurosci. Bull., 24:66-72; Stefanova et al. (2007) Mov. Disord., 22:2196-2203; Xiao et al. (2007) J. Neurochem., 102:2008-2019). Thus, for PD, nitrated-α-syn (N-α-syn)-mediated microglial activation and accelerated neuronal death are closely related (Benner et al. (2008) PLoS ONE 3:e1376; Hodara et al. (2004) J. Biol. Chem., 279:47746-47753; Reynolds et al. (2008) J. Neurochem., 104: 1504-1525; Reynolds et al. (2008) J. Neuroimmune Pharmacol., 3: 59-74; Thomas et al. (2007) J. Neurochem., 100:503-519).

Abundant evidence indicates a significant role for adaptive immunity in neuroregulatory activities (Benner et al. (2004) Proc. Natl. Acad. Sci., 101:9435-9440; Garg et al. (2008) J. Immunol., 180:3866-3873; Laurie et al. (2007) J. Neuroimmunol., 183: 60-68; Reynolds et al. (2007) J. Leukocyte Biol., 82:1083-1094). Such effects are seen in experimental neurodegenerative models, including PD (Reynolds et al. (2007) J. Leukocyte Biol., 82:1083-1094; Gorantla et al. (2008) Glia 56:223-232; Banerjee et al. (2008) PLoS ONE 3:e2740). Principally, these data found that neuronal degeneration or protection is linked to the microglial phenotype and that N-α-syn-specific effector T cells exacerbate microglial activation and DA neurodegeneration, whereas CD4+ CD25+ regulatory T cells (Treg) attenuate those processes; however, how microglia activation is regulated by regulatory and effector T cell subsets is not known. To address this, aggregated N-α-syn was used as an inducer of microglial activation (Reynolds et al. (2008) J. Neurochem., 104:1504-1525; Reynolds et al. (2008) J. Neuroimmune Pharmacol., 3:59-74), then studied the microglial immune response as it is affected by activated Treg and CD4+ CD25+ effector T cells (Teff). The observations demonstrate, for the first time, that Treg modulate a broad range of microglial activities, including redox biology, migration, phagocytosis, energy metabolism, and cytokine secretions. Differential outcomes of microglial processes are dependent on the temporal engagement of Treg with N-α-syn and microglia. The findings provide insights into disease pathobiology and how the adaptive immune system may be harnessed for therapeutic benefit.

Materials and Methods

Animals

C57BL/6J male mice (7 wk old) were purchased from The Jackson Laboratory and used for CD4+ T cell isolations. All animal procedures were in accordance with National Institutes of Health guidelines and were approved by the Institutional Animal Care and Use Committee of the University of Nebraska Medical Center.

Cell Isolates

Microglia were prepared from neonatal mice (1-2 days old) using previously described techniques (Dobrenis et al. (1998) Methods 16:320-344). Adherent microglia were cultured in DMEM complete medium for 7-14 days and then replated for experiments. Cultures were consistently >98% CD11b+ microglia as determined by morphology and flow cytometric analysis (Enose et al. (2005) Glia 51:161-172). CD4+ T cell subsets were isolated from lymph nodes and spleens using previously described techniques (Reynolds et al. (2007) J. Leukocyte Biol., 82: 1083-1094; Banerjee et al. (2008) PLoS ONE 3:e2740). Teff and Treg isolates used in these studies were >95% enriched. Following CD3 activation, T cells were added in coculture with primary microglia for 24 hours. All analyses of microglia phenotypic changes were performed after removal of T cells by vigorous washings from the microglial cocultures.

Flow Cell Analysis

Samples from cell fractions were labeled with fluorescently labeled Abs to CD4, CD8, CD25, CTLA-4, CD62L, Fas ligand (FasL), Fas (APO-1), CD11b, and intracellular FoxP3 (eBioscience) and active caspase-3 (Abcam) and analyzed with a FACSCalibur flow cytometer (BD Biosciences). FITC-latex beads (1 mM, 2.5% solids; Sigma-Aldrich) were added to microglial cultures for 30 minutes. Microglia were then detached and acid-washed (PBS, pH 6.0) to quench fluorescence of nonphagocytosed beads, and cells were analyzed by flow cytometry and gated to CD11b+ cells. Fluorescence intensity was normalized to beads alone.

Quantitative PCR (qPCR)

RNA was extracted with TRIzol® reagent (Invitrogen), column-purified (Qiagen), and RNA (2 μg) was reverse-transcribed with random hexamers and SSII reverse transcriptase (Applied Biosystems) for cDNA synthesis. Real-time qPCR was performed with cDNA using an ABI PRISM 7000 sequence detector (Applied Biosystems), using the SYBR Green detection system and murine-specific primers. Values were normalized to Gapdh expression.

Recombinant α-syn

Purification, nitration, and aggregation of recombinant mouse α-syn were performed as described previously (Reynolds et al. (2008) J. Neurochem., 104:1504-1525; Thomas et al. (2007) J. Neurochem., 100:503-519; Reynolds et al. (2007) J. Leukocyte Biol., 82:1083-1094). N-α-syn was added to cultures at 100 nM (14.5 ng/ml).

Cytokine/Chemokine Analysis

Fifty microliters of culture supernatants were analyzed using the BD Cytometric Bead Array Mouse Inflammation kit (BD Biosciences) and measured with a FACSCalibur flow cytometer (BD Biosciences). Cytokine concentration was determined from a standard curve prepared from cytokine standards. The multianalyte cytokine ELISArrays (Superarray) were performed according to the manufacturer's protocol. Culture inserts (0.4-μm pore size; BD Biosciences) and neutralizing Abs to mouse IL-10 (5 μg/ml; BD Pharmingen), TGF-β1 (5 μg/ml; R&D Systems), and CTLA-4 (CD152, 5 μg/ml; BD Biosciences) were used.

2D SDS-PAGE

Cell lysate fractionation, sample labeling, 2D DIGE, image acquisition, and Decyder analysis were performed as described previously. The selection criteria for spots were based on gel image quantitative analysis using DeCyder software (GE Healthcare) with the threshold for analysis at >1.5-fold difference between spot intensities. Protein spots were analyzed by biological variance analysis (BVA) software (GE Healthcare), then matched to a preparative 2D gel and excised using an Ettan robotic spot picker (Rozek et al. (2007) J. Proteome Res. 6:4189-4199). In-gel tryptic digestion and LC-MS/MS were performed as described previously. Proteins identified by peptides having a Unified Score >3000 were targeted for further analysis (Enose et al. (2005) Glia 51:161-172).

Western Blot Analysis

Ten micrograms of protein were loaded onto 4-12% gradient Bis-Tris NuPAGE® Novex gels (Invitrogen), electrophoresed, and transferred onto polyvinylidene difluoride membranes (Bio-Rad). Blots were probed with the respective primary Abs and secondary Abs (1/10,000; Invitrogen) and were detected using a Super-Signal West Pico Chemiluminescent substrate (Pierce). Band intensity was measured using ImageJ and normalized to Gapdh or β-actin (1/5000; Santa Cruz Biotechnology).

Immunofluorescence

Intracellular reactive oxygen species (ROS) production was detected using the ImageItLive ROS Detection kit (Invitrogen) according to the manufacturer's protocol. Abs included active caspase-3 (Abcam) and NF-κB p65 (Cell Signaling Technology), and nuclei were stained with TO-PRO-3 iodide or 4',6-diamidino-2-phenylindole (DAPI; Invitrogen). Images were taken with a Nikon swept field confocal microscope (Nikon). Cathepsin B (CB) activity was determined using the CV-Cathepsin B Detection kit (BIOMOL) according to the manufacturer's protocol and was visualized with an inverted fluorescent microscope. The mean fluorescence intensity (MFI) was determined using ImageJ software.

Glutathione (GSH) Assay

Microglia were cultured with and without N-α-syn for 24 hours in media without exogenous glutamine. Intracellular GSH levels were determined with the Biovision GSH Assay kit (Biovision) according to the manufacturer's protocol, and assessed using a SpectraMAX GEMINI fluorometer (Molecular Devices) at excitation/emission of 340/450 nm and normalized to a GSH standard curve.

Apoptosis

Apoptotic cells were detected using the TACS TdT Fluorescein In Situ Apoptosis Detection kit (R&D Systems) according to the manufacturer's protocol and were visualized by a fluorescent microscope. MFI of TUNEL+ cells was determined per field using ImageJ and was normalized to DAPI-stained nuclei (n=3, six fields per well). Caspase activity was determined using the SensoLyte Homogeneous R110 Caspase-3/7 Assay kit (AnaSpec) according to the manufacturer's protocol. Cell viability was determined by 3-(4,5-dimethylthiazol-2-yl)-2,5-diphenyl tetrazolium bromide (MTT) activity as described previously. Functional grade Abs to mouse FasL (2 μg/ml; eBioscience) and Fas (5 μg/ml; BD PharMingen) and CA074ME (BIOMOL) were used.

Statistics

All values are expressed as means±SEM and are representative of three to four separate experiments. Differences among means were analyzed by one-way ANOVA, followed by Tukey's post-hoc testing for pairwise comparison. For identification of statistically significant proteins, three to four analytical gels were analyzed using BVA software by one-way ANOVA for pairwise comparison between treatment groups.

Results

Treg Affect N-α-Syn microglial NF-κB Responses

Figure 12:
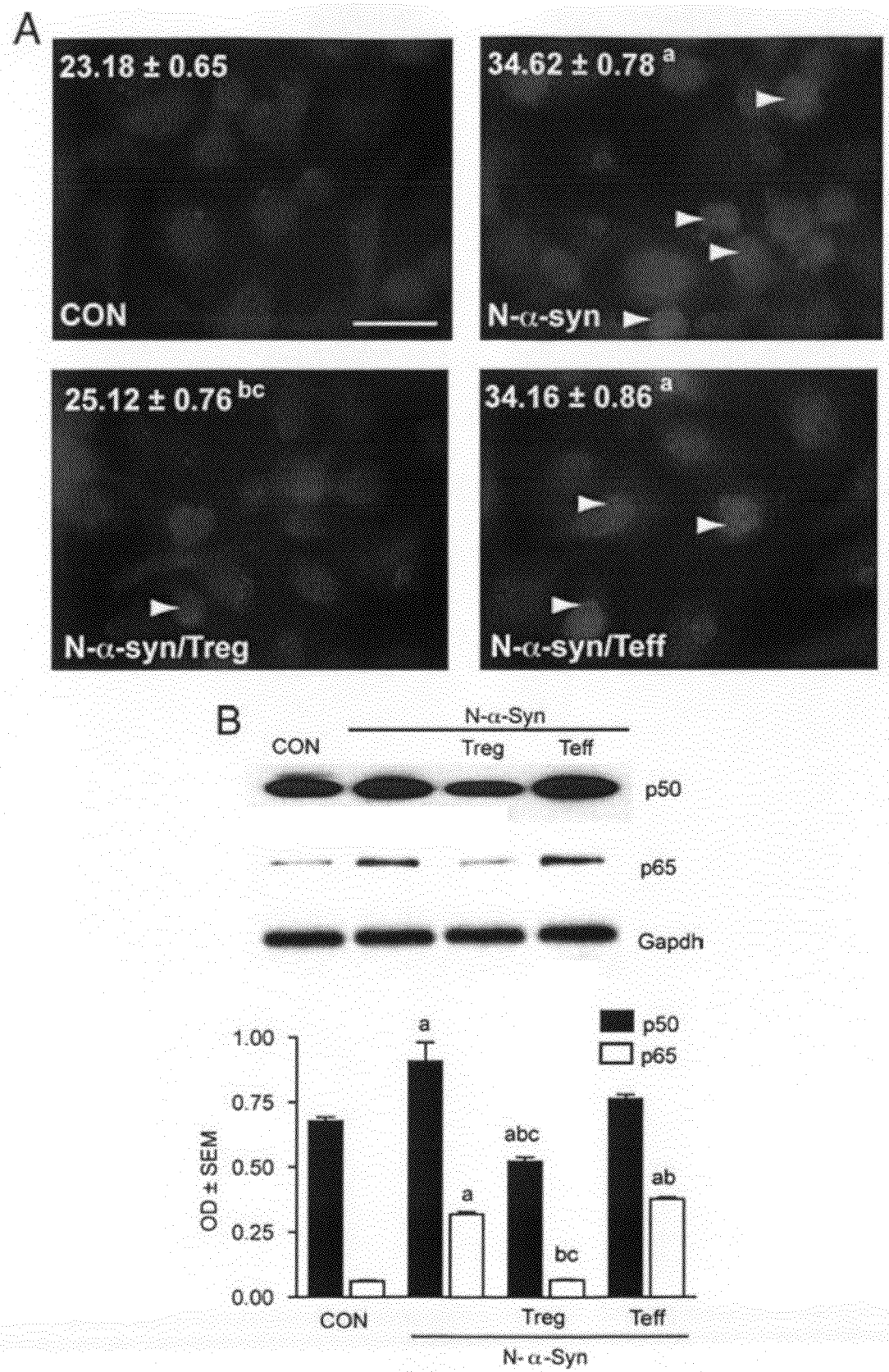
FIGS. 12A-12C demonstrate CD4+ T cells modulate NF-κB activation in N-α-syn-stimulated microglia. Microglia were pretreated without or with CD4+ T cells, and NF-κB activity was assessed following 90 minutes of stimulation with N-α-syn.
Figure 12:
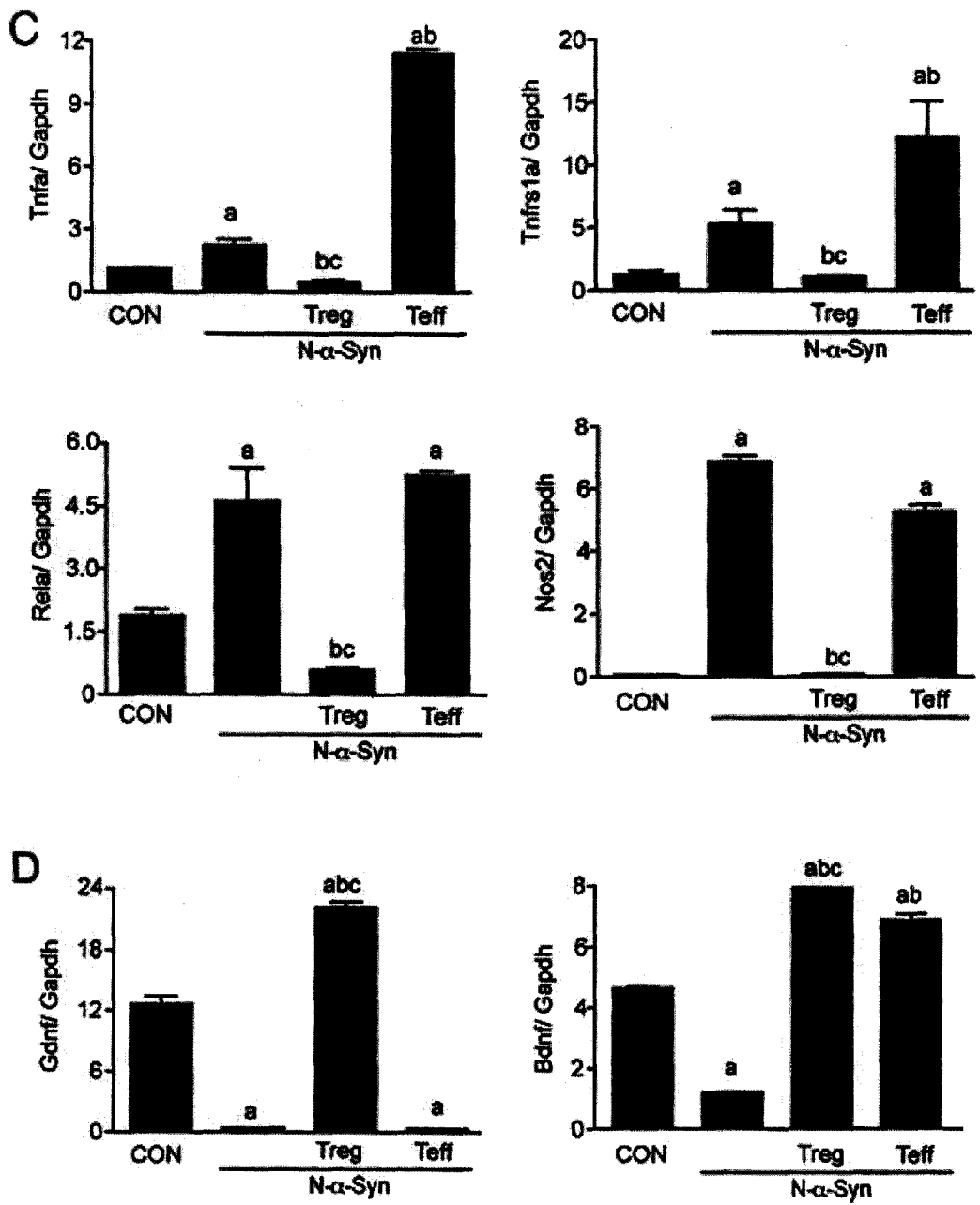

To test the notion of Treg control of microglial activities in preclinical and overt disease, two experimental paradigms were developed. One reflects early or asymptomatic disease where Treg would engage microglia before exposure to N-α-syn and the second, where Treg are added to N-α-syn-activated microglia. Tests of cell surface Ags, cytokine gene expression, and suppression of Teff proliferation indicated that T cell isolates were characteristic of distinct Treg and Teff populations. To determine the effect of CD4+ T cells on microglial responses to N-α-syn, CD3-activated Treg or Teff were cocultured with primary microglia at a 1:1 ratio for 24 hours, removed the T cells, and stimulated the microglia with aggregated N-α-syn. Microglial uptake of Cy5-labeled N-α-syn by flow cytometry for Cy5-N-α-syn-containing microglia between control and T cell-treated microglia revealed that neither Treg nor Teff treatment significantly altered microglia uptake of N-α-syn. In situ analysis for NF-κB p65 expression in cultured microglia revealed that N-α-syn stimulation resulted in an increase in NF-κB p65 expression compared with unstimulated controls. In contrast, pretreatment with Treg, but not Teff, attenuated the induction of NF-κB p65 expression by N-α-syn stimulation (FIG. 12A). Western blot analysis for NF-κB activation was determined by translocation of the subunits RELA/p50 and NFκB1/p65 to the nucleus. N-α-syn stimulation induced translocation of the NF-κB subunits to the nucleus, whereas translocation was inhibited by pretreatment with Treg (FIG. 12B). After Teff pretreatment, translocation of NF-κB subunits was comparable to N-κ-syn stimulation. Diminished expression of NF-κB-related genes following pretreatment with Treg in stimulated microglia, including Tnfa, Tnfrs1a, Rela, and Nos2, was also observed (FIG. 12C). Expression of neurotrophins Bdnf and Gdnf was increased following Treg pretreatment to greater levels relative to all other treatments (FIG. 12D).

Figure 13:
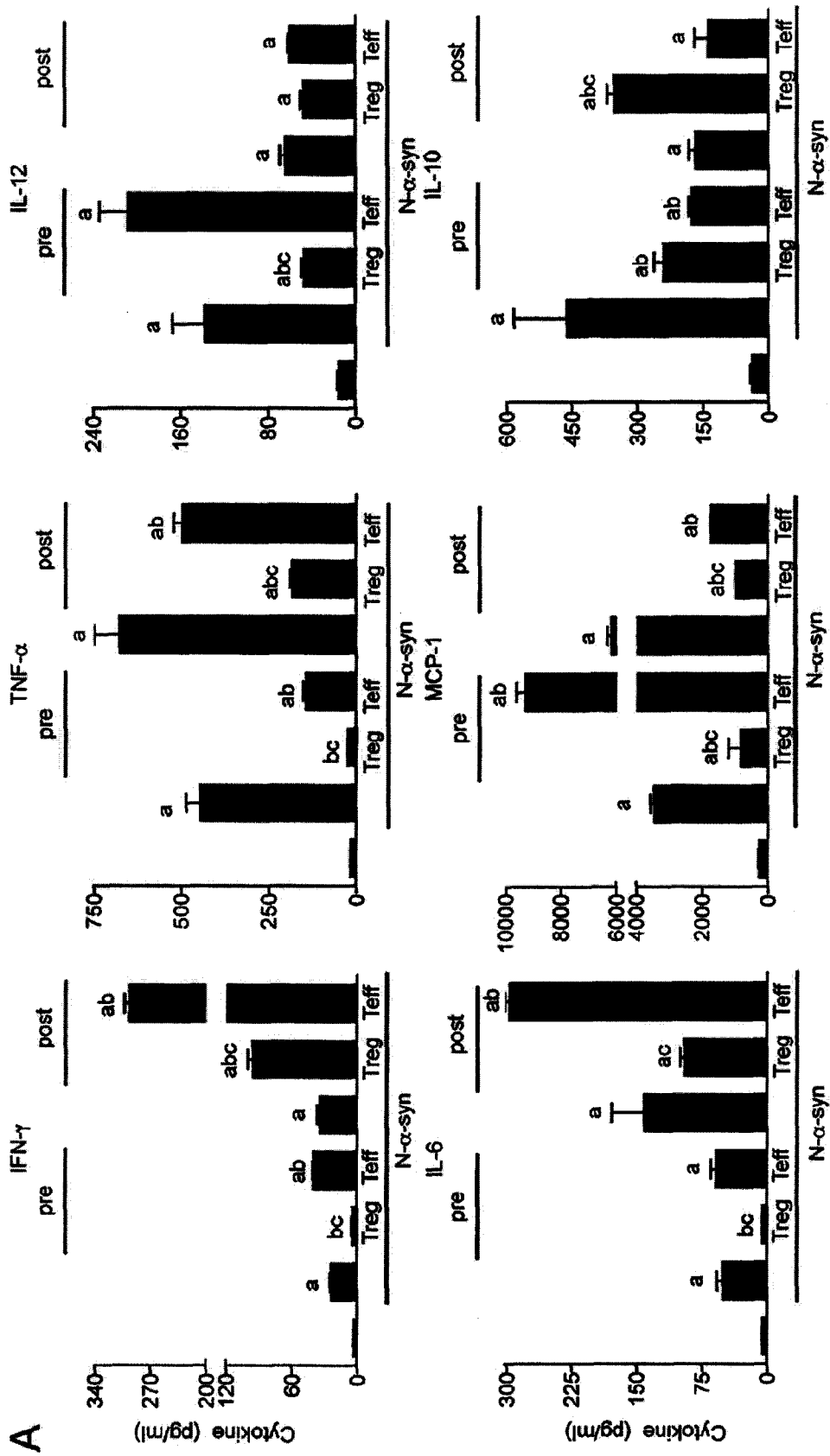
FIGS. 13A-13F demonstrate the inhibition of proinflammatory cytokine/chemokine production requires both cell contact and soluble factors.
Figure 13:
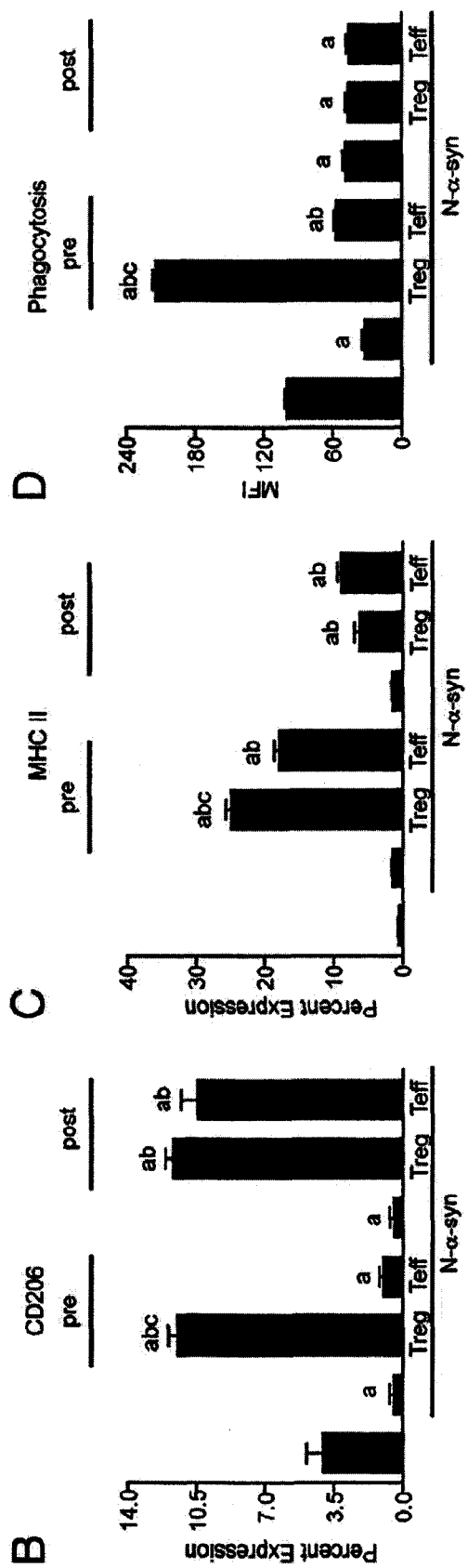
Figure 13:
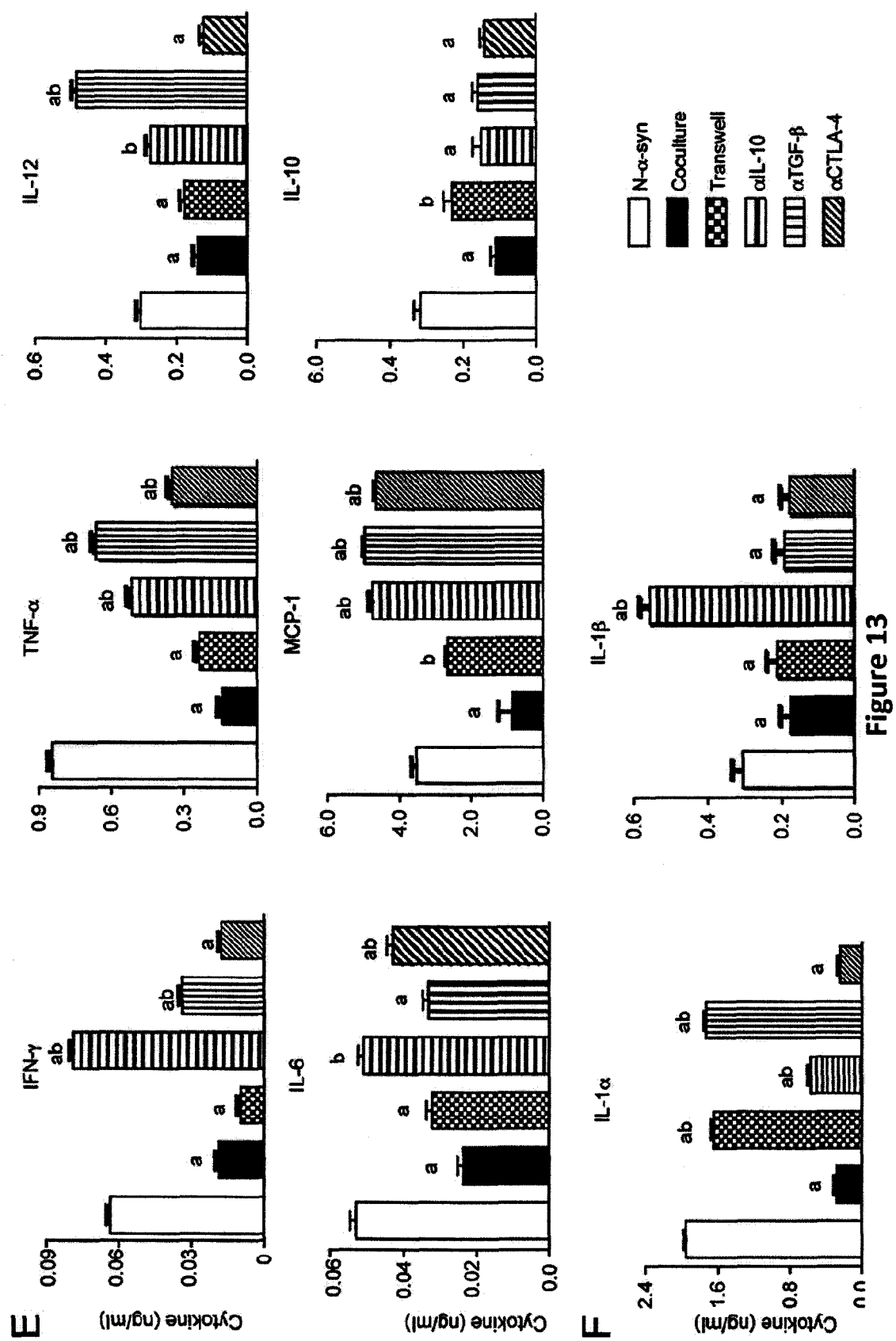

Microglial cytokine/chemokine analysis revealed that pretreatment with Treg suppressed production of IFN-γ, TNF-α, IL-12, IL-6, IL-10, and MCP-1 compared with untreated or Teff-treated microglia, whereas only TNF-α was reduced by Teff pretreatment (FIG. 13A). To mirror interactions that would occur between CD4+ T cells and microglia in disease, microglia were first stimulated with aggregated N-α-syn for 12 hours before addition of Treg or Teff (post-treatment). Treg posttreatment resulted in diminished production of all assayed proinflammatory cytokines, except IFN-γ, which was increased as a result of Treg or Teff coculture compared with N-α-syn stimulation alone, although concentration was less after treatment with Treg than with Teff. Assessment of CD206 (macrophage mannose receptor) and MHC class II expression revealed that pre- or posttreatment with Treg up-regulated both markers for alternative activation, as did post-treatment with Teff (FIGS. 13B and 13C). N-α-syn stimulation reduced microglial phagocytosis of FITC-labeled latex beads as determined by a 68% decrease in MFI compared with unstimulated microglia (FIG. 13D). However, Treg-pretreated microglia consistently engulfed more beads compared with N-α-syn-stimulated microglia (+6.8-fold) or Teff-pretreated microglia (+1.9-fold). In contrast, post-treatment with Treg or Teff had no significant effect on phagocytosis compared with N-α-syn stimulation.

Treg-modulated Microglial Responses Require Factor Secretion and Cell Contact

To determine whether Treg-mediated attenuation of microglial inflammation depends on T cell-microglia contact or on cytokine support, microglia were cocultured with Treg either in Transwell™ or with neutralizing Abs to IL-10, TGF-β, or CTLA-4. After 24 hours, inserts, Abs, and Treg were removed, and the microglia were stimulated with N-α-syn for 24 hours. Inhibition of IFN-γ secretion was not affected by physical contact but was abrogated or reduced in the presence of neutralizing Ab to IL-10 and TGF-β, respectively (FIG. 13E). Suppression of TNF-α was partially reversed in the presence of neutralizing Abs for IL-10, TGF-β, or CTLA-4 but not in Transwell™ cultures, whereas inhibition of IL-12 production was dependent on both IL-10 and TGF-β. In contrast, inhibition of MCP-1 was seen in Transwell™ cultures or with neutralizing Ab against IL-10, TGF-β, or CTLA-4, suggesting that both cell contact and soluble factors attenuate MCP-1 production. Suppression of IL-1α was dependent, in part, on cell contact and TGF-β, whereas inhibition of IL-1α was IL-1α dependent (FIG. 13F). Modulation of phagocytic activity of microglia was primarily dependent on cell contact and was reduced 12-fold in Transwells™ compared with coculture. Neither blockade of IL-10 nor CTLA-4 altered phagocytic function compared with coculture; however, inhibition of TGF-β resulted in a 2-fold reduction in FITC-gated cells compared with coculture without Ab (p<0.05).

Treg and the Microglial Proteome

Figure 14:
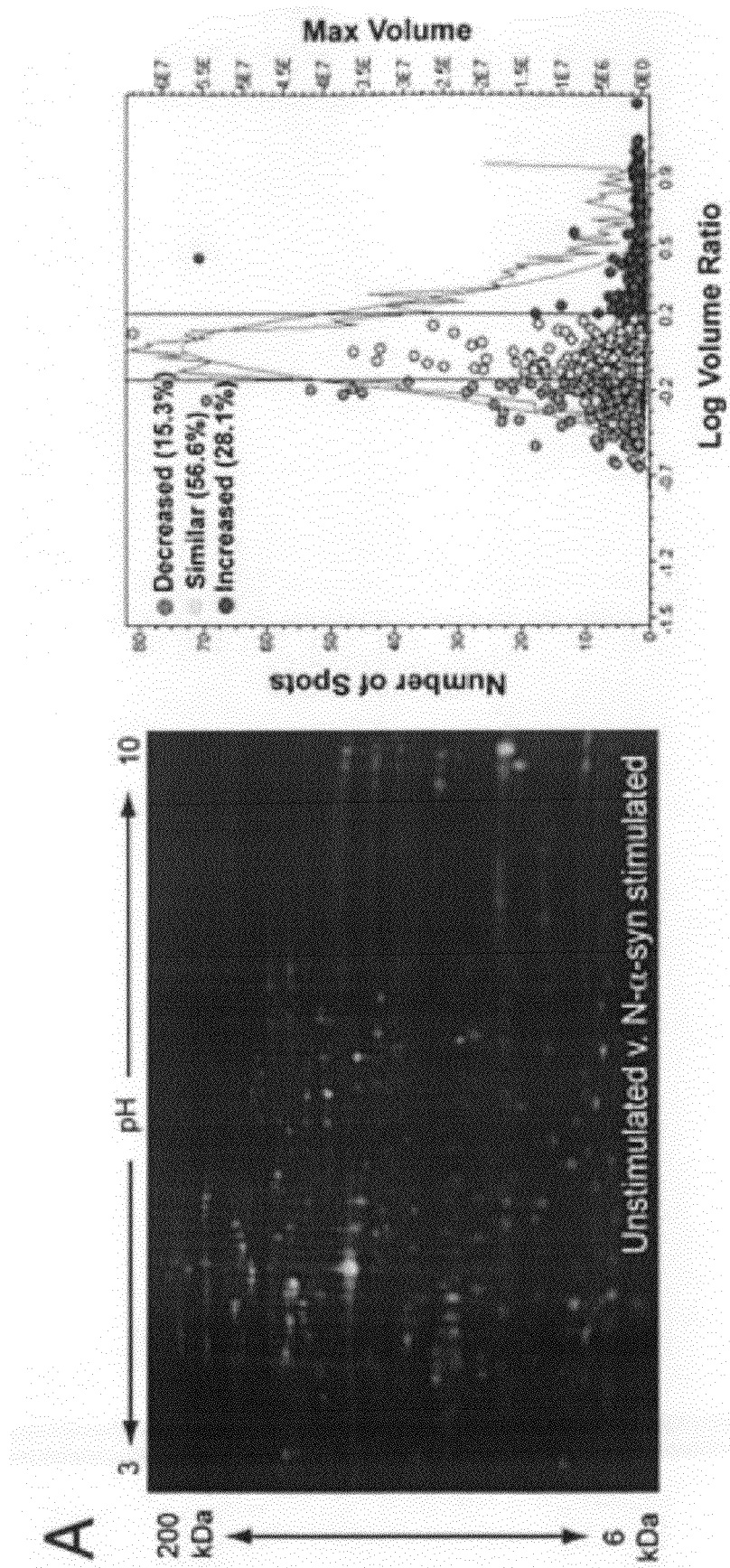
FIGS. 14A-14D provide an analysis of microglial proteome.
Figure 14:
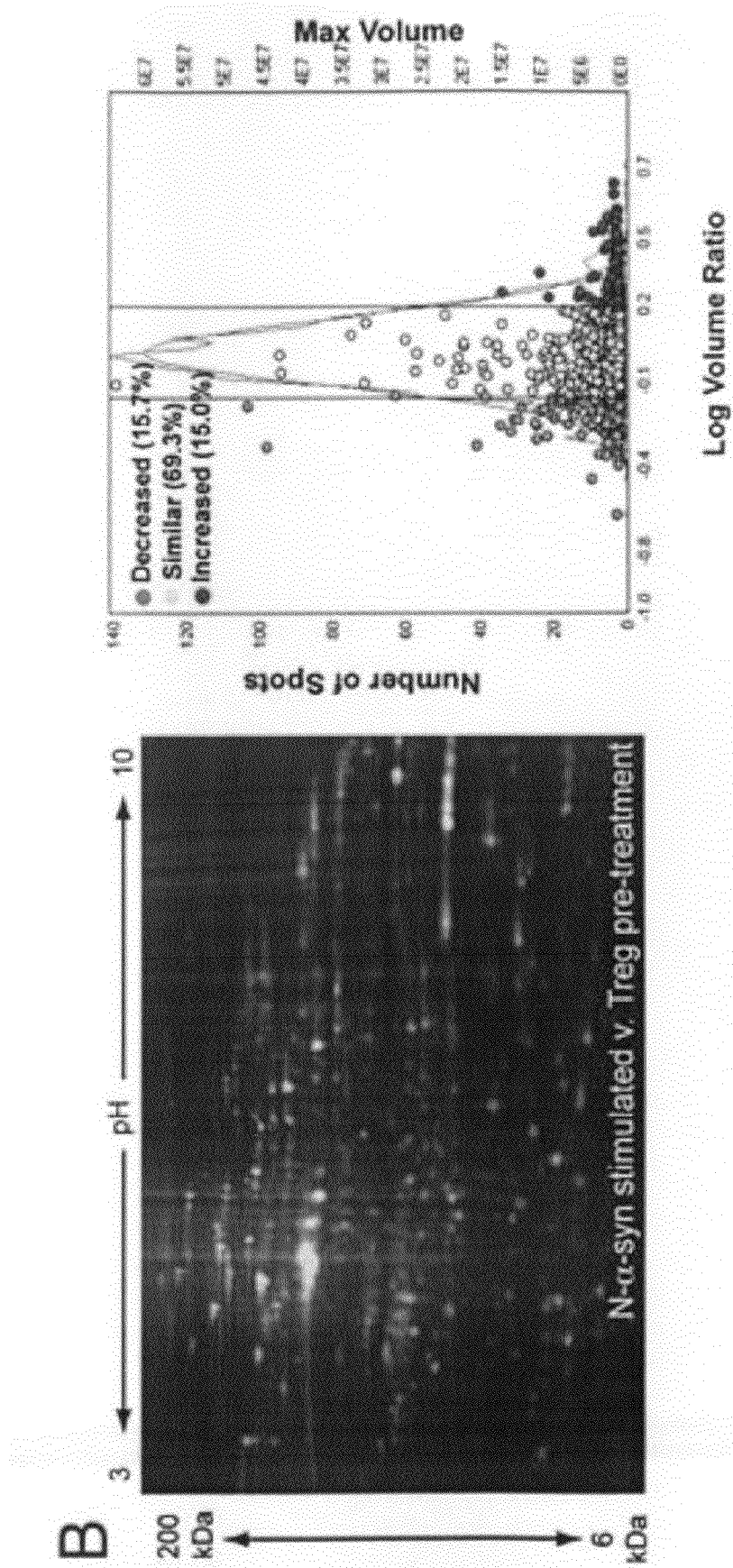
Figure 14:
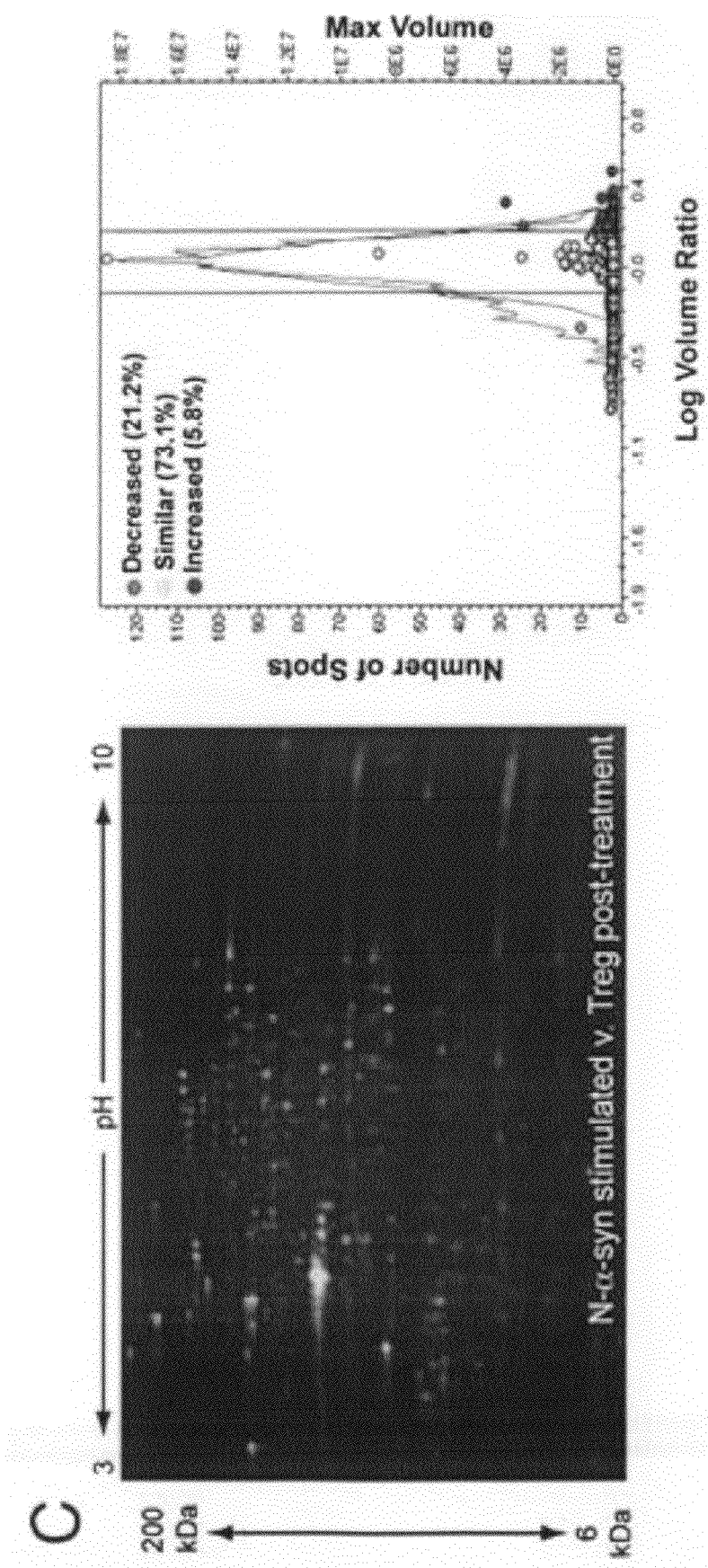
Figure 14:
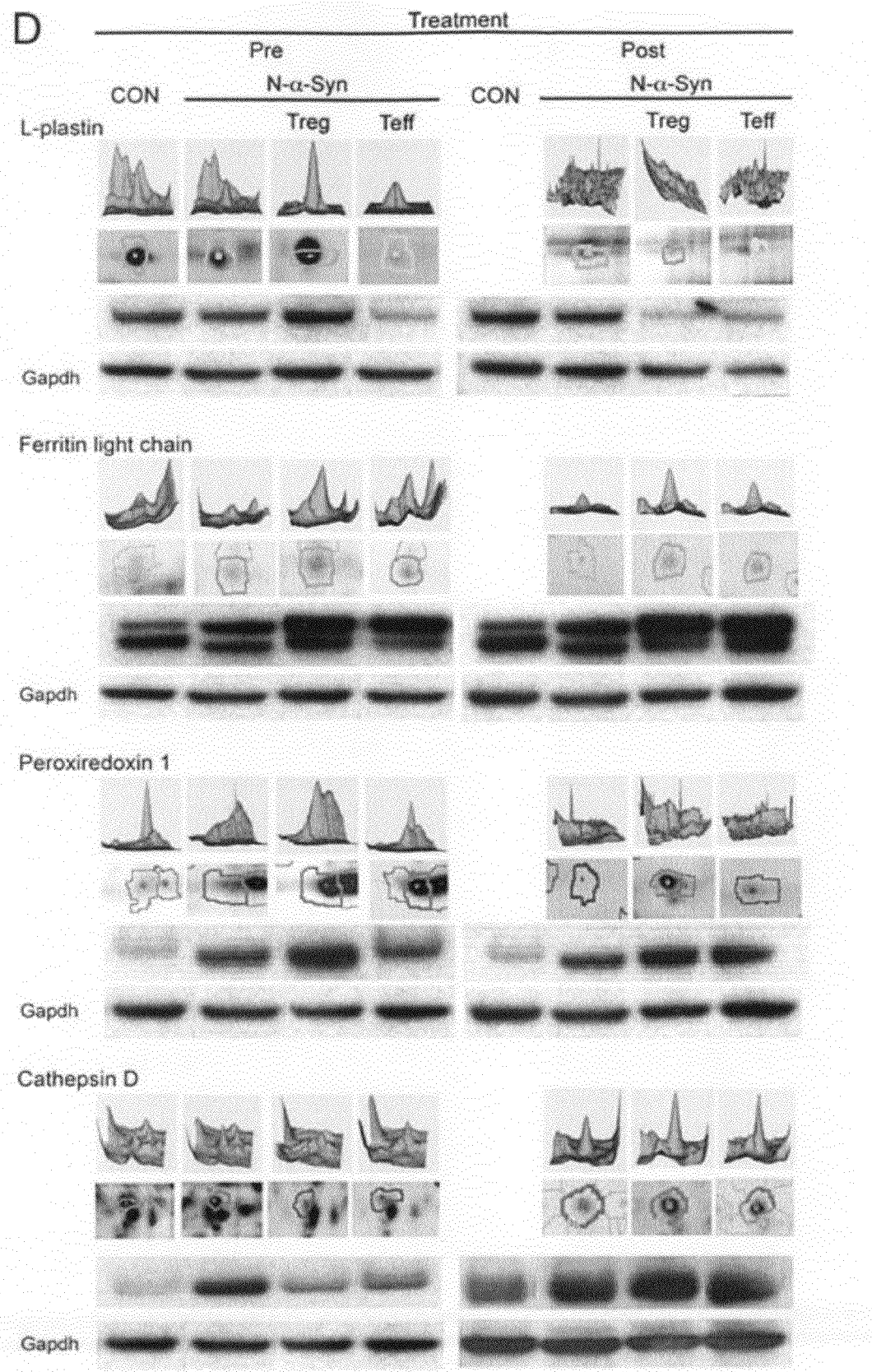

To facilitate quantitative detection and to maximize identification of changes in the microglial proteome in response to N-α-syn following coculture with Treg, microglial cell lysates were subjected to 2D gel electrophoresis and LC-MS/MS proteomic analyses. Representative analytical 2D gels and Decyder™ analyses are shown for cell lysates of N-α-syn-stimulated microglia compared with unstimulated controls (FIG. 14A). In comparison to N-α-syn-stimulated microglia, coculture with Treg before stimulation resulted in a different proteomic profile (FIG. 14B), as did coculture with Treg post-activation (FIG. 14C). Analysis was performed on analytical gels from separate lysates comparing microglia cultures stimulated with media alone, N-α-syn, or cocultured with Treg by BVA software to identify differentially expressed proteins (p≤0.05). Proteomic analyses of N-α-syn/Teff cocultures vs N-α-syn stimulation alone following pre- and posttreatment were also performed to facilitate cross-comparisons between treatments by BVA. All analytical gels were cross-compared by BVA and matched to a preparative gel consisting of pooled protein from the experimental groups. Identified spots were compared for area and peak height (3D plots) by BVA. Western blot analyses and densitometry confirmed differential expression of several proteins, including L-plastin (+1.5-fold), ferritin L chain (+1.3-fold) and peroxiredoxin 1 (+1.5-fold), and cathepsin D (−2.0-fold) in microglial lysates following pretreatment with Treg compared with stimulated with N-α-syn alone (FIG. 14D).

Among the proteomic changes induced by pretreatment of microglia with Treg and compared with N-α-syn stimulated microglia were decreased expression in several cytoskeletal proteins such as β-actin, vimentin, cofilin 1, and gelsolin, whose function is to regulate cell motility and vesicle transport. Treatment with Treg also resulted in increased expression of microglial proteins involved in exocytosis such as annexin A1 and annexin A4, and phagocytosis such as L-plastin. Stimulation with N-α-syn decreased expression of proteins associated with the ubiquitin-proteasome system (UPS) >1.5-fold compared with unstimulated microglia, whereas pretreatment with Treg increased expression of UPS-related proteins, including proteosome subunit α type 2, proteasome subunit β type 2, ubiquitin specific protease 19, and ubiquitin fusion degradation. Treatment with Treg also increased the expression of molecular chaperones, including heat shock proteins (HSP) and calreticulin; most of which were decreased following stimulation with N-α-syn compared with unstimulated controls. Lysosomal proteases, including cathepsins B and D, were increased by N-α-syn stimulation alone; however, microglia pretreated with Treg showed decreased abundance of the same proteins. Regulatory proteins involved in cellular metabolism (transaldolase 1) and catabolism (α-mannosidase) were increased in Treg-pretreated cultures.

Changes in several proteins associated with mitochondrial function were observed as a result of stimulation with N-α-syn. Of interest, proteins of the electron transport chain (ETC), specifically complex V, involved in ATP synthesis were decreased in expression. Whereas ETC proteins such as nicotinamide adenine dinucleotide dehydrogenase (ubiquinone) Fe—S protein 2 of complex I, cytochrome c oxidase of complex III, and the subunits that make up the components of ATP synthase were increased by microglia in response to N-α-syn stimulation following Treg pretreatment. Changes in the mitochondrial response to Treg were not limited to proteins involved in cellular energetics but included redox proteins, chaperones, and structural proteins. Other proteins that increased as a result of treatment with Treg were mitochondrial redox proteins, including peroxiredoxins, superoxide dismutase (SOD)2, thioredoxin 1 (THX 1), and catalase. In addition, cytoplasmic redox proteins were also increased, including peroxiredoxin 1, SOD1, biliverdin reductase B (BVR B), and glutaredoxin 1 (GLU 1). Interestingly, all were decreased by N-α-syn stimulation compared with unstimulated controls.

For comparison of the microglial phenotype after commitment to activation by N-α-syn stimulation and modulation by CD3-activated T cells, microglia were first stimulated with N-α-syn for 12 hours before the addition of Treg or Teff for an additional 24 hours, and the T cells were removed before microglial cell lysis. Similar proteins were affected by posttreatment with Treg as with pretreatment; interestingly, some exhibited opposite expression patterns observed after pretreatment with Treg. Western blot analysis and densitometry confirmed differential expression of L-plastin (−1.6 fold), ferritin L chain (+1.2-fold), peroxiredoxin 1 (+1.5-fold), and cathepsin D (+1.5-fold) by posttreatment with Treg compared with N-α-syn alone (FIG. 14D).

Akin to pre-treatment, post-treatment with Treg yielded increased redox-active protein expression by activated microglia, including SOD1 and peroxiredoxins 1 and 5. Several proteins that were differentially expressed in the pretreatment analysis were also identified in post-treatment analysis but were opposite in direction, including increased expression of structural proteins involved in cell motility, such as β-actin and γ-actin, decreased expression of mitochondrial proteins, including ETC complex V, and decreased expression in L-plastin. Induction of proapoptotic protein expression was observed, including increased expression of apoptosis-associated speck-like protein containing a caspase recruitment domain, galectin 3, gelsolin, eukaryotic translation elongation factor 1, and cathepsins B and D. Decreased expression of proteins involved in cellular metabolism such as aldolase I and aldehyde dehydrogenase 2 was also observed in response to Treg post-treatment.

Treg Affect Microglial Oxidative Stress

Figure 15:
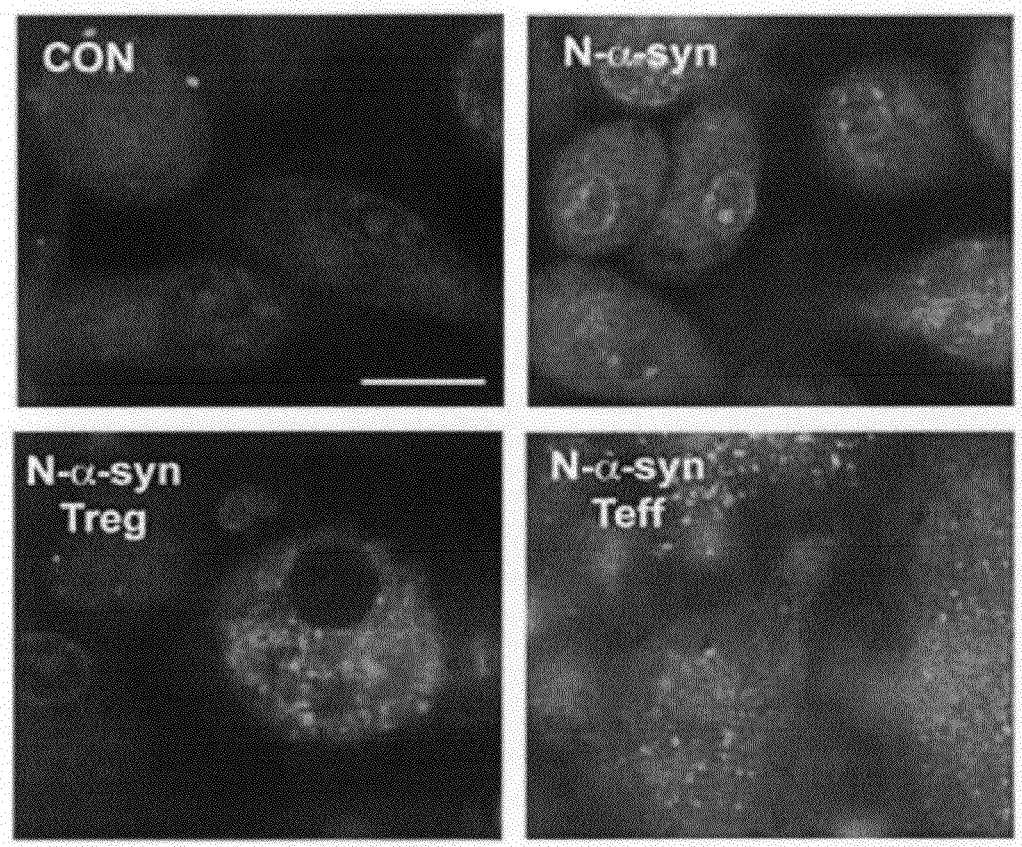
FIGS. 15A-15J demonstrate CD4+ T cells modulate microglial oxidative stress and CB activity.
Figure 15:
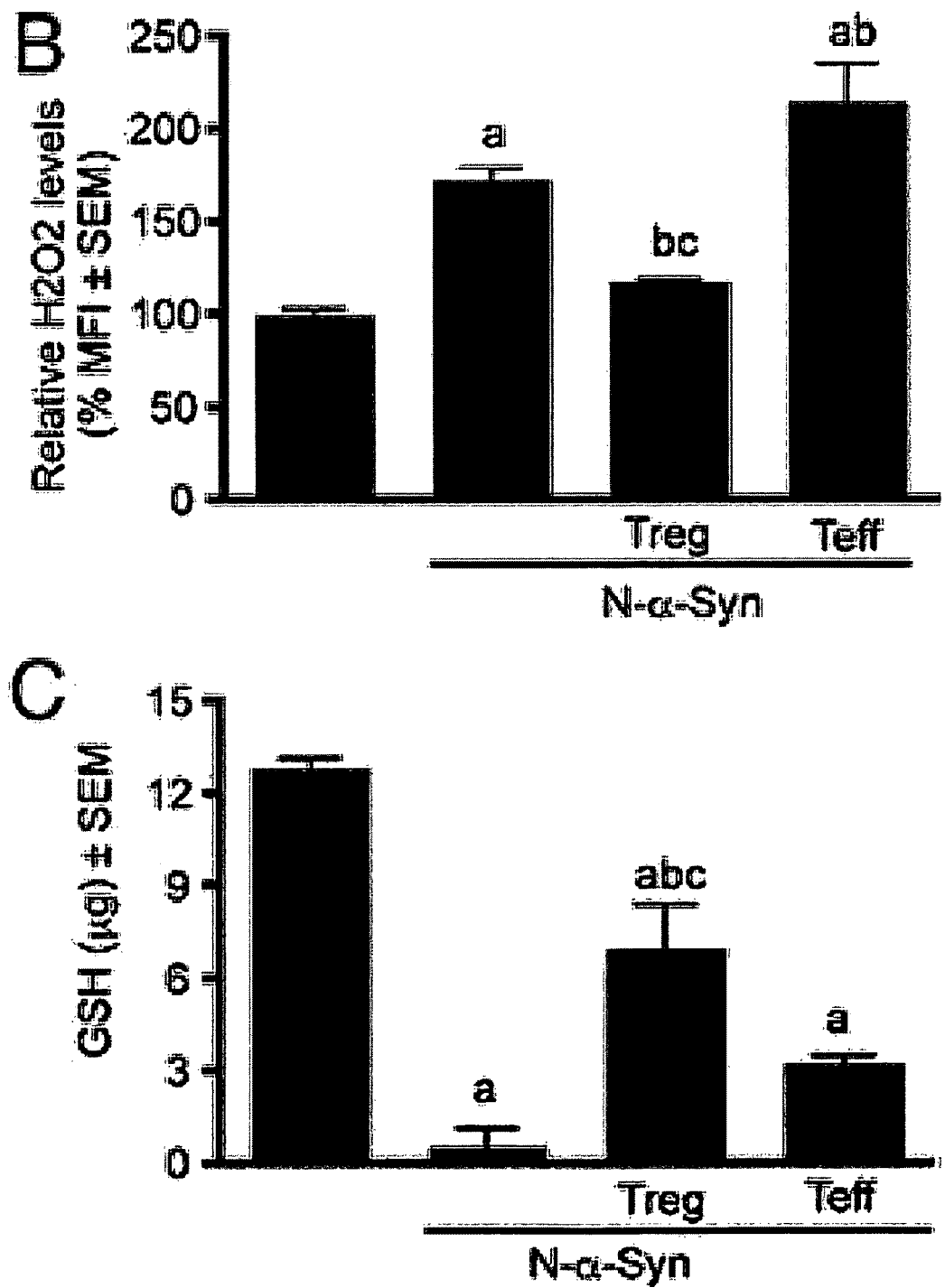
Figure 15:
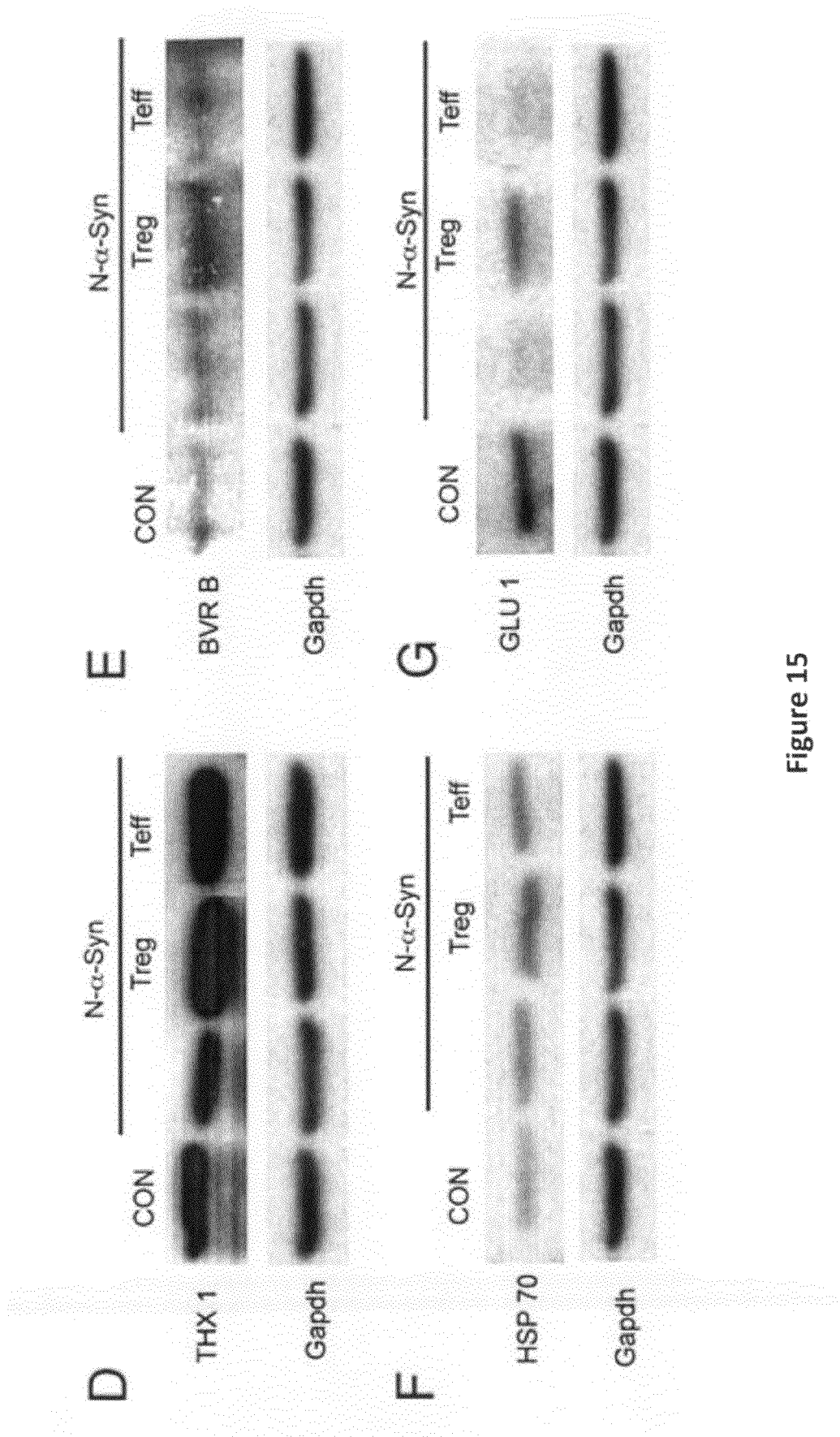
Figure 15:
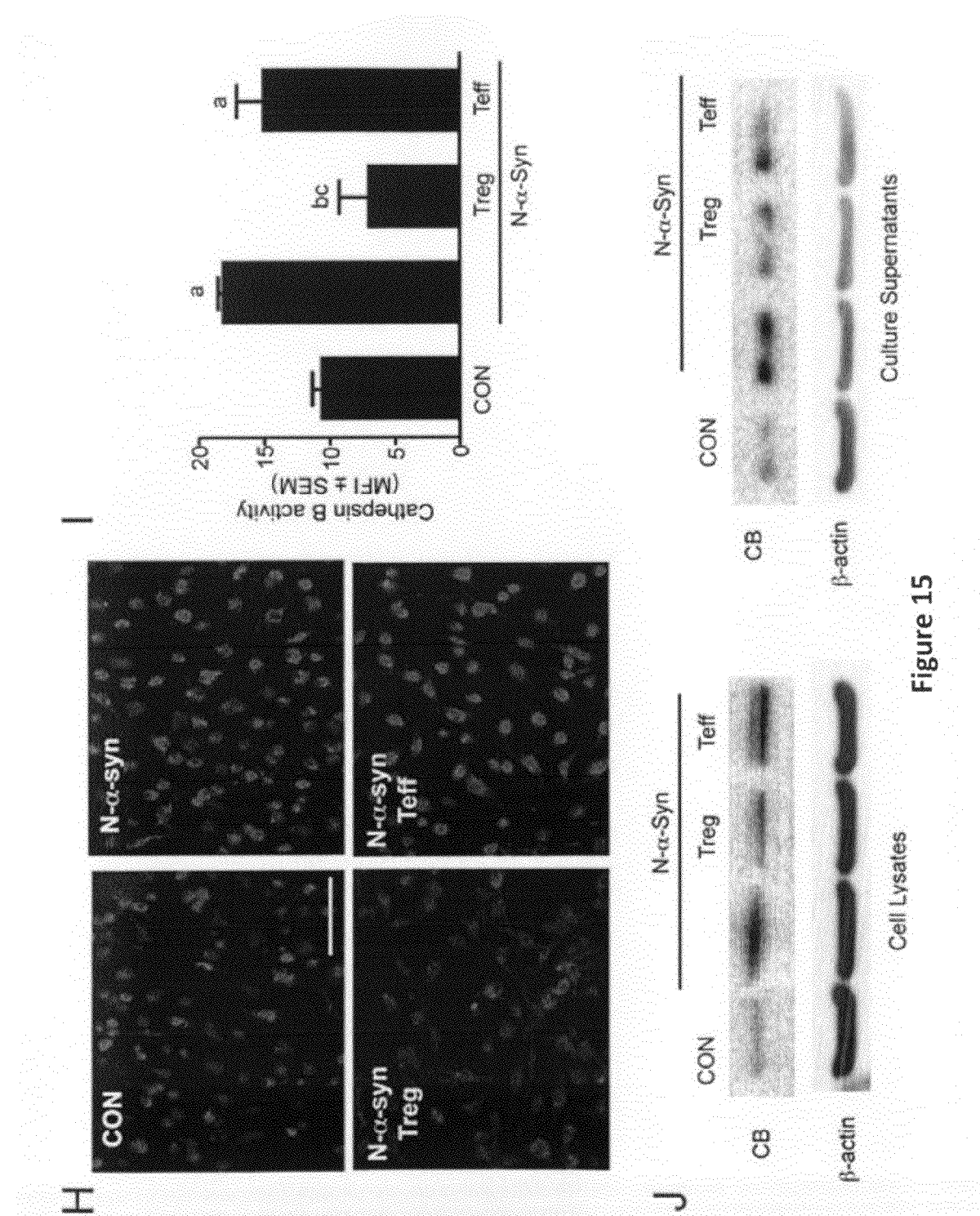

To validate that changes in expression of redox-active proteins accurately reflect changes in the oxidative balance of microglia, oxidative stress levels were measured in N-α-syn-activated microglia pretreated with Treg or Teff. N-α-syn-stimulated microglia consistently produced greater levels of $H_2O_2$ compared with unstimulated controls, whereas Treg pretreatment of microglia diminished the levels of $H_2O_2$ (FIGS. 15A and 15B). In contrast, pretreatment with Teff exacerbated $H_2O_2$ production by microglia. Analysis of intracellular GSH levels revealed that microglia stimulated with N-α-syn were depleted of intracellular GSH, a key oxidative buffer in cells, following 24 hours of stimulation as previously shown (Reynolds et al. (2008) J. Neuroimmune Pharmacol., 3:59-74). However, pretreatment with Treg buffered the loss of GSH stores in stimulated microglia, whereas Teff provided no significant protection from GSH loss (FIG. 15C). Western blot and densitometric analyses validated protein expression trends identified by proteomics for select redox-active proteins, including THX 1 (+1.7-fold; FIG. 15D), biliverdin reductase B (BVR B) (+1.8-fold; FIG. 15E), HSP 70 (+1.4-fold; FIG. 15F), and GLU 1 (+2.0-fold; FIG. 15G).

Treg Modulate Microglial CB Activity

Treg pretreatment revealed decreased expression of cellular proteases, including cathepsin B (CB). Therefore, it was investigated whether differential protein expression paralleled inhibition of CB enzymatic activity. N-α-syn stimulation of microglia for 24 hours increased CB activity compared with unstimulated controls, whereas pretreatment with Treg before stimulation diminished CB activity (FIGS. 15H and 15I). In contrast, stimulated microglia pretreated with Teff exhibited CB activity similar to that of N-α-syn stimulation alone. Western blot analysis revealed increased abundance of CB both in cell lysates and culture supernatants of N-α-syn-stimulated microglia compared with unstimulated controls and cultures pretreated with either Treg or Teff, whereas pretreatment with Treg diminished intracellular (−1.6-fold) and secreted (−1.8-fold) CB levels (FIG. 15J).

Proapoptotic Treg Responses are Mediated Through Fas-FasL Interactions

Figure 16:
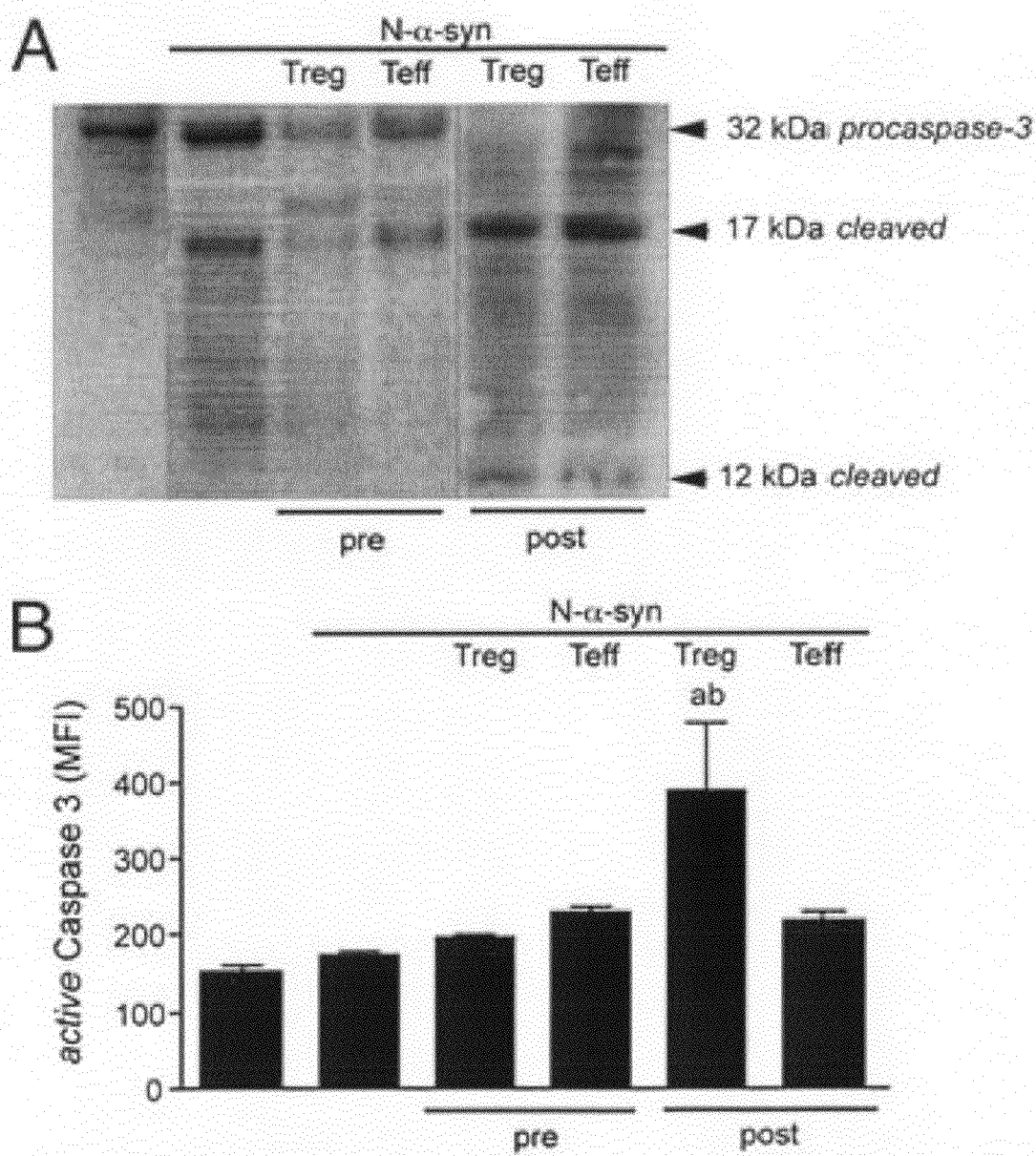
FIGS. 16A-16I demonstrate Treg induce microglial apoptosis through Fas-FasL interactions.
Figure 16:
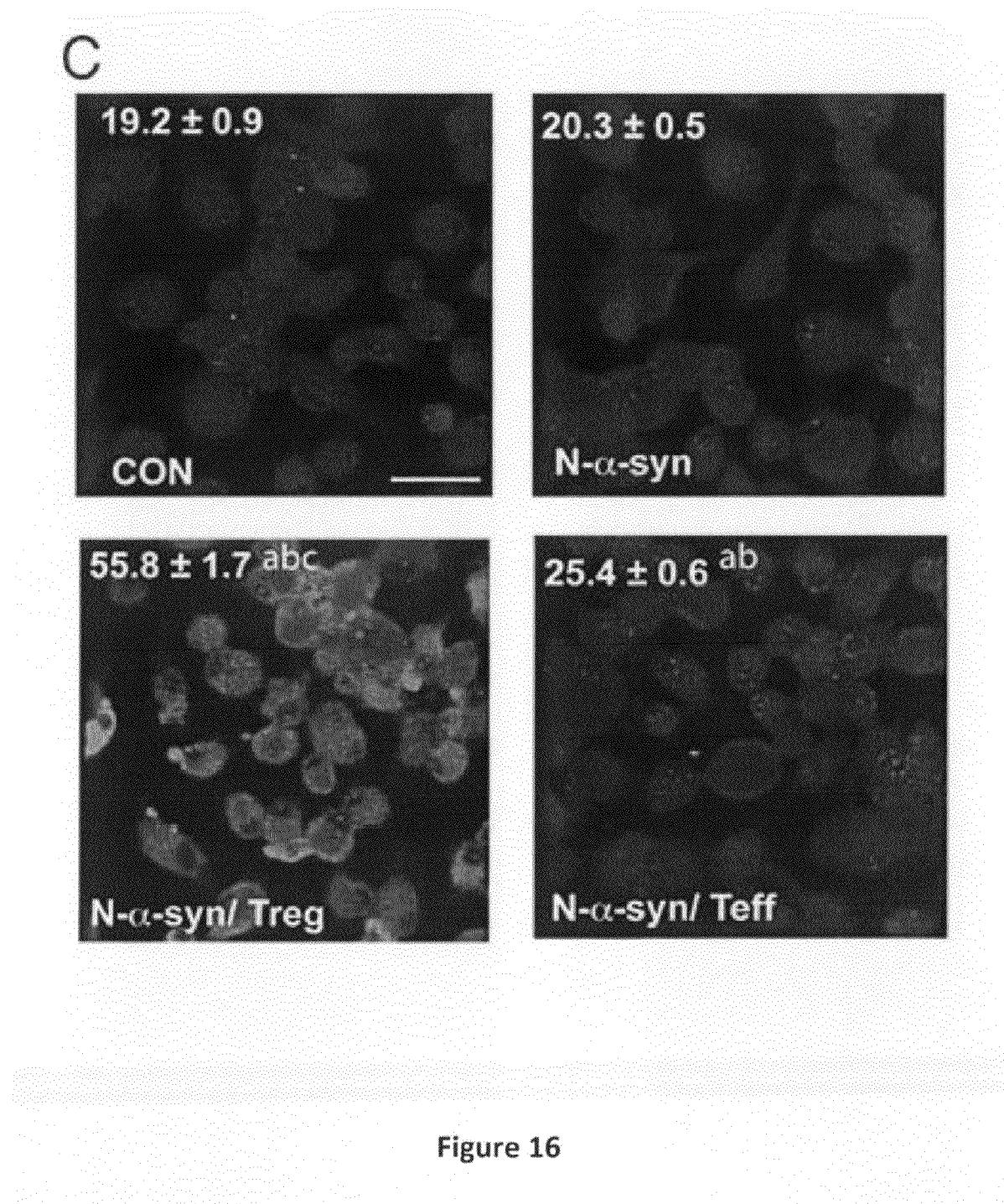
Figure 16:
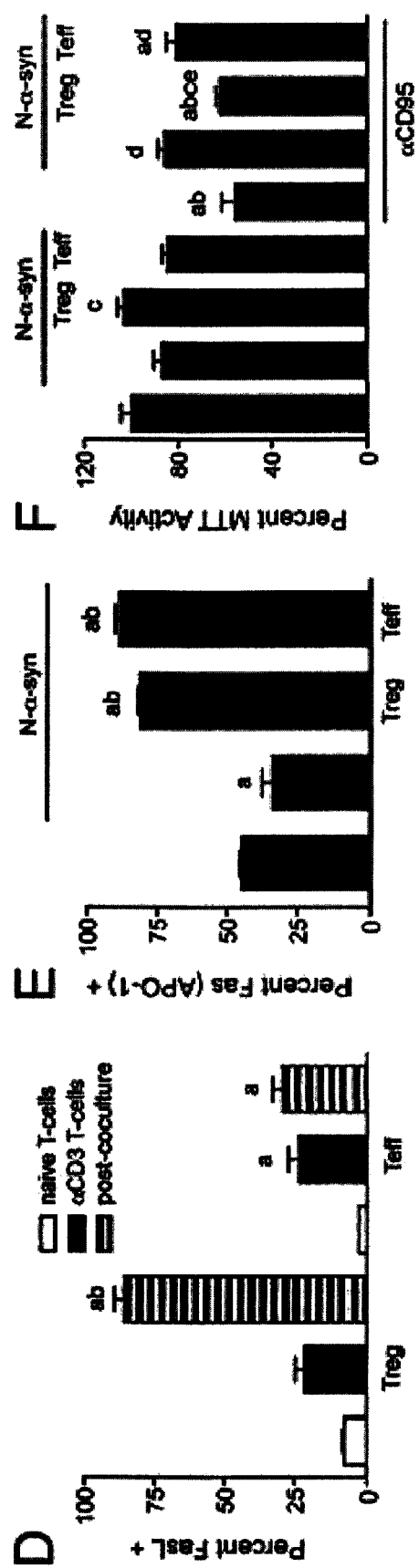
Figure 16:
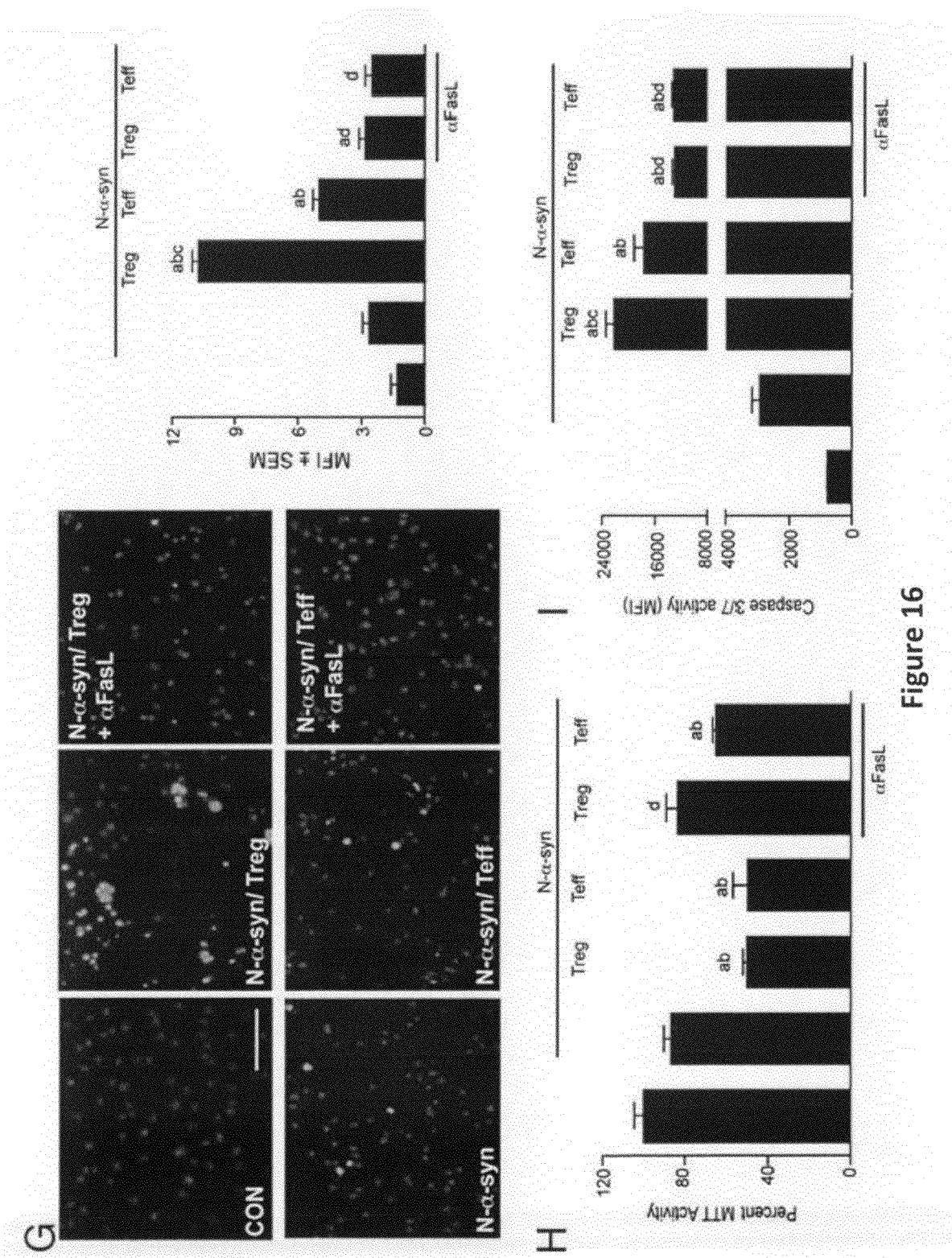

Evidence that Treg regulate inflammation through induction of apoptosis in activated effector cells, including monocytes/macrophages (Glanzer et al. (2007) J. Neurochem., 102:627-645; Liu et al. (2009) J. Immunol., 182:3856-3866), led to the investigation of whether post-treatment with Treg induced microglial apoptosis. Microglial cell viability was monitored using independent markers for apoptosis and cell viability: caspase-3 activation, MTT activity, and TUNEL. By Western blot analysis, lysates from microglia cultured for 24 hours in the presence of N-α-syn exhibited increased caspase-3 activation compared with unstimulated controls (FIG. 16A). Pretreatment with Treg or Teff resulted in diminished caspase-3 activation in response to N-α-syn, whereas posttreatment with Treg or Teff increased levels of cleaved caspase-3 products. To confirm those results, analysis of active caspase-3 by flow cytometry revealed that pretreatment of microglia with either Treg or Teff failed to significantly increase caspase-3 activation (FIG. 16B). In contrast, posttreatment with Treg, but not Teff, resulted in a significant increase in active caspase-3+ cells. In situ staining for active caspase-3+ cells revealed that posttreatment with Treg resulted in profound induction of active caspase-3 relative to any other treatment paradigm (FIG. 16C).

To investigate the proapoptotic factors involved in the Treg effect on microglia, the relative expression of FasL on Treg and Teff was assessed by flow cytometry after fresh isolation (naive), anti-CD3 activation, or after coculture with N-α-syn-stimulated microglia. Numbers of FasL+Treg and Teff were increased following anti-CD3 activation (FIG. 5D). In comparison, coculture with N-α-syn-activated microglia induced >80% of Treg to express FasL, whereas microglial coculture had no significant additive effect on Teff. N-α-syn activation diminished Fas (CD95) expression by microglia; however, coculture of microglia with either activated T cell subset resulted in significant up-regulation of Fas expression among activated microglia (FIG. 16E). Moreover, reduced expression of Fas by N-α-syn-stimulated microglia paralleled reduced susceptibility to anti-CD95-induced apoptosis compared with unstimulated controls (FIG. 16F). Although pretreatment with Treg did not reduce microglial viability, pretreatment with Treg, but not Teff, restored susceptibility of N-α-syn-stimulated microglia to anti-CD95-induced apoptosis. In contrast, post-treatment with T cells resulted in significant apoptosis of microglia compared with unstimulated and N-α-syn-stimulated microglia, with Treg inducing >2-fold increase in MFI of TUNEL+microglia (FIG. 16G). T cell-mediated apoptosis of N-α-syn-stimulated microglia was mediated through Fas-FasL interactions as anti-FasL returned levels of TUNEL staining to those of N-α-syn-stimulated controls. These results were essentially confirmed by MTT assays of microglia, showing reduction of microglial cell viability after posttreatment with Treg and Teff and increased viability after blocking of Treg with anti-FasL (FIG. 16H). This apoptotic response was at least partially caspase-dependent as Treg and Teff posttreatment increased activation of caspase-3/7 in N-α-syn-stimulated microglia compared with controls, whereas incubation with anti-FasL partially blocked caspase activation (FIG. 16I).

Figure 17:
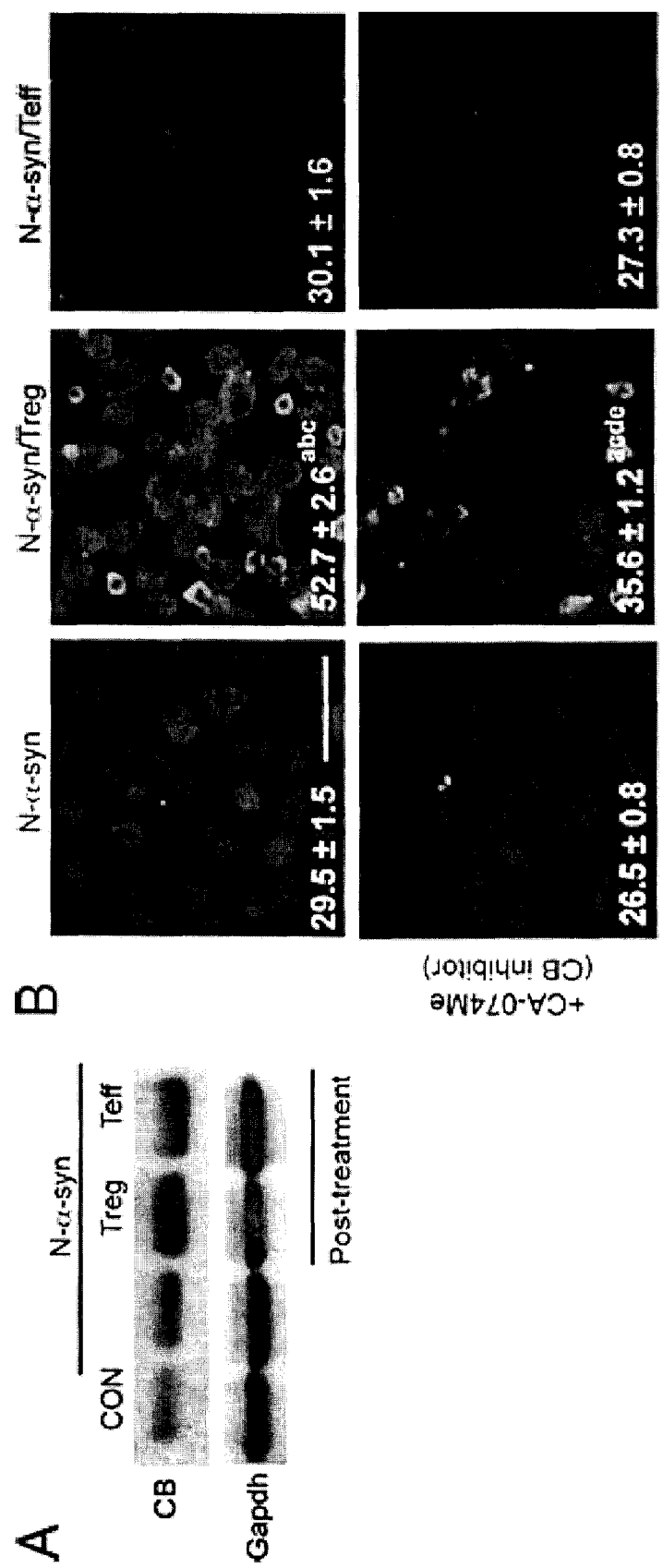
FIG. 17A-17D demonstrate CB regulates microglial apoptosis.
Figure 17:
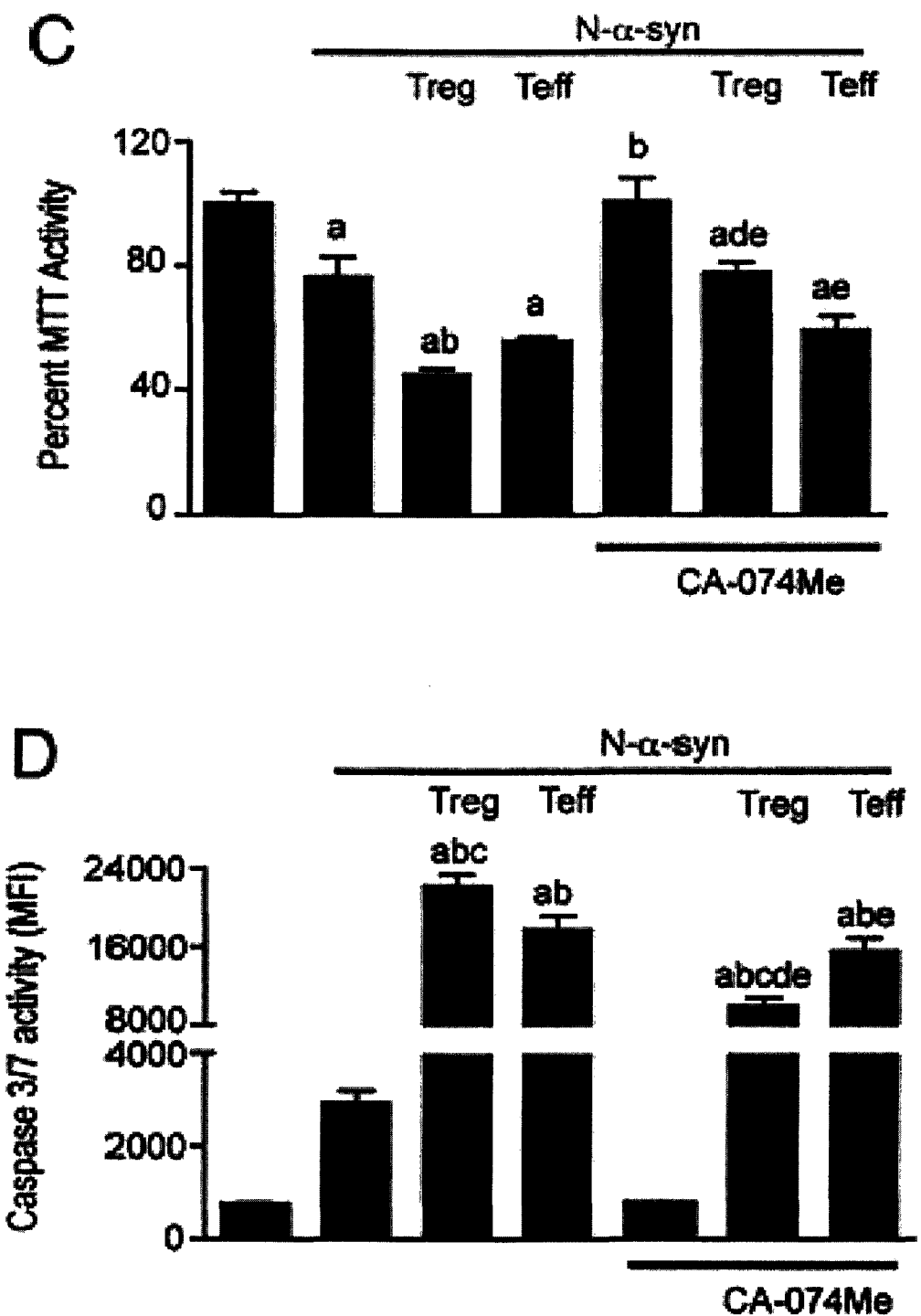

Analysis of the N-α-syn microglial proteome following post-treatment with Treg revealed increased abundance of CB in cell lysates compared with N-α-syn stimulation alone. Treg-induced expression of CB was validated by Western blot and densitometry analyses (+1.6-fold; FIG. 17A). The role for CB activation in Treg-mediated microglial apoptosis was investigated using the cell-permeable inhibitor of CB, CA-074ME. In situ staining for active caspase-3+ cells revealed that inhibition of CB partially diminished active caspase-3 expression following stimulation with N-α-syn (FIG. 17B). In comparison, CB inhibition during Treg post-treatment resulted in significant suppression of active caspase-3 expression relative to Treg post-treatment without CB inhibitor. Decreased active caspase-3 was also observed in Teff-treated cultures in response to CB inhibitor. Inhibition of CB partially inhibited loss of Treg-mediated N-α-syn microglial MTT activity but had no significant affect on Teff-mediated cytotoxicity (FIG. 17C). Similarly, inhibition of CB diminished caspase-3/7 activation in N-α-syn-stimulated microglia treated in the presence or absence of Treg or Teff (FIG. 6D). Analysis by flow cytometry confirmed these observations as inhibition of CB diminished active caspase-3+ cells on average by 11.1±0.5% in N-α-syn-stimulated cultures. Moreover, flow cytometric analysis revealed that neutralization of FasL during posttreatment resulted in decreased CB protein expression in Treg-treated microglia by 40.2±4.0% ($p<0.05$ compared with N-α-syn/Treg posttreatment), whereas blocking of FasL interactions produced no significant effect on diminishing CB expression in Teff-treated cultures (4.8±1.7%). Taken together, these data support a role for the Fas-FasL proapoptotic pathway and the induction of CB to promote apoptosis in the effect of Treg poststimulation on activated microglia.

EXAMPLE 3

Parkinson's disease (PD) is a progressive neurodegenerative disease characterized clinically as gait and motor disturbances such as rigidity, resting tremor, slowness of voluntary movement, and postural instability. In some cases these evolve to frank dementia (Dauer et al. (2003) Neuron 39:889-909; Fahn et al. (2000) In Merritt's Neurology, Rowland, L. P., Ed. Lippincott Williams & Wilkins: New York, pp 679-693; Fahn, et al. (2004) NeuroRx 1:139-54; Mayeux, R. (2003) Annu. Rev. Neurosci., 26:81-104). A plethora of host and environmental factors affect the onset and progression of PD including genetics, environmental cues, aging, peripheral immunity, impaired energy metabolism, and oxidative stress (Baba et al. (2005) Parkinsonism Relat. Disord., 11:493-8; Klockgether, T. (2004) Cell Tissue Res., 318:115-20; Linton et al. (2004) Nat. Immunol., 5:133-9; Naylor et al. (2005) J. Immunol., 174:7446-52; Orr et al. (2005) Brain 128:2665-74; Reale et al. (2009) Brain Behav. Immun., 23:55-63; Rosenkranz et al. (2007) J. Neuroimmunol., 188:117-27; Sian et al. (1994) Ann. Neurol., 36:348-55; Taki et al. (2000) Eur. J. Nucl. Med., 27:566-73; Tanner, C. M. (1992) Occup. Med., 7:503-13; Tanner, C. M. (1992) Neurol. Clin., 10:317-29). Pathologically, PD is characterized by nigrostriatal degeneration precipitated by progressive loss of dopaminergic neuronal cell bodies in the substantia nigra pars compacta (SNpc) and their projections to the dorsal striatum (Homykiewicz et al. (1987) Adv. Neurol., 45:19-34). This degeneration is associated with alterations in innate, microglial activation and adaptive T cell immunity (Baba et al. (2005) Parkinsonism Relat. Disord., 11:493-8; Banati et al. (1998) Mov. Disord., 13:221-7; Block et al. (2004) Faseb J., 18:1618-20; Cicchetti et al. (2002) Eur. J. Neurosci., 15:991-8; Formo et al. (1992) Prog. Brain Res., 94:429-436; Hong, J. S. (2005) Ann. NY Acad. Sci., 1053:151-2; McGeer et al. (1998) Alzheimer Dis. Assoc. Disord., 12:S1-6; Mirza et al. (2000) Neuroscience 95:425-432; Wang et al. (2005) Mech. Ageing Dev., 126: 1241-54; Benner et al. (2008) PLoS ONE 3:e1376; Brochard et al. (2009) J. Clin. Invest., 119:182-92; Theodore et al. (2008) J. Neuropathol. Exp. Neurol., 67:1149-58). Precipitation of immune dysfunction in PD is thought to ensue from the release of cytoplasmic inclusions of fibrillar, misfolded proteins encased in Lewy bodies (LB) and composed principally of aggregated α-synuclein (α-syn) (Spillantini et al. (1997) Nature 388:839-40). Such misfolded proteins can engage innate and adaptive immunity (Spillantini et al. (1997) Nature 388:839-40; Croisier et al. (2005) J. Neuroinflammation 2:14). Indeed, substantive evidence supports the notion that nigrostriatal degeneration is manifest by α-syn mediated microglial activation, oxidative stress and disease inciting adaptive immune responses (Benner et al. (2008) PLoS ONE 3:e1376; Brochard et al. (2009) J. Clin. Invest., 119:182-92; Theodore et al. (2008) J. Neuropathol. Exp. Neurol., 67:1149-58; Reynolds et al. (2008) J. Neurochem., 104:1504-25; Reynolds et al. (2008) J. Neuroimmune Pharmacol., 3:59-74; Thomas et al. (2007) J. Neurochem., 100: 503-19; Zhang et al. (2005) Faseb J., 19:533-42). It is the pathogenic spiral of dopaminergic neuronal death, release of extracellular aggregated α-syn, microglial activation, peripheral immune activation, collateral neuronal injury, sustained α-syn release with ingress into lymphatics, and engagement of specific T cell responses that further damage dopamine neurons.

It has been demonstrated that microglia associated degenerative responses are triggered by nitrated α-syn (N-α-syn)-specific effector T cells (Teff); whereas, CD4+ CD25+ regulatory T cells (Treg) attenuate microglial activation and promote dopaminergic neuronal survival (Reynolds et al. (2007) J. Leukoc. Biol., 82:1083-94). Lacking from the prior works was a mechanism for CD4+ T cell-mediated modulation of microglial function. Based on these observations, it was hypothesized that CD4+ T cells have dual roles, and as such, influence microglial responses to evoke biological activities that ultimately effect neuronal survival or loss. In attempts to decipher the mechanisms underlying such responses, aggregated N-α-syn was used as an inducer of microglial activation (Reynolds et al. (2008) J. Neurochem., 104:1504-25; Reynolds et al. (2008) J. Neuroimmune Pharmacol., 3:59-74; Thomas et al. (2007) J. Neurochem., 100: 503-19), then examined the microglial proteome affected by interactions with CD4+ T cell subsets (Reynolds et al. (2009) J. Immunol., 182:4137-49). Using proteomic approaches, it is demonstrated that Treg regulatory activities extend beyond inhibition of cellular activation and include modulation of a broad range of microglial activities involving regulation of phagocytosis and proteasome function, induction of redox-active and bioenergetic proteins, and apoptotic cell processes. Such regulatory events lead to the attenuation of microglial inflammatory neurotoxic responses. Importantly, the data demonstrate that the effects of Treg on N-α-syn-mediated immune activities are multifaceted and of potential therapeutic benefit.

Materials and Methods

Animals

C57BL/6J male mice (7 weeks old) were purchased from The Jackson Laboratory (Bar Harbor, Me.) and used for CD4+ T cell isolations. C57BL/6J neonates were obtained from breeder colonies housed in the University of Nebraska Medical Center animal facilities. All animal procedures were in accordance with National Institutes of Health guidelines and were approved by the Institutional Animal Care and Use Committee of the University of Nebraska Medical Center.

Cell Isolates

Microglia were prepared from neonatal mice (1-2 days old) using previously described techniques (Dobrenis, K. (1998) Methods 16:320-44). Cultures were consistently >98% CD11b+ microglia (Enose et al. (2005) Glia 51:161-72). CD4+ T cell subsets were isolated using previously described techniques (Reynolds et al. (2007) J. Leukoc. Biol., 82:1083-94; Banerjee et al. (2008) PLoS ONE 3:e2740). Treg and Teff isolates were >95% enriched (Reynolds et al. (2009) J. Immunol., 182:4137-49). CD3-activated T cells were co-cultured with microglia at 1:1 ratio. All analyses of microglia were performed after removal of the T cells from the cultures.

Recombinant α-syn

Purification, nitration and aggregation of recombinant mouse α-syn were performed as previously described (Reynolds et al. (2008) J. Neurochem., 104:1504-25; Reynolds et al. (2008) J. Neuroimmune Pharmacol., 3:59-74; Thomas et al. (2007) J. Neurochem., 100:503-19). N-α-syn was added to cultures at 100 nmol/L (14.5 ng/ml).

2D Difference Gel Electrophoresis (DIGE) and Image Analysis

Protein prepared from microglial cell lysates was labeled with the respective CyDyes, followed by separation in the first and second dimension, and the gels were scanned using a Typhoon 9400 Variable Mode Imager. Analyses of Cy3-Cy5 image pairs, adjustment to Cy2 control images and detection of protein spots were performed using DeCyder™ software (GE Healthcare). Statistical significance ($P<0.05$) was determined with Biological Variance Analysis (BVA).

Mass Spectrometry

In gel trypsin digestion were performed as previously described (Ciborowski et al. (2004) J. Neuroimmunol., 157:11-6). The resulting peptides were sequenced using Electrospray Ionization-Liquid Chromatography Mass Spectrometry (ESI-LC MS/MS) (Proteome X System with LCQDecaPlus mass spectrometer, ThermoElectron, Inc.) with a nanospray configuration. The spectra were searched against the NCBI.fasta protein database narrowed to murine proteins using SEQUEST search engine (BioWorks 3.1 SR software from ThermoElectron, Inc.). Validation of select proteins identified by LC-MS/MS was performed using immunocytochemistry or Western blot.

Cytotoxicity

The Live/Dead Viability/Cytotoxicity kit (Invitrogen) was performed according to manufacturer's protocol. Images were taken using fluorescence microscopy. Cell counts were normalized as the percentage of surviving cells from unstimulated culture controls.

Statistics

For identification of statistically significant proteins, three-to-four analytical gels were analyzed using BVA software by one-way ANOVA for pair-wise comparison between treatment groups. Differences between means±SEM were analyzed by one-way ANOVA followed by Tukey's post-hoc test for pair-wise comparisons.

Results

Figure 18:
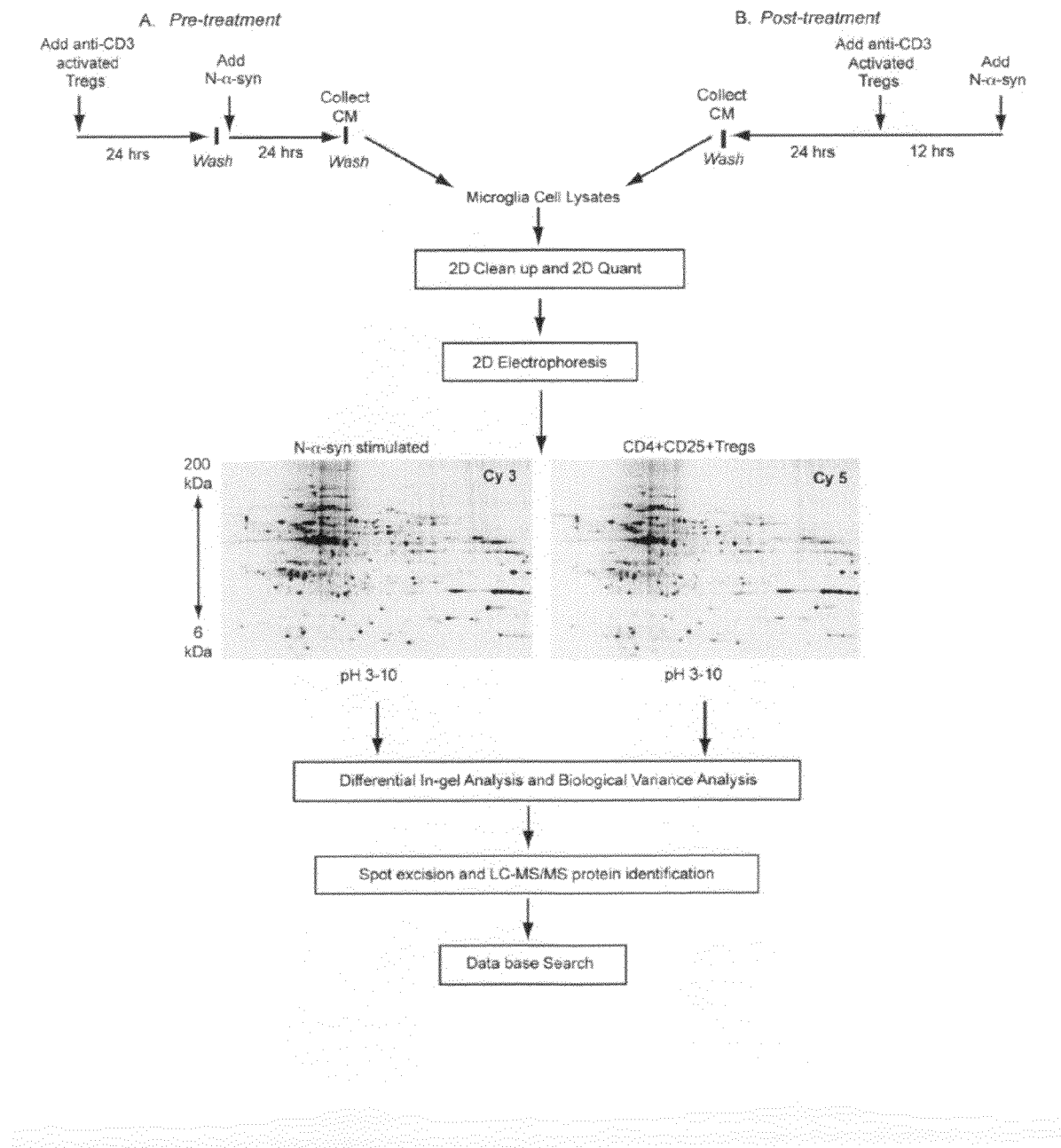
FIG. 18 provides the experimental design for microglial proteomics protein discovery. Microglia were co-cultured for 24 hours with CD4+ CD25+Treg (or Teff) or without as control. Treg (or Teff) were removed from the cultures and the microglia stimulated with aggregated N-α-syn for 24 hours [pre-treatment] to represent asymptomatic disease (A). Alternatively, microglia were stimulated with N-α-syn for 12 hours prior to the addition of Treg [post-treatment] to represent more overt disease (B). Twenty-four hours later microglial cell protein lysates were prepared and subjected to 2D electrophoresis. Decyder™ analysis software was used to match spots and identify expression patterns. Selected protein spots were excised, digested with trypsin and identified by nano-LC-MS/MS peptide sequencing. Database searches were performed using SEQUEST with criteria thresholds set to afford greater than 95% confidence level in peptide identification.

Microglial Protein Profiling Techniques Following N-α-Syn Stimulation and Treg Co-cCultivation It has been demonstrated that aggregated N-α-syn induces activation of the NF-κB pathway in microglia resulting in a robust inflammatory response characterized by increased production of TNF-α, IFN-γ, IL-6, and IL-1β among others (Reynolds et al. (2008) J. Neurochem., 1041504-25; Reynolds et al. (2008) J. Neuroimmune Pharmacol., 3:59-74). Co-culture of microglia with Treg either pre- or post-stimulation significantly attenuates NF-κB activation as well as inflammatory cytokine and superoxide production in response to N-α-syn, whereas Teff exacerbate these responses (Reynolds et al. (2007) J. Leukoc. Biol., 82:1083-94; Reynolds et al. (2009) J. Immunol., 182:4137-49). Therefore, to uncover putative mechanisms for CD4+ T cell-mediated modulation of the microglial phenotype, 2D DIGE was used to identify differences in protein expression of N-α-syn stimulated of microglia alone and cocultured with CD4+ T cells. 2D DIGE analysis of microglial cell lysates was repeated three separate times with three independent cell isolations and cultures. Analyses of 2D images from protein lysates of $15\times10^6$ microglial cells identified an average of approximately 2000 "putative" protein spots. DeCyder™ DIGE Analysis of Cy3-labeled proteins from unstimulated microglia and Cy5-labeled proteins from N-α-syn stimulated microglia obtained from three independent experiments showed an average of 2072 detected spots. Representative analyses revealed 43% differentially expressed protein spots after setting a threshold mode of quantitative differences $\geq 2$ standard deviations (SD). Of those uniquely identifiable spots (582), 28% were upregulated and (318) 15% were downregulated in microglial cell lysates in response to 24 hour stimulation with N-α-syn. To assess how CD4+ T cells modulate the N-α-syn microglial phenotype, microglia were co-cultured with either Treg or Teff for 24 hours either prior to stimulation with N-α-syn (pre-treatment) or following 12 hours of stimulation (post-treatment), and comparisons were made using 2D DIGE and nano-LC-MS/MS peptide sequencing (FIG. 18). Co-cultivation with Treg prior to stimulation with N-α-syn (pre-treatment) altered the microglial phenotypic response to N-α-syn stimulation. An analysis of Cy3-labeled proteins from N-α-syn stimulated microglia and Cy5-labeled proteins from N-α-syn stimulated microglia pre-treated with Treg obtained from three independent experiments showed an average of 2326 detected spots. Representative analysis revealed 31% differentially expressed protein spots after setting a threshold mode of quantitative differences $\geq 2$ SD. Of those uniquely identifiable spots (348), 15% were increased and (365) 16% were decreased in microglial cell lysates in response to Treg treatment prior to N-α-syn stimulation. Pre-treatment with Teff had less robust affects on the microglial phenotype in response to N-α-syn. Of the >2000 uniquely identifiable spots, approximately 32 (1.8%) were decreased and 22 (1.3%) increased in abundance compared to N-α-syn stimulation alone.

To mimic what may occur during overt disease, CD4+ T cells were added to N-α-syn microglial cultures 12 hours post-stimulation. Co-cultivation with Treg post-stimulation with N-α-syn (post-treatment) also altered the microglial phenotype. An analysis of Cy3-labeled proteins from N-α-syn stimulated microglia and Cy5-labeled proteins from N-α-syn stimulated microglia post-treated with Treg obtained from three independent experiments showed an average of 1905 detected spots. Representative analysis revealed 27% differentially expressed protein spots after setting a threshold mode of quantitative differences ≧2 SD. Of those uniquely identifiable spots, (110) 6% were increased and (403) 21% were decreased in microglial cell lysates in response to Treg treatment following N-α-syn stimulation. By comparison, post-treatment with Teff resulted in significant modulation of the microglial proteome in response to N-α-syn stimulation. Of the >2000 uniquely identifiable spots, approximately 318 (15%) were decreased and 325 (16%) were increased in abundance compared to N-α-syn stimulation alone.

Figure 19:
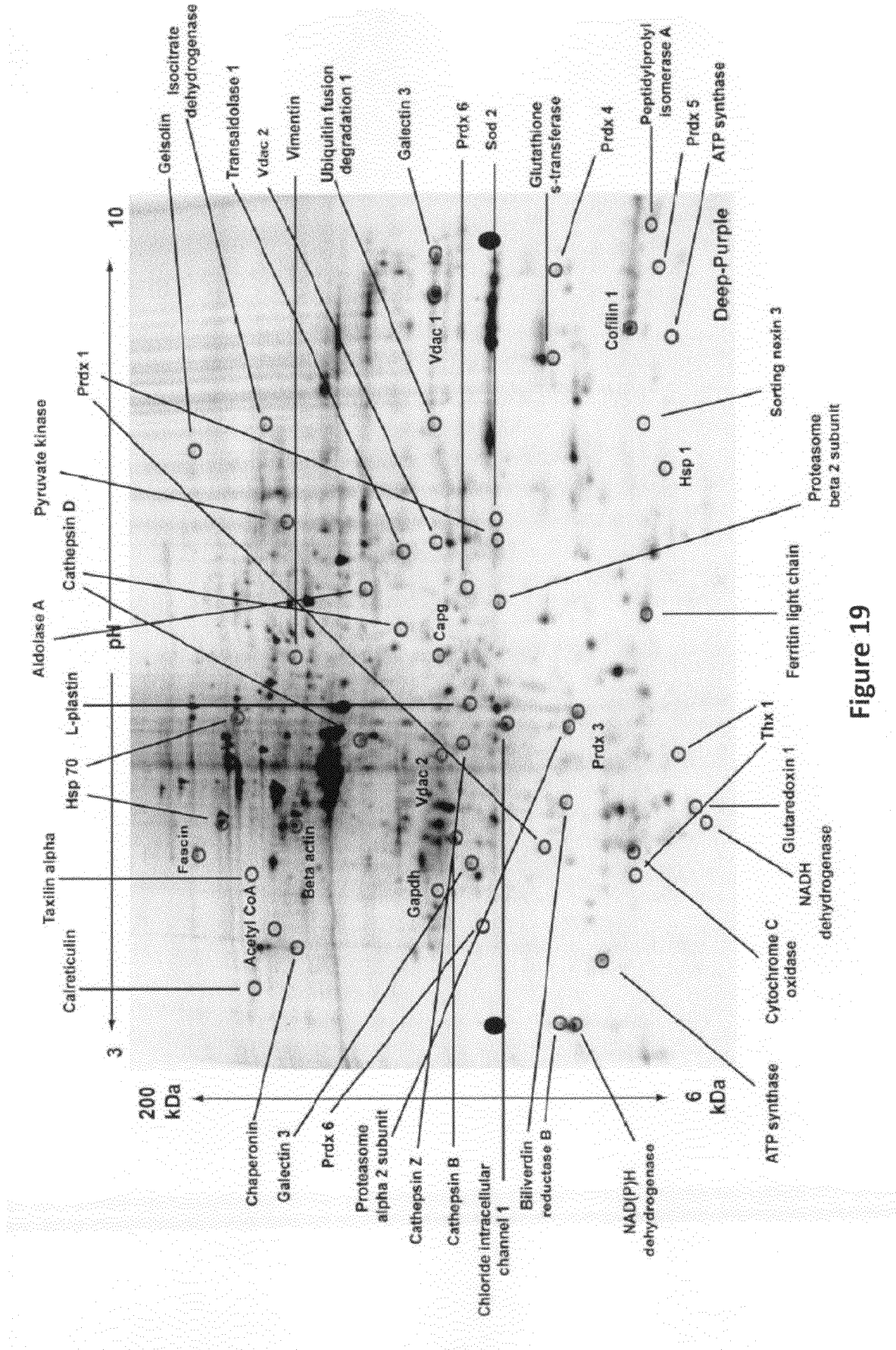
FIG. 19 provides 2D-DIGE of proteins from all experimental groups with matched spots picked for sequencing identifications by nano-LC-MS/MS. A representative preparative gel is shown. Equal amounts of protein were pooled from all experimental groups (unstimulated, N-α-syn-stimulated, pre- and posttreatment with Treg or Teff) and replicates for a total concentration of 450 μg. The pooled sample was applied to a pH gradient strip and separated with isoelectric focusing for the first dimension. For the second dimension, the strip was loaded onto a large format gradient gel and separated based on molecular weight. Following electrophoresis, the gel was fixed and post-stained with Deep Purple for positive detection of protein spots. Circled spots identified by BVA using Decyder™ analysis software were selected for excision. Proteins with the most peptides positively identified within a specific spot are labeled on the gel. (Abbreviations: Prdx, peroxiredoxin; Thx, thioredoxin, Vdac, voltage-dependent anion channel; Sod, superoxide dismutase; Hsp, heat shock protein; Capg, macrophage capping protein; NAD, nicotinamide adenine dinucleotide).

To identify differentially expressed proteins (P<0.05), analyses with BVA software were performed on analytical gels from separate lysates comparing microglia cultures stimulated with media alone, N-α-syn or co-cultured with Treg or Teff to facilitate cross-comparisons between treatments by BVA whereby identified spots were compared for area and peak height (3D plots). The 3D peak of each protein spot, comprised of Cy3-labeled and Cy5-labeled cell lysates, was generated based on the pixel intensity versus pixel area, where peak area correlated with the distribution of the protein spot on the gel. 3D images were obtained using 2D Master Imager and were evaluated independently based on their differential fluorescent signal within a constant area for the spot. Their relative peak volumes were normalized to the total volume of the spot (Cy2-labeled). All analytical gels were cross-compared by BVA and matched to a preparative gel consisting of pooled protein from the experimental groups. The proteins identified consisted of structural or cytoskeletal proteins, regulatory proteins, redox-active proteins and enzymes. FIG. 19 shows the location of these proteins on the preparative gel selected for LC-MS/MS sequencing.

N-α-syn Stimulation and the Microglial Proteome

Figure 20:
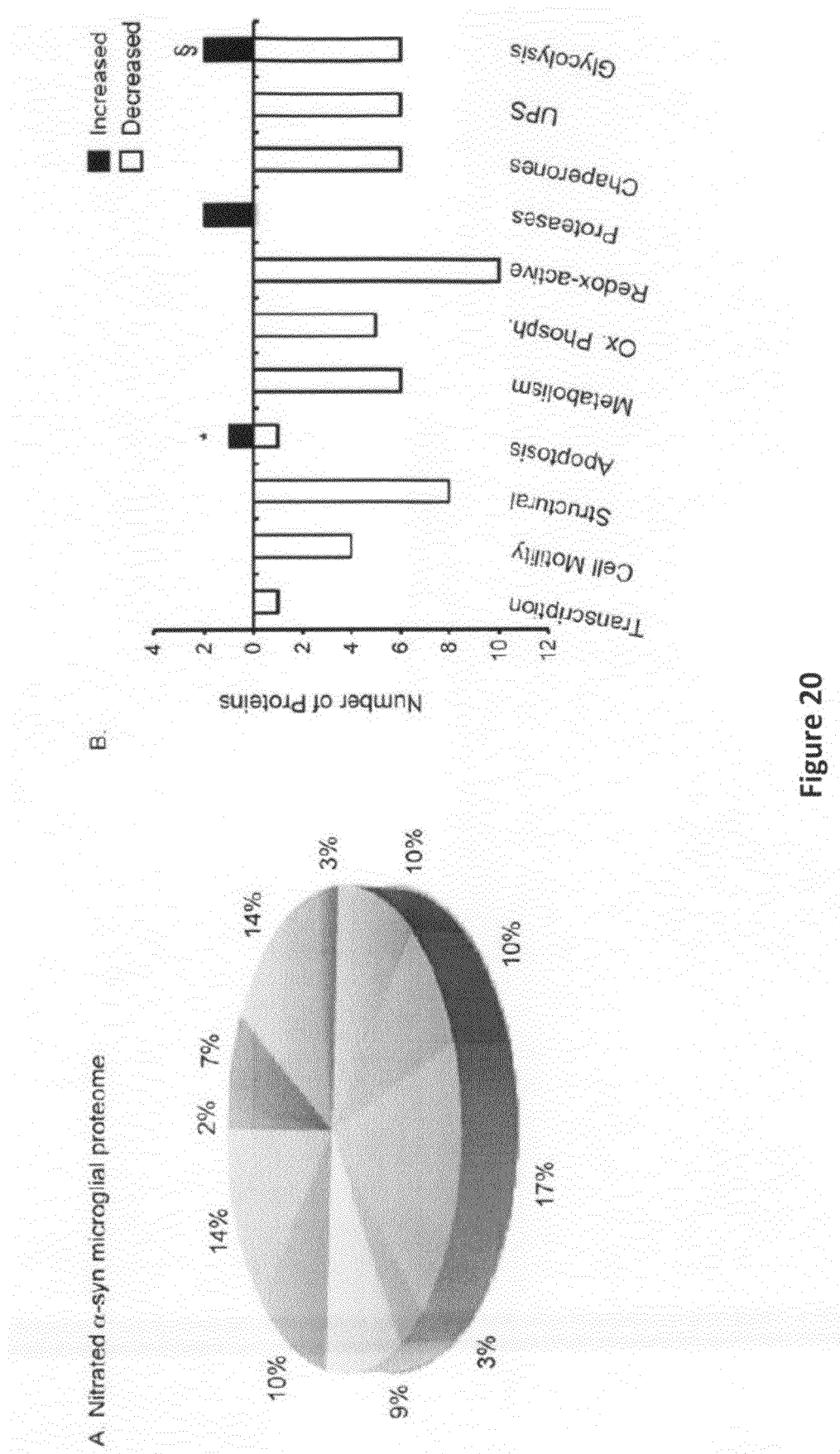
FIG. 20 E provides the proportion of microglial proteins differentially expressed in response to N-α-syn following Treg post-treatment and the relative expression trends are shown in FIG. 20F. Categories associated with metabolism ([#]phosphoglycerate mutase 1 increased; aldolase 1 and aldehyde dehydrogenase 2 decreased), oxidative phosphorylation (§ATP synthase D increased; H+-transporting two-sector ATPase alpha chain decreased), and chaperones ([#]cyclophilin A increased; protein disulfide isomerase decreased) consisted of both increased and decreased expression of proteins.
Figure 20:
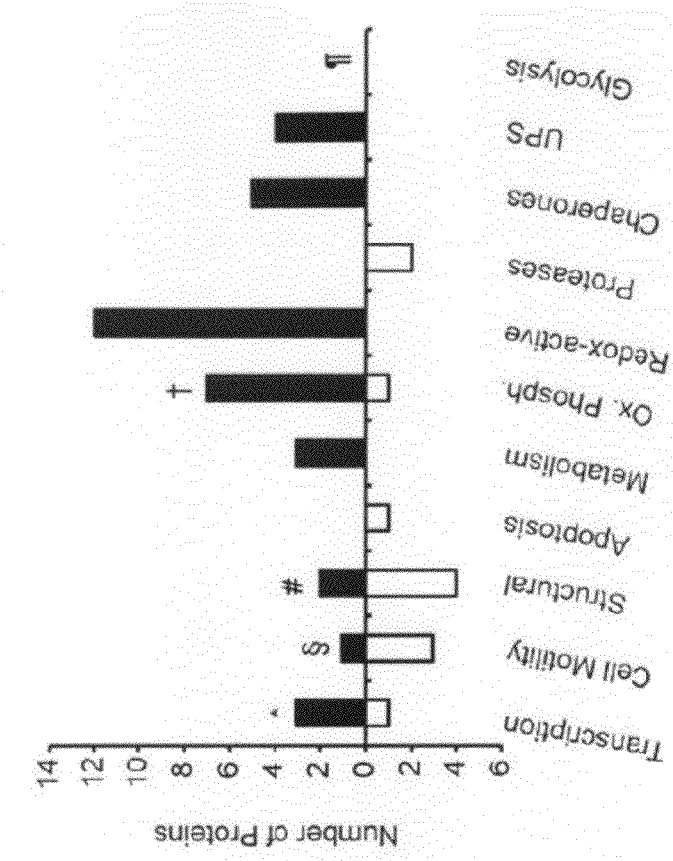
Figure 20:
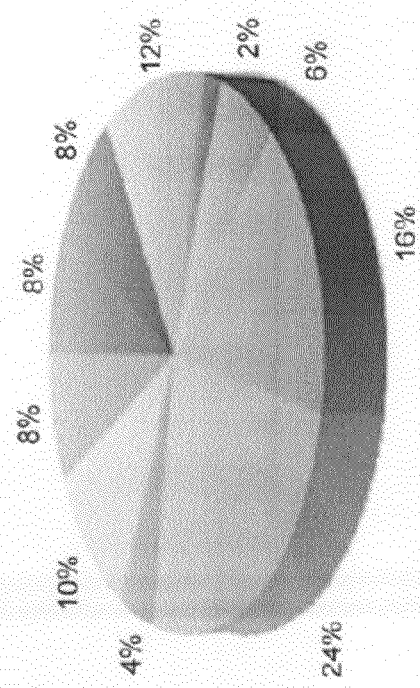
Figure 20:
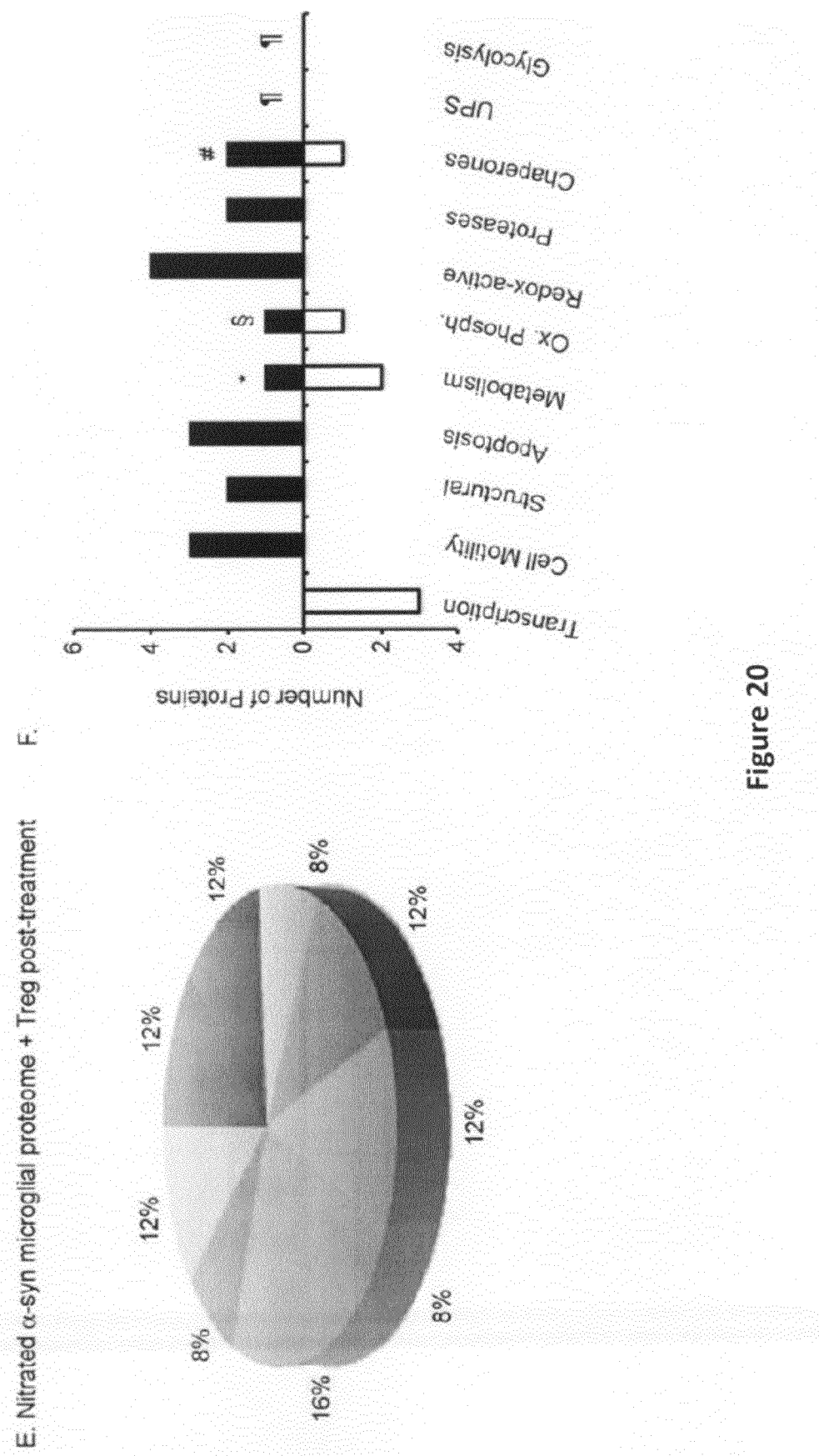

It has been demonstrated that N-α-syn is capable of inducing the temporal activation of a neurotoxic microglial phenotype (Reynolds et al. (2008) J. Neurochem., 104:1504-25; Reynolds et al. (2008) J. Neuroimmune Pharmacol., 3:59-74). To extend these works, the time course of activation was extended from 2 hours, 4 hours, and 8 hours to 24 hours for the current study. FIGS. 22A-22G shows proteins differentially expressed in microglia that were stimulated in media alone or with N-α-syn. Proteins were considered identified with high confidence with at least two peptides sequenced and met the threshold peptide criteria. Such threshold criteria have been determined previously to result in a 95% confidence level in peptide identification (Ciborowski et al. (2007) Virology 363: 198-209; Ricardo-Dukelow et al. (2007) J. Neuroimmunol., 185:37-46). The categories of proteins included regulatory, cytoskeleton/structural, enzymes, mitochondrial, redox-active and others. FIG. 20A shows the relative percentages of proteins within each classification based on protein function that were modulated by N-α-syn stimulation and expression trends.

A majority of the proteins positively identified by mass spectrometry were decreased in expression. A large percentage of the proteins that were decreased in response to N-α-syn stimulation following 24 hours were cytoskeletal associated including vimentin, cofilin 1, beta-actin and alpha-tubulin (FIGS. 22A-22G). N-α-syn stimulation also resulted in decreased expression of proteins involved in protein processing, transport, and folding. These included cryptochrome 2, 14-3-3 zeta, and annexin A1, as well as several molecular chaperones including heat shock protein (Hsp) 10, Hsp 60, and Hsp 70. Moreover, stimulation with N-α-syn decreased expression of proteins associated with the ubiquitin-proteasome system (UPS) greater than 1.5-fold compared to unstimulated microglia (FIGS. 22A-22G). Several proteins associated with mitochondrial function and redox biology were also decreased as a result of stimulation with N-α-syn. Of interest, proteins of the electron transport chain (ETC), specifically complex V involved in adenosine triphosphate (ATP) synthesis, were decreased in expression. Redox-active proteins were also decreased following 24 hours of exposure to N-α-syn including superoxide dismutase (Sod)1, biliverdin reductase B, peroxiredoxin (Prdx) 1 and glutaredoxin 1 (FIGS. 22A-22G). Other proteins decreased following stimulation with N-α-syn stimulation were metabolic proteins such as acetylcoenzyme A and aldehyde dehydrogenase, and proteins involved in glycolysis such as alpha enolase, pyruvate dehydrogenase, and pyruvate kinase (FIGS. 22A-22G). Despite the even-distribution of up- and down-regulated proteins identified in the initial analysis, many of the proteins that were increased in expression did not reach the confidence interval threshold for adequate identification by mass spectrometry. Nonetheless, those identified included lysosomal proteases cathepsins B and D, gelsolin implicated in inflammation and proteins involved in catabolism including aldo-keto reductase family 1 member B8 and catechol o-methyltransferase (FIGS. 22A-22G).

Treg-microglial Co-cultivation Followed by N-α-Syn Stimulation (Pre-treatment)

To simulate preclinical disease and assess putative mechanisms for early affects of CD4+ T cells on the microglial phenotype in response to N-α-syn, microglial cells were co-cultured with CD3-activated CD4+ T cells for 24 hours prior to exposure to N-α-syn. FIGS. 22H-22M show those proteins differentially expressed in microglia stimulated with N-α-syn alone or pre-treated with Treg. The relative percentages of proteins within each classification based on protein function that were modulated by Treg pretreatment together with N-α-syn stimulation and expression trends are shown in FIG. 20B. Among the proteomic changes induced by pre-treatment of microglia with Treg prior to N-α-syn stimulation were decreased expression in several cytoskeletal proteins such as β-actin, vimentin, cofilin 1, and gelsolin, involved in regulation of cell motility and vesicle transport. Treatment with Treg also resulted in increased expression of microglial proteins involved in exocytosis such as annexin A1 and annexin A4, and phagocytosis such as L-plastin (FIGS. 22H-22M). In addition, pre-treatment with Treg increased expression of UPS-related proteins including proteasome subunit alpha type-2, proteasome subunit beta type-2, ubiquitin specific protease 19 and ubiquitin fusion degradation. Treatment with Treg also increased the expression of molecular chaperones including HSPs and calreticulin. Whereas lysosomal proteases cathepsins B and D were increased by N-α-syn stimulation alone, microglia pre-treated with Treg showed decreased abundance of the same proteins. Regulatory proteins involved in cellular metabolism (transaldolase 1) and catabolism (α-mannosidase) were increased in Treg pre-treated cultures (FIGS. 22H-22M).

ETC proteins such as nicotinamide adenine dinucleotide (NADH) dehydrogenase (ubiquinone) Fe—S protein-2 of complex I, cytochrome c oxidase of complex III and the subunits that comprise the components of ATP synthase were increased by microglia in response to N-α-syn stimulation following Treg pre-treatment. Changes in the mitochondrial response to Treg were not limited to proteins involved in cellular energetic, but included redox proteins, chaperones, and structural proteins. Other proteins increased as a result of pre-treatment with Treg were mitochondrial redox-active proteins including peroxiredoxins, Sod 1, Sod 2, thioredoxin (Thrx) 1 and catalase. In addition, cytoplasmic redox-active proteins were also increased including Prdx 1, biliverdin reductase B and glutaredoxin 1 (FIGS. 22H-22M).

Cross-comparison of Teff pre-treatments was facilitated by the BVA module to compare protein expression trends. In contrast to pre-treatment with Treg, pre-treatment with Teff did not alter the expression of structural proteins including cofilin 1 and 2, taxilin alpha or beta actin in response to N-α-syn stimulation. Expression of lysomal proteases including cathepsin B and D were also not changed. In addition, pre-treatment with Teff did not affect expression of redox-active proteins such as Prdx 5, cytochrome c reductase, Thrx 1, or biliverdin reductase B. However, enzymatic proteins that were involved in glycolysis and metabolism were decreased in expression following Teff pre-treatment included pyruvate kinase M, phosphoglycerate kinase and aldolase A. Proteins of the ETC were also decreased including ATP synthase (Complex V). Compared to N-α-syn stimulation alone, Teff pretreatment resulted in greater than 1.5 fold increased expression of voltage-dependent anion channel-1 (Vdac-1), the interferon α/β receptor, and Prdx 1, whereas Hsp 90, chaperonin, galectin 3 and gelsolin were decreased greater than 1.5 fold in expression.

N-α-syn Stimulation Followed by Treg-microglial Co-cultivation (Post-treatment)

For comparison of the microglial phenotype after commitment to activation by N-α-syn stimulation and modulation by CD3-activated CD4+ T cells, microglia were first stimulated with N-α-syn for 12 hours prior to the addition of Treg or Teff for an additional 24 hours and the T cells removed prior to microglial cell lysis. FIGS. 22N-22Q show those proteins differentially expressed in microglia stimulated with N-α-syn alone or post-treated with Treg. The relative percentages of proteins within each classification based on protein function that were modulated by Treg post-treatment together with N-α-syn stimulation and expression trends is shown in FIG. 20C.

Similar proteins were affected by post-treatment with Treg as with pre-treatment; interestingly, some exhibited opposite expression patterns observed after pre-treatment with Treg. Akin to pre-treatment, post-treatment with Treg yielded increased redox-active protein expression by activated microglia including Sod1 and Prdx1 and 5. Several proteins differentially expressed in the pre-treatment analysis were also identified in post-treatment analysis, but were expressed in opposite directions, including increased expression of structural proteins involved in cell motility, such as β-actin and γ-actin, decreased expression of mitochondrial proteins including ETC complex V, and decreased expression of L-plastin (FIGS. 22N-22Q). Induction of pro-apoptotic protein expression was observed and included increased expression of apoptosis-associated speck-like protein containing a caspase recruitment domain, gelsolin, eukaryotic translation elongation factor 1, and cathepsins B and D. Decreased expression of proteins involved in cellular metabolism such as aldolase I and aldehyde dehydrogenase 2 was also observed in response to Treg post-treatment (FIGS. 22N-22Q).

Cross-comparison of protein expression trends following post-treatment with Teff revealed that in contrast to pre-treatment, post-treatment with Teff increased expression of redox-active proteins including Prdx 1, Thrx 1, and cytochrome c oxidase in N-α-syn stimulated microglia compared to N-α-syn stimulation alone. Ferritin light chain, Hsp 70, and transaldolase 1 were also increased. Similar to pre-treatment, expression of cathepsins B and D were not affected. Moreover, expression of proapoptotic proteins was not affected with Teff post-treatment.

Validation of Protein Identification and Biological Significance

Figure 21:
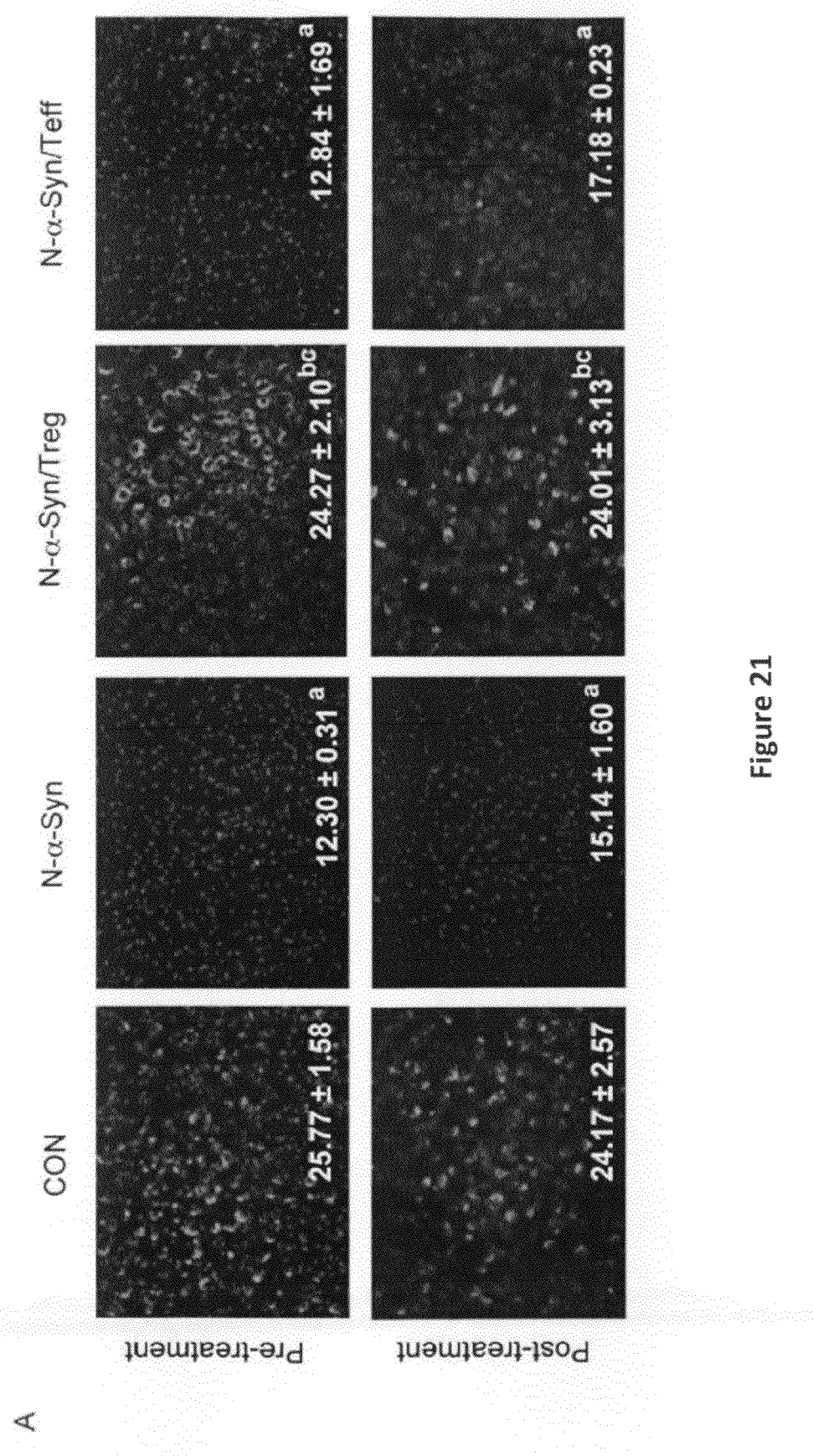
FIGS. 21A-21D demonstrate that Treg modulate microglial inflammation to attenuate the neurotoxic phenotype of N-α-syn stimulated microglia.
Figure 21:
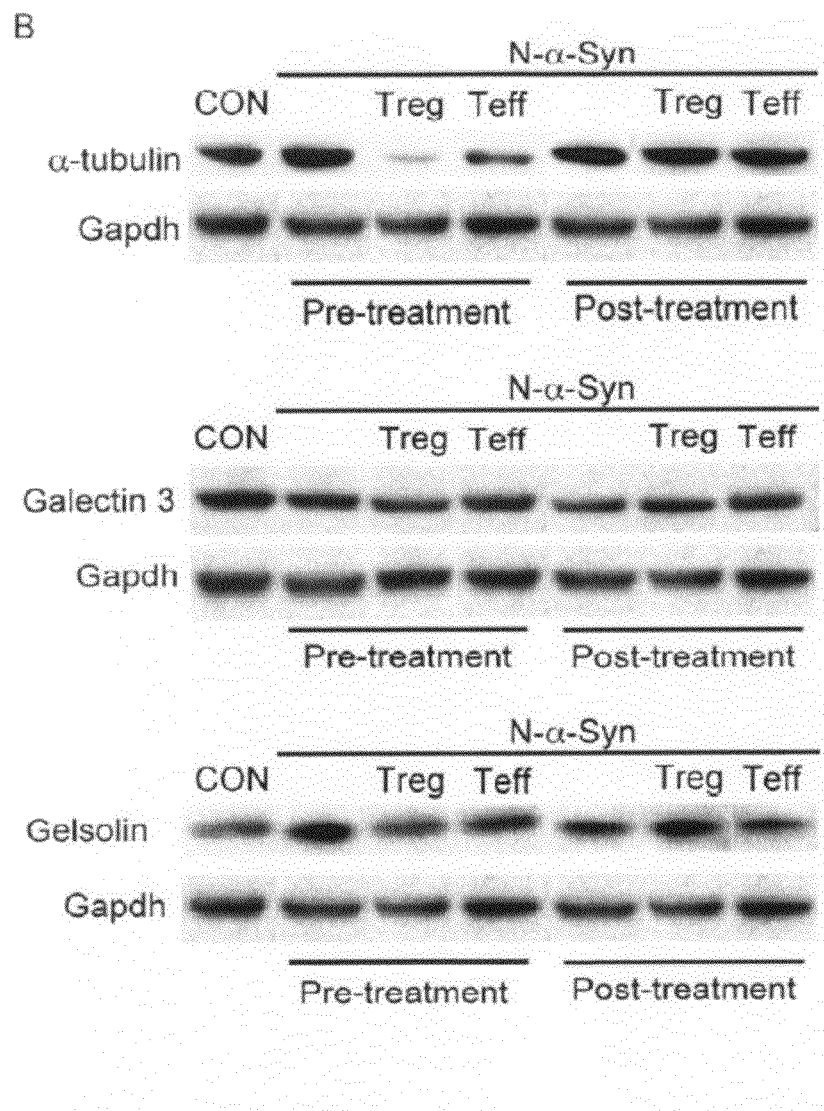
Figure 21:
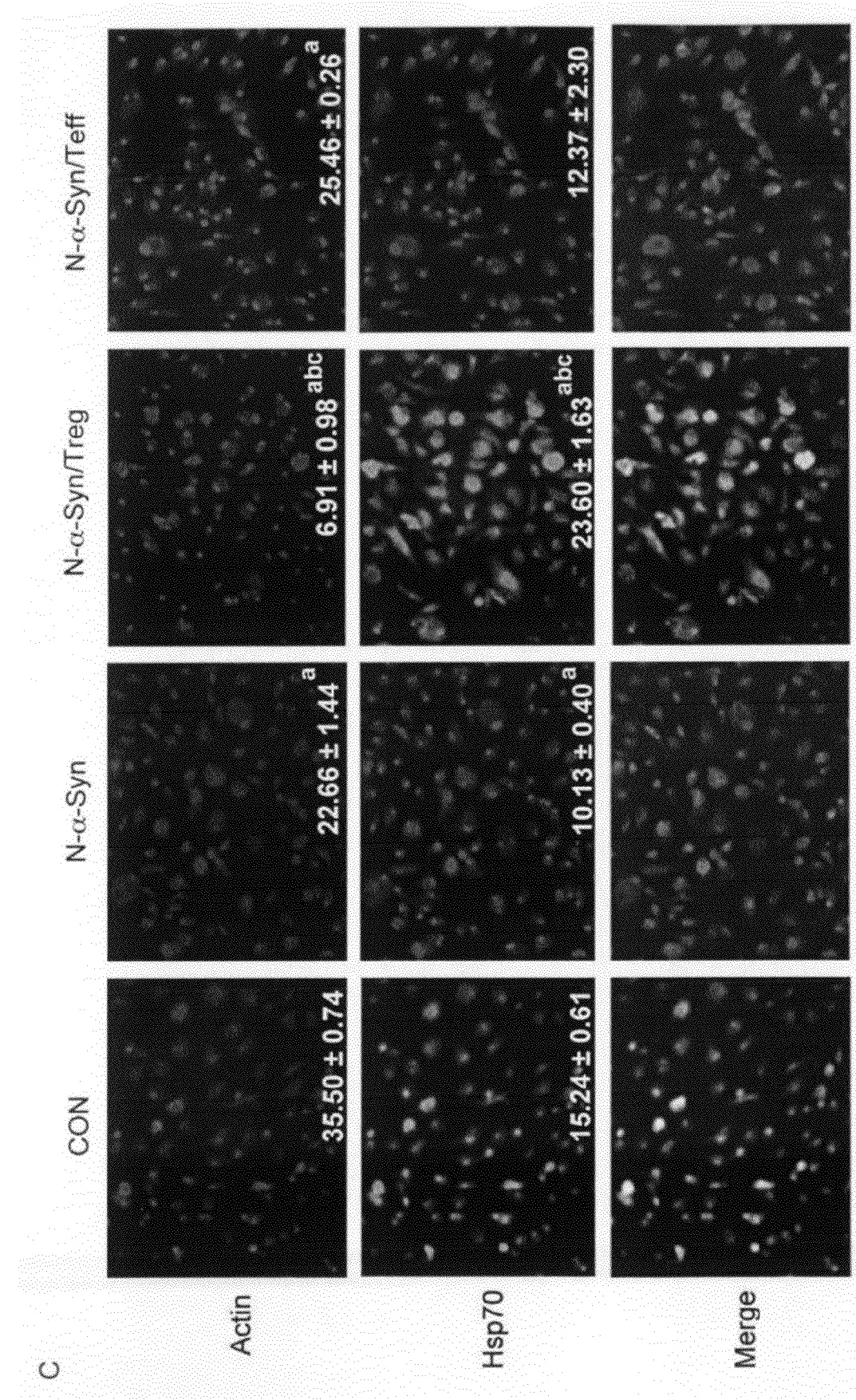
Figure 21:
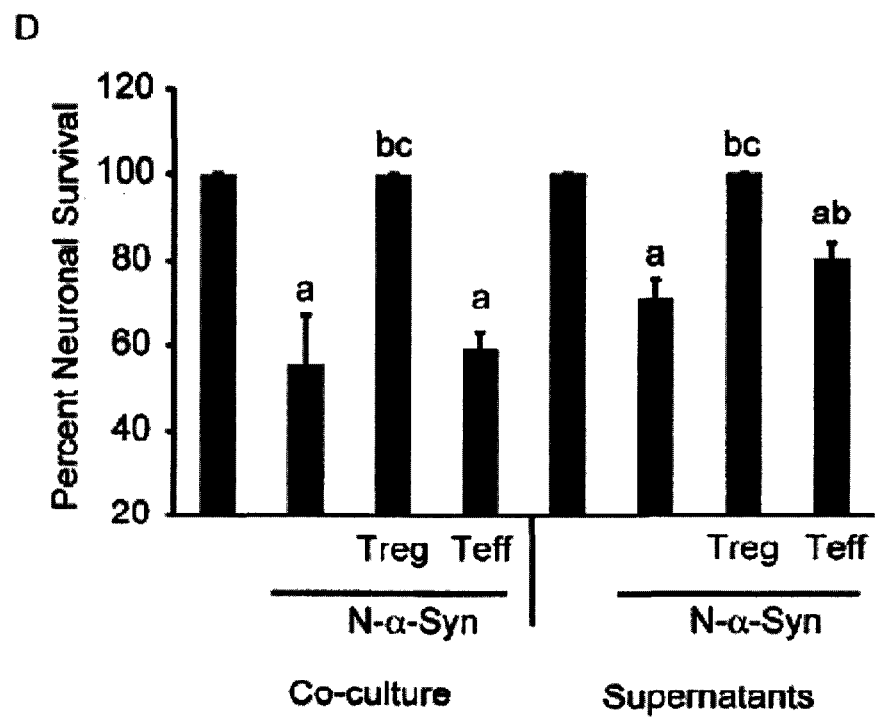

Immunocytochemistry and Western blot analyses were used to validate protein expression trends identified in the proteomic analyses. Immunoflourescent cytochemistry revealed that stimulation with N-α-syn significantly reduced Prx1 expression in microglial cells compared to unstimulated microglia. In contrast, Treg pre-treatment protected against a decrease in Prx1 expression (FIG. 21A). In comparison, post-treatment with Treg rescued microglial Prx1 expression and restored expression levels to near 100% of the unstimulated control. The effect of Teff was more variable and depended on the temporal engagement of Teff with stimulated microglia. Pre-treatment with Teff did not effectively alter Prx1 expression in response to N-α-syn stimulation, however Prx1 expression appeared to be partially rescued following post-treatment with Teff although this did not reach statistical significance.

Western blot validation for cytoskeletal and inflammatory proteins that were involved both in cell mobilization as well as survival, confirmed expression trends of select proteins following different culture conditions (FIG. 21B). Expression of alpha-tubulin was decreased nearly 6-fold following Treg pre-treatment, and compared to a 1.5 fold increase by N-α-syn stimulation alone. In comparison, alpha tubulin expression in N-α-syn-stimulated microglia following Teff pre-treatment was reduced by 2-fold. Post-treatment with Treg or Teff failed to alter alpha-tubulin expression levels in N-α-syn stimulated microglia. Analysis of gelsolin confirmed the increased expression in N-α-syn stimulated microglial lysates compared to control (1.5 fold). Pre-treatment with Treg reduced gelsolin expression to control levels, while, post-treatment increased gelsolin expression compared to N-α-syn stimulation alone. Albeit pre-treatment with Treg had no effect on galectin 3 expression, post-treatment with Treg resulted in a 1.4 fold increase compared to N-α-syn stimulation alone. No change in expression of gelsolin or galectin 3 was detected in response to Teff treatment by Western blot.

Immunofluorescence cytochemistry for actin and Hsp70 also confirmed differential expression of these proteins following N-α-syn stimulation and pre-treatment with CD4+ T cells. Whereas pretreatment with Treg significantly decreased fluorescence intensity of beta-actin expression in response to N-α-syn stimulation, expression of Hsp70 was increased compared with N-α-syn stimulation alone to levels and exceeded those observed in unstimulated controls. By comparison, pre-treatment with Teff had no observed affect on either actin or Hsp70 expression compared with N-α-syn stimulation alone (FIG. 21C).

Deleterious microglial activation is postulated to affect a neurodegenerative process in PD. For this reason, suppression of microglial activation by Treg may be responsible for the profound protection observed in vivo (Reynolds et al. (2007) J. Leukoc. Biol., 82:1083-94). To investigate whether phenotypic modulation of microglia by Treg co-culture affected neuronal survival, an in vitro model of microglia-mediated cytotoxicity was established using N-α-syn-activated microglia and the dopaminergic cell line MES23.5. A 56% loss of MES23.5 cells was observed after co-culture for 24 hours with N-α-syn stimulated microglia compared to control cocultures of MES23.5 with unstimulated microglia (FIG. 21D). In contrast, co-culture of N-α-syn stimulated microglia with Treg inhibited microglial-mediated MES23.5 cytotoxicity, while activated Teff afforded no cytotoxic protection. These data suggested that Treg modulation of microglia attenuates the neurocytotoxic responses mediated by activated microglia. In addition, supernatants from microglia stimulated with N-α-syn alone or N-α-syn and cultured in the presence of Teff were cytotoxic to MES23.5 cells, whereas neurocytotoxicity was abrogated in supernatants from stimulated microglia co-cultured with Treg. Surprisingly, there was less cytotoxicity induced from culture supernatants from N-α-syn microglia treated with Teff than seen in supernatants from N-α-syn microglia alone. These data demonstrate the potential of Tregs to suppress cytotoxicity afforded by N-α-syn-activated microglia, and suggest that direct modulation of microglial responses provides a primary mechanism for Treg-mediated neuronal protection.

EXAMPLE 4

Parkinson's disease (PD) is a progressive neurodegenerative disorder characterized by resting tremor, rigidity, bradykinesia, and gait disturbances (Fahn et al. (1998) Mov. Disord., 13:759-767; Mayeux, R. (2003) Annu. Rev. Neurosci., 26:81-104; Fahn et al. (2004) NeuroRx., 1:139-154). Presently, 1.5 million Americans are afflicted. Disease incidence rises with increasing age, with 120/100 000 contracting PD over the age of 70 (Dauer et al. (2003) Neuron 39:889-909). Pathologically, PD is characterized by the progressive loss of dopaminergic neuronal cell bodies in the substantia nigra pars compacta (SNpc) and their termini in the dorsal striatum (Hornykiewicz et al. (1987) Adv. Neurol., 45:19-34). These pathological findings commonly parallel microglial activation observed in association with deposits of aggregated alpha synuclein (α-syn) in intracellular inclusions, known as Lewy bodies (LB) (Spillantini et al. (1997) Nature 388:839-840; Croisier et al. (2005) J. Neuroinflammation 2:14). Although host genetics and environmental factors affect the onset and progression of PD (Tanner, C. M. (1992) Occup. Med., 7:503-513) significant clinical, epidemiologic, and experimental data also support a role for microglial inflammation in disease pathogenesis (Formo et al. (1992) Prog. Brain Res., 94:429-436; Banati et al. (1998) Mov. Disord., 13:221-227; McGeer et al. (1998) Alzheimer Dis. Assoc. Disord., 12(Suppl. 2):S1-S6; Mirza et al. (2000) Neuroscience, 95:425-432; Cicchetti et al. (2002) Eur. J. Neurosci., 15:991-998; Block et al. (2005) Prog. Neurobiol., 76:77-98; Hong, J. S. (2005) Ann. NY Acad. Sci., 1053:151-152; Wang et al. (2005) Mech. Ageing Dev., 126:1241-1254).

The mechanisms underlying microglial activation in PD and how it affects neuronal survival is incompletely understood. One line of investigation is that neuronal death itself drives microglial immune responses (Giasson et al. (2000) Science 290:985-989; Przedborski et al. (2001) J. Neurochem., 76:637-640; Mandel et al. (2005) Ann. NY Acad. Sci., 1053:356-375). Alternatively, it has been proposed that activation occurs as a consequence of release of aggregated proteins from the cytosol or within LB to the extracellular space. In this way, the death of dopaminergic neurons leads to release of modified protein aggregates that activate microglia inciting a lethal cascade of neuroinflammation and neuronal demise (Zhang et al. (2005) FASEB J., 19:533-542; Wersinger et al. (2006) Curr. Med. Chem., 13:591-602). Several lines of experimental evidence support this contention (Spillantini et al. (1997) Nature 388:839-840; Goedert, M. (1999) Philos. Trans. R. Soc. Lond. B Biol. Sci., 354:1101-1118; Giasson et al. (2000) Science 290:985-989; Kakimura et al. (2001) Eur. J. Pharmacol., 417:59-67; Croisier et al. (2005) J. Neuroinflammation 2:14; Lee et al. (2005) J. Neurosci. 25:6016-6024). First, aberrant expression of α-syn and PD pathogenesis are linked. This is derived from the discovery that mutations and multiple copies of the gene encoding α-syn (SNCA and PARK1) are linked to familial early onset PD (Kruger et al. (1998) Nat. Genet., 18:106-108; Spira et al. (2001) Ann. Neurol., 49:313-319; Zarranz et al. (2004) Ann. Neurol., 55:164-173; Singleton et al. (2003) Science 302:841; Chartier-Harlin et al. (2004) Lancet 364:1167-1169). Second, oxidation and nitration of α-syn leads to formation of aggregates and filaments that comprise LB (Giasson et al. (2000) Science 290, 985-989; Souza et al. (2000) J. Biol. Chem., 275:18344-18349). Third, portions of α-syn are secreted rendering it more vulnerable to aggregation (Lee et al. (2005) J. Neurosci., 25:6016-6024) and oxidative modification (Kakimura et al. (2001) Eur. J. Pharmacol., 417:59-67). Fourth, α-syn itself can activate microglia, inducing reactive oxygen species (ROS) (Thomas et al. (2007) J. Neurochem., 100:503-519) and subsequent neurotoxicity (Zhang et al. (2005) FASEB J., 19:533-542). Fifth, microglial products including cytokines, chemokines, excitotoxins, and proteins of the classical complement cascade affect a broad range of neurological diseases (McGeer et al. (1998) Alzheimer Dis. Assoc. Disord., 12(Suppl. 2):S1-S6; Bal-Price et al. (2001) J. Neurosci., 21:6480-6491; Liu et al. (2003) J. Pharmacol, Exp. Ther., 304:1-7; Block et al. (2005) Prog. Neurobiol., 76:77-98). Sixth, endogenous activators of microglia show a neuroinflammatory fingerprint reflective of what can occur during PD (Zhou et al. 2005; McLaughlin et al. 2006). Lastly, attenuation of microglial activation can protect up to 90% of dopaminergic neurons in PD animal models (Du et al. (2001) Proc. Natl. Acad. Sci. USA, 98:14669-14674; Teismann et al. (2003) Proc. Natl. Acad. Sci. USA, 100:5473-5478; Wu et al. (2002) J. Neurosci., 22:1763-1771; Teismann et al. (2001) Synapse 39:167-174; Kurkowska-Jastrzebska et al. (2004) Int. Immunopharmacol., 4:1307-1318; Choi et al. (2005) J. Neurosci., 25:6594-6600; Vijitruth et al. (2006) J. Neuroinflammation 3:6).

Based on these observations, changes in the microglial transcriptome and proteome as a consequence of the cells' engagement with nitrated and aggregated α-syn (N-α-syn) was investigated. N-α-syn stimulation of microglia induced morphological cell transformation and neurotoxic secretions. A N-α-syn-activated 'microglial signature' was determined by gene microarrays, 2D differential in-gel electrophoresis (DIGE), and by cytokine profiling. N-α-syn induced a microglia inflammatory phenotype characterized by the expression of neurotoxic and neuroregulatory factors. Importantly, the inflammatory signature seen in laboratory assays were mirrored in parallel tests performed on postmortem brain tissues from PD patients. These observations, taken together, indicate a 'putative' role for N-α-syn-activated microglia in disease.

Materials and Methods

Parkinson's Disease Brain Tissues

Autopsy materials from the substantia nigra (SN) and basal ganglia (BG; caudate nucleus and putamen) of 10 patients who died with signs and symptoms of PD, three with Alzheimer's disease (AD), and 10 age-matched controls were secured from the National Research Brain Bank Tissue Consortium. The 10 controls ranged in age from 62 to 91 and died of diseases unrelated to neurological impairments. This included atherosclerotic and metabolic diseases, infections, and cancer.

An antibody to N-α/β-syn (clone nSyn12, mouse ascites; Upstate, Charlottesville, Va.) that recognizes nitrated human N-α-syn (14.5 kDa) and N-α-syn (17 kDa) was used for immunoprecipitation. Samples of SN from control, AD, and PD autopsy brain tissues were homogenized in ice-cold radioimmunoprecipitation (RIPA) buffer, pH 7.4 and centrifuged at 10 000 g for 10 minutes at 4° C. to remove cellular debris. Protein A/G PLUS-agarose beads (Santa Cruz Biotechnology Inc., Santa Cruz, Calif., USA) were added to 1 mg total cellular protein and incubated for 30 minutes at 4° C. Beads were pelleted by centrifugation at 1000 g for 5 minutes at 4° C. The supernatants were incubated overnight at 4° C. with 2 μg of primary antibody, then with Protein A/G PLUS-agarose beads for 6 hours on a rotating device at 4° C. Immunoprecipitates (IP) were collected after centrifugation at 1000 g for 5 minutes at 4° C., washed with phosphate-buffered saline (PBS), and resuspended in 20 μL of 1× electrophoresis sample buffer.

Nitrated-α-Syn IP (20 μL) were fractionated by 16% Tricine sodium dodecyl sulfate-polyacrylamide gel electrophoresis (PAGE) (Jule Inc., Milford, Conn., USA and BIO-RAD Laboratories Inc., Los Angeles, Calif., USA) at constant voltage for 1.5 hours. The gels were fixed and stained with Coomasie Blue to visualize protein bands. Bands corresponding to the molecular weights encompassing 14.5 kDa (α-syn) were excised, digested by trypsin, column purified, and sequenced by liquid chromatography-tandem mass spectrometry (LC-MS/MS) for protein validation. Sequenced peptides were distinguished by peptide matches to the human α-syn sequence (NCBI Accession:AA108276).

Purification, Nitration, and Aggregation of Recombinant Mouse α-Syn

Purification, nitration, and aggregation of recombinant mouse α-syn were performed as previously described (Thomas et al. (2007) J. Neurochem., 100:503-519). Five individual lots of α-syn were tested for endotoxin by *Limulus amebocyte* lysate tests and all were below the limit of detection for endotoxin (<0.05 endotoxin units). Amino acid analysis to determine protein concentration using HPLC was performed by the University of Nebraska Medical Center Protein Structure Core Facility. Proteins were separated by PAGE using 4-12% NuPAGE gels (Invitrogen, Carlsbad, Calif., USA). After electrophoresis, the gels were transferred onto polyvinylidene fluoride (PVDF) membranes (Millipore, Billerica, Mass., USA) and probed with primary mouse IgG1 anti-α-syn (1:500; Transduction Laboratories/BD Biosciences, Franklin Lakes, N.J., USA) or primary rabbit IgG antinitrotyrosine (1: 2000; Upstate). Signal was detected with horseradish peroxidase-conjugated anti-mouse IgG or anti-rabbit IgG (both from Zymed Laboratories, South San Francisco, Calif., USA) using chemiluminescence systems (SuperSignal® West Pico Chemiluminescent Substrate; Pierce Biotechnology Inc., Rockford, Ill., USA). For visualization of the protein by atomic force microscopy (AFM), samples were deposited on mica, glued to a glass slide, and dried under argon gas flow. The image was taken in air, height, amplitude, and phase modes using a Molecular Force Probe 3D controller (Asylum Research Inc., Santa Barbara, Calif., USA).

Isolation, Cultivation, and N-α-syn Activation of Murine Microglia

Microglia from C57BL/6 mice neonates (1-to-2-days old) were prepared according to well described techniques (Dobrenis 1998). All animal procedures were in accordance with National Institutes of Health guidelines and were approved by the Institutional Animal Care and Use Committee of the University of Nebraska Medical Center. Brains were removed and placed in Hanks' Balanced Salt Solution at 4° C. The mixed glial cells were cultured for 7 days in Dulbecco's Modified Eagle's Medium (DMEM) containing 10% fetal bovine serum (FBS), 10 μg/mL gentamicin, and 2 μg/mL macrophage colony stimulating factor (Wyeth Inc., Cambridge, Mass., USA). To obtain homogenous microglial cell populations, culture flasks were gently shaken and non-adherent microglia were transferred to new flasks. The flasks were incubated for 30 minutes to allow the microglia to adhere, and loose cells removed by washing with DMEM. Microglia were plated at $2\times10^6$ cells per well in six-well plates in DMEM containing 10% FBS, 10 μg/mL gentamicin, and 2 μg/mL macrophage colony stimulating factor. One week later, cells were stimulated with 100 nmol/L of aggregated N-α-syn/well or no stimulation for 4 hours. Media were replaced with serum-free DMEM without phenol red or other additives (Invitrogen) and incubated for 24 hours in a 37° C., 5% $CO_2$ incubator.

Inflammatory Genomic and PCR Assays

RNA from N-α-syn stimulated primary murine microglial cells and unstimulated control was extracted with TRIzol® (Invitrogen), column purified (Qiagen, Valencia, Calif., USA), precipitated with ammonium acetate, amplified and labeled using the T7-based TrueLabeling-AMP™ 2.0 kit (Superarray, Frederick, Md., USA). The resultant cRNA was hybridized to an oligo-based microarray for mouse general pathway (Superarray #OMM-014) and nuclear factor-kappa B (NF-κB)-related genes (Superarray #OMM-025). The arrays were washed, incubated sequentially with streptavidin-bound alkaline phosphatase and chemiluminescent substrate before exposure to X-ray film. Subsequent analysis of the microarrays was performed using the GEArray expression analysis suite (Superarray).

Total RNA obtained from analysis of the microglial transcriptome was reverse transcribed with random hexamers and SSII reverse transcriptase (Applied Biosystems, Foster City, Calif., USA). Murine-specific primer pairs were: Ccl2: CCCCAAGAAGGAATGGGTCC (SEQ ID NO: 3) and GGTTGTGGAAAAGGTAGTGG (SEQ ID NO: 4); Il1b: GTTCCTTTGTGGCACTTGGT (SEQ ID NO: 5) and CTAT-GCTGCCTGCTCTTACTGACT (SEQ ID NO: 6); Il10: CAGTTATTGTCTTCCCGGCTGTA (SEQ ID NO: 7) and CTATGCTGCCTGCTCTTACTGACT (SEQ ID NO: 8); Ifng: TTTGAGGTCAACAACAACCCACA (SEQ ID NO: 9) and CGCAATCACAGTCTTGGCTA (SEQ ID NO: 10); and Nos2:5'-GGCAGCCTGTGAGACCTTTG-3' (SEQ ID NO: 11) and 5'-GAAGCGTTTCGGGATCTGAA-3' (SEQ ID NO: 12). TaqMan® gene expression assays specific for murine Tnf, Tnfrsf1a, Stat1, Rela, Bdnf, and Gdnf were purchased from Applied Biosystems, and normalized to glyceraldehyde-3-phosphate dehydrogenase (Gapdh) expression. Tissue samples obtained from PD and control patients were snap frozen on dry ice and stored at −80° C. RNA was prepared from the samples using TRIzol® reagent (Invitrogen) and purified with the RNeasy Mini Kit (Qiagen), prior to cDNA synthesis. Human specific primers for TNF, TNFRSF1A, STAT1, NFKB1, RELA, BDNF, and GDNF were analyzed using TaqMan gene expression assays. Gene expression was normalized to the housekeeping gene Gapdh. Real-time quantitative PCR was performed with cDNA using an ABI PRISM 7000 sequence detector (Applied Biosystems). Reverse SYBR Green I detection system was used, and the reactions generated a melting temperature dissociation curve enabling quantitation of the PCR products.

Cytokine Arrays

Microglia were plated at a density of $2\times10^6$ cells/well in a six-well plate and stimulated with 100 nmol/L aggregated N-α-syn, and 100 ng/mL lipopolysaccharide (LPS, *Escheri-*

*chia coli*; Sigma-Aldrich, St. Louis, Mo., USA) in serum-free media. Fifty microliter aliquots were collected at 8, 24, and 72 hours of incubation in triplicate and frozen at −80° C. For assay, the samples were analyzed using the BD Cytometric Bead Array Mouse Inflammation Kit (BD Biosciences, San Jose, Calif., USA) according to the manufacturer's protocol. Samples of culture supernatants from microglia were diluted 1:3 and 1:10 in assay diluent and analyzed for cytokine concentration with a FACSCalibur flow cytometer (BD Biosciences). Concentrations of cytokines were determined from a standard curve created with serial dilutions of the cytokine standards provided by the manufacturer.

Neurotoxicity Assays

MES23.5 cells were cultured in 75-$cm^2$ flasks in DMEM/F12 with 15 mmol/L HEPES (Invitrogen) containing N2 supplement (Invitrogen), 100 U/mL of penicillin, 100 µg/mL streptomycin, and 5% FBS. Cells were grown to 80% confluence then co-cultured at 1:1 ratio with previously plated microglial cells. To assess cell viability microglia cells were plated at a density of $5\times10^4$ cells on sterile glass coverslips, and co-cultures were prepared with a 1:1 ratio microglia:MES23.5 cells. After 24-48 hours, cells were stimulated with aggregated 100 nmol/L N-α-syn or 100 nmol/L α-syn for 4, 8, 24, and 72 hours. CD11b+ microglial cells were distinguished from MES23.5 cells by APC-conjugated CD11b (1:200; Invitrogen) immunocytochemistry. For tyrosine hydroxylase (TH) cytostaining, cells were fixed in 4% p-formaldehyde, permeablized, and blocked in 2% normal goat serum with 0.25% Triton X-100 in PBS for 30 minutes, and probed with rabbit polyclonal anti-TH (1:1000; EMD Biosciences Inc., San Diego, Calif., USA), followed by FITC goat anti-rabbit IgG. For western blot analysis, 10 lg of protein sample from cell lysates of each treatment group was loaded onto a 12% NuPAGE Bis-Tris gel (Invitrogen). Following transfer onto a PVDF membrane, the membrane was blocked and then probed overnight with anti-TH (1:1000). Signal was detected with horseradish peroxidase-conjugated anti-rabbit IgG (1:10 000; Zymed Laboratories) using chemiluminescence system (SuperSignal® West Pico Chemiluminescent substrate; Pierce Biotechnology Inc.). Densitometric analysis was performed using IMAGEJ software and normalized to β-actin (1:1000; Abcam, Cambridge, Mass., USA). Assays for viable and dead mammalian cells (Live/Dead Viability/Cytotoxicity; Invitrogen) were performed according to manufacturer's protocol. The protocol was revised so that the concentration of each dye was 1 µmol/L to avoid high background. Live cells were distinguished by the uptake of calcein acetoxymethyl ester to acquire a green fluorescence [excitation/emission (ex/em) 495/515 nm], while dead cells acquired a red fluorescence (ex/em 495/635 nm) because of the uptake of ethidium homodimer-1. Cell enumerations were performed using fluorescence microscopy (200· magnification) and a M5 microplate fluorometer (Molecular Devices, Sunnyvale, Calif., USA) (Limit 1 ex/em 490/522 nm and Limit 2 ex/em 530/645 nm). The number of viable MES23.5 cells in each treatment group was normalized as the percentage of surviving cells in unstimulated culture controls.

Protein Purification, 2D DIGE, and DeCyder Analyses

Cell lysates of microglia were prepared with 5 mmol/L Tris-HCl, pH 8.0, 1% 3-[(3-cholamidopropyl)-dimethylammonio]-1-propane sulfonate and a cocktail of protease inhibitors (Sigma-Aldrich). Protein content was quantitated using a DC Protein Assay (BioRad, Hercules, Calif., USA). Factors known to interfere with isoelectric focusing (first dimension separation in 2D sodium dodecyl sulfate-PAGE) such as salts and detergents were removed from cell lysates using the 2D Cleanup kit (GE Healthcare, Piscataway, N.J., USA) according to manufacturer's protocol. Protein concentration was determined using 2D Quant (GE Healthcare). Samples of control and stimulated cell lysates (25 µg of each lysate) were labeled with 400 pmol of CyDyeo 2. A 50 µg protein sample of control cell lysate was labeled with 400 µmol of CyDye 3; and a 50 µg protein sample of stimulated cell lysate was labeled with 400 µmol of CyDye 5. Labeling was performed following the manufacturer's protocols. The samples were pooled, resuspended in rehydration buffer to a total volume of 450 µL, then loaded onto an immobilized pH gradient strip, and left for 18 hours for rehydration. In the first dimension, samples were run in IPGphor and in Ettan DALTsix electrophoresis apparatus (GE Healthcare) for the second dimension. CyDye 3- and CyDye 5-derivatized proteins were detected in gels using a Typhoon 9400 Variable Mode Imager with ex-em filters at 540/590 nm for CyDye 3 dyes and 620/680 nm for CyDye 5 dyes (GE Healthcare). Analysis of CyDye 3-CyDye 5 image pairs, adjustment to CyDye 2 control images, and detection of protein spots with relative spot volumes were performed using DeCyder software (GE Healthcare) to locate and analyze multiplexed samples within the gel. Selected protein spots of interest were excised from the 2D gel using an Ettan Spot Picker. The proteins from gel pieces were digested with trypsin, as described below, and resultant peptides were analyzed using LC-MS/MS system (ThermoElectron Inc., Waltham, Mass., USA). Protein identification was completed using BIOWORKS 3.1 software.

In Gel Tryptic Digestion and Protein Identification by LC-MS/MS

Specific protein spots were excised from the gels by an automated Ettan spot picker. Following column purification (ZipTip CU-18; Millipore) with 50% acetonitrile (ACN), 50 mmol/L $NH_4HCO_3$/50% ACN, and 10 mmol/L $NH_4HCO_3$/50% ACN, gel pieces were dried and incubated with trypsin (100 ng/1L) (Promega, Sunnyvale, Calif., USA) for 12-18 hours. Samples were extracted by 0.1% trifluoroacetic acid/60% ACN, pooled, and dried.

Dried peptide samples were reconstituted in 0.1% formic acid/HPLC-grade water, detected on a ProteomeX LCQ™ DECA XP Plus mass spectrometer (ThermoElectron Inc.), and identified using BIOWORKS 3.1 SR software. Proteins identified by peptides having a Unified Score (BIOWORKS 3.1 SR, ThermoElectron Inc.) greater than 3000 were marked for further analysis.

Nuclear/Cytosol Fractionation

Cell lysates were prepared from SN of PD and control patients by homogenization in PBS. Cells were collected following centrifugation at 500 g for 5 minutes. Cytosol and nuclear fractions were prepared using the Nuclear/Cytosol Fractionation Kit (BioVision, Mountain View, Calif., USA) according to manufacturer's protocol.

Western Blot Assays

Protein was prepared from cell lysates in RIPA buffer supplemented with protease inhibitors (Pierce Biotechnology Inc.). Protease inhibitor cocktail was added to each conditioned media sample fraction prior to processing. Following centrifugation at 10 000 g for 10 minutes, the supernatants were removed and allowed to dialyze against water overnight. Tissue samples obtained from PD and control patients were snap frozen on dry ice and stored at −80° C. Protein lysates were prepared from individual samples through homogenization in RIPA buffer supplemented with protease inhibitors (Pierce Biotechnology Inc.). Protein quantification was performed using the bicinchoninic acid kit (Pierce Biotechnology Inc.). Protein concentration of each sample was determined using a calibration curve generated from purified bovine serum albumin. A total of 20 µg of each sample was loaded onto 4-12% Bis-Tris NuPAGE gels (Invitrogen) and transferred onto PVDF membranes (BioRad). Primary antibodies to calmodulin (1:1000) and 14-3-3σ (1:200) (Millipore), biliverdin reductase (1:5000), thioredoxin (1:2000), β-actin (1:5000), and α-tubulin (1:5000) purchased from Abcam, L-plastin (1:1000), α-enolase (1:1000), glutathione-S-transferase (1:1000), and NF-κB p65 and p50 (1:200) purchased from Santa Cruz Biotechnology Inc. were used for analyses. Blots were probed with the respective horseradish peroxidase-conjugated secondary:antibodies (1:5000; Invitrogen) and detected using SuperSignal® West Pico Chemiluminescent substrate (Pierce Biotechnology Inc.). The intensity of protein bands was quantified using IMAGEJ and normalized to Gapdh (1:5000; Santa Cruz Biotechnology Inc.) level in the same sample.

Statistical Analyses

All values are expressed as mean±SEM. Differences among means were analyzed by Student's t-test or by one-way ANOVA followed by Bonferroni post hoc testing for pair-wise comparison.

Results

Figure 23:
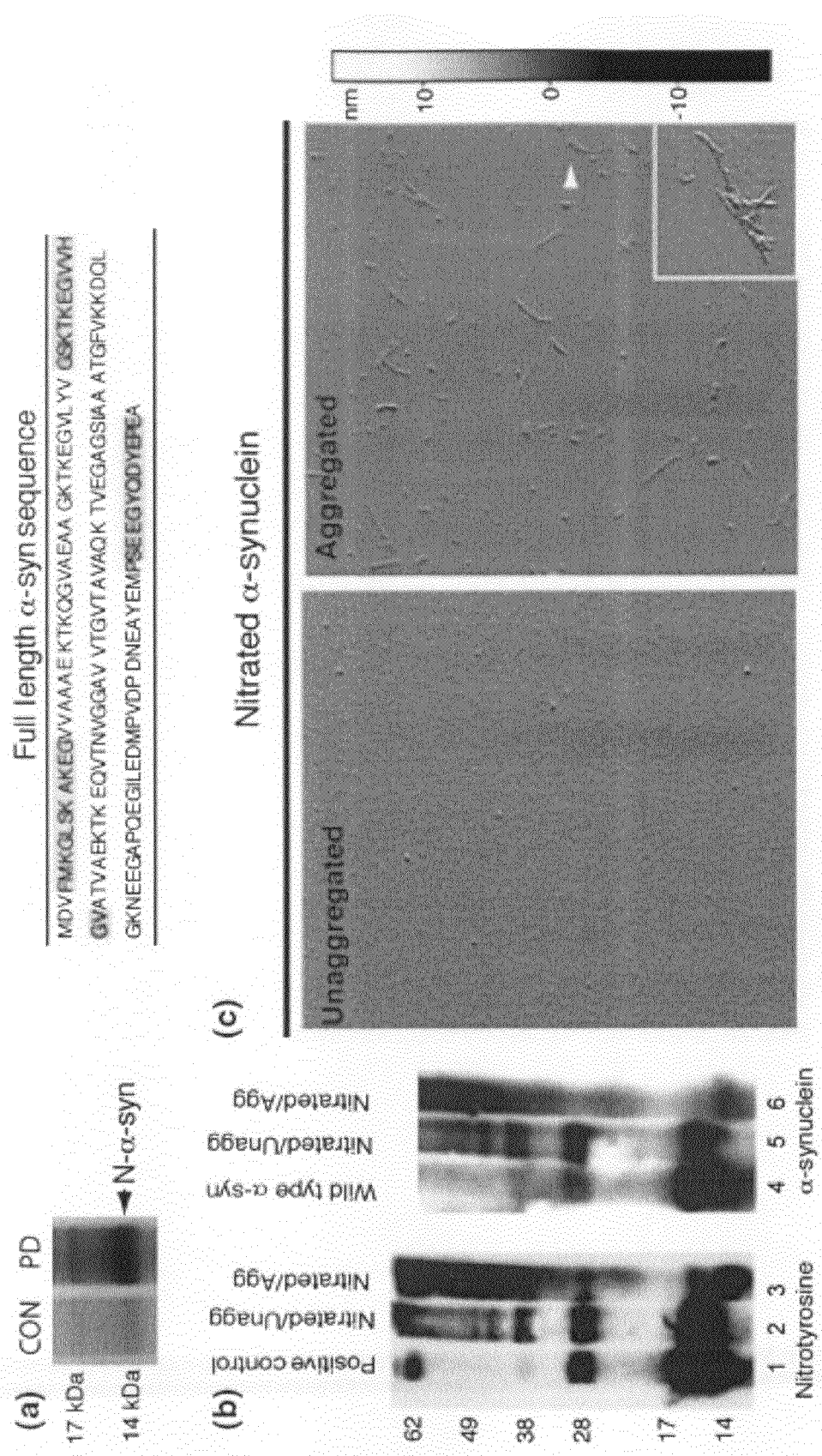
FIG. 23 E provides cytokine bead arrays were used for flow cytometric analysis of supernatants from unstimulated microglia (control, open box) and microglia stimulated with either 100 nmolIL N-α-syn (closed triangle) or 100 ng LPS (closed circle) (n=3, p<0.01 vs. [a]control and [b]LPS at each corresponding time point).
Figure 23:
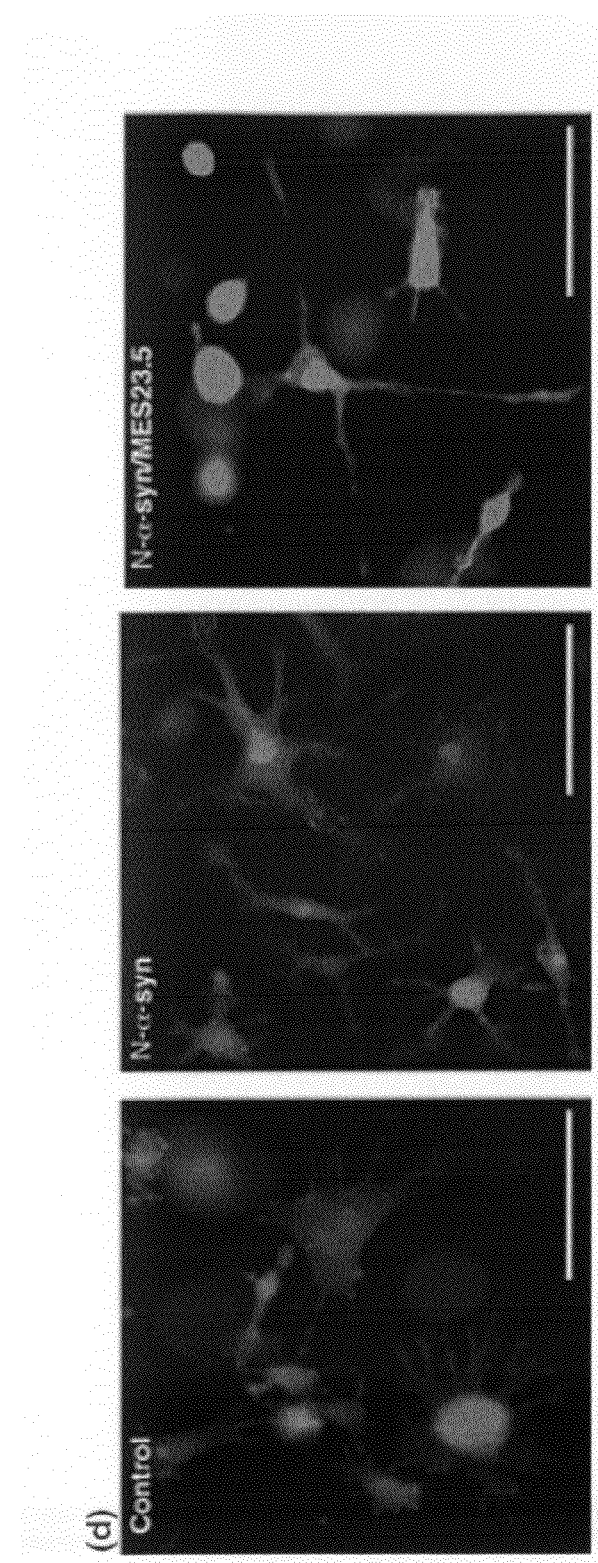
Figure 23:
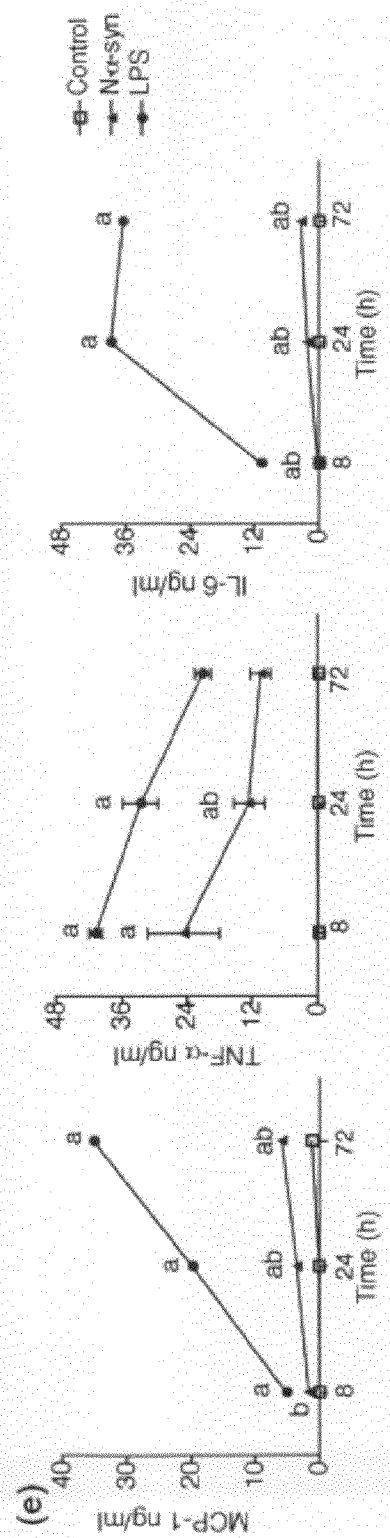

Aggregated N-α-syn and Microglial Activation: Laboratory and Pathological Studies To investigate the mechanisms by which N-α-syn-mediated microglial activation affects dopaminergic neurodegeneration, a cellular model was created that would reflect the salient features of neuroinflammation as it could occur in PD. To this end, it was first determined if N-α-syn was present in regions of brain where microglial activation is known to be present in PD. Whole cell lysates consisted of several protein bands following gel electrophoresis and Coomassie staining. IP assays performed from SN tissues of PD patients using a primary antibody against nitrated α/β-synulcein showed a greater than twofold increase in intensity of the protein band corresponding to 14-14.5 kDa ($p<0.001$) than that present in control patients (FIG. 23A) or in patients diagnosed with AD along with higher molecular weight species greater than 17 kDa. Peptide sequence analyses by LC-MS/MS revealed that the protein band encompassing the 14-14.5 kDa of the anti-N-α-syn IP contained peptides with sequence homology to human α-syn in SN samples recovered from PD brains (FIG. 23A, highlighted sequences). Interestingly, such sequence homologies to α-syn were not identified from 14 to 14.5 kDa proteins in either control or AD samples. Thus, an in vitro model was developed to reflect conditions present in an affected human host, but using the murine analog. Here, recombinant mouse α-syn was purified, nitrated, and aggregated for use as a microglial stimulant. Western blot assays showed cross-linking of N-asyn monomers (Souza et al. (2000) J. Biol. Chem., 275:18344-18349) and higher molecular weight aggregates, thus verifying the nitration and aggregation of α-syn (FIG. 23B). The aggregated N-α-syn contained a substantially reduced monomeric band (corresponding to a band at ~14 kDa) but higher molecular weight banding aggregates. Analysis of protein aggregation was also assessed by AFM. Samples of N-α-syn contained low numbers of globular aggregates (2-6 nm in height) prior to aggregation. However, following aggregation, N-α-syn was present predominately as oligomers (2-6 nm in height). In addition, there were few protofibrils (1.5-2.5 nm in height), filaments, and fibrils (~5-8 nm in height) present (FIG. 23C). Non-nitrated α-syn was present in similar configurations.

The stimulatory effects of N-α-syn on microglia was then evaluated. The dose of 100 nmol/L (14.5 ng protein/mL) was selected based on previous extensive works performed demonstrating that, following a dose-response of N-α-syn, 100 nmol/L (50% over control) is required to induce substantive ROS from activated microglial cells (Zhang et al. (2005) FASEB J., 19:533-542; Thomas et al. (2007) J. Neurochem., 100:503-519.) as well as cytotoxicity. ROS production was slightly decreased in comparison with either 50 or 500 nmol/L of N-α-syn. While native α-syn is ubiquitously expressed, the physiological concentration of N-α-syn in disease has not been elucidated. However, based on concentrations of modified α-syn in affected PD brain tissues, 100 nmol/L concentration is at physiologically relevant levels (Halliday et al. (2005) Brain 128, 2654-2664) and is below that detectable by immunohistochemistry in neuronal inclusions within the SN of PD brains ($\geq 100$ ng). Phenotypic transformation into an ameboid morphology commonly follows microglial activation with different pro-inflammatory stimuli (Giulian et al. (1995) J. Neurosci., 15:7712-7726; Vilhardt, F. (2005) Int. J. Biochem. Cell Biol., 37:17-21). Thus, it was examined if changes in microglial morphology would be elicited following N-α-syn activation. Resting microglia were both round and ellipsoid shaped with retracted processes that were characteristic of a relatively quiescent phenotype (FIG. 23D). In contrast, N-α-syn activated microglia assumed a more ameboid appearance with extensive processes, characteristic, in part, of an activated phenotype. N-α-syn-stimulated microglia co-cultured with MES23.5 cells acquired a rod-like appearance and further extension of processes.

It has been demonstrated that 100 nmol/L of aggregated N-α-syn could activate microglia to produce copious amounts of ROS (Thomas et al. (2007) J. Neurochem., 100: 503-519). In contrast, unaggregated N-α-syn or minced neuronal membrane fractions failed to induce significant amounts of ROS above control levels. This suggested that the microglial response to N-α-syn was specific and could not be elicited in response to unaggregated protein or by phagocytosis under the same conditions. Therefore, the extent of the neuroinflammatory phenotype induced by N-α-syn stimulation of microglia was assessed. Quantification of common cytokines and chemokines that are secreted in response to inflammatory stimuli was performed by cytometric bead array. LPS-activated microglia served as a positive control. Stimulation with N-α-syn enhanced the secretion of TNF-α, IL-6, MCP-1 (FIG. 23E), and IFN-γ compared with basal levels observed in unstimulated microglia. These results are consistent with the induction of an inflammatory microglial phenotype following N-α-syn stimulation. The parallels between N-α-syn and LPS-induced cellular effects support a commonality for innate immune responses in disease and suggest that these pro-inflammatory processes may be common among mononuclear phagocytes that recognize disparate activators.

N-α-syn-stimulated Microglia are Neurotoxic to MES23.5 Dopaminergic Cells

Figure 24:
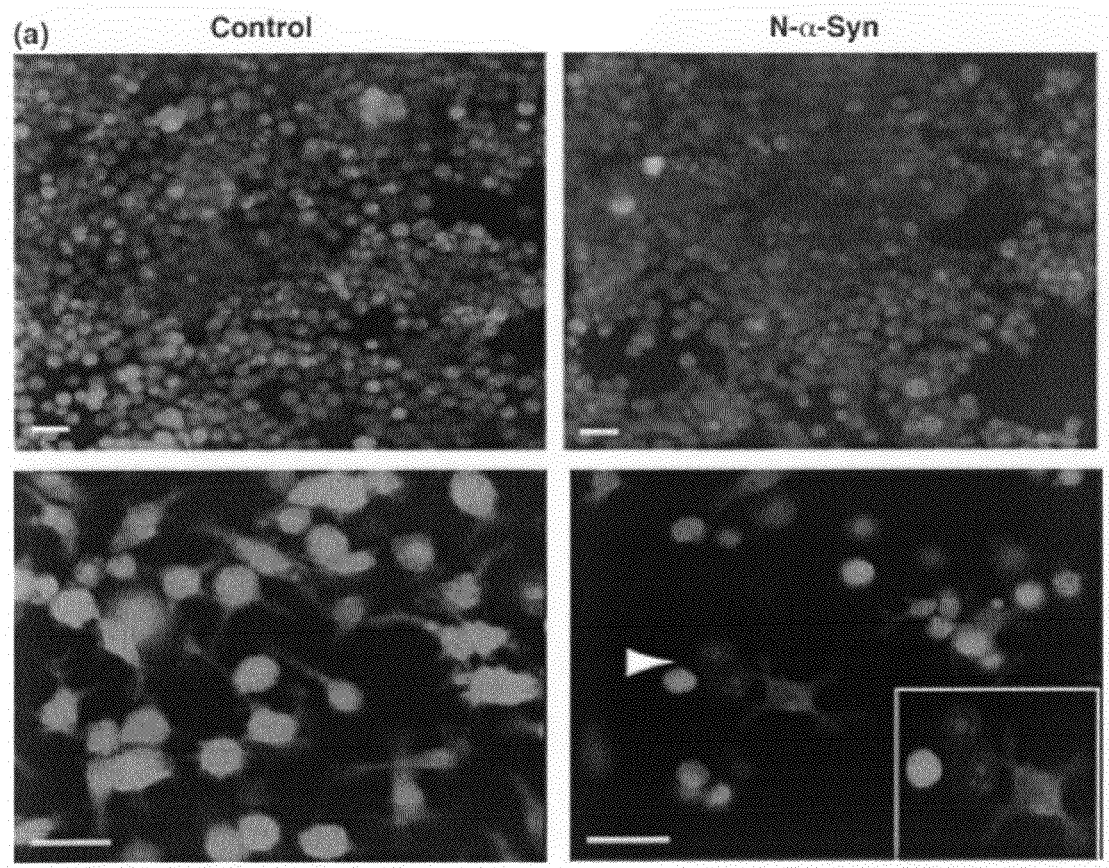
FIGS. 24A-24E demonstrate N-α-syn-stimulated microglia decrease dopaminergic cell survival.
Figure 24:
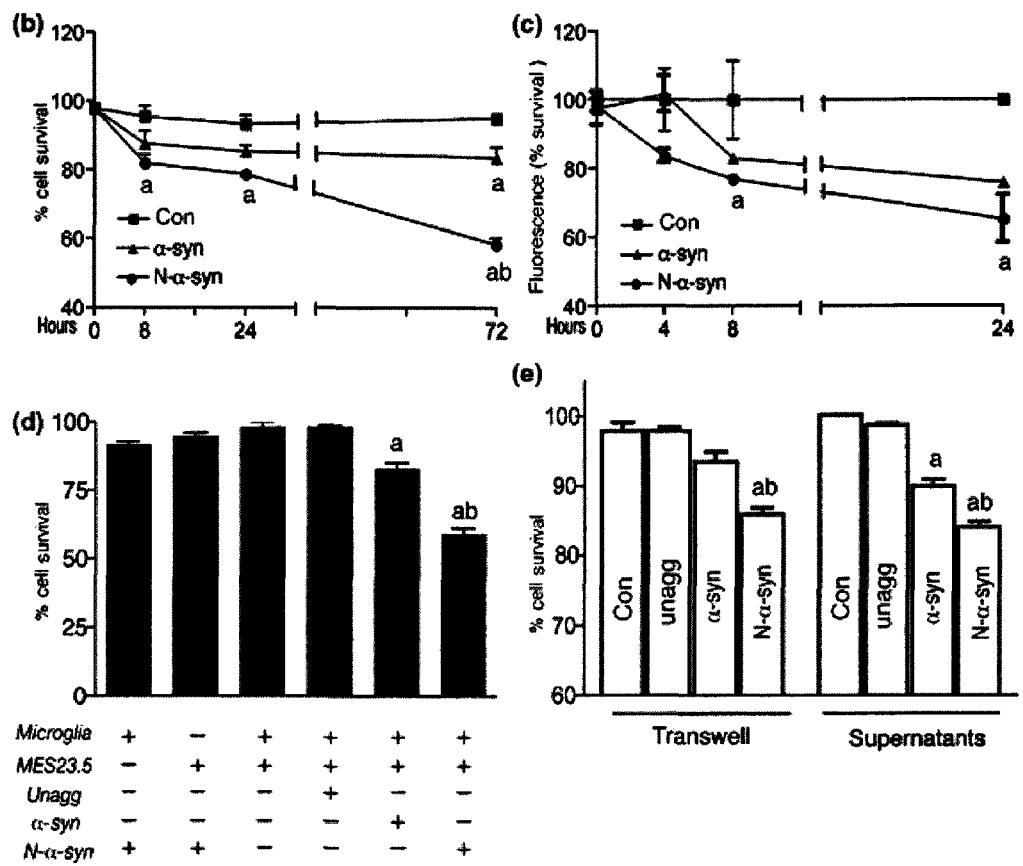

To determine the effect of N-α-syn-activated microglia on neuronal survival, the dopaminergic MES23.5 cell line was used as an indicator for cytotoxicity measurements by co-culture with stimulated and unstimulated microglia. MES23.5 cell death was determined by measuring immunoreactivity for the rate-limiting enzyme in dopamine synthesis, TH, expressed by MES23.5 cells, and the Live/Dead cell assay. During stimulation with 100 nmol/L N-α-syn, the number of TH+ cells declined in the stimulated cultures, resulting in a significant diminution in TH-immunoreactive cells (8 hours: 74.6% of control; 24 hours: 53.4% of control, $p<0.01$; 72 hours: 48.5% of control, n=6, $p<0.01$). Western blot analysis confirmed this observation, as TH expression decreased in a time-dependent manner over the course of N-α-syn stimulation (TH+/β-actin ratio at 8 hours: 94.6% of control; 24 hours: 86.2% of control; 72 hours: 64.9% of control, p<0.01). Analysis of cell viability with the Live/Dead cell assay demonstrated that stimulation of microglia with 100 mmol/L of N-α-syn followed by MES23.5 co-culture resulted in remarkable reduction of viable cells with concomitant increase in dead MES23.5 cells; whereas, fewer dead cells were observed in co-cultures with microglia stimulated with α-syn (non-nitrated) after 24 hours (FIG. 24A). Percentage of MES23.5 cell survival was less in co-cultures with microglia stimulated with α-syn (83%) and N-α-syn (58%) compared with unstimulated controls (95%) at 72 hours (FIG. 24B). The more sensitive fluorometric analysis revealed as early as 24 hours after stimulation a similar pattern of progressive decline in viable cells in the presence of α-syn and N-α-syn stimulated microglia to 76% and 65% of controls at 24 hours of stimulation, respectively (FIG. 24C). Moreover, N-α-syn-mediated cytotoxicity was restricted to MES23.5 cells, as stimulation of microglia in the absence of MES23.5 cells neither affected microglial survival (FIG. 24D) nor yielded a significant difference in the number of dead CD11b+ cells between control and stimulated cultures. In addition, cytotoxicity of MES23.5 cells was not elicited with N-α-syn in the absence of microglia (FIG. 24D). Furthermore aggregation of N-α-syn was necessary for inducing microglia cytotoxicity (FIG. 24D). Importantly, a decrease in the cell survival was observed when microglia were stimulated with either aggregated α-syn (93%) or N-α-syn (86%) for 24 hours, and co-cultured with MES23.5 cells in Transwell™ inserts, but not unaggregated protein. MES23.5 cultures incubated with supernatants obtained from microglia stimulated with either α-syn or N-α-syn resulted in decreased cell survival (89% and 84%, respectively) compared with supernatants from unstimulated microglia (FIG. 24E).

NF-κB Gene Expression and Nuclear Translocation in Pd

Figure 25:
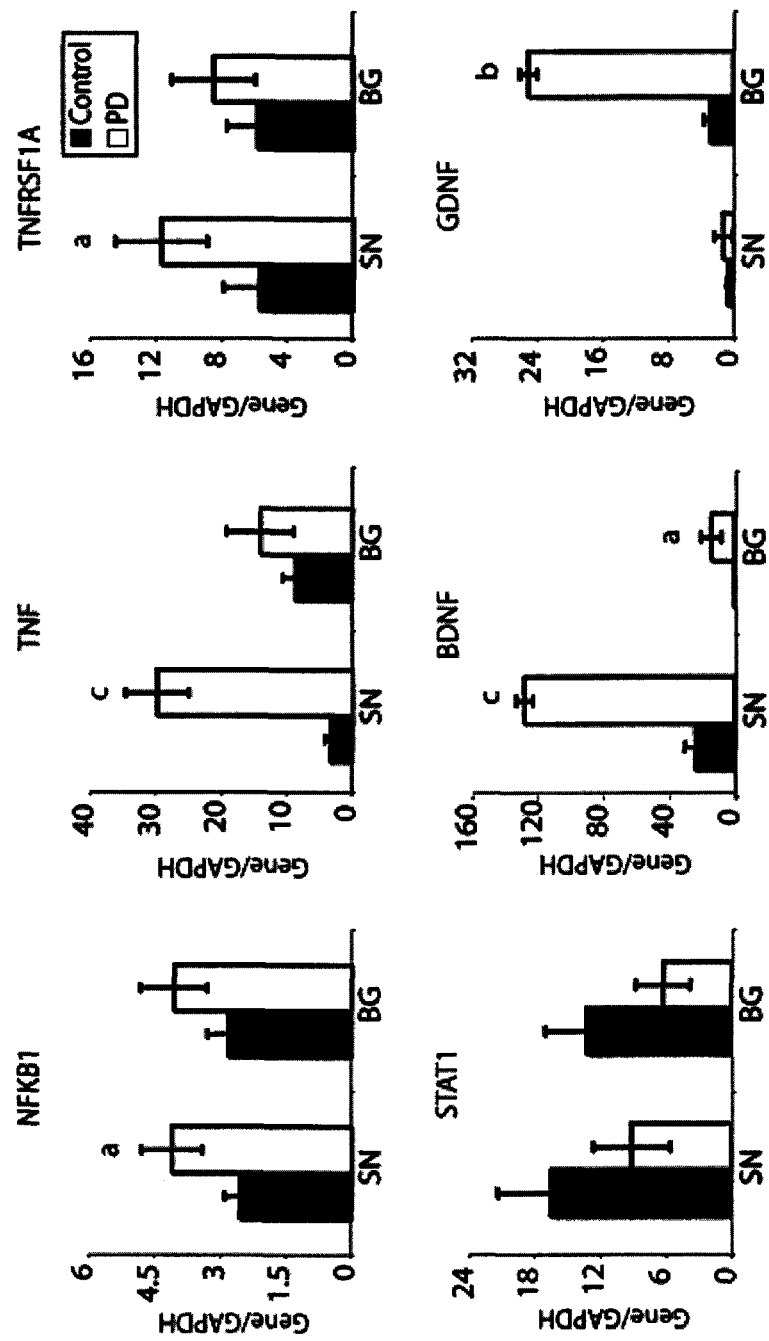
FIG. 25 demonstrates cellular activation and oxidative stress pathways in PD brain tissues. Tissue samples from the SN and BG of control (filled bars) and PD patients (open bars) were evaluated by qRT-PCR for expression of NF-κB pathway associated genes. The relative expression of a gene was normalized to GAPDH in the same sample and values are represented as mean±SEM ([a]p<0.05, [b]p<0.01, and [c]p<0.001 compared with samples from control patients, n=8-10 patients per group).

NF-κB pathway activation is critical for the initiation of inflammatory events including the production of inflammatory cytokines and chemokines linked to inflammation and microglial activation. Acquisition of such an inflammatory phenotype may begin with induction of gene products that ultimately leads to neurotoxic factor production, cell migration, and apoptosis. To determine the extent to which this pathway was operative in PD, the SN and BG of PD brains and controls (those without neurological disease) were analyzed for NF-κB-related genes as well as neurotrophin expression (FIG. 25). Increases, albeit modest, were seen in NFKB1 expression from samples of SN from PD patients compared with controls; whereas, no significant difference was observed for RELA expression. However, an eightfold increase in TNF expression was observed in the SN and BG together with a twofold increase in expression of its receptor TNFRSF1A. STAT1 was minimally decreased in PD brains. Similarly, analysis of AD brain tissues as a control for neuroinflammatory pathology also revealed a moderate induction of NF-κB transcription factors NFκB1 and RELA, while TNF expression was increased 40- and 10-fold in the SN and BG along with modest elevations of STAT1 in AD brain tissues compared with controls. Based on these findings, it was reasoned that a compensatory trophic mechanism could be operative in PD. Indeed, BDNF was shown to be increased greater than sixfold in the SN and twofold in the BG in PD. Consistent with recent observations (Backman et al. (2006) Mol. Cell. Endocrinol., 252:160-166), GDNF was increased greater than 10-fold in the BG but no significant changes were observed in the SN.

Figure 26:
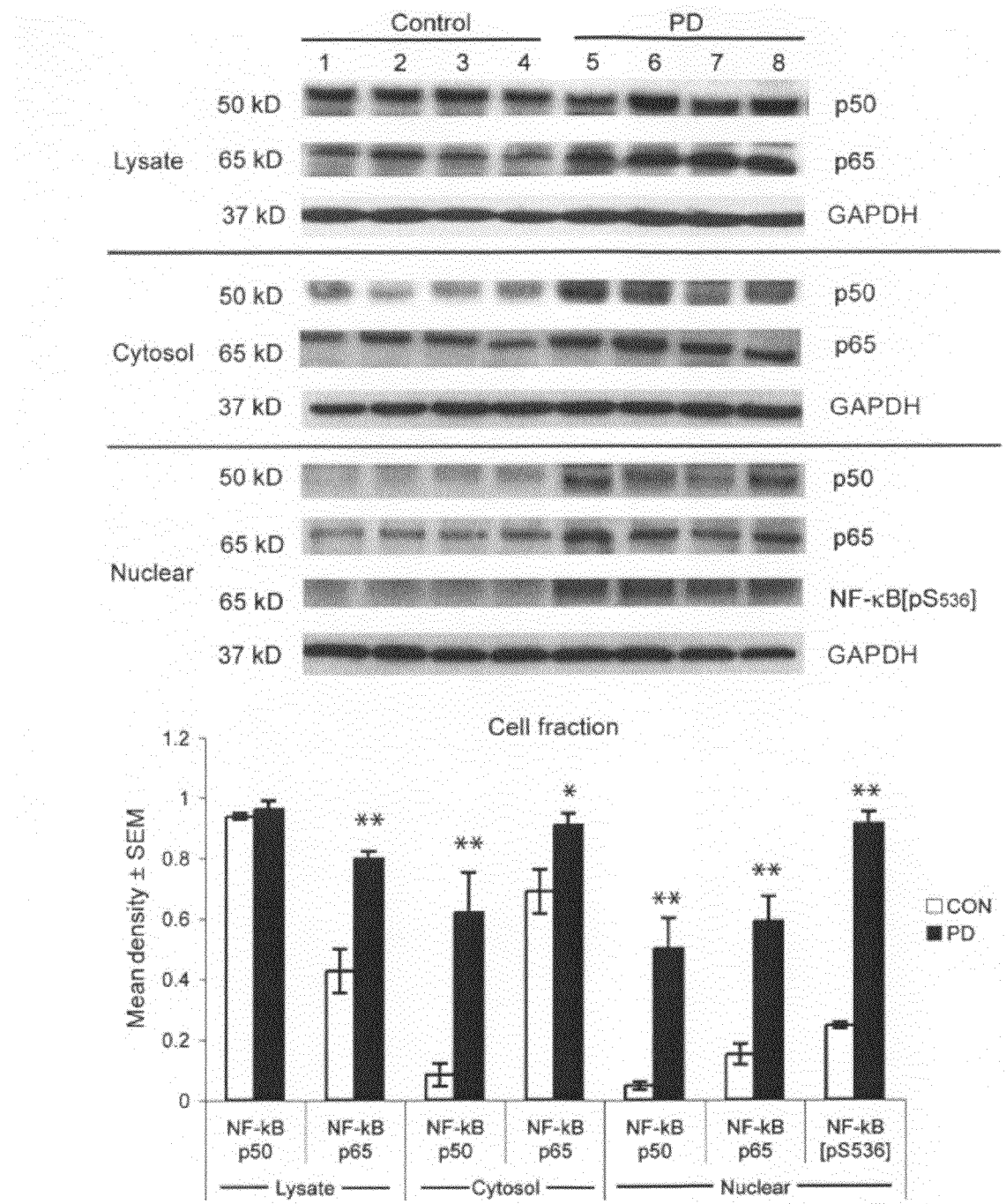
FIG. 26 shows NF-κB translocation in PD. Expression of NF-κB subunits p50/NFKB1 and p65/RELA proteins were evaluated by western blot analysis from whole tissue lysates (top), cytosolic fractions (middle), and nuclear fractions (bottom) of SN from control and PD patients. Expression of phosphorylated RELA/p65 [NF-κB pS536] within the nuclear fraction was also assessed. The mean densitometric values were determined with IMAGEJ software and normalized to GAPDH expression in the same sample (bottom). Values are represented as the mean density±SEM for four patients/group and p-values of Student's t-test for pair-wise comparisons of densities from control (open bars) and PD (filled bars) patients are *p<0.05 and **p<0.005. Blots are representative of two independent experiments (n=4 patients per group).

A recent investigation by immunofluorescence analysis of midbrain sections revealed a marked increase in expression of NF-κB p65 in the SN of PD patients compared with controls, which co-localized to CD11b+ microglia in addition to affected neurons. In the current study, cytosolic and nuclear fractions were prepared from the lysates of SN of PD and control brain tissues, and lysates analyzed for NF-jB protein subunits p50 and p65. Increased expression of NF-jB subunits in both the cytosolic fractions and nuclear fractions were observed in PD brain tissues (FIG. 26). Phosphorylation of serine 536 (pS536) critical for RelA/p65 transcriptional activity was also increased in PD brain tissues.

N-α-syn-activated Microglia and the PD Transcriptome are Linked through NF-κB

The increased expression of NF-κB transcription identified in the SN of PD brains and the microglial response to N-α-syn stimulation that were consistent with inflammatory responses suggested that one major signaling pathway induced by N-α-syn involves NF-jB activation. Use of a general microarray confirmed that NF-κB expression was increased by stimulation with N-α-syn (FIG. 27A). Using NF-κB-focused microarrays (FIGS. 27B, 27D, and 27E), increased expression of genes encoding pro-inflammatory cytokines was shown, including Tnf, Ccl2, Il6, and Il1b. Also induced were those genes encoding the NF-jB transcription factor subunits, Nfkb1, Nfkb2, and Rela. In addition, N-α-syn induced genes involved in other pathways, particularly those of the mitogen-activated pathway, as indicated by the induction of the immediate early genes, Fos and Raf1. At 4 hours post-stimulation, expression of most NF-κB-related genes peaked. The majority of genes induced at 1 hour remained elevated, with the addition of the apoptosis-regulatory genes Card10 and Casp8. The NF-κB inhibitor, Nfkbia, was also induced but may become apparent only after removal or clearance of the stimulus, as Ikbkb expression was also induced at this time. Removal of N-α-syn from microglial cells after 4 hours of stimulation reduced most NF-κB genes to pre-stimulatory levels. At 8 and 16 hours following removal of N-α-syn from culture, several apoptosis-regulatory genes (Card10, Card11, and Cflar) were induced as well as genes for receptors of cell activation and NF-κB stimulation including Tnfrsf1a and Cd40. These results were similar but lesser in magnitude than stimulation of microglia with LPS (FIGS. 27B and 27F-H). Consistent with microarray analyses, quantitative RT-PCR analyses of Tnf, Il1b, and Ccl2 genes indicated very high levels of transcripts for these cytokines during stimulation by N-α-syn (10-, 3097-, and 16-fold increases, respectively) over pre-stimulatory levels (FIG. 27C). Verification of gene expression during stimulation of other, less abundant, NF-κB-related genes were achieved, including Tnfrsf1a (6.2-fold increase), Stat1 (2.3-fold increase), and Rela (3.6-fold increase). N-α-syn stimulation also increased expression of Nos2 (inducible nitric oxide synthase) and Ifng, both regulated by NF-κB activation. Expression of the neurotrophins Bdnf and Gdnf were also increased following N-α-syn stimulation.

N-α-syn-activated Microglial Proteome Shows a Reactive Inflammatory Phenotype

Analysis of the N-α-syn microglial transcriptome showed differential gene regulation and induction of the NF-κB pathway, indicative of an inflammatory microglial phenotype. Activation of this pathway influences downstream expression of proteins involved in processes including inflammation, immune regulation, survival, and proliferation. Protein expression obtained from cell lysates were analyzed following 2, 4, and 8 hours of stimulation with 100 nmol/L N-α-syn to assess the translation of differences in gene induction to intracellular protein expression. Two-dimensional DIGE was used to compare protein expression profiles of unstimulated microglia (control) and N-α-syn-stimulated microglia (FIG.

28). A complete listing of all proteins identified by LCMS/MS is contained within FIG. 27.

Stimulation with N-α-syn resulted in differential expression of several proteins that are likely a consequence of NFκB-related signaling pathways (FIG. 27) as soon as 2 hours after stimulation. Many proteins differentially expressed could be attributed to oxidative stress, including the down-regulation of aconitase as well as the up-regulation of peroxiredoxin-1, -4, -5, superoxide dismutase, and heat-shock protein 70.

Figure 27:
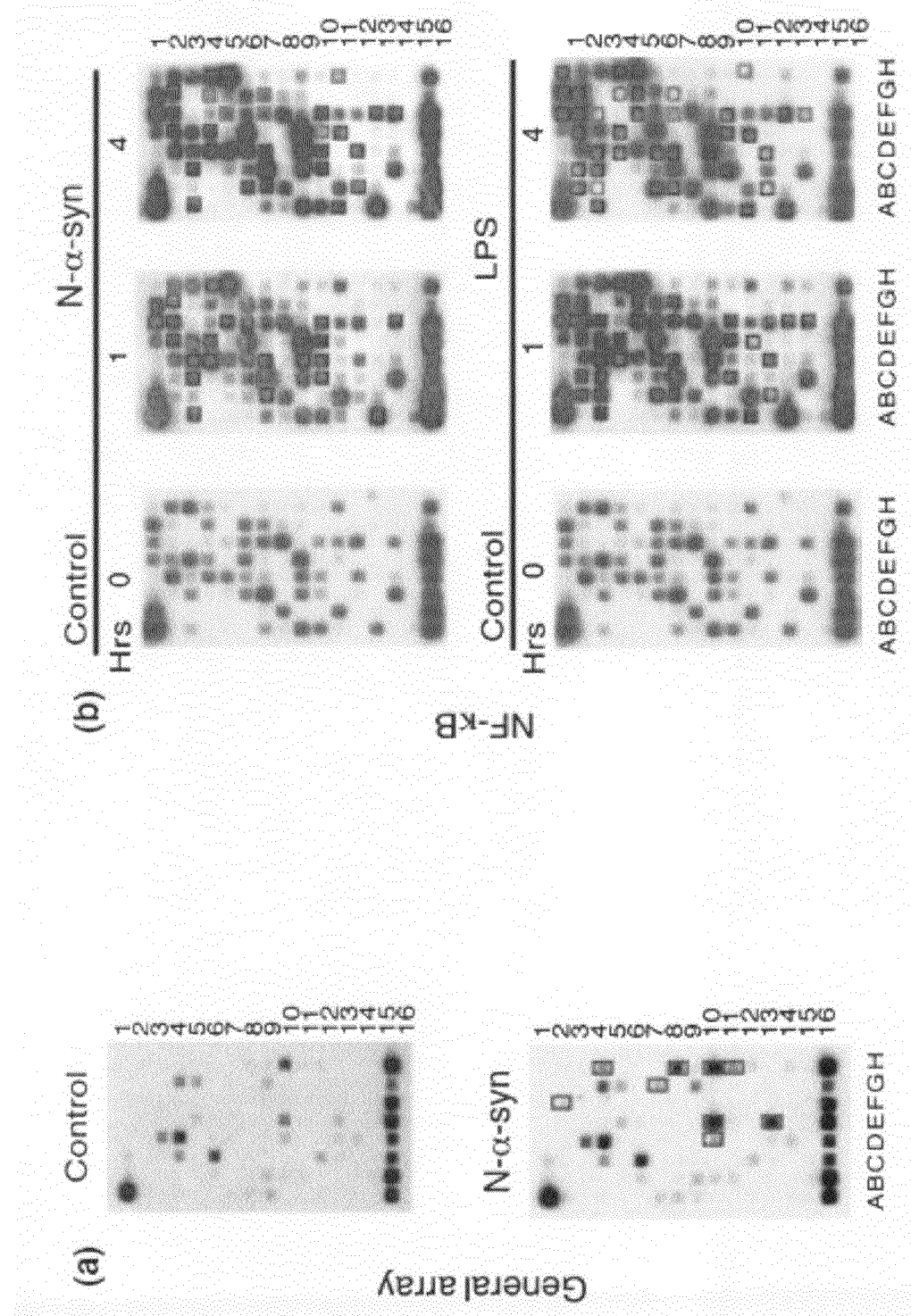
FIG. 27 provides microarray analysis of N-α-syn-stimulated microglia. RNA was isolated from microglial cells stimulated with 100 nmol/L N-α-syn or 100 ng/mL LPS from which cDNA was made and amplified.
Figure 28A:
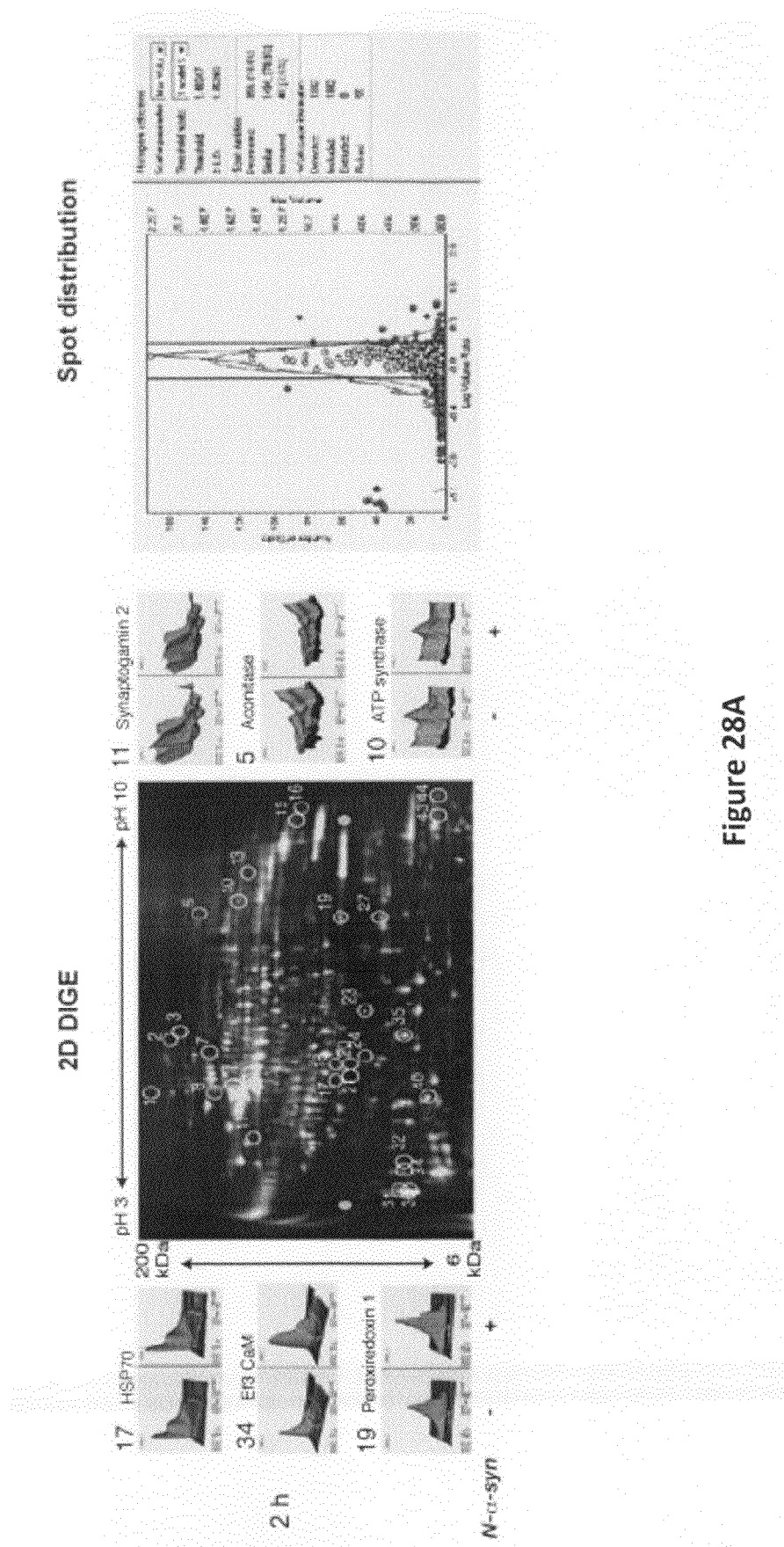
FIGS. 28A-28C provide 2DE and LC-MS/MS analysis of the N-α-syn-stimulated microglia proteome. Fluorescence 2D DIGE analysis of N-α-syn-activated microglial cell lysates. Fluorescence 2D DIGE (2DE) analysis of activated microglial cell lysates at 2, 4, and 8 hours after N-α-syn stimulation. Proteins from cell lysates of unstimulated microglia labeled with Cy3 appear green on the 2 dimensional gels, while proteins of N-α-syn stimulated microglia labeled with Cy5 appear red, and proteins common to both appear yellow. Three-dimensional DeCyder interpretation for six representative proteins per time-point are shown. The numbers correspond to the protein spot labeled on gels. Analysis of spot distribution to locate and define protein spots (right panel). Protein spots from samples of stimulated cell lysates were identified as decreased, increased, or common versus non-stimulated cell lysates. Spots picked for sequencing analysis with LC-MS/MS are shown. Abbreviations: HSP70, heat-shock protein 70; Cyt c oxidase, cytochrome c oxidase; SOD, superoxide dismutase. A complete listing of all proteins identified through 2DE is contained within FIG. 27.
Figure 28B:
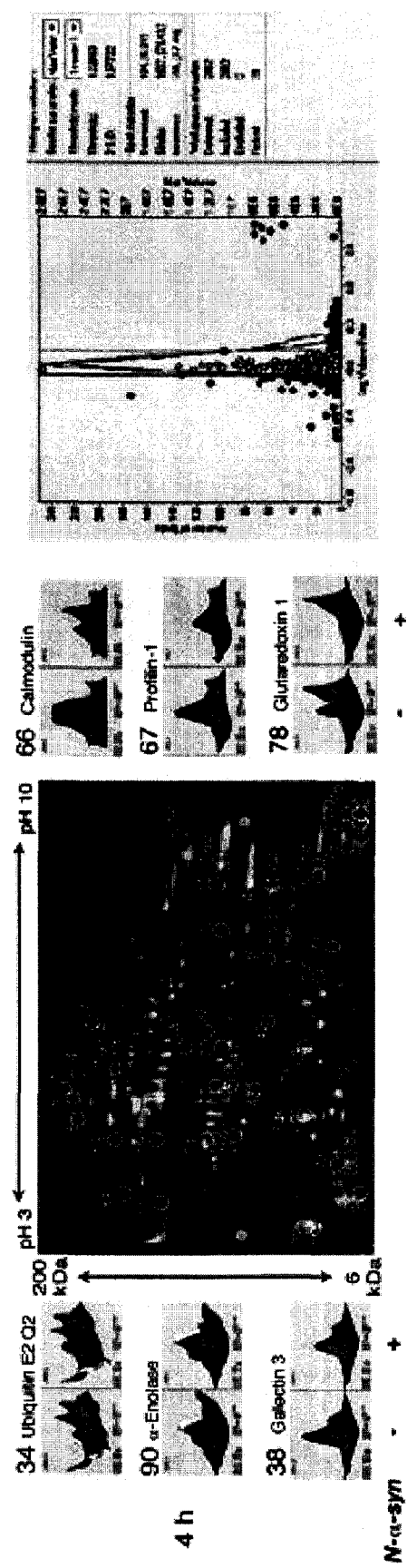
Figure 28C:
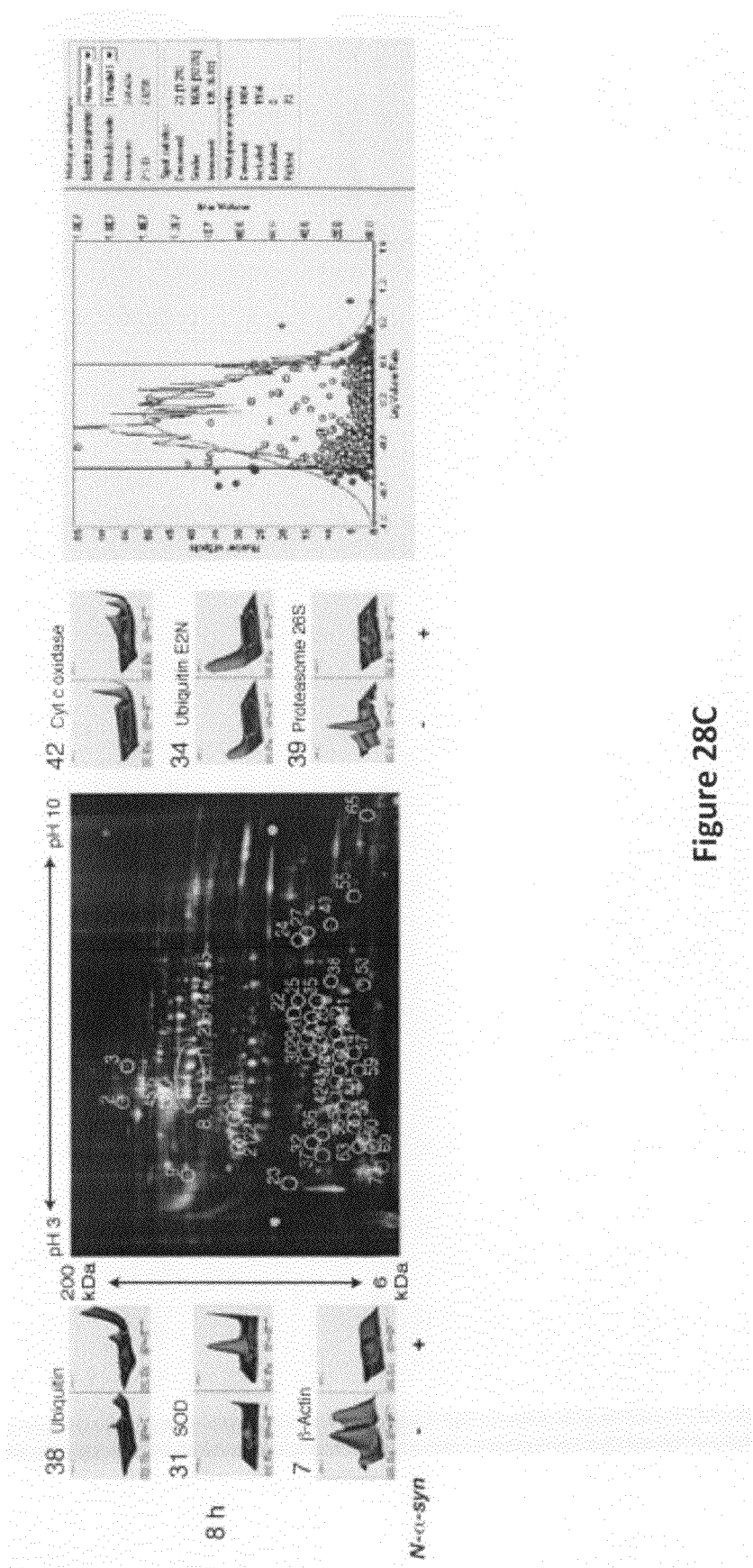

After 4 hours of N-α-syn-stimulation, proteins decreased included several cytoskeletal proteins including β-actin, cofilin-1, profilin-1, tropomysin-3, and vimentin. The putative functions of other proteins decreased in N-α-syn-stimulated microglial lysates were found to be involved in cell adhesion and actin microfilament attachment to the plasma membrane (vinculin, coronin-1A, and adenylyl cyclase-associated protein 1), glycolysis and growth control (α-enolase), and migration (galectin 3 and macrophage migration inhibitory factor) (Walther et al. (2000) J. Neurosci. Res., 61:430-435; Chandrasekar et al. (2005) J. Cell Sci., 118:1461-1472). Annexin A3 is an inhibitor of phospholipase A2 and a promoter of apoptosis of inflammatory cells (Parente et al. (2004) Inflamm. Res., 53:125-132), and was also down-regulated. The antioxidant glutaredoxin-1 was also decreased in cell lysates compared with unstimulated controls (FIG. 27). Four of the proteins increased in stimulated cell lysates affect intracellular calcium signaling, storage, and cell cycle regulation (swiprosin 1, calmodulin, calreticulum, and nucleophosmin 1) (Parente et al. (2004) Inflamm. Res., 53:125-132; Vuadens et al. (2004) Proteomics 4:2216-2220; Meini et al. (2006) Eur. J. Neurosci., 23:1690-1700).

By 8 hours, 73 proteins were differentially expressed. Thirty three proteins were decreased including all cytoskeletal proteins down-regulated at 4 hours, vimentin and β-actin. Up-regulated proteins included the antioxidants superoxide dismutase, thioredoxin, and cytochrome c reductase. Oxidative stress can also lead to dysfunction of the proteasome and is implicated in PD pathogenesis (Gu et al. (2005) Cell Death Differ., 12:1202-1204). Indeed, as a result of N-α-syn stimulation the proteasome 26S subunit was decreased in these cell lysates, although ubiquitin and the ubiquitin conjugating enzyme E2N were increased, suggesting that the microglia may be compensating for decreased proteasomal activity (FIG. 27).

Neuroinflammatory Parkinson's Disease Phenotype

Figure 29:
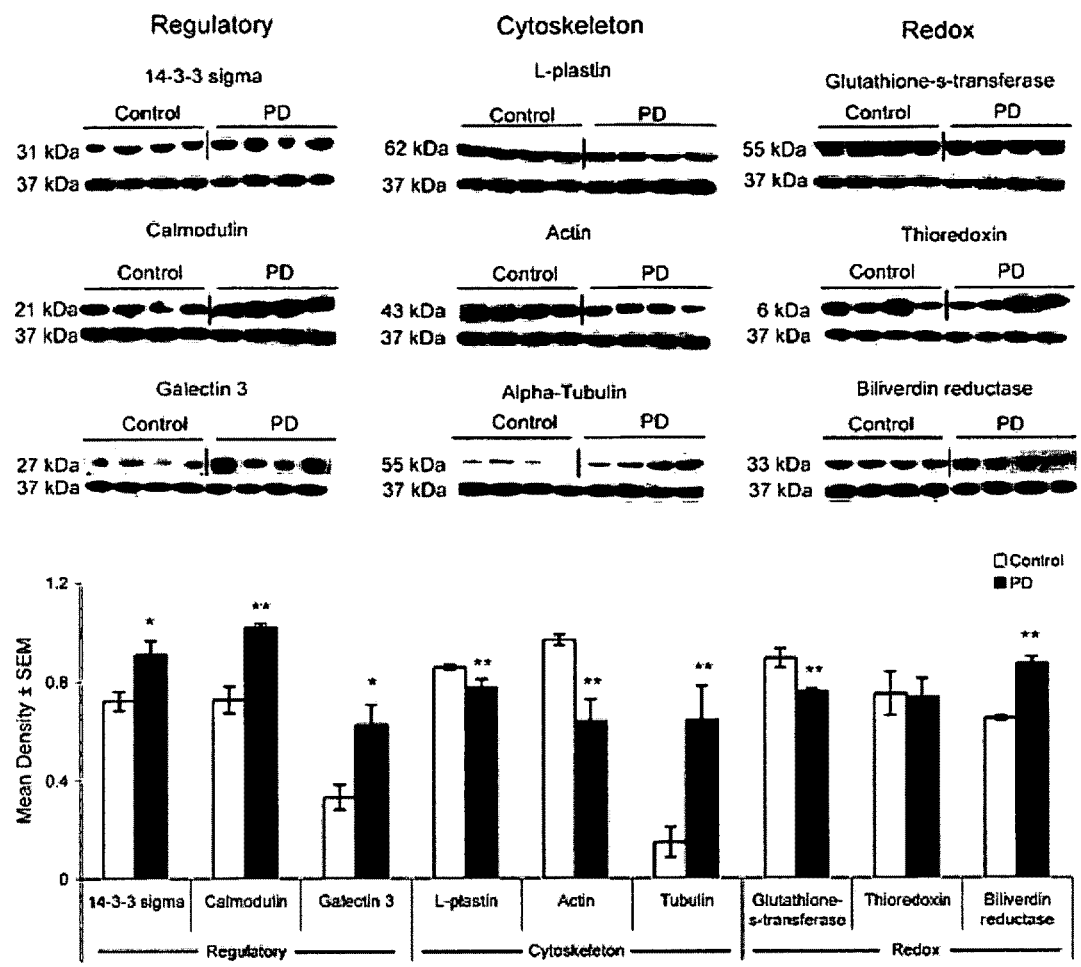
FIG. 29 provides N-α-syn-stimulated microglial proteins in PD brain tissue. Immunoblot identification of proteins in the SN and BG of PD brains that were previously observed in N-α-syn-stimulated microglia. This includes 14-3-3σ, calmodulin, galectin-3, L-plastin, actin, tubulin, glutathione-S-transferase, thioredoxin, and biliverdin reductase. The proteins are divided into regulatory, cytoskeleton, or redox functions. The mean densitometric values were determined with IMAGEJ software and normalized to GAPDH expression in the same sample (bottom). Values are represented as the mean density±SEM for four patients/group and p-values of Student's t-test of pair-wise comparisons of densities from Control (open bars) and PD (closed bars) patients are *p<0.05 (**p<0.05 and congruent results with the N-a-syn-microglial proteomic and western blot assays).

Analysis of the proteome of N-a-syn-stimulated microglia revealed the induction of NF-κB-related signaling pathways and initiation of several proteins involved in the cellular response to inflammation and oxidative stress. To investigate whether differential expression of proteins identified in the proteomic analyses of in vitro stimulated microglia was reflected in PD, protein expression of lysates prepared from the SN and BG of control and PD brains were assessed by western blot assays (FIG. 29). Proteins increased in abundance within the secretome as a result of N-α-syn stimulation were cross-validated in PD patients including calmodulin and the redox-associated secreted proteins biliverdin reductase and thioredoxin; whereas, secretion of the regulatory proteins glatectin-3 and 14-3-3σ, structural protein actin, and the redox protein glutathione-S-transferase were decreased following N-α-syn stimulation. These analyses verified the increased expression of calmodulin as well as the antioxidant biliverdin reductase in the SN of PD compared with age-matched controls without neurological disease. Actin expression appeared decreased in PD brains relative to controls, which coincided with the analysis of the N-α-syn-stimulated microglia secretome. In contrast to the in vitro results, expression of 14-3-3σ and galectin 3 were increased in PD brains. Glutathione-S-transferase expression was decreased in PD brains relative to control. Although expression of thioredoxin did not appear to be different within the SN, expression in the BG was significantly decreased in PD. Proteins that were identified in the proteome of N-α-syn-stimulated microglia were, in part, also cross-validated in SN of PD and control brains. Akin to the laboratory model, expression of calmodulin was increased whereas expression of α-enolase, L-plastin, α-tubulin, and actin were decreased in PD relative to control. The discrepancies between the cellular model and expression in the human tissue underscore the complexity of human disease and the multiple cell components that are involved. Indeed, comparing non-affected brains to PD brains may be misleading as already the proportion of cellular components are different, especially at end stage where greater than 80% of the dopaminergic neurons have died and substantial gliosis is present. However, overall these results support that the molecular and biochemical analyses of N-α-syn microglial activation appear, in part, applicable to human PD.

EXAMPLE 5

Activated microglia are linked to Parkinson's disease (PD) pathobiology (McGeer et al. (1988) Neurology 38:1285-1291; Hald et al. (2007) Subcell. Biochem., 42:249-279; Whitton, P. S. (2007) Br. J. Pharmacol., 150:963-976; Wilms et al. (2007) Curr. Pharm. Des., 13:1925-1928; Yuan et al. (2007) Neurosci. Bull., 23:125-130). The primary mediators of neuroinflammatory responses in PD are activated microglia. How such microglial activation can be regulated could present diagnostic and therapeutic options for PD (Hermanowicz, N. (2007) Semin. Neurol., 27:97-105; Klegeris et al. (2007) Curr. Opin. Neurol., 20:351-357; Lipton et al. (2007) Int. Rev. Neurobiol., 82:1-27; Reynolds et al. (2007) Int. Rev. Neurobiol., 82:297-325). This is of importance as PD remains the second most common neurodegenerative disorder among the elderly and will increase in incidence and prevalence as the baby boomer generation ages (Khandhar et al. (2007) Dis. Mon., 53:200-205). PD is characterized by progressive loss of dopaminergic neurons in the substantia nigra pars compacta (SNpc) and their projections to the caudate-putamen of the basal ganglia (BG). A pathological hallmark of disease is the presence of fibrillar α-synuclein (α-syn) inclusions known as Lewy bodies (LB) in the SN that are associated with degenerating neurons (Hodaie et al. (2007) Neurosurgery 60:17-28. 28-30). Although the etiology of PD remains unknown, a large body of evidence links inflammation, mitochondrial dysfunction, oxidative stress, and diminished neurotrophic support to disease (Przedborski, S. (2005) Parkinsonism Relat. Disord., 11(Suppl 1):S3-7; Zhang et al. (2005) Faseb J., 19:533-542; Mandemakers et al. (2007) J. Cell Sci., 120:1707-1716).

Activated microglia are closely associated with dying or damaged dopaminergic (DA) neurons (McGeer et al. (1988) Neurology 38:1285-1291; Czlonkowska et al. (1996) Neurodegeneration 5:137-143). A link between microglial secretory activities and neurodegeneration is made through the plethora of neurotoxic factors they produce following activation including tumor necrosis factor alpha (TNF-α, reactive oxygen species (ROS), interferons, excitatory amino acids, interleukin (IL)-1β, IL-6, nitric oxide (NO), and leukotrienes (Rogove et al. (1998) Curr. Biol., 8:19-25; Wu et al. (2002) J. Neurosci., 22:1763-1771). There is compelling evidence that the release of aggregated and nitrated α-syn (N-α-syn) from dying or damaged SN dopaminergic neurons serves, in part, to provoke a neuroinflammatory response (Zhang et al. (2005) Faseb J., 19:533-542; Thomas et al. (2007) J. Neurochem., 100:503-519) that, left uncontrolled, contributes to neurodegenerative activities and the tempo of disease.

The mechanism of microglia-mediated DA neurotoxicity is linked to the generation of oxidative insult from microglia. DA neurons, in particular, possess reduced antioxidant capacity as a result of low intracellular glutathione, which renders DA neurons vulnerable to oxidative stress relative to other cell types (Loeffler et al. (1994) Clin. Neuropharmacol., 17:370-379). Ongoing investigations have identified cellular properties including ROS production, morphological transformation, inflammatory cytokine secretion, nuclear factor-kappa B (NF-κB) activation, and a proteome characteristic of an inflammatory response that accompany microglial stimulation with N-α-syn and DA degeneration. Nonetheless, PD progresses slowly over the span of several years to decades suggesting that in addition to neuroinflammation, a compensatory regulatory mechanism is operative for disease (Przedborski, S. (2005) Parkinsonism Relat. Disord., 11(Suppl 1):S3-7).

Activated microglia possess dual roles for neural repair and disease that are dependent upon specific environmental cues, degree of injury, stage of disease, and brain regions involved. In previous works, it has been demonstrated that stimulation of microglia with sciatic and optic nerve fragments, in addition to inducing expression of pro-inflammatory cytokines, incites a neuroprotective phenotype by upregulation of several signal transducer and activator of transcription (STAT) genes, cytoskeletal proteins, lysosomal proteins, and immunoregulatory proteins, and enhanced expression of neurotrophins including brain derived neurotrophic factor (BDNF) and glial derived neurotrophic factor (GDNF) (Glanzer et al. (2007) J. Neurochem., 102:627-645). Based on those observations, it was reasoned that microglial response to N-α-syn might also induce underlying compensatory or protective mechanisms to circumvent the injurious effects. Herein, a dual profile for both a toxic and trophic microglial cell in response to N-α-syn is demonstrated. This profile indicates modulation of the glutamate-glutamine cycle and an upregulation of cytoskeletal proteins, regulatory and redox-active proteins. Most importantly, high levels of cysteine were produced in parallel to reduced cathepsin and high cystatin levels. It is demonstrated herein that microglia acquire a neurotoxic phenotype after aggregated N-α-syn stimulation. However, a tandem compensatory response through regulation of cysteine secretion, cystatin expression, cathepsin activity, and NF-κB activation was observed. These data provide a yet undefined regulatory role for microglia in PD pathobiology.

Materials and Methods
Purification, Nitration, and Aggregation of Recombinant Mouse α-Syn Purification, nitration, and aggregation of recombinant mouse α-syn were performed as previously described. Protein concentration was determined from the dry weight of the lyophilized protein.

Isolation, Cultivation, and N-α-syn Activation of Murine Microglia

Microglia from C57BL/6J mice neonates (1-2 days old) were prepared using previously described techniques (Dobrenis, K. (1998) Methods 16:320-344). All animal procedures were in accordance with National Institutes of Health guidelines and were approved by the Institutional Animal Care and Use Committee of the University of Nebraska Medical Center. Brains were removed and placed in Hanks' balanced salt solution (HBSS) at 4° C. The mixed glial cells were cultured for 7 days in complete Dulbecco's modified Eagle's medium (DMEM) containing 10% FBS (fetal bovine serum), 10 μg/ml gentamicin and 2 μg/ml macrophage colony stimulating factor (MCSF; Wyeth, Inc., Cambridge, Mass.). To obtain homogenous microglial cell populations, culture flasks were gently shaken and nonadherent microglia were transferred to new flasks. The flasks were incubated for 30 minutes to allow the microglia to adhere, and loose cells removed by washing with DMEM. Microglia were plated at $2\times10^6$ cells/well in 6-well plates in complete DMEM. The adherent microglia obtained using this method was assessed for purity by immunocytochemical analysis for CD11b positive cells and by morphological examination. As previously reported, the microglial cell population was >98% CD11b+ (Enose et al. (2005) Glia 51:161-172). One week following re-plating, cells were stimulated with 100 nM of aggregated N-α-syn/well or no stimulation for 4 hours and 24 hours. Media were replaced with serum free DMEM without phenol red or other additives (Invitrogen/GIBCO) and incubated for 24 hours in a 37° C., 5% $CO_2$ incubator.

Surface Enhanced Laser Desorption Ionization-Time of Flight (SELDI-TOF)

Protein profiling of culture supernatants was performed using SELDI-TOF ProteinChip® assays (Enose et al. (2005) Glia 51:161-172; Kadiu et al. (2007) J. Immunol., 178:6404-6415) (Ciphergen Biosystems, Fremont, Calif.). The normal phase NP20 protein chip was selected to profile culture supernatants for low and high abundant proteins based on the non-discriminating binding affinity of its hydrophobic surface to proteins regardless of their chemical structure. An aliquot of culture supernatant (2 μg of protein) was applied onto each spot and air-dried. To each air-dried spot, 0.5 μl of 50% sinapic acid (SPA) was added and air-dried. The 50% SPA was prepared as a saturated solution in solvent containing 30% acetonitrile (ACN), 15% isopropanol, 0.5% trifluoroacetic acid, and 0.05% Triton X-100. SELDI-TOF spectra were generated on supernatants collected from three separate microglia cultures. Supernatants collected at each time point were run in triplicate, on three protein chips at different spots to control for instrumental and experimental variability. Molecular mass/charge (m/z) ratios of laser beam ionized proteins were measured in a ProteinChip® PBS II reader. The ProteinChip® Reader was externally calibrated for each analysis using the four standard proteins: bovine insulin (5,733.6 Da), cytochrome C (12,230.9 Da), superoxide dismutase (SOD) (15,591.4 Da), and beta-lactoglobulin (18,363.3 Da). Acquired spectra were analyzed using ProteinChip® software 3.2 (Ciphergen Biosystems). The ProteinChip®& analyses were performed in three independent experiments, and the data set from each microglia comprised a minimum of 8 spectra. All spectra were combined in one file and normalized to total ion current. Peaks were automatically detected using the Biomarker Wizard of ProteinChip® software 3.2. Peak detection parameters were first pass signal/noise (S/N) ratio=5, second pass S/N ratio=2, mass tolerance=0.5%, and estimated peaks were included in completion of clustering.

Protein identification by LC-MS/MS

Following in gel tryptic digestion and column purification, dried peptide samples from cell supernatant fluids were reconstituted in 0.1% formic acid/HPLC-grade water, detected on a ProteomeX LCQ™ DECA XP Plus mass spectrometer (ThermoElectron, Inc. Waltham, Mass.), and identified using BioWorks 3.1 SR software. Proteins identified by peptides having a Unified Score (BioWorks 3.1 SR, Thermo-Electron, Inc. Waltham, Mass.) >3000 were marked for further analysis (Enose et al. (2005) Glia 51:161-172; Kadiu et al. (2007) J. Immunol., 178:6404-6415).

Extracellular Supernatant Fractionation

Culture supernatants were concentrated using Centriplus™ centrifugal filter devices (Millipore, Billerica, Mass.) and dialyzed against MiliQ water using Cellu-Sep® H1 cellulose membranes (Membrane Filtration Products). Samples of culture supernatants were fractionated using 1D SDS-PAGE. Each 200 μg sample was diluted with NuPAGE® loading buffer and separated using NuPAGE® Novex 10% Bis-Tris (Invitrogen) gel. After electrophoresis, the gels were stained with Coomassie Brilliant blue G-colloidal concentrate (Sigma-Aldrich, St. Louis, Mo.).

Nuclear/Cytosol Fractionation

Cell lysates were prepared from N-α-syn-stimulated and control microglia. Cells were rinsed 3× with PBS, following gentle scraping, cells were collected following centrifugation at 600×g for 5 minutes. Cytosol and nuclear fractions were prepared using the Nuclear/Cytosol Fractionation Kit (BioVision; Mountain View, Calif.) according to manufacturer's instructions.

Western Blot Assays

A total of 20 μg of each sample was loaded onto 4-12% Bis-Tris NuPAGE Novex gels (Invitrogen) and transferred onto PVDF membranes (BioRad, Hercules, Calif.). Primary antibodies to calmodulin (1:1000) and 14-3-3σ (1:200) (Millipore), biliverdin reductase (1:5000), thioredoxin (1:2000), β-actin (1:5000), ferritin light:chain (1:1000), galectin 3 (1:1 000) (Abcam, Cambridge, Mass.), NF-κB p65 and p50 (1:200) (Santa Cruz Biotechnology, Inc., Santa Cruz, Calif.), cystatin B (1:500), and cathepsin B (1:1000) (R & D Systems) were used for analyses. Blots were probed with the respective horseradish peroxidase-conjugated secondary antibodies (1:5000; Invitrogen) and detected using SuperSignal® West Pico Chemiluminescent substrate (Pierce Biotechnology, Inc). The intensity of protein bands was quantified using ImageJ and normalized to Gapdh (1:5000, Santa Cruz Biotechnology, Inc.).

Metabolite Assays

Microglia were cultured with and without N-α-syn in media without added glutamine for 2, 4, 8, and 24 hours during stimulation. For analysis of extracellular metabolites, culture supernatants were collected at each time point and mixed with equal volumes of metaphosphoric acid solution (16.8 mg/ml $HPO_3$, 2 mg/ml EDTA and 9 mg/ml NaCl). For analysis of intracellular metabolites, cells were washed three times with ice cold PBS, maintained on ice in PBS, and detached with a tissue culture scraper. To measure protein concentration, an aliquot of the cell suspension was mixed with an equal volume of lysis buffer (0.1 M sodium phosphate, pH 7.4, containing 0.1% Triton-X100, 10 μl/ml protease inhibitor cocktail (Sigma), 25 μg/ml tosyllysine chloromethylketone and 5 μg/ml phenylmethylsulfonyl fluoride). Samples were stored at −80° C. until further use. Data are representative of three independent experiments performed in triplicate.

High Performance Liquid Chromatography (HPLC) Analyses

For analysis of metabolites, the metaphosphoric acid fixed samples of cells or culture supernatant were thawed, vortexed, and clarified by centrifugation at 14000×g for 10 minutes at 4° C. Thiol metabolites in protein free extracts were derivatized with monoiodoacetic acid (7 mM) followed by mixing with an equal volume of 2,4-dinitrofluorobenzene solution (1.5% v/v in absolute ethanol) and analyzed by HPLC using u-Bondapak-NH2 300×3.9 mm column (Waters) with a methanol-acetate gradient as described previously (Mosharov et al. (2000) Biochemistry 39:13005-13011). The concentration of metabolites in the samples was determined using a standard curve generated for each metabolite of interest. Results were normalized to protein concentration in each sample. The protein concentration in samples was measured using the Bradford reagent (Bio-Rad; Hercules, Calif.) with bovine serum albumin as standard.

Intracellular Glutathione (GSH)

Microglia were cultured with and without N-α-syn for 24 hours in media without added glutamine. Cells were washed three times with ice cold PBS, and detached with a tissue culture scraper. Cell suspensions were collected in triplicate and assayed for GSH, GSSG, and total glutathione levels with the Biovision Glutathione Assay Kit (Biovision, Mountain View, Calif.) according to manufacturer's protocol. Briefly, cells were homogenized in 100 μl assay buffer, and glutathione was stabilized with 6N perchloric acid. For assay, a standard curve was performed with GSH standard. Samples were prepared according to protocol for determination of GSH, GSSG, and total glutathione. Reducing Agent Mix (Biovision) was added to convert GSSG to GSH. An o-phthalaldehyde probe was added to the samples for 40 minutes. Samples were then assessed in a 96 well fluorometer plate using a SpectraMAX GEMINI (Molecular Devices, Sunnyvale, Calif.) at excitation/emission of 340/450 nm.

Cathepsin B Activity

Microglia were seeded onto sterile glass coverslips at $10^5$ cells per well and allowed to adhere for 24 hours prior to stimulation with aggregated N-α-syn. Cathepsin B activity was determined using the CV-Cathepsin B Detection Kit (BIOMOL International LP). For measurement of cathepsin B activity, arginine conjugated cresyl violet [CV-$(RR)_2$, a red fluorogenic substrate when unconjugated] was added to the culture media and allowed to incubate for 60 minutes in a 37° C., 5% $CO_2$ incubator. The attached ArgArg group is a substrate for cathepsin B cleavage. Hoechst stain was added at 0.5% v/v and incubated with cells for an additional 5 minutes to stain nuclei. Fluorescence intensity of unconjugated CV was determined at 550 nm for excitation and 610 nm for emission of 3 wells/10 fields per well/experimental group. Mean Fluorescence intensity of unconjugated CV was normalized to the mean intensities of Hoechst staining at 480 nm for excitation and 540 nm for emission for each sample.

Cathepsin B Inhibition and Neurotoxicity

MES 23.5 cells were cultured in 75-$cm^2$ flasks in DMEM/F12 with 15 mM HEPES (Invitrogen) containing N2 supplement (Invitrogen), 100 U/ml of penicillin, 100 μg/ml streptomycin, and 5% FBS. MES23.5 cells is a cell line derived using somatic cell fusion of rat embryonic mesencephalon cells and the murine neuroblastoma-glioma cell line N18TG2 that produce dopamine and express tyrosine hydroxylase (Crawford et al. (1992) J. Neuroscience 12:3392-3398). Cells were grown to 80% confluence then plated at a density of $10\times10^4$ cells on sterile glass coverslips. Microglia were plated in 6 well plates and incubated for 1 hour with or without 1 μM of cathepsin B inhibitors, CA-074 [cell impermeable] or CA-074 Me [cell permeable] (Sigma), in a 37° C., 5% $CO_2$ incubator to inhibit residual cathepsin B expression (Gan et al. (2004) J. Biol. Chem., 279:5565-5572). N-α-syn (100 nM) was then added directly to this media for 24 hours. Unstimulated microglia and N-α-syn stimulation alone served as controls. Following stimulation, supernatants were removed and added to cultures of MES23.5 cells for an additional 24 hours. MES 23.5 cell viability was assessed using the Live/Dead cytotoxicity assay (Invitrogen) as previously described. Live cells were distinguished by the uptake of calcein AM to acquire a green fluorescence [excitation/emission (ex/em)

495/515=m], while dead cells acquired a red fluorescence (ex/em 495/635 μm) due to the uptake of ethidium homodimer-1 (EthD-1). Cell enumerations were performed using fluorescence microscopy (200× magnification, n=6 wells per group, 3 frames per well).

Statistical Analyses

All values are expressed as means±SEM. Differences among means were analyzed by oneway ANOVA followed by Bonferroni post-hoc testing for pair-wise comparison.

Results

N-α-syn-Activated Microglia Secretions and Neuroinflammatory Responses

Figure 30:
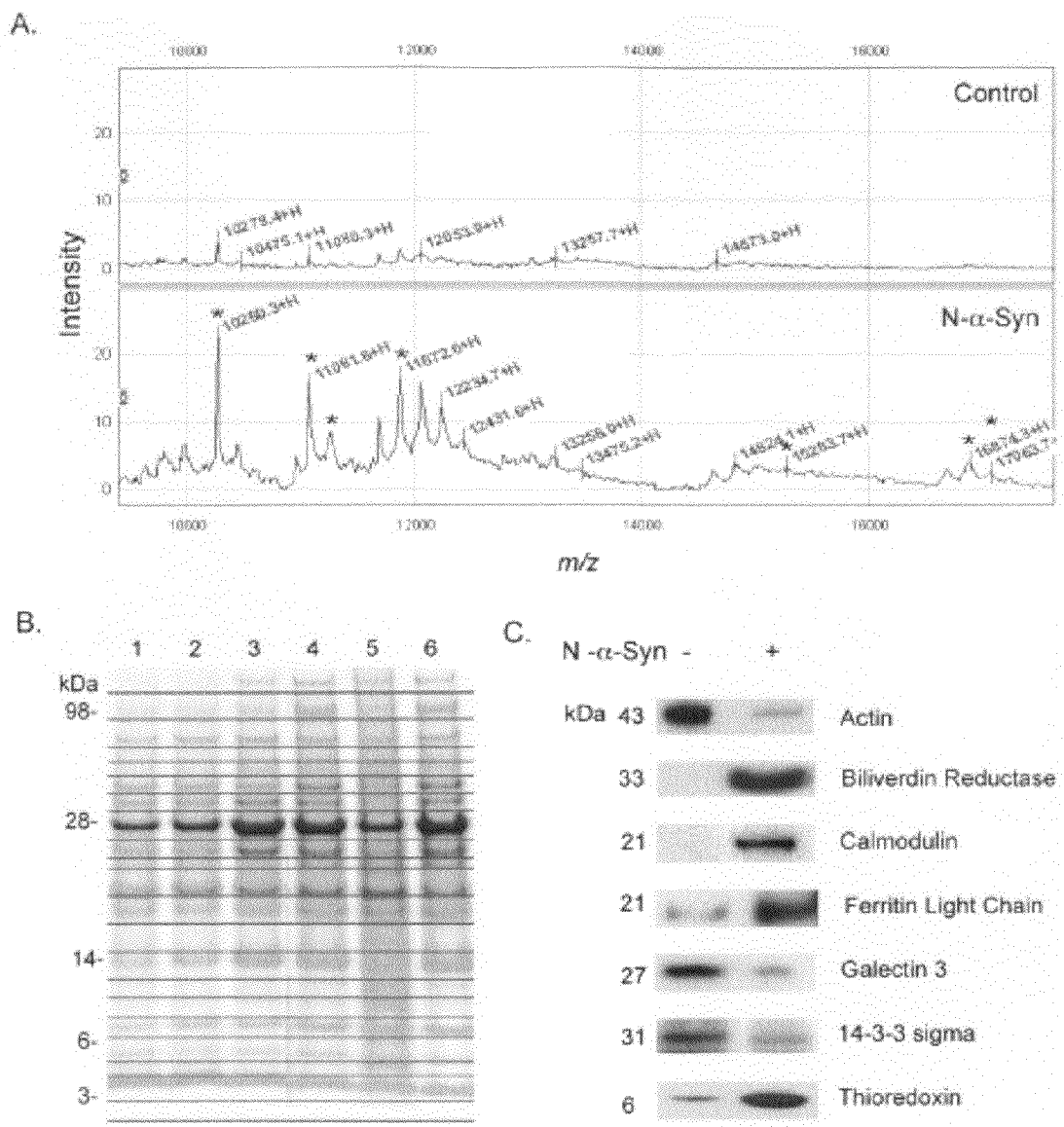
FIGS. 30A-30C provide SELDI-TOF, 1D SDS PAGE, and Western blot analyses of supernatant fluids obtained from N-α-syn-activated microglial. Representative SELDI-TOF spectral analysis (region 10-20 kDa) of untreated-control (top panel) and N-α-syn-stimulated microglia (bottom panel) at 16 hours post-stimulation, shown in FIG. 30A. Marked by an asterisk are upregulated and uniquely expressed peaks corresponding in molecular weight within 1% of mass tolerance to proteins identified by LC-MS/MS. These include calcyclin (10,051 Da), thioredoxin (11,544 Da), calvasculin (11,721 Da), calmodulin (16,706 Da), and TNF-α (17,907 Da). Bands were excised from 1D SDS PAGE gel, digested by trypsin, and sequenced by LC-MS/MS. Lanes are supernatant fluids obtained from control (unstimulated) microglial=[Lanes 1-3] and supernatants from N-α-syn-activated microglia [Lanes 4-6] collected 8 hours, 16 hours, and 24 hours post-stimulation, respectively (FIG. 30B). Representative Western blots of supernatant fluids from control and N-α-syn-stimulated microglia 16 hours post-stimulation for proteins identified by LC-MS/MS (FIG. 30C).
FIGS. 30D and 30E provide the secretome of N-α-syn-stimulated microglia. **The CID spectra were compared against those of the EMBL nonredundant protein database by using SEQUEST (ThermoElectron, San Jose, Calif.). After filtering the results based on cross correlation Xcorr (cutoffs of 2.0 for [M+H] 1+, 2.5 for [M+2H]2+, and 3.0 for [M+3H]3+), peptides with scores greater than 3000 and meeting delta cross-correlation scores (Cn)>0.3, and fragment ion numbers >60% were deemed valid by these SEQUEST criteria thresholds, which have been determined to afford greater than 95% confidence level in peptide identification. $^a$Theoretical molecular mass. $^b$Isoelectric point. $^c$Accession numbers for UniProt (accessible at www.ipr.uniprot.org/search/textSearch.shtml). $^d$Number of peptides identified for each protein selected based on the above mentioned criteria. Proteins were considered if 2 or more peptides were identified. $^e$Proteins were increased or decreased in supernatants of microglia stimulated with N-α-syn for 4 hours when compared to unstimulated microglia (controls).

In previous studies it has been demonstrated that a temporal pattern of microglial activation occurs following stimulation of microglia with N-α-syn, and consists of increased expression of factors attributed to inflammatory responses, oxidative stress and significant neurocytotoxicity (Zhang et al. (2005) Faseb J., 19:533-542). The secretion of potentially neurotoxic compounds characterizes the progression of an activated microglial phenotype to a neurotoxic phenotype, while secretion of trophic factors that support neuronal survival and cell-cell communication characterizes a quiescent microglial phenotype. To analyze the secretory profile induced upon N-α-syn stimulation, supernatants from microglia stimulated for 4 hours with N-α-syn were collected at 8, 16, and 24 hours post-stimulation. Supernatants were first screened for low and high abundant proteins using SELDI-TOF analysis. In these experiments, spectra were generated from cell supernatants collected from control and stimulated cultures at each time-point in three separate experiments using a NP20 Protein Chip. Signal to noise ratios of 5 and 2 for first and second passes respectively and 0.5% mass tolerance (Enose et al. (2005) Glia 51:161-172). Representative spectra of culture supernatants obtained from microglia simulated with aggregated N-α-syn revealed that microglial secretory constituents were significantly altered compared to those of unstimulated microglial controls (FIG. 30A), and consisted of several peaks coinciding with molecular masses of calcium regulatory proteins (calcyclin, 10,051; calmodulin, 16,706 Da; calvasculin, 11,721 Da), redox-active proteins (thioredoxin, 11,544 Da), and TNF-α (17, 907 Da). In contrast, secretory profiles of microglia cultured in the presence of unaggregated N-α-syn revealed similar profiles to unstimulated control microglia. These results determined that microglial secretory products were significantly changed by stimulation with N-α-syn, and encouraged the pursuit of 1D SDS PAGE methods to isolate and identify differentially secreted proteins upon stimulation. Use of 1D SDS PAGE followed by LC-MS/MS analysis has been shown to be reliable in identifying differentially expressed proteins (Enose et al. (2005) Glia 51:161-172; Glanzer et al. (2007) J. Neurochem., 102:627-645; Ciborowski et al. (2007) Virology 363: 198-209) and identification of N-α-syn following immunoprecipiation with confirmatory western blot analyses. LCMS/MS analyses of SDS-PAGE fractions identified 30 proteins common to supernatants from both stimulated and control microglia. Analysis of proteins secreted from N-α-syn-stimulated microglia by LC-MS/MS identified those proteins detected by SELDI-TOF. Microglial expressed proteins were considered using criteria that at least two peptides from a protein were detected with a unified score (BioWorks, 3.1 SR) greater than 3000 as previously described (Glanzer et al. (2007) J. Neurochem., 102:627-645). Proteins were identified as either greater or lower in abundance based on the number of peptides detected by LC-MS/MS, or the presence of a protein identified with high confidence in culture supernatants of one group but not in culture supernatants of the other. Altogether, LC-MS/MS analysis revealed 40 increased and 34 decreased in abundance within culture supernatants when compared to unstimulated controls (FIGS. 30D and 30E); seven of which were validated by western blot analysis (FIG. 30C) including decreased secretion of actin, galectin 3, and 14-3-3 sigma along with increased expression of biliverdin reductase, calmodulin, ferritin light chain, and thioredoxin in culture supernatants of N-α-syn-stimulated microglia. Sixteen proteins found in greater abundance in supernatants of aggregated N-α-synstimulated microglia were classified as being involved in both cellular activation and regulation. For example, regulators of oxidative stress including thioredoxin, biliverdin reductase, and ferritin light chain were abundantly secreted by stimulated microglia. Also found in these supernatants were cell-morphogenesis proteins L-plastin, actin-related protein 3 homolog B (ARP3) and adenylyl cyclase-associated protein 1 (CAP 1); the lysosomal proteins, α-N-acetylglucosaminidase (NAGLU) and N-acetylgalactosamine-6-sulfate sulfatase (GALNS); and the calcium binding proteins EF-hand domain-containing protein 2 (EFHD2, swiprosin1) and nucleobindin (Islam et al. (2006) J. Biol. Chem., 281:6860-6873). Proteins less abundant in supernatant fluids from N-α-syn-stimulated microglial supernatants including calcyclin, β-actin, histone H4, triose-phosphate isomerase, phosphoglycerate mutase 1, cathepsin S, 14-3-3σ, and ubiquitin were reported to be associated with exosomal vesicles, whereas only three of the proteins (ferritin light chain, CAP1, and L-plastin) that were more abundant in N-α-syn-stimulated microglial supernatants have been associated with exosomes (Thery et al. (2001) J. Immunol., 166:7309-7318; Wubbolts et al. (2003) J. Biol. Chem., 278:10963-10972; Pisitkun et al. (2004) Proc. Natl. Acad. Sci., 101:13368-13373; Potolicchio et al. (2005) J. Immunol., 175:2237-2243; Faure et al. (2006) Mol. Cell. Neurosci., 31:642-648).

Metabolic Response of Microglia to N-α-Syn Stimulation

Figure 31:
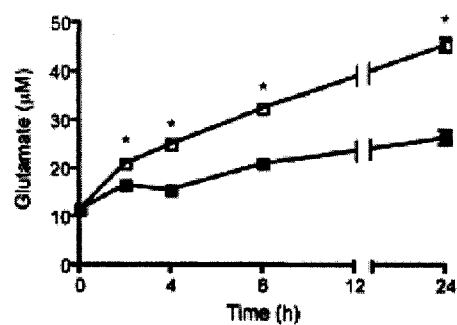
FIG. 31 provides N-α-Syn activated microglial metabolic responses. Microglia were stimulated with N-α-syn over the course of 24 hours and culture supernatants were collected at specified times following stimulation for analysis of extracellular metabolites, shown in FIG. 31A. Analysis of intracellular metabolites following engagement with N-α-syn is shown in FIG. 31B. Mean metabolite concentrations are presented as values±SEM, and are representative of three separate experiments, (*P<0.001, v. unstimulated control).
Figure 31:
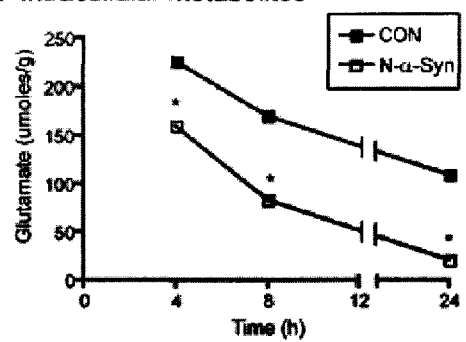
Figure 31:
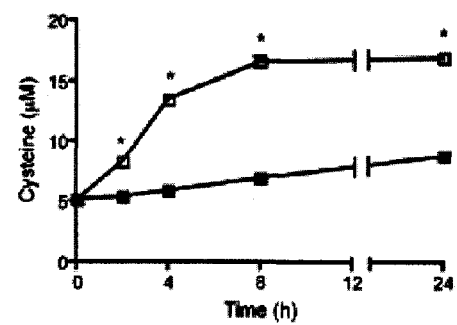
Figure 31:
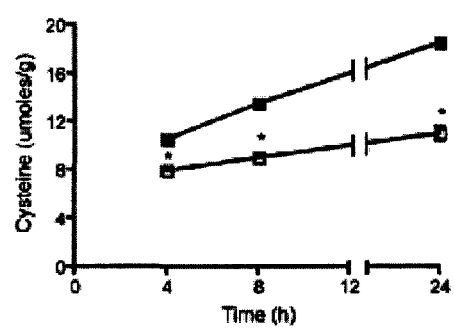
Figure 31:
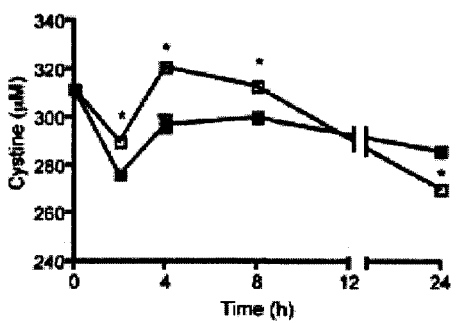
Figure 31:
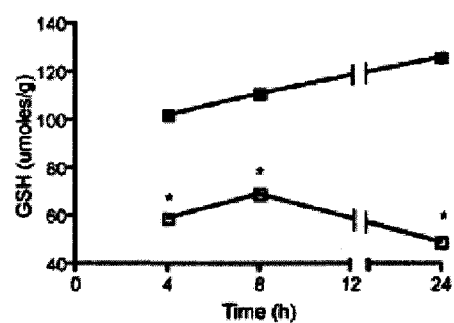

In addition to activation of signaling pathways that incite neuroinflammatory responses, increased expression and secretion of redox-active proteins suggested that a multifaceted microglial response to N-α-syn may affect PD, and that regulatory mechanisms which counter oxidative stress may accompany the inflammatory response. To assess the latter possibility, the concentrations of metabolites involved in the glutamate-glutamine cycle were determined. It was theorized that as a result of stimulation with N-α-syn, changes in the levels of microglial metabolites would occur relative to unstimulated controls (FIG. 31A). Stimulation with N-α-syn resulted in increased secretion of glutamate in supernatants collected at time points measured over a 24 hour time period compared to supernatants collected from unstimulated control cells (32.5±0.5 μM versus 21.0±1.0 μM, P<0.0001 at 8 hours of stimulation) and continued to rise, so that by 24 hours the concentration was 45.5±1.5 μM compared to 26.5±2.5 μM for control (P<0.0001). Moreover, extracellular cysteine was also found significantly elevated in response to N-α-syn compared to controls (16.6±0.7 μM versus 6.96±0.03 μM, P<0.0001; 8 hours). As expected, increased extracellular cysteine was accompanied by decreased cystine. This was seen at 24 hours following exposure to N-α-syn (270.0 μM versus 286.0±3.0 μM in controls, P<0.0001 at 24 hours). Intracellular concentrations of both glutamate and cysteine were decreased in stimulated microglia compared to controls (FIG. 31B).

Determination of intracellular GSH concentration by HPLC indicated that exposure to N-α-syn resulted in its 2 fold rapid depletion at 2 hours to 31.3±0.6 μmoles/g protein compared to controls with 60.0±3.3 μmoles/g protein (data not shown, P<0.001). During continuous exposure with N-α-syn, glutathione levels rose to nearly pre-stimulatory levels by 8 hours (69.0±2 μmoles/g protein versus 111±2 μmoles/g protein), and the levels again dropped by 24 hours (49±1 μmoles/g protein). In contrast, glutathione levels steadily rose in cell lysates of unstimulated microglia to 126±1 μmoles/g protein (P<0.0001, FIG. 2B) by 24 hours. In addition, the ratio of GSH to oxidized glutathione (GSSG), an indicator of cellular redox status, declined steeply within 2 hours in response to N-α-syn stimulation (34.2±1.0 versus 89.4±2.6, P<0.001), however this ratio gradually rebounded (70.0±2.0 and 65.0±1.0 by 8 and 24 hours respectively) but remained at about 2 fold lower throughout the course of stimulation in comparison to unstimulated control (114.0±3.0 and 163.0±1.0 by 8 and 24 hours respectively). Investigation of GSH and GSSG levels using the Biovision glutathione assay kit confirmed these results, and revealed that by 24 hours the GSH levels were significantly decreased (P<0.001), and corresponded with decreased GSH/GSSG ratio and total GSH plus GSSG levels compared to levels in unstimulated cell lysates.

Cathepsin B Activity and N-α-Syn Microglial Activation and Cytotoxicity

Figure 32:
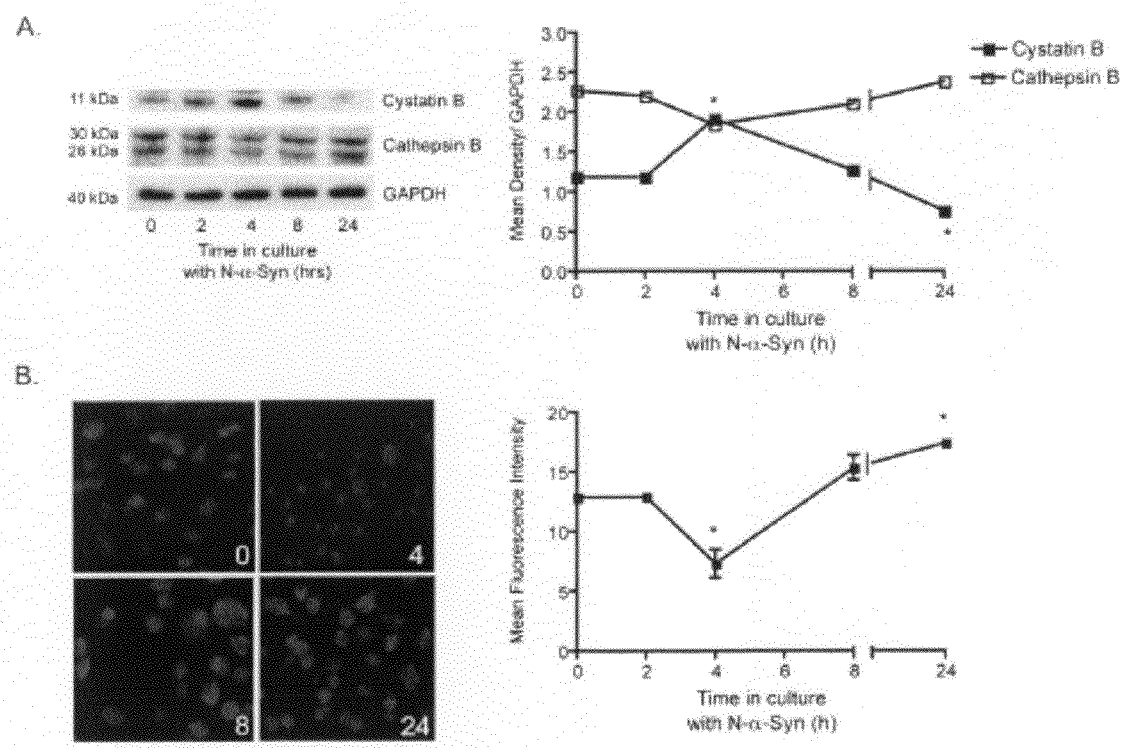
FIG. 32 shows cathepsin B expression and functional activity following N-α-syn-microglial activation. Comparative analysis of cystatin B and cathepsin B protein expression in microglia at several time points during stimulation with aggregated N-α-syn by western blot, shown in FIG. 32A. Mean density of protein bands (±SEM) were normalized to GAPDH expression on the same blot (*P<0.05 compared to unstimulated microglia at 0 hour) (FIG. 32B). Cathepsin B enzymatic activity prior to stimulation (0 hour) and at 2 hours, 4 hours, 8 hours, and 24 hours after stimulation with N-α-syn. Enzymatic activity is visualized with the red fluorogenic substrate, CV-(RR)$_2$ and nuclei are stained blue with Hoechst dye. Fluorescence intensities were determined by ImageQuant and are presented as mean±SEM for n=3 fields for 4 replicates (P<0.05 compared to mean at 0 hour).
Figure 33:
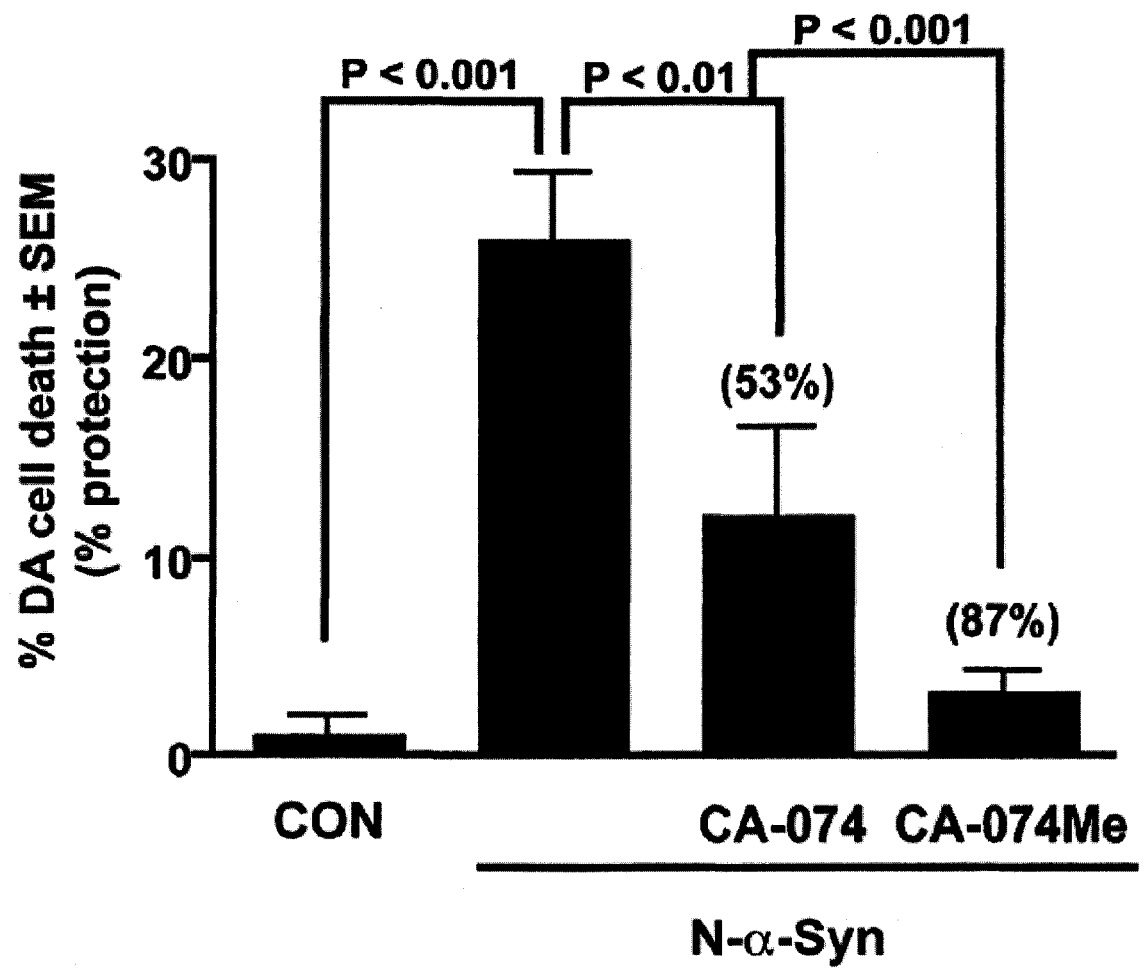
FIG. 33 shows the effect of Cathepsin B inhibition on N-α-syn-mediated cytotoxicity. Supernatants from N-α-syn stimulated microglia induced significant DA cell death. Whereas, inhibition of cathepsin B activity by either the cell impermeable inhibitor CA-074 or the cell-permeable inhibitor CA-074 Me resulted in partial protection from N-α-syn mediated DA cell death, shown. Values are shown as mean dead DA cells±SEM for n=6 replicates per treatment paradigm.

Microglia have been shown to express a number of proteases, including the cysteine protease cathepsin B, where it may play a role in degradation of matrix proteins and associated signal transduction molecules that can induce neuronal apoptosis (Kingham and Pocock, 2001). To further investigate the microglial response to N-α-syn in regulating neurotoxicity a series of tests were performed to assess the differential expression of cathepsin B, and the cysteine protease inhibitor cystatin B, over the course of stimulation. Western blot analysis revealed a significant increase in expression of cystatin B in microglial cell lysates following 4 hours of N-α-syn stimulation compared to unstimulated controls and decreased expression of cathepsin B (FIG. 32A). However, by 24 hours of N-α-syn stimulation, cystatin B expression was decreased, whereas expression of cathepsin B in cell lysates was not significantly changed. Since regulation of cathespin B is primarily post-translational, increased expression of cystatin B would more closely correspond to decreased cathepsin B activity rather than decreased protein expression, therefore it was investigated the enzymatic activity of cathespin B before and during stimulation with N-α-syn. Activity of intracellular cathepsin B was significantly decreased in microglia following 4 hours of stimulation with N-α-syn compared to basal activity before stimulation, and then enzymatic activity increased significantly over pre-stimulatory level by 24 hours (FIG. 32B). It was next investigated whether cathepsin B could also contribute to N-α-syn stimulated microglial cytotoxicity. Microglia were stimulated with N-α-syn in the presence of either the selective cathepsin B inhibitor CA-074 or the cell permeable form CA-074 Me for 24 hours, when cathepsin B activity was elevated following N-α-syn stimulation alone. The resultant supernatants were then added to cultures of dopaminergic MES23.5 cells, for an additional 24 hours for cell death measurement (FIG. 33). Supernatants from unstimulated microglia did not induce DA cell death, while N-α-syn stimulation alone resulted in significant cytotoxicity (26% of control, P<0.001). Inhibition of secreted Cathepsin B by the cell impermeable inhibitor, CA-074, partially protected DA cells against N-α-syn microglial mediated cell death (53% protection v. N-α-syn alone, P<0.01), while the cell permeable form, CA-074 Me resulted in heightened DA cell protection (87%, P<0.001).

NF-κB Subunit Translocation and N-α-syn Microglial Activation

Figure 34:
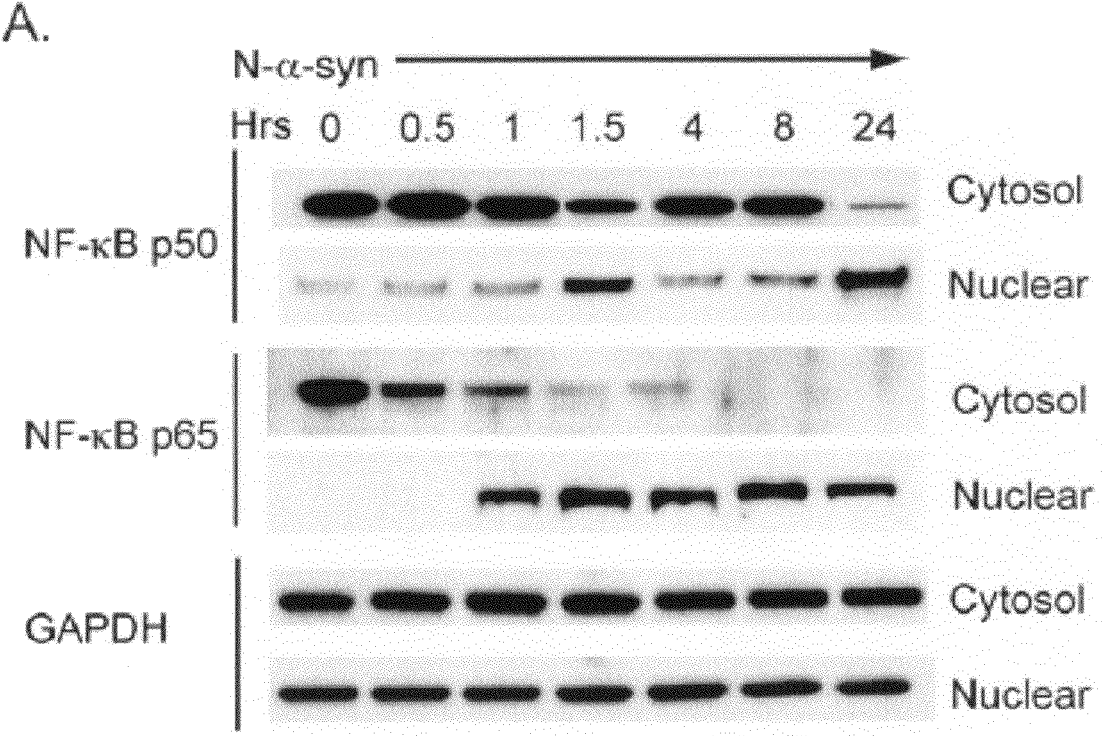
FIG. 34 shows nuclear translocation of NF-κB subunits. Cytosol (top) and nuclear (bottom) fractions were prepared from microglia stimulated with N-α-syn for subsequent timepoints and assessed for expression of NF-κB subunits NFκB1/p50 and RelA/p65 by western blot (FIG. 34A). Mean density of protein bands for NFκB1/p50 (FIG. 34B) and RelA/p65 (FIG. 34C) by western blot were normalized to GAPDH in the same sample. Values are shown mean±SEM for n=3 replicates per time point (*P<0.01 compared to 0 hour).

Activation of the NF-κB pathway leads to the production of inflammatory mediators implicated in inducing neuronal injury (Qin et al. (2005) Blood 106:3114-3122). Indeed, upregulation of NF-κB transcription is induced upon stimulation with N-α-syn activation, as well as being significantly increased in the SN of post-mortem brains from PD patients. In addition, analysis of the microglial secretome identified many proteins, including for example phosphatidylethanolamine-binding protein, thioredoxin, and FK506-binding protein 12 (FKBP1A) that are downstream of either the NF-κB or mitogen-signaling pathways, suggesting the involvement of NF-κB pathway to initiate not only the inflammatory response, but also regulation of the response. To investigate whether this dual toxic and trophic reaction to N-α-syn by microglia was contingent on activation of the NF-κB pathway, NF-κB translocation to the nucleus was assessed where it can bind DNA and activate transcription of genes encoding proteins involved in an inflammatory response. As early as 1-1.5 hours stimulation of microglia with N-α-syn, NF-κB p50 and p65 were increased in the nucleus, and coincided with decreased expression of these subunits within the cytosolic fractions (FIG. 34A). By 4 hours stimulation however, the nuclear localization of NF-κB subunit p50 was decreased compared to 1.5 hours stimulation, and remained repressed through 8 hour. By 24 hours of stimulation, the p50 subunit was once again diminished in the cytosol and increased within the nucleus (FIG. 34B). Notably, compared to 0 hour, p65 levels in the nucleus were high with correspondingly diminished levels within the cytosolic fraction by 1 hour stimulation (FIG. 34C). These data suggest that the microglial compensatory response, albeit temporary, is also reflective of discontinuous activation of the NF-κB pathway and downstream inflammatory cascades.

EXAMPLE 6

An inciting event that underlies Parkinson's disease (PD) neurobiology is the accumulation of aggregated proteins within neuronal cell bodies and microglia is associated with microglial activation and neuronal death. Deposition of misfolded and nitrated alpha-synuclein (N-α-syn) into Lewy bodies (LB) within nigral dopaminergic neurons of the substantia nigra pars compacta (SNpc) (Spillantini et al. (1997) Nature 388:839-840; Giasson et al. (2000) Science 290:985-989), with subsequent release into extracellular spaces and draining cervical lymph nodes affect neuronal loss by engaging innate and adaptive immune responses (Lee et al. (2008) Biochem. Biophys. Res. Commun., 372:423-428; Theodore et al. (2008) J. Neuropathol. Exp. Neurol., 67:1149-1158). This leads to oxidative stress, microglial and APC activation, and neuronal degeneration (Thomas et al. (2007) J. Neurochem., 100:503-519). Interestingly, α-syn immunization was shown to generate humoral responses for clearing protein aggregates (Masliah et al. (2005) Neuron 46:857-868). However, using nitrated forms of α-syn (N-4YSyn) as an immunogen profound effector T cell (Teff) responses were shown to exacerbate neuroinflammation, and neurodegeneration analogous to the untoward T cell-mediated meningoencephalitic responses observed by Aβ immunization (Smith et al. (2002) Lancet 359:1864-1865). Others reported that T cell responses elicited during the course of 1-methyl-4-phenyl-1, 2,3,6-tetrahydropyridine (MPTP) intoxication led to accelerated neurodegeneration (Theodore et al. (2008) J. Neuropathol. Exp. Neurol., 67:1149-115).

Interestingly, components of adaptive immunity affect neural repair and protection. Indeed, regulatory T cells (Treg) protect against MPTP-induced dopaminergic degeneration. This raised the specter of opposing effects for CD4+ T cell subsets on brain disease where auto-aggressive Teff responses speed the tempo of disease Treg attenuate neurodegeneration. This is in keeping with known anti-inflammatory and neurotrophic function of Treg, their essential role in controlling immune-mediated inflammation and mononuclear phagocyte phenotype (Cederbom et al. (2000) Eur. J. Immunol., 30:1538-1543; Thornton et al. (2000) J. Immunol., 164:183-190; Tiemessen et al. (2007) Proc. Natl. Acad. Sci., 104:19446-19451). Thus, it was investigated whether an adjuvant to promote specific adaptive immune responses could be used with N-α-syn as a vaccine for PD. Using vasoactive intestinal peptide (VIP), a neuropeptide known to induce Treg responses (Delgado et al. (2005) J. Leukoc. Biol., 78:1327-1338; Gonzalez-Rey et al. (2006) Blood 107:3632-3638), it is now show that replacement of functional Treg within the N-α-syn splenocyte mixture results in neuroprotection and is modulated through altered Th17 expression.

Materials and Methods

Animals, Immunizations, and MPTP Intoxication

Recombinant C-terminal tail of α-syn (4YSyn) was purified, nitrated (N-4YSyn), and tested for endotoxin as described. Male C57BL/6J mice and FoxP3-GFP knock in C57BL/6J mice (5 weeks old, The Jackson Laboratory) were immunized with N-4YSyn emulsified in adjuvant as described. Donor mice that did not receive immunizations were injected i.p. with 15 μg of VIP (Sigma-Aldrich) in PBS. Recipient mice received four i.p. injections at 2 hour intervals of either vehicle (PBS, 10 mL/kg bodyweight) or MPTP-HCl (16 mg MPTP/kg bodyweight of free base in PBS; Sigma-Aldrich). Twelve hours after the last injection, MPTP-intoxicated mice received adoptive transfers of whole SPC, Treg or no cells (n=5-7 mice per group per time point). On days 2 and 7 post-MPTP, mice were sacrificed and brains were processed for analysis. All animal procedures were in accordance with National Institutes of Health guidelines and were approved by the Institutional Animal Care and Use Committee of the University of Nebraska Medical Center. MPTP safety measures were in accordance with published guidelines (Przedborski et al. (2001) J. Neurochem., 76:1265-1274).

Isolation and Adoptive Transfer of SPC and CD4+ CD25+T Cells.

Seven days following treatment, mice were sacrificed and single cell suspensions were prepared from inguinal lymph nodes and spleens. CD4+ T cell populations from spleens and lymph nodes were enriched by negative selection with CD4-enrichment columns (R & D Systems) followed by CD25-PE positive selection with AutoMACS (Miltenyi Biotec). T cells were cultured in RPMI medium 1640 (Invitrogen) supplemented with 10% FBS, 2 mM L-glutamine, 25 mM HEPES, 1 mM sodium pyruvate, 1× nonessential amino acids, 55 μM 2-mercaptoethanol, 100 units/ml penicillin, 100 μg/ml streptomycin (Mediatech) in the presence of anti-CD3 (145-2C11; BD Pharmingen), 4YSyn or N-4YSyn. Proliferation and inhibition assays were performed as described. MPTP-intoxicated mice received an i.v. tail injection of $5 \times 10^7$ SPC or $1 \times 10^6$ Treg in 0.25 ml of HBSS.

In Vitro Polarization of CD4+ T Cells

CD4+ T cells were isolated from N-4YSyn immunized donors and cultured $1 \times 10^6$/ml CD4+ T cells with $2 \times 10^6$/ml irradiated SPC and 10 mg/ml N-4YSyn in 20 ml of complete RPMI 1640 supplemented with 10% FBS, 2 mM L-glutamine, 10 mM HEPES, 55 μm 2-mercaptoethanol, 100 units/ml penicillin, and 100 μg/ml streptomycin in T25 flasks. For polarization the CD4+ T cells were cultured with 10 ng/ml IL-2 for Th0; 10 ng/ml IL-12 and 2 μg/ml anti IL-4 for Th1; 10 ng/ml IL-4 and 2 μg/ml anti-IL-12 for Th2; and 3 ng/ml TGF-0, 10 ng/ml IL-6, 5 ng/ml IL-1b, 10 ng/ml IL-23, 2 μg/ml anti-IL-4, 2 μg/ml anti-IL-12, 2 μg/ml anti-IFN-g, and 2 μg/ml anti-IL-2 (Laurence et al., 2007 Immunity 26:371) for 5 days. The Th subsets were then harvested, and $10 \times 10^6$ T cells transferred to each recipient. For stimulation of cytokine production, Th subsets were stimulated with 20 ng/ml PMA and 1 μM ionomycin (Sigma-Aldrich) for 5 hours and supernatants collected 24 hours later for analysis.

Flow Cytometric Analysis

Samples from cell fractions were labeled with fluorescently labeled antibodies (eBiosciences) and analyzed by flow cytometry with a FACSCalibur flow cytometer (BD Biosciences).

RNA Isolation and Real-Time PCR Arrays

RNA was purified using TRIzol reagent (Invitrogen Corp) and the RNeasy Mini Kit (QIAGEN Sciences), prior to cDNA synthesis. Real-time PCR analysis using pathway-focused gene expression profiling arrays (SA Biosciences) was performed according to manufacturer's protocol.

Cytokine Analyses

A multi-analyte cytokine ELISArray (SA Biosciences) was used for cytokine analysis within cell culture supernatants according to manufacturer's protocol, Absorbance values were read at 450 nm after stopping the reaction. A cytometric bead array for Th1/Th2 cytokines and an IL-17a Flex set were used to quantitate cytokine concentrations within culture supe matants. The bead arrays were performed according to maunfaturer's protocol and the data acquired on a BD FACSArray bioanalyzer and analyzed using the FCAP Array Software (BD biosciences).

Immunohistochemistry

Mice were transcardially-perfused with PBS followed by 4% paraformaldehyde (PFA, Sigma). Frozen midbrain sections (30 μm) were immunostained for Mac-1 (CD11b, 1:1000; Serotec). Fluorojade C staining (Millipore) was performed on adjacent sections according to manufacturer's protocol to assess degenerating neurons and quantified using ImageJ. Overall dopaminergic neuron survival was assessed seven days following MPTP intoxication and resolution of cell death processes with polyclonal antibody to mouse Tyrosine hydroxylase (TH), 1:1000 (Calbiochem) and counterstained for Nissl substance by thionin staining (Tieu et al. (2003) J. Clin. Invest., 112:892-901) as previously described (Benner et al. (2004) Proc. Natl. Acad. Sci., 101:9435-9440). Total numbers of Mac-1+ cells, TH- and Nissl-stained neurons in the SNpc were estimated by stereological analysis with StereoInvestigator software (MicroBrightfield) using the optical fractionator module (Liberatore et al. (1999) Nat. Med., 5:1403-1409). Quantitation of striatal TH (1:500; Calbiochem) was performed by densitometric analysis as described (Benner et al. (2004) Proc. Natl. Acad. Sci., 101: 9435-9440). Adjacent midbrain sections were immunostained for CD4 (L3T4; 1:200, BD Pharmingen). Sections were incubated in streptavidin-horseradish peroxidase (HRP) solution (ABC Elite vector kit, Vector Laboratories), and color developed using a generation system consisting of diaminobenzidine (DAB) chromogen (Sigma-Aldrich) as described (Benner et al. (2004) Proc. Natl. Acad. Sci., 101: 9435-9440).

Statistical Analyses

All values are expressed as means±SEM. Differences among means were analyzed by one-way ANOVA followed by Fisher's least significant post-hoc testing for multiple comparisons (SPSS, Inc.). All effects of treatment were tested at the 95% confidence level.

Results

N-4YSyn Immunity Exacerbates the MPTP-Induced Nigrostriatal Lesion

Figure 35:
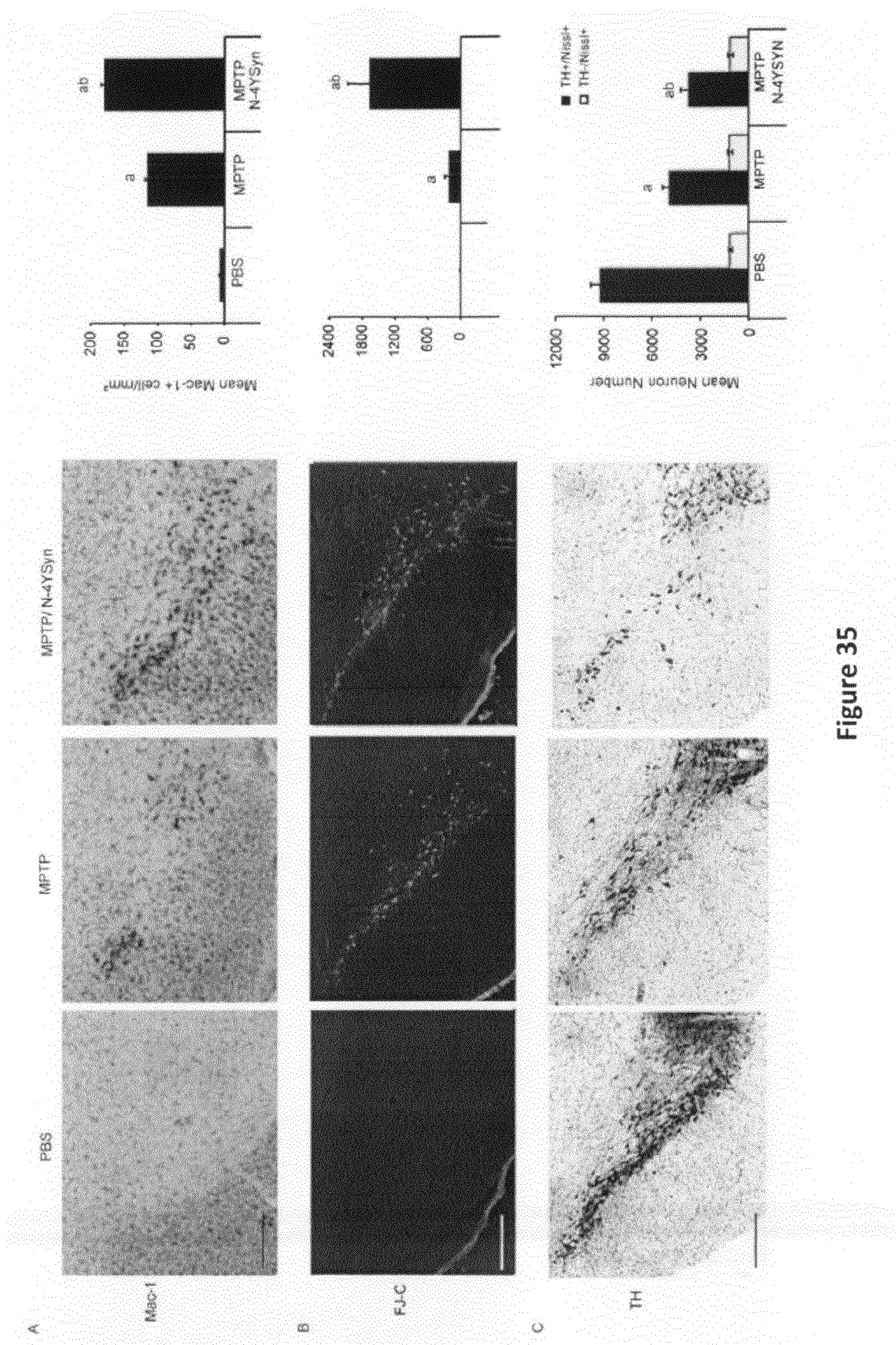
FIG. 35 shows N-α-syn adaptive immunity accelerates MPTP-nigrostriatal degeneration.
Figure 35:
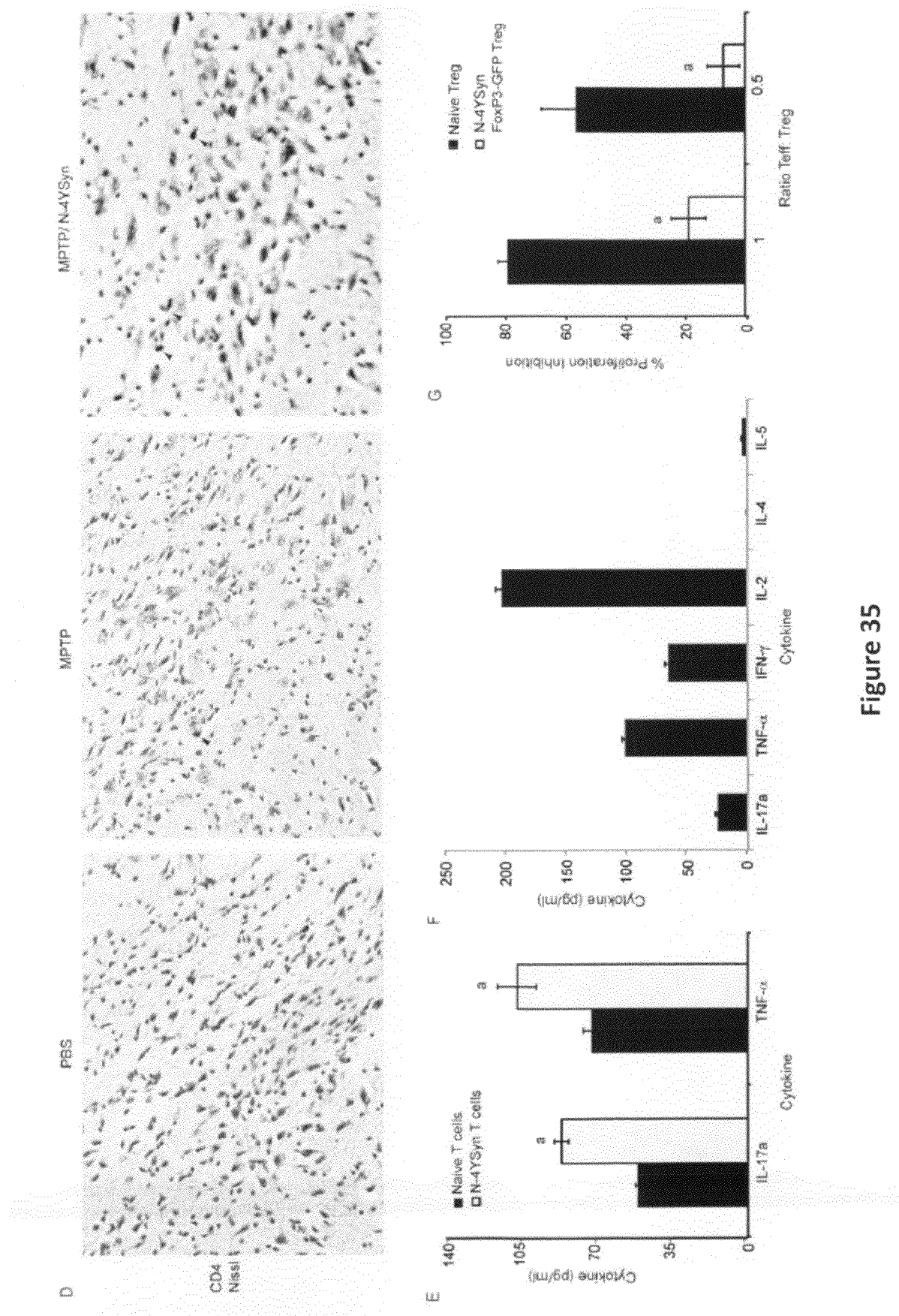

To test whether N-α-Syn-induced immunocytes could exacerbate MPTP-induced inflammation and dopaminergic neurodegeneration, splenocytes (SPC) from donors immunized with N-4YSyn were adoptively transferred to MPTP-recipients and the extent of inflammation and neurodegeneration. Stereological analysis of Mac-1+ cells within the SNpc 2 days post-MPTP showed greater than 16-fold increase in numbers of Mac-1+ cells compared with PBS controls (FIG. 35A), while adoptive transfer of N-4YSyn SPC to MPTP-recipients exacerbated reactive Mac-1+ cell numbers/mm$^2$ by 35% greater than that observed with MPTP alone and 96% greater than PBS controls. Fluorojade C (FJ-C) staining of dead or dying neurons revealed that adoptive transfer of N-4YSyn SPC accelerated MPTP-induced neuronal death by 7.2-fold (FIG. 35B). Analysis of surviving nigral TH$^+$ neurons 7 days after MPTP intoxication indicated a 45% overall neuronal loss compared with PBS controls, whereas MPTP-treated recipients receiving N-4YSyn SPC exhibited a 63% reduction of TH$^+$ neurons (FIG. 35C). PBS mice that received N-4YSyn SPC showed no change in TH$^+$ neuron numbers compared to PBS controls. MPTP mice that received SPC from PBS/adjuvant- or non-nitrated α-syn (4YSyn)/adjuvant-immunized donors showed no significant additive or protective effect on microglial activation or neuronal survival compared to MPTP alone as previously described. No significant effects of any treatment were observed among numbers of non-dopaminergic neurons (TH-Niss1+). Analysis for CD4+ T cell infiltration revealed that MPTP-intoxicated recipients of N-4YSyn SPC had increased infiltration of CD4+ cells within the SNpc following adoptive transfers, whereas MPTP-intoxication alone showed limited infiltrates at 48 hour-post intoxication and no CD4+ cells were identified in PBS-treated controls (FIG. 35D). These data demonstrate that adaptive immune responses against N-α-syn exacerbate MPTP-induced neuroinflammation and nigrostriatal degeneration and support the previous works above.

T cells isolated from N-4YSyn donors stimulated in vitro with anti-CD3 for 24 hours produced greater concentrations of IL-17a and TNF-α relative to naïve T cells (FIG. 35E). N-4YSyn antigenic stimulation of CD4+ effector T cells isolated from immunized mice induced the production of IL-17a, TNF-α, IFN-γ and IL-2, but not IL-4 or IL-5 (FIG. 35F) indicating that immunization partially polarized the CD4+ T cells in vivo towards either a Th1 or Th17 phenotype. Functional characterization of Treg isolated from immunized FoxP3-GFP mice revealed that Treg were functionally deficient in the capacity to inhibit effector T cell proliferation to anti-CD3 stimulation following immunization with N-4YSyn (20%) as compared to Treg isolated from naïve donors (80%) at a ratio of 1:1 (FIG. 35G).

N-4YSyn Immunity Toxic Effect is Mediated by CD4+ T Cell Subsets

Figure 36:
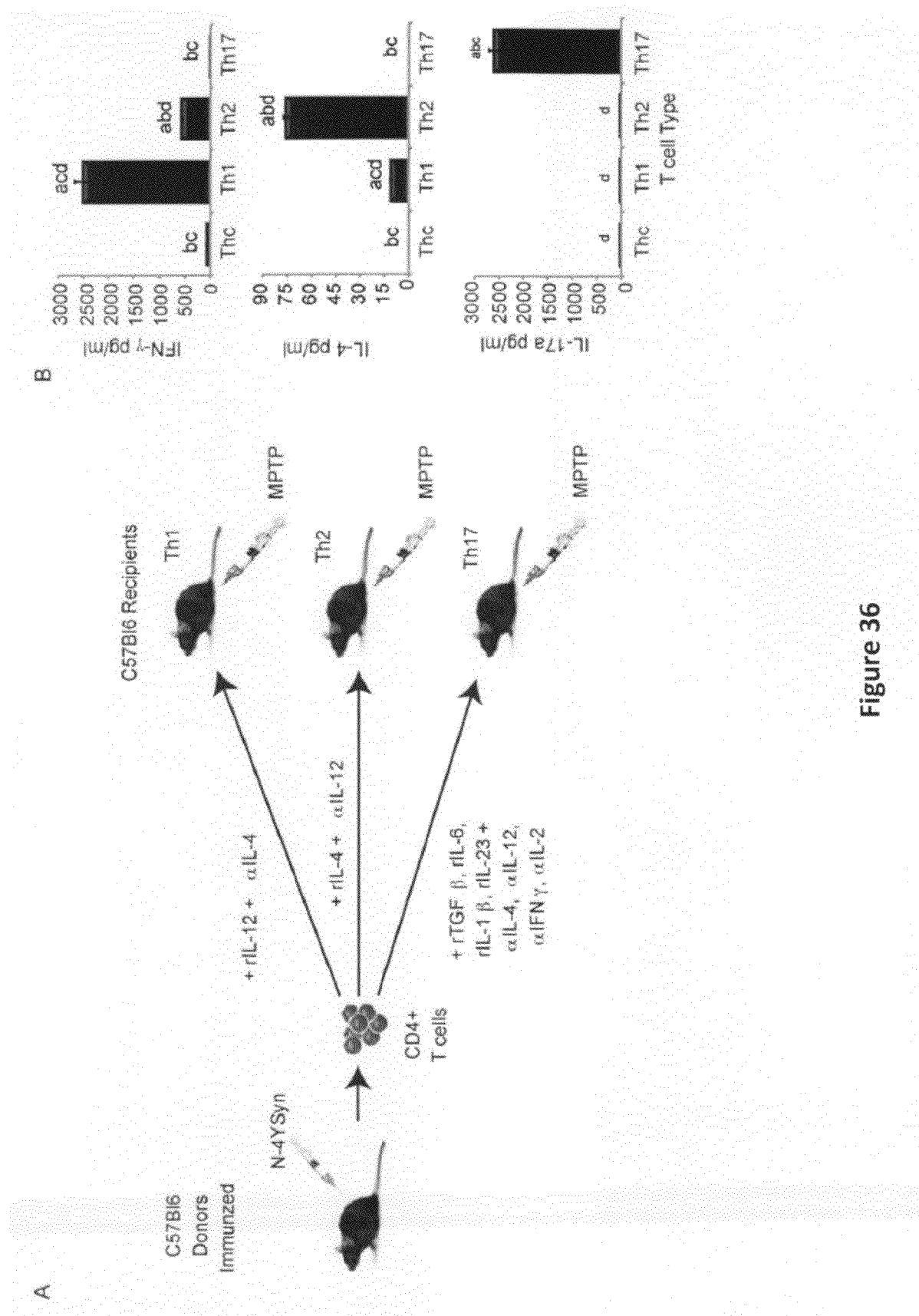
FIG. 36A is a schematic of the adoptive transfer protocol.
FIG. 36B provides graphs demonstrating a cytometric bead array analysis confirming that the CD4+ T cell subtypes were indeed polarized to the designated phenotype.
FIG. 36C provides images of TH immunostained ventral midbrain and striatum 7 days after MPTP treatment and adoptive transfers. The adoptive transfer of both N-4YSyn Th1 and Th17 subsets resulted in decreased numbers of surviving TH+ neurons within the SNpc; whereas, only N-4YSyn Th17 cells resulted in diminished TH termini density within the striatum.
FIG. 36D is a graph showing that the adoptive transfer of N-4YSyn Th17 cells induced a 53% decrease in the number of surviving TH+ neurons relative to MPTP-intoxication alone.
FIG. 36E is a graph of the TH density within the striatum. Adoptive transfer of N-4YSyn Th17 cells significantly exacerbated the MPTP-induced loss of striatal TH density to 5% of PBS-treated controls.
Figure 36:
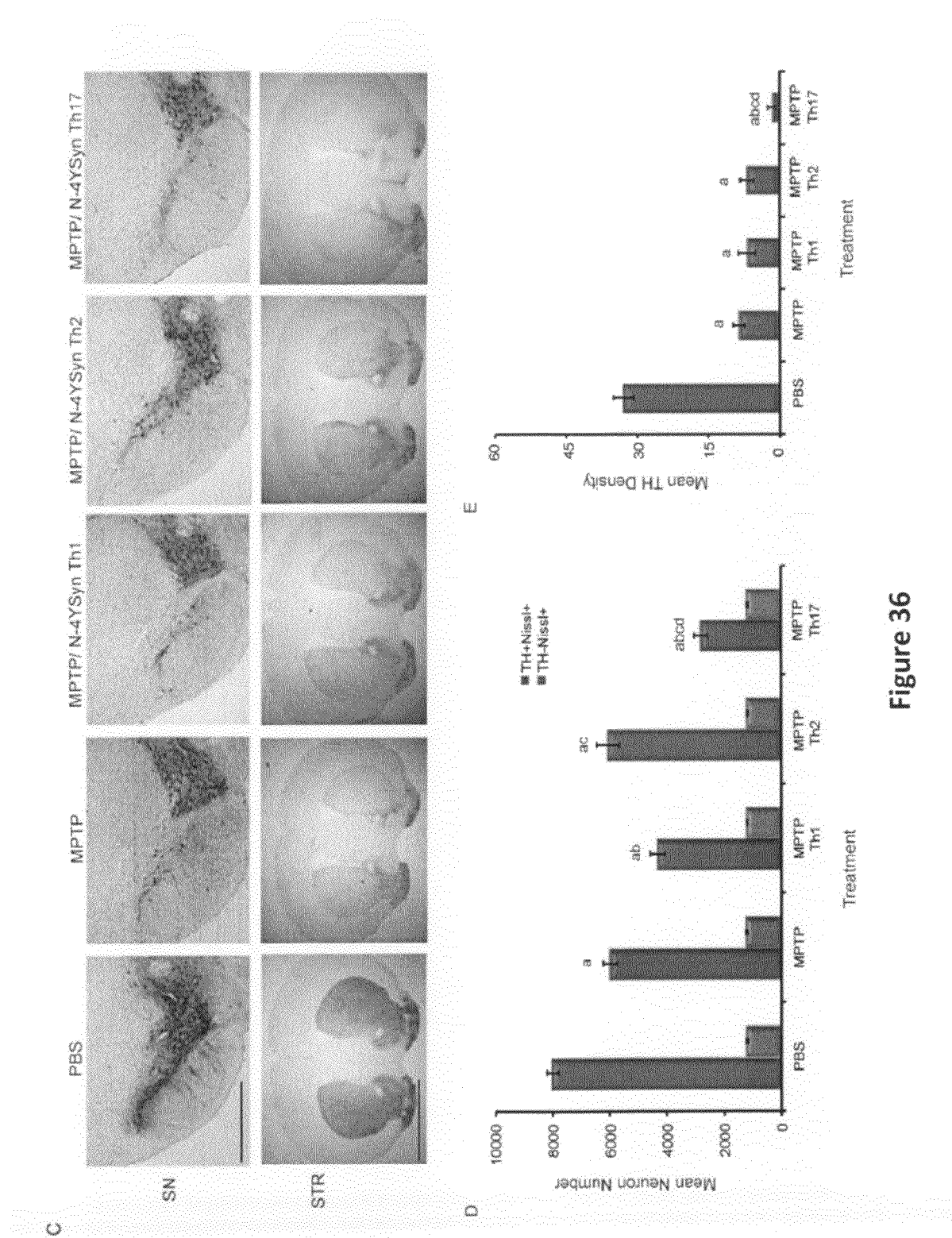

In order to identify the CD4+ T cell subset responsible for the toxic effects mediated by N-4YSyn immunity, CD4+ T cells were isolated from N-4YSyn immunized donors and polarized in vitro for 5 days in culture conditions to favor either a Th1, Th2 or Th17 phenotype and then adoptively transferred into MPTP-intoxicated recipients as shown (FIG. 36A). CD4+ T cells not adoptively transferred were re-stimulated for 4 hours with PMA and ionomycin then supernatants collected for analysis of cytokine production after 24 hours. Cytometric bead array analysis confirmed that the CD4+ T cell subtypes were indeed polarized to the designated phenotype characterized by IFN-γ production by Th1 cells, IL-4 by Th2 cells, and IL-17a by Th17 cells (FIG. 36B).

Analysis of TH immunostained ventral midbrain and striatum 7 days after MPTP treatment and adoptive transfers revealed that adoptive transfer of both N-4YSyn Th1 and Th17 subsets resulted in decreased numbers of surviving TH+ neurons within the SNpc; whereas, only N-4YSyn Th17 cells resulted in diminished TH termini density within the striatum (FIG. 36C). Stereological analysis of ventral midbrain sections indicated that while PBS-treated controls averaged 7994±212 total TH+ neurons within the SNpc, MPTP-intoxication induced a 25% loss of TH+ neurons to 5971±250. Adoptive transfer of N-4YSyn Th1 cells increased the lesion induced with MPTP by 28% resulting in 4320±252 total TH+ neurons; whereas, adoptive transfer of N-4YSyn Th2 cells had no significant additive or exacerbative effect on the total TH+ neurons in response to MPTP-intoxication. In contrast, adoptive transfer of N-4YSyn Th17 cells induced a 53% decrease in the number of surviving TH+ neurons (2800±243) relative to MPTP-intoxication alone reaching statistical significance relative to all other treatment groups (FIG. 36D). Analysis of TH density within the striatum showed that TH density within the striatum of MPTP-intoxicated mice was 26% relative to PBS-treated controls. Adoptive transfer of neither N-4YSyn Th1 nor Th2 cells did not significantly affect the striatal density relative to MPTP-intoxication alone. In contrast, adoptive transfer of N-4YSyn Th17 cells significantly exacerbated the MPTP-induced loss of striatal TH density to 5% of PBS-treated controls (FIG. 36E).

Figure 37:
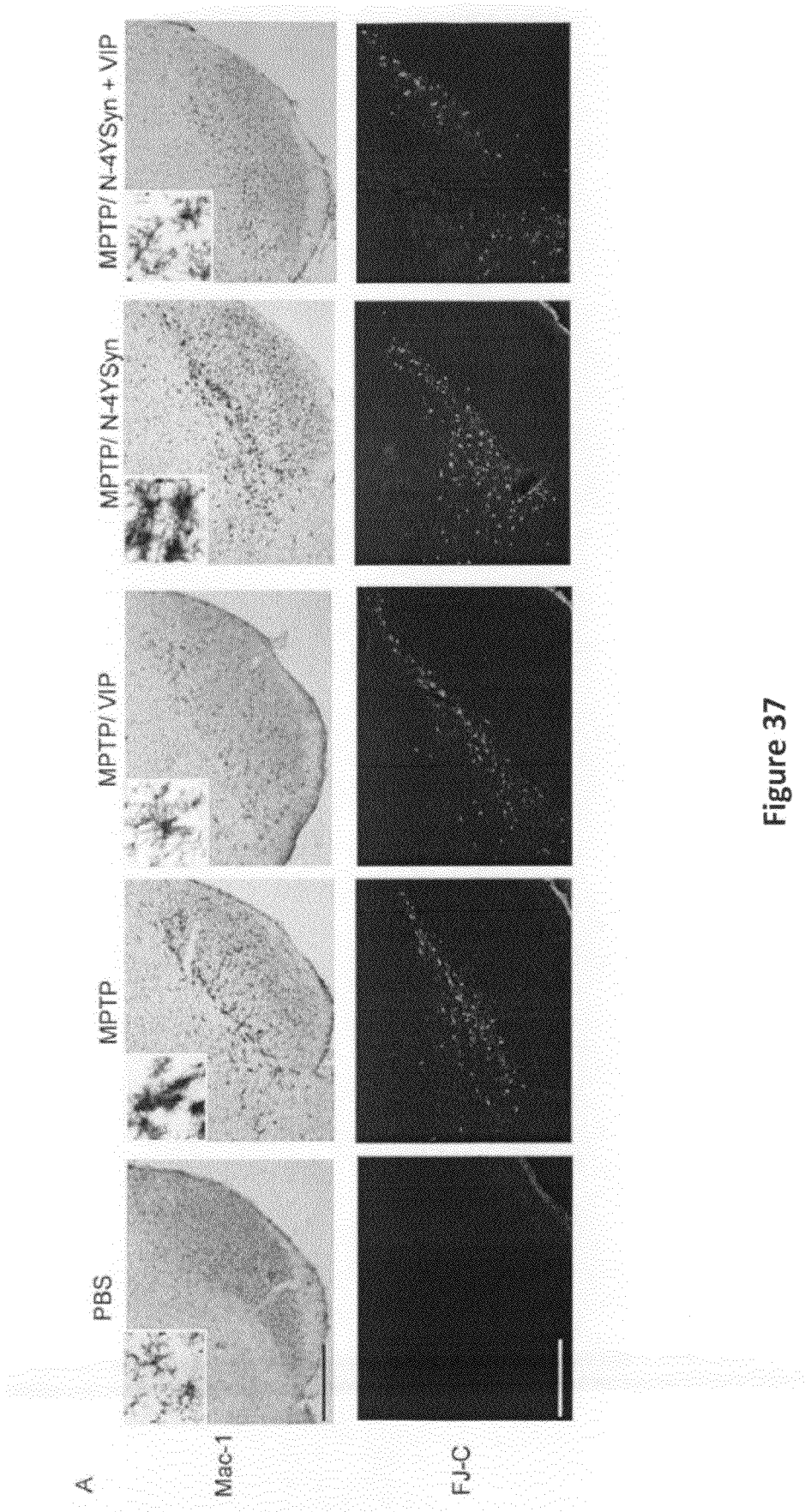
FIG. 37 shows microglial activation and dopaminergic neuroprotection and degeneration.
Figure 37:
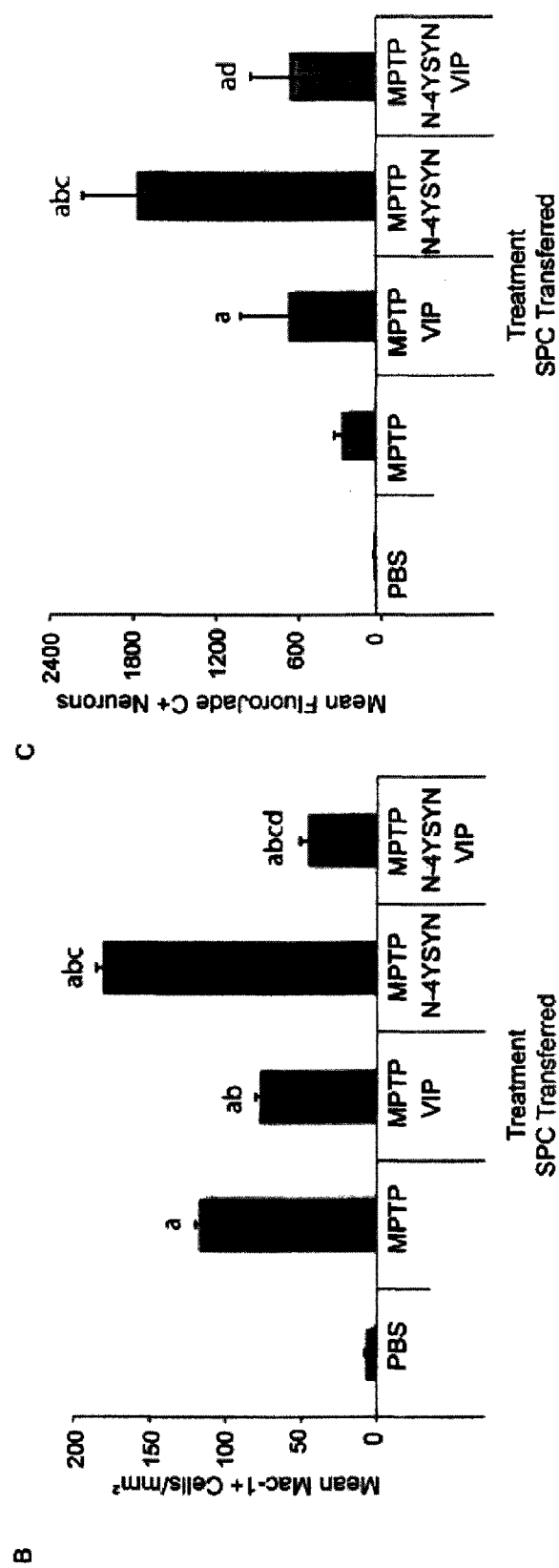

Co-Transfer of VIP SPC with N-4YSyn SPC Attenuates N-4YSyn Mediated Microglial Responses As VIP increases Treg numbers or suppressive function (Delgado et al. (2005) J. Leukoc. Biol., 78:1327-1338; Gonzalez-Rey et al. (2006) Blood 107:3632-3638) or through abrogation of Th17 differentiation (Leceta et al. (2007) Neuroimmunomodulation 14:134-138), it was determined whether VIP modulation of N-α-syn-directed immune responses could affect neurodegenerative activities. SPC populations from VIP-treated or N-4YSyn-immunized mice were adoptively transferred either separately or together to MPTP-recipients and the neuroinflammatory and neurodegenerative responses were evaluated. MPTP mice that received N-4YSyn SPC exhibited an exacerbated nigral Mac-1 response, which was diminished in mice treated with VIP SPC (FIG. 37A). Similarly, FJ-C staining was increased in N-4YSyn SPC-treated MPTP mice; whereas, the FJ-C staining in mice treated with pooled VIP and N-4YSyn SPC was diminished. In validation of these observations in MPTP-intoxicated mice, transfer of VIP SPC reduced the numbers of activated microglia by 33%; whereas, transfer of N-4YSyn SPC numbers increased Mac-1+ densities by 35% (FIG. 37B). Importantly, co-transfer of VIP SPC with N-4YSyn SPC not only attenuated the exacerbative effects mediated by N-4YSyn SPC by 75%, but diminished numbers of Mac-1+ microglia 39% less than MPTP alone. Analysis of nigral Mac-1+ microglia 7 days post-MPTP demonstrated sustained microglial activation in both mice that received N-4YSyn SPC alone or in combination with naïve SPC; whereas, significant numbers of Mac-1+ cells were not observed within any other treatment group. Analysis of total nigral FJ-C$^+$ cells revealed a 7-fold increase in MPTP-recipients that received N-4YSyn SPC compared with MPTP alone; while 36% fewer neurons were injured or dead after transfer of combined VIP- and N-4YSyn-SPC (FIG. 37C). Adoptive transfer of naïve SPCs alone or together with N-4YSyn SPC showed no significant detrimental or protective effect on microglial activation, and numbers of FJ-C+ neurons were not significantly different compared with MPTP alone. These data indicated that a cell population within the VIP, but not naïve SPC, was better able to inhibit or suppress N-4YSyn mediated effector cells and abrogate neuropathology.

VIP SPC Modulate N-4YSyn Immunity to Confer Neuroprotection

Figure 38:
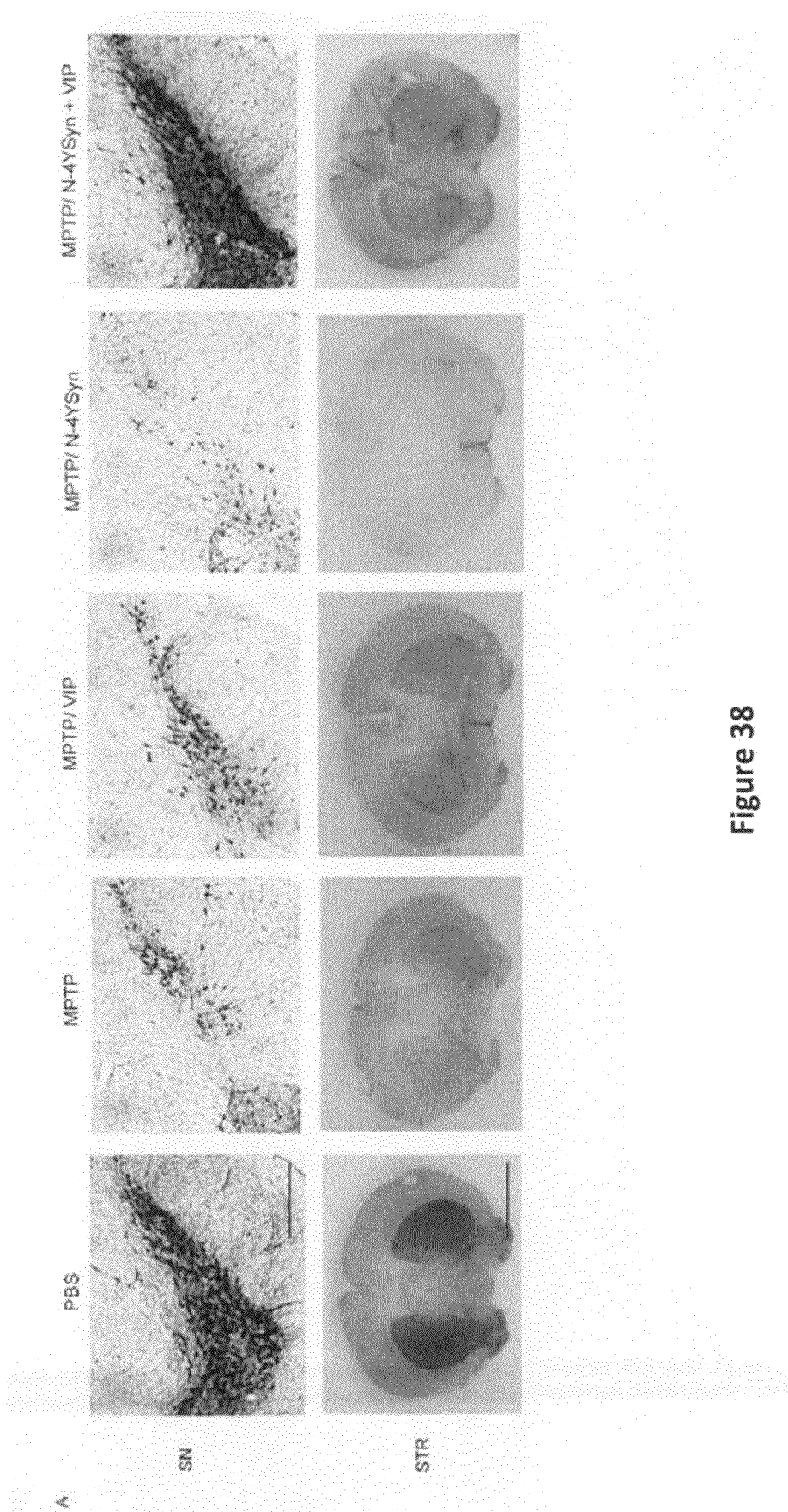
FIG. 38 shows Treg mediated dopaminergic neuroprotection in N-α-syn-immunized MPTP-intoxicated animals.

To validate that neuroprotection was not a transient effect, TH immunostained ventral midbrain and striatal sections were assessed 7 days after MPTP treatment and adoptive transfers. MPTP mice that received VIP SPC showed a modest increase in TH+ neuronal density. In contrast, TH+ neurons within the SNpc of N-4YSyn SPC recipients were diminished compared with MPTP alone; whereas, those that received pooled VIP and N-4YSyn SPC exhibited TH+ neuronal densities reminiscent of PBS controls (FIG. 38A). Although lesions of the dopaminergic striatal termini are typically more severe, similar patterns of dopaminergic loss are observed in mice treated with MPTP alone and with separate SPC populations, while those treated with N-4YSyn SPC and VIP SPC exhibited discernable increases in the density of TH+ striatal termini. Stereological analysis and comparison with PBS controls showed that MPTP reduced SNpc TH+ neurons by 48%, while MPTP and N-4YSyn SPC reduced those neurons by 64% (FIG. 38B). MPTP recipients of VIP SPC showed a modest, yet significant 18% increase in TH+ neuron number compared to MPTP alone. In comparison, 91% of TH+ neurons survived in mice receiving SPC from N-4YSyn-immunized and VIP-treated donors. Striatal TH+ density in MPTP-intoxicated mice was 16% of PBS controls, whereas transfer of N-4YSyn SPC to MPTP recipients reduced densities to 7% of PBS controls (FIG. 38C). Although transfer of VIP SPC to MPTP-mice showed no significant additive or protective, co-transfer of VIP and N-4YSyn SPC increased striatal termini survival to 39% of PBS controls. Adoptive transfer of naïve SPC alone showed no significant detrimental or protective effect on dopaminergic neuronal survival.

To elucidate the neuroprotective cell populations within the SPC pools, Treg from naïve and VIP-treated donors were enriched and each population was adoptively transferred with N-4YSyn SPC into MPTP mice. Co-transfer of N-4YSyn and VIP SPC to MPTP-recipients provided 100% protection of TH+ nigral dopaminergic neurons; whereas, significant protection was not observed in MPTP mice that received SPC from N-4YSyn-immunized and naïve donors (45% TH+ neuron survival) compared with percentages of surviving neurons after treatment with MPTP alone (49%) or in combination with N-4YSyn SPC (34%) (FIG. 38D). In comparison, adoptive transfer of Treg from either naïve or VIP-treated donors with N-4YSyn SPC afforded significant protection with VIP-Treg being more effective (96% survival) than naïve Treg (80% survival). Analysis striatal dopaminergic termini were comparable, showing that N-4YSyn SPC exacerbated the MPTP-induced lesion to 13% of PBS controls (FIG. 38E). Co-transfer of naïve with N-4YSyn SPC was not effective in perturbing N-4YSyn exacerbative effects; whereas co-transfer of VIP and N-4Syn SPC increased survival to 47% of PBS controls, as did co-transfer of naïve Treg and N-4YSyn SPC (50% of PBS controls). Co-transfer of Treg from VIP-treated mice with N-4YSyn SPC was the most efficacious increasing the mean terminal density to 62% of PBS controls. These results demonstrate that VIP-Treg can protect against N-4YSyn adaptive immune degenerative activities.

Figure 39:
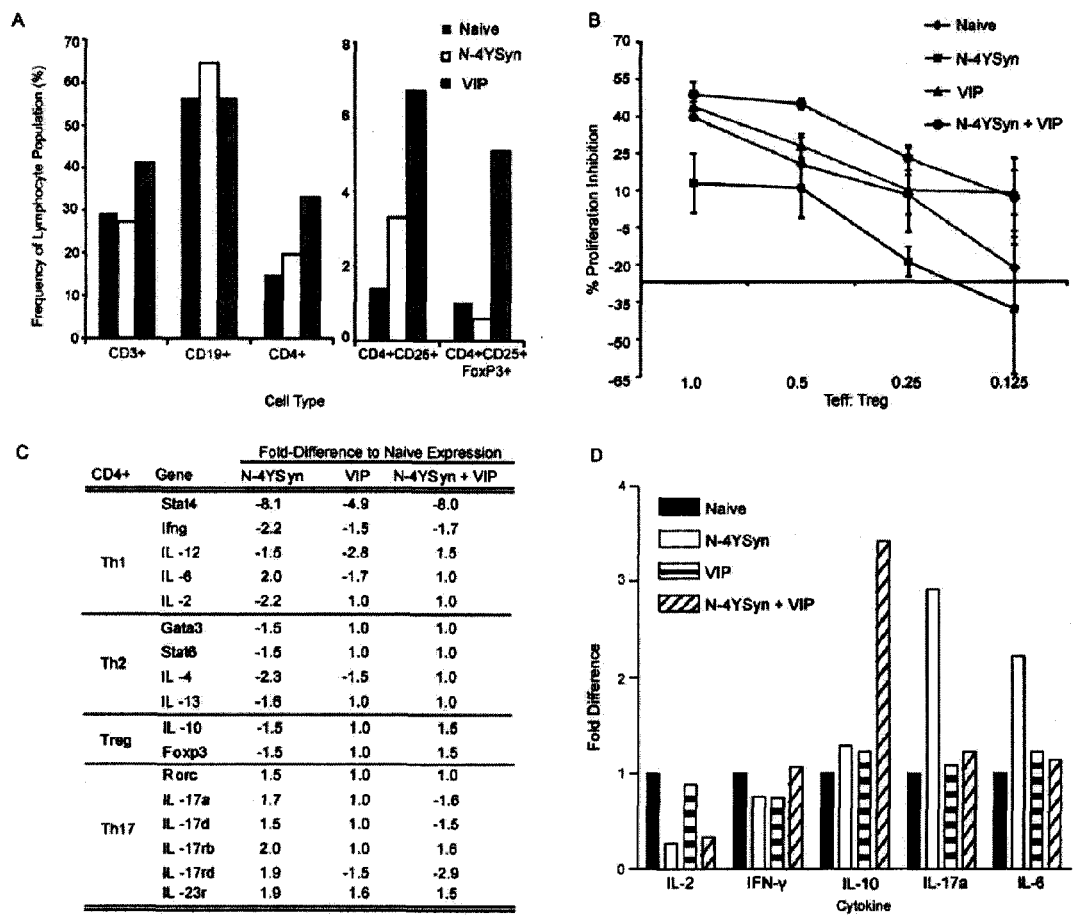
FIG. 39 shows phenotypic and functional characterization of neuroprotective Treg.
Figure 39:
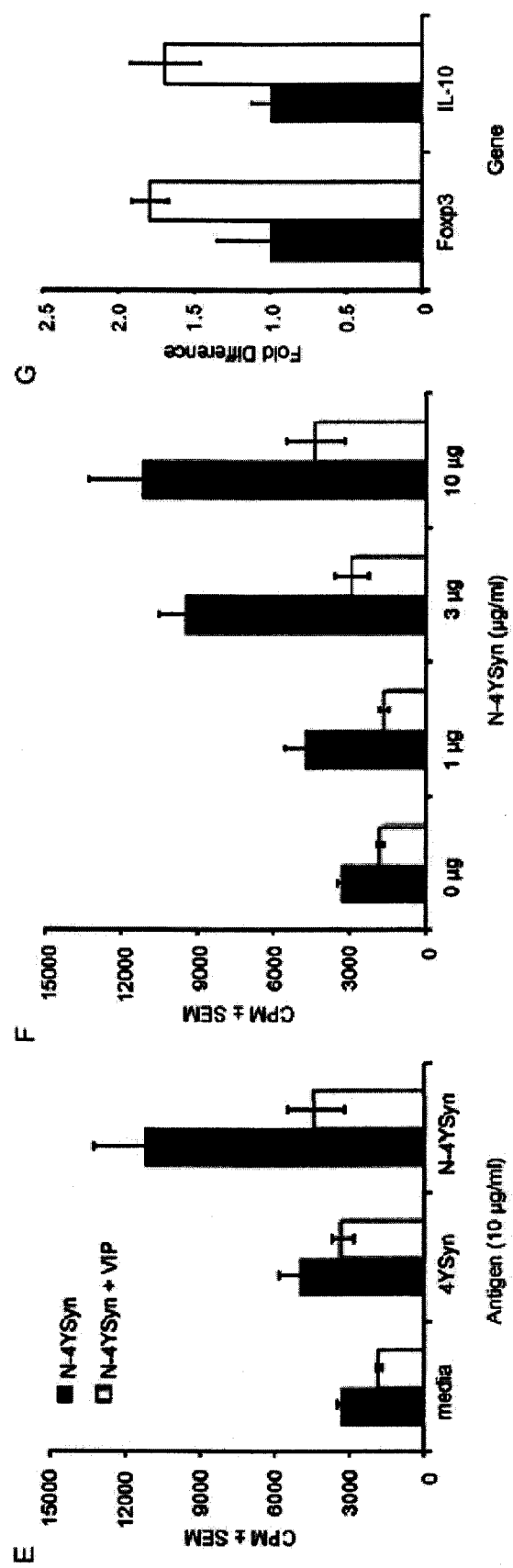

Immunization with N-4YSyn or treatment with VIP altered the frequencies of splenic CD3, CD19+, CD4+, and CD4+ CD25+ cells (FIG. 39A). Flow cytometric analysis for CD4+ CD25+T cells within SPC populations revealed that VIP-treated donors had increased percentages of CD4+ CD25+T cells with greater than 95% of this population also being FoxP3+. Analysis of antigen-induced proliferative responses showed that while N-4YSyn T cells proliferated in response to N-4YSyn, naïve or VIP-treated donors did not. In contrast, anti-CD3 stimulation of T cells from all donor groups induced proliferative responses in excess of 10-fold. Such responses, however, were not observed against non-nitrated α-syn in any of the experimental or control groups.

To assess whether VIP SPC suppress effector T cell proliferative responses, SPC co-cultures from N-4YSyn immunized and VIP treated donors were evaluated for their proliferative capacity in the presence of either anti-CD3 or N-4YSyn. At a one-to-one ratio of N-4YSyn SPC to VIP SPC, proliferation to both anti-CD3 stimulation and N-4YSyn were suppressed by 67% and 81%, respectively and diminished in a dose dependent fashion with the diminution of VIP SPC number. Given the dichotomy between Treg and Th17 differentiation, it was hypothesized that Treg function or development may be inhibited by immunization with N-4YSyn. To test this hypothesis, CD4+ CD25+CD62L$^{low}$ Treg isolated from naïve, N-4YSyn-immunized, and VIP-treated mice were evaluated for their capacity to inhibit CD3-mediated proliferation of CD4+ CD25-naïve T cells (FIG. 39B). VIP-Treg were increased in their functional capacity to suppress T cell proliferation compared with naïve Treg showing a 5% greater inhibition of proliferation. Importantly, N-4YSyn-Treg were functionally deficient in their suppressive function of Teff proliferation showing 3-fold less percent inhibition of Teff proliferation compared to naïve Treg. In contrast, pooled VIP- and N-4YSyn-Treg showed enhanced suppressive capacity compared to all other Treg populations, with 10% greater inhibition versus naïve Treg at a one-to-one responder:Treg ratio. These data indicate that restoration of functional Treg with VIP abrogates N-4YSyn-immunity.

To characterize effector and regulatory T cell subsets from N-4YSyn-immunized or VIP-treated mice, isolated CD4+ T cells separately or pooled at a 1:1 ratio were stimulated to induce cytokine expression. Quantitative RT-PCR revealed that N-4YSyn T cells showed increased expression of Th17 and Th17-associated genes relative to naïve T cells. This included interleukin (IL)-21, IL-17A and transcription activator RAR-related orphan receptor c (Rorc), whereas genes linked to Th1 [signal transducer and activator of transcription (Stat)4, IL-6, and interferon (Ifn)-γ], Th2 [Gata3, Stat6, IL-4, IL-10, and IL-13], and Treg [forkhead box P3 (Foxp3) and IL-10] (Kaiko et al., 2008) were decreased (FIG. 39C). The increased expression of IL-17 and Rorc with concomitant decrease in Th1, Th2, and Treg associated genes, suggested that N-4YSyn immunization polarized CD4+ T cells toward a Th17 phenotype. Moreover, genes encoding cytokines known to inhibit Th17 differentiation including IL-2, IL-4, IL-15, and IFN-γ were decreased in N-4YSyn T cells compared with naïve T cells. Interestingly, VIP T cells showed few changes in gene expression relative to naïve T cells, with predominately genes associated with a Th1 phenotype decreased in expression whereas expression of Th2, Treg, or Th17 related genes were not affected. In comparison, pooled N-4YSyn- and VIP-T cells showed decreased expression of Th1 and Th17 related genes; whereas, genes for Treg were increased (FIG. 39C).

Analysis of cytokine production in response to anti-CD3 stimulation showed increased production of IL-17A and IL-6 from N-4YSyn T cells relative to naïve T cells; while, production of IL-2, IFN-γ (FIG. 39D), and IL-4 were decreased. TNF-α production was also increased greater than 2.5-fold relative to naïve T cells. Analysis of cytokine production by VIP-T cells revealed that the cytokine production was not significantly different to that of naïve T cells, although production of Th2-related cytokines IL-10 (FIG. 39D), IL-4, and IL-13 (data not shown) were marginally increased. In comparison, co-culture of N-4YSyn and VIP-T cells resulted in increased production of regulatory cytokines including IL-10, IFN-γ (FIG. 39D), and IL-13, with concomitant decreased production of IL-17a and IL-6 compared with N-4YSyn T cells. TGF-β1 production was increased 2-fold relative to naïve T cells in supernatants of N-4YSyn-immunized, VIP-treated, and pooled T cell populations.

It was next theorized that VIP could induce antigenic tolerance when given with N-4YSyn immunization. To test this idea, T cells from N-4YSyn immunized donors treated with or without VIP were assessed for proliferation capacity to N-4YSyn antigen. T cell proliferation to N-4YSyn was suppressed 2.5-fold in T cells isolated from N-4YSyn and VIP immunized donors compared to N-4YSyn alone (FIGS. 39E and F). These data indicate that VIP and N-4YSyn immunization induce antigen-specific tolerance to N-4YSyn. Moreover, T cells from N-4YSyn-immunized and VIP-treated mice showed a 2-fold increase in expression of genes encoding Foxp3 and IL-10. This demonstrated that VIP favors the induction of Treg responses (FIG. 39G). Possible mechanisms could include divergent transcriptional regulation either in favor of RORγt/RORc or FoxP3 pathways, as induction of one activator of transcription may inhibit the induction of the other (Awasthi et al. (2008) J. Clin. Immunol., 28:660-670; Kom et al. (2008) Proc. Natl. Acad. Sci., 105:18460-18465).

EXAMPLE 7

A spectrum of neurological dysfunctions is associated with advanced HIV-1 infection and termed HIV-1-associated neurocognitive disorders (HAND) (Antinori et al. (2007) Neurology 69:1789-1799). In the era of antiretroviral therapy and increased patient survival, nervous system impairment is more subtle with low level infection and focal neuroinflammation more closely correlated with mild neuropsychological signs and symptoms. The pathological correlate of HAND is encephalitis. Before the widespread use of antiretroviral drugs, encephalitis was characterized by the presence of multinucleated giant cells, profound viral replication, astrogliosis, microgliosis, myelin pallor, and neuronal dropout with severe compromise of dendritic arbor (Hult et al. (2008) Int. Rev. Psychiatry., 20: 3-13; Chemer et al. (2002) Neurology 59:1563-1567; Masliah, E. (1996) Am. J. Pathol. 149: 745-750). HIV encephalitis (HIVE) remains prevalent, although attenuated by effective drug treatments. Patients show significant CNS lymphocytic infiltrates as a consequence of disease or immune reconstitution syndrome. Moreover, HIVE depends on the continuous flux of activated leukocytes toward the brain parenchyma rather than simply autonomous HIV infection and inflammation per se. CD4+ T cells as well as CD8+ T lymphocytes accumulate in brains of patients with progressive HIV-1 infection and AIDS (Gisslen et al. (2007) J. Neuroimmune Pharmacol., 2:112-119; Yilmaz et al. (2008) J. Acquir. Immune. Defic. Syndr., 47:168-173; Spudich et al. (2005) BMC Infect. Dis., 5:98). Prior work examined T lymphocyte subsets in the CA1, CA3, and CA4 regions of the hippocampus of AIDS patients with and without HIVE and showed that hippocampal activated/memory CD45RO+T lymphocytes were significantly increased in diseased hippocampal subregions (Petito et al. (2003) J. Neurovirol., 9:36-44). This led to the notion that perineuronal location of CD4+ cells provides the potential for lymphocyte-mediated neuronal injury or trans-receptor-mediated neuronal infection (Petito et al. (2003) J. Neurovirol., 9:36-44).

The presence of activated microglia and brain macrophages with lower levels of virus remains a central pathological feature of disease. Increased inflammation can occur as a consequence of secreted viral and cellular proteins from activated or infected mononuclear phagocytes (MP; perivascular brain macrophages and microglia) (Persidsky et al. (2003) J. Leukocyte Biol., 74:691-701) and include proinflammatory cytokines, chemokines, and arachidonic acid and its metabolites NO, quinolinic acid, and glutamate as well as HIV-1 proteins such as Tat, Nef, and gp120 (Smith et al. (2001) J. Neurovirol., 7:56-60; Kaul et al. (2005) Cell Death Differ. 12(Suppl. 1):878-892; Kaul et al. (2005) Neurotox. Res., 8:167-186; Rostasy et al. (2005) J. Neurol. Neurosurg. Psychiatry 76:960-964; Rostasy, K. M. (2005) Neuropediatrics 36:230239; Kadiu et al. (2005) Neurotox., Res. 8:25-50).

Host immune surveillance against persistent viral infection includes CD8+ CTL and humoral and innate secretory responses (Rosenberg et al. (1997) Science 278:1447-1450; Petito et al. (2006) J. Neurovirol., 12:272-283; Poluektova et al. (2004) J. Immunol., 172:7610-7617; Poluektova et al. (2002) J. Immunol., 168:3941-3949). However, the mechanisms by which the virus escapes clearance remain unknown. Included in these responses are attempts to purge the infected host of latently infected cells (Rosenberg et al. (1997) Science 278:1447-1450; Petito et al. (2006) J. Neurovirol., 12:272-283). Nonetheless, of all immune responses, CD8+ T cells are among the most effective and were previously investigated in prior reports in rodent models of neuroAIDS (Poluektova et al. (2004) J. Immunol., 172:7610-7617; Poluektova et al. (2002) J. Immunol., 168:3941-3949; Gorantla et al. (2007) J. Immunol., 179:4345-4356). It is posited herein that in addition to CTL, CD4+ CD25+ regulatory T cells (Treg) as well as effector T cells (Teff) play an important role in HAND control. Treg, a subset of CD4+ T cells, are now well recognized for their immune modulatory function and play pivotal roles in maintaining immunological tolerance. Their principal role is to attenuate T cellmediated immunity and suppress autoreactive T cells (Curiel et al. (2004) Nat. Med. 10:942-949; Wang et al. (2004) Immunity. 20:107-118; Sakaguchi, S. (2004) Annu. Rev. Immunol., 22:531-562). Teff promote inflammatory responses and speed recognition and immunity (Eggena et al. (2005) J. Immunol., 174:4407-4414). It is now reported that Treg modulate immune responses in the brain and lead to neuronal protection in murine HIVE. Neuroprotection was found to be mediated by attenuating HIV-1-induced microglia activation and enhancing of neurotrophic factors. These results indicate the importance of Treg in the control of HIV-1-associated neurodegeneration in the antiretroviral era and when adaptive immune responses remain operative.

Materials and Methods

Animals, Infection of Bone Marrow-Derived Macrophages (BMM), and Induction of HIVE Four- to 6-wk-old male C57BL/6J mice (The Jackson Laboratory) were maintained in accordance with guidelines for the care of laboratory animals from the National Institutes of Health and with approval of the Institutional Animal Care and Use Committee of the University of Nebraska Medical Center (Omaha, Nebr.). BMM were derived after a 7-day culture of bone marrow cells with macrophage CSF (M-CSF; Wyeth) and were infected as previously described (Gorantla et al. (2007) J. Immunol., 179:4345-4356). Briefly, vesicular stomatitis virus (VSV)-pseudotyped HIV-1$_{Ba2}$ (HIV-1/VSV) was used to infect BMM at a concentration of 1 pg of HIV-1 p24 per cell for 24 hours. After a continuous 5-day culture, >90% of BMM were virus positive according to HIV-1 p24 immunochemical tests (Dako-Cytomation). Reverse transcriptase activity as a function of [$^3$H]deoxythymidine triphosphate from BMM culture supernatants confirmed the extent of infection as previously described (Gendelman et al. (1994) Adv. Neuroimmunol., 4:189-193). To induce HIVE, HIV-1/VSV-infected BMM ($1\times10^6$ cells/5 µl/mouse) were delivered by intracerebral (i.c.) injection into the basal ganglia of 4-wk-old C57BL/6J mice using stereotactic coordinates as previously described (Persidsky et al. (1996) Am. J. Pathol., 149: 1027-1053). Mice injected i.c. with PBS served as sham-injected controls.

Isolation, activation, and transfer of Treg and Teff

From pooled splenic and lymph node CD3+ CD4+ T cells enriched from negative selection columns (R&D System), Treg-enriched CD4+ CD25+ and naive CD4+ CD25− T cells were prepared by positive and negative selection for CD25+ T cells, respectively, using PE-anti-CD25 (BD Pharmingen) magnetic beads conjugated to anti-PE mAb and passage over autoMACS columns (Miltenyi Biotech) as previously described (Reynolds et al. (2007) J. Leukocyte Biol., 82:1083-1094). By flow cytometric analyses, T cells were shown to be >95% enriched for each T cell subset. Isolated CD4+ CD25+Treg and CD4+ CD25− T cells were activated by culture in the presence of 0.5 µg/ml anti-CD3 (145-2C11; BD Pharmingen) and 100 U/ml mouse rIL-2 (R&D Systems). Three days later, $1.0\times10^6$ activated Treg or Teff (anti-CD3 stimulated CD4+ CD25− T cells) were harvested and adoptively transferred i.v. to HIVE mice.

BMM and Treg/Teff Cocultivations

BMM were seeded at $1\times10^6$/well in 6-well plates containing a 1:1 ratio mixture of BMM and T cell medium. BMM and HIV-1/VSV-infected BMM were cocultivated with Treg or Teff for 6 days. Supernatants were collected as conditioned medium (CM). BMM viability was measured using the LIVE/DEAD viability cytotoxicity kit (Invitrogen) after removal of the cocultured Treg and Teff. Cell viability was measured by MTT assay (Dou et al. (2007) Virology 358:148-158).

Measures of Oxidative Stress

To assess hydrogen peroxide ($H_2O_2$) production from uninfected or infected BMM, cells were plated at $1\times10^5$/0.2 ml tissue culture medium/well in a 96-well fluorometer plate and stimulated for 24 hours with 200 ng/ml mouse rTNF-α (R&D Systems) as previously described (Reynolds et al. (2007) J. Leukocyte Biol., 82:1083-1094). The medium was removed and replaced with Krebs-Ringer buffer (Sigma-Aldrich) containing 10 µM PMA, 0.1 U/ml HRP, and 50 µM Amplex Red (Sigma-Aldrich). BMM cultured in the absence of TNF-α or PMA served as baseline controls. Fluorescence intensity was measured at 563 nm (excitation)/587 nm (emission) 90 minutes after the addition of Amplex Red using a microplate spectrophotometer (µQuant; BioTek Instruments) interfaced with analysis software (KC Junior; BioTek Instruments).

Isolation and Characterization of Primary Mouse Neurons

Eighteen-day-old embryonic fetuses were harvested from terminally anesthetized pregnant C57BL/6J mice. Cerebral cortices were dissected and digested using 0.25% trypsin (Invitrogen). Cortical digests were seeded at a density of $1.5\times10^5$ cells/well in 24-well plates containing poly-D-lysine-coated cover slips and cultured in neurobasal medium supplemented with 2% B27, 1% penicillin/streptomycin, 0.2% FBS, and 0.5 mM L-glutamine (Invitrogen). After 10-14 days, neuron-enriched cultures contained >90% microtubule-associated protein (MAP)-2-positive cells with <2% glial fibrillary acidic protein (GFAP)-positive cells as determined by immunocytochemistry. Mature neurons were treated with CM collected from 24-hour cocultures of HIV-1/VSV-infected BMM in the presence or absence of Teff or Treg.

Immunohistochemistry

Brain tissues were derived from perfused mice and processed as previously described (Gorantla et al. (2007) J. Immunol., 179:4345-4356). Murine microglia were detected with rabbit polyclonal Abs to Iba1 (ionizing calcium-binding adaptor molecule 1) (1/500; Wako) or Mac-1 (CD11b; 1/500; Serotec). Astrocytes were visualized with antirabbit GFAP Ab (1/1,000; DakoCytomation). Anti-HIV-1 p24 Abs (1/10; DakoCytomation) were used to identify HIV-1-infected cells. Putative Treg were identified by dual staining with anti-CD4 (1/100; DakoCytomation) and anti-Forkhead box P3 (FoxP3) (1/100; ProMab Biotechnologies) Abs (Reynolds et al. (2007) J. Leukocyte Biol., 82:1083-1094). Abs to neuronal nuclei protein (NeuN) (1/100) and MAP-2 (1/1,000; Chemicon) were used to identify neurons, and mouse cross-reactive chicken anti-human brain-derived neurotrophic factor (BDNF) and antiglial cell line derived neurotrophic factor (GDNF) (1/50; Promega) were used for growth factor expression. Primary Abs were visualized with Alexa Fluor 488 (green)- and Alexa Fluor 594 (red)-conjugated secondary Abs (Invitrogen; Molecular Probes). Images were obtained by an Optronics digital camera fixed to Nikon Eclipse E800 (Nikon Instruments) using MagnaFire 2.0 software (Optronics). Fluorescence intensity in the stained area of serial brain sections encompassing the i.c. injection sites was analyzed under ×400 magnification using NIH Image J software. To detect apoptotic neurons in vitro and infected BMM in brain sections, a Roche Applied Sciences in situ cell death detection kit with alkaline peroxidase was used according to the manufacturer's instructions to stain for TUNEL-positive neurons and 4',6'-diamidino-2-phenylindole (DAPI) as a nuclear stain. Laser-scanning images were obtained using a Nikon swept-field laser confocal microscope with a ×200 power field (Nikon Instruments). A minimum of 10 images were taken from each brain section obtained from infected controls and groups treated by adoptive transfer of Treg or Teff. The total TUNEL-positive cells and DAPI nuclei staining in each field were counted and the percentage of apoptotic neurons was determined from the ratio of the number of TUNEL-positive cells to the total number of DAPI-positive cells.

Western Blot Assays

Twenty µg of protein harvested from brain or cell lysates was separated on 10-20% Tris-Tricine gels and blotted onto polyvinylidene fluoride membranes (Bio-Rad Laboratories). Membranes were probed overnight at 4° C. with primary Abs including rabbit polyclonal anti-caspase-3 (1/1000; Cell Signaling), rabbit polyclonal anti-GFAP (1/1000; DakoCytomation), rabbit polyclonal anti-Iba1 (1/500; Wako), chicken monoclonal anti-human BDNF, and biotin-conjugated anti-TNF-α. Primary Abs and β-actin were detected with HRP-conjugated goat anti-mouse (1/10,000), goat anti-rabbit (1/10,000), goat anti-chicken (1/10,000), and mouse anti-α-actin mAb (1/10,000, Sigma-Aldrich). Proteins were visualized with an ECL kit (Bio-Rad Laboratories).

Cytokine Arrays

Equal volumes of cell culture supernatants were incubated with the precoated cytokine Ab array according to the manufacturer's instructions (AAM-CYT-3-2; RayBiotech). Densitometric analysis of the array was performed using the NIH Image J software.

Statistical Analyses

The results were expressed as mean±SEM for each group. Statistical significance between groups was analyzed by Student's t test using Microsoft Excel. Differences were considered statistically significant at p<0.05.

Results

HIVE Mice

Figure 40:
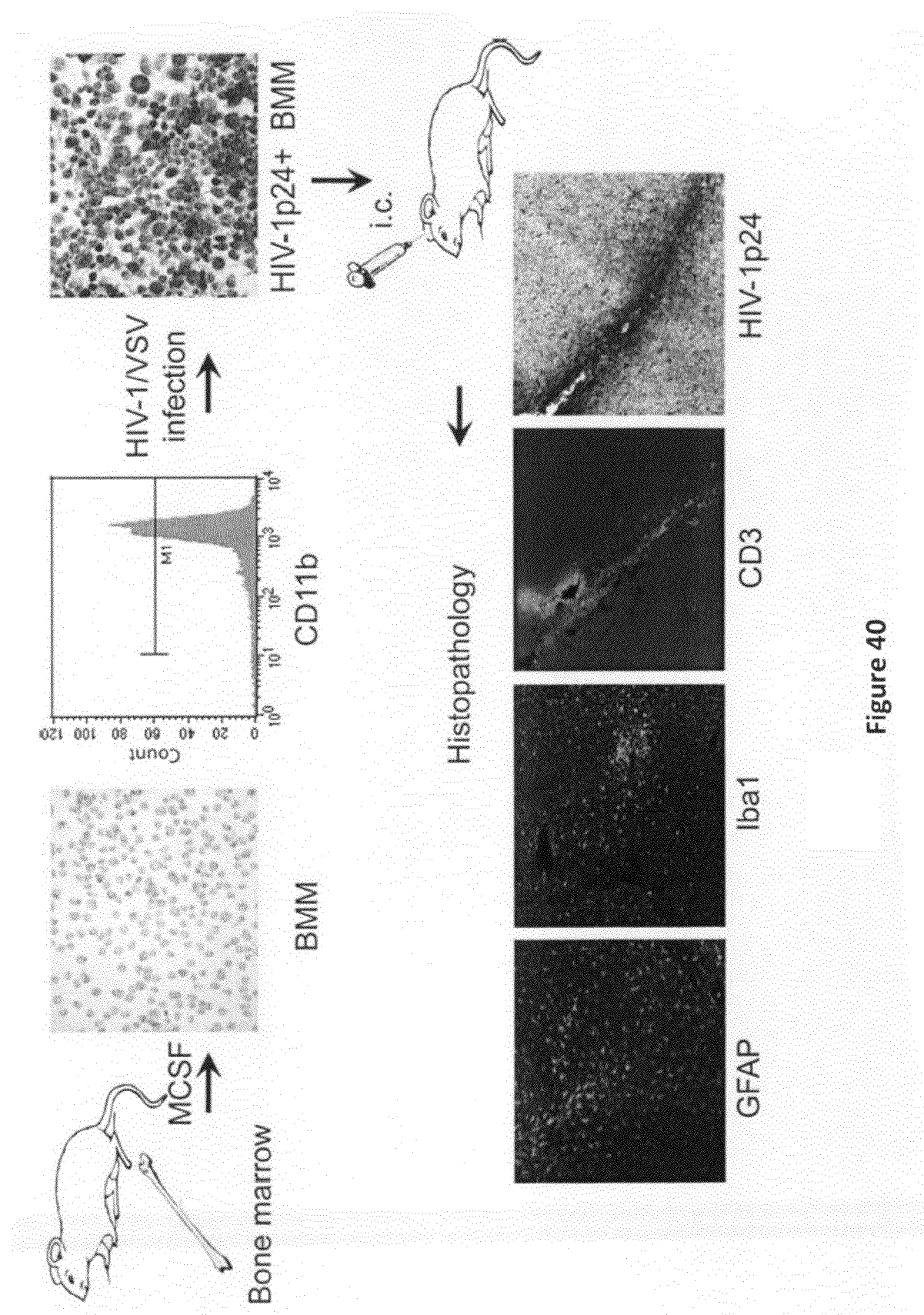
FIG. 40 shows HIV-1/VSV-infected BMM induce HIVE pathology. Inflammatory pathological effects of virally infected BMM in brains of immune competent mice were evaluated. BMM infected with HIV-1NVSV were tereotactically injected via the i.c. route into the basal ganglia of syngeneic C57BL/6J mice. Brain tissues were dissected on day 7 and HIVE pathology was analyzed after immunostaining for expression of HIV-1 p24, anti-CD3, GFAP, and Iba1 Ags. Representative micrographs are shown at the original magnification of ×100 for HIV-1 p24, CD3, GFAP, and Iba1 and at ×400 for bone marrow cell and HIV-1 p24-positive BMM. Flow cytometric analysis demonstrated >95% CD11b+ BMM.

HIVE was established using BMM infected with HIV-1/VSVpseudotyped virus and injected i.c. into the basal ganglia of syngeneic C57BL/6J mice (FIG. 40). This led to the induction of HIV-1 induced focal encephalitis along the injection track as shown by HIV-1 immunostained cells, robust astrogliosis and microgliosis, and T cell infiltrate as evidenced by positive staining for expression of HIV-1 p24, GFAP, Iba1, and CD3.

Treg and Teff Modulate Neural Responses in HIVE Mice

Figure 41:
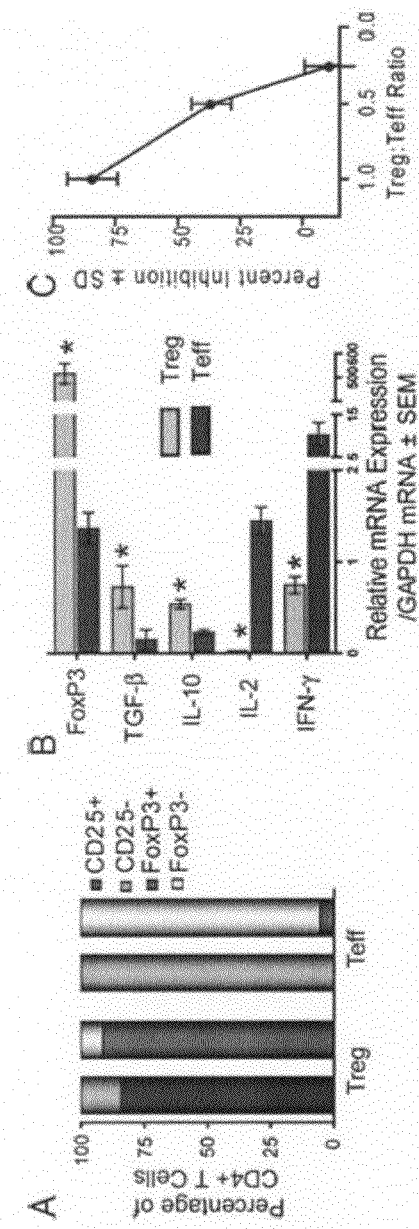
FIG. 41 shows Treg attenuate chronic neuroinflammatory responses in HIVE mice.

Treg have been shown to have a potential role in modulating the immune response to HIV infection (Oswald-Richter et al. (2004) PLoS Biol., 2:E198; Kinter et al. (2004) J. Exp. Med., 200:331-343). In an effort to assess the role of Treg in a mouse model of HIVE, Treg and Teff T cell subsets from naive mice were isolated and characterized. Flow cytometric analyses indicated that Tregs were >85% CD4+ CD25+ FoxP3+ and naive Teff were >95% CD4+ CD25-FoxP3− T cells (FIG. 41A). Three days after CD3 activation, >95% of CD4+ Teff showed CD25 up-regulation without concomitant FoxP3 expression. Additionally, mRNA levels for FoxP3, TGF-β, and IL-10 from Treg were significantly elevated over those from Teff, whereas expression of IL-2 and IFN-γ mRNA levels was diminished by activated Treg and increased in Teff (FIG. 41B). Treg suppressed the proliferative response of CD3-activated Teff in a dose-dependent fashion (FIG. 41C). Taken together, the T cells used in these studies showed appropriate Treg and Teff phenotypes.

Figure 41D:
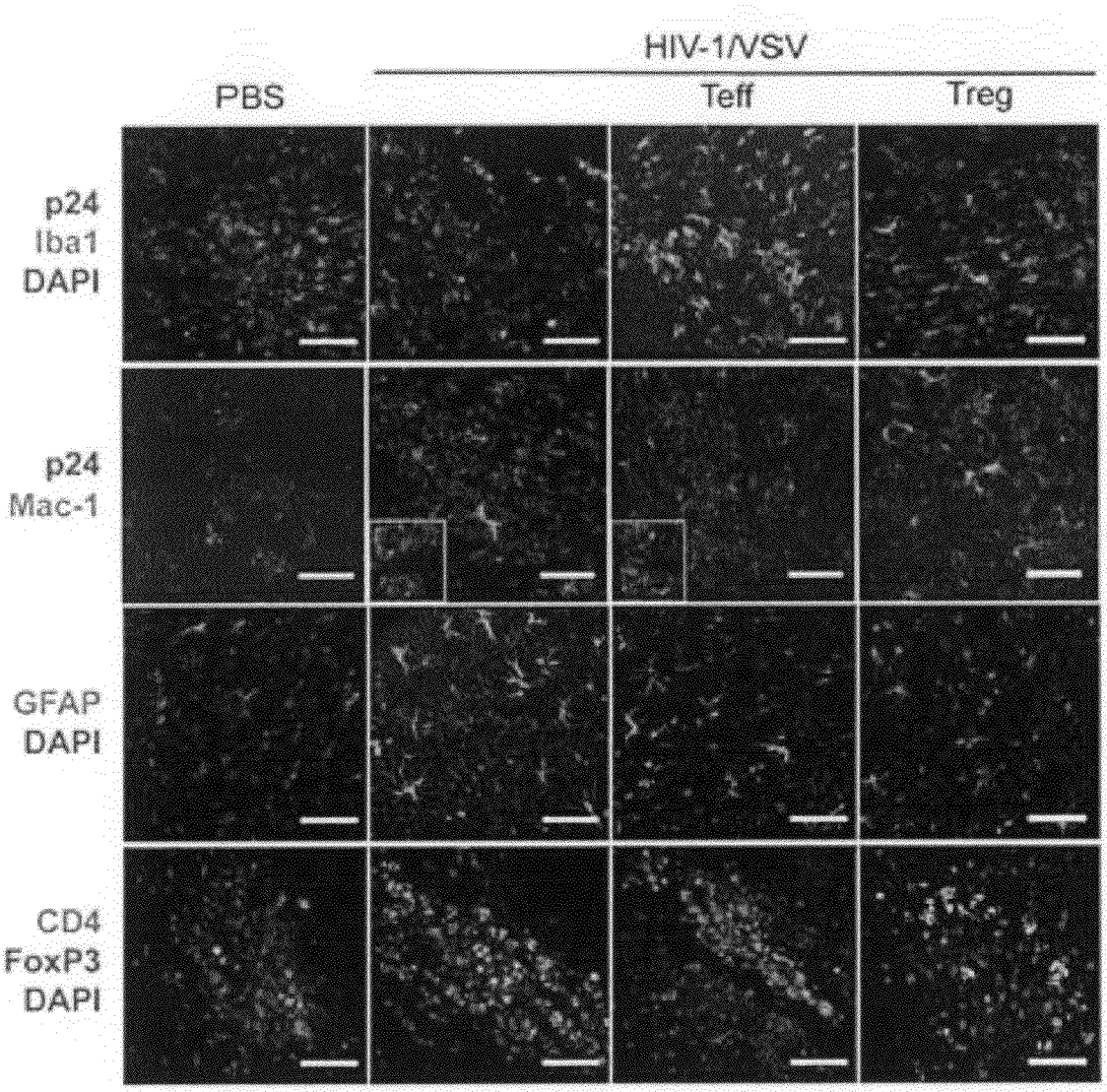
FIG. 41D are images of HIVE, HIV-1/VSV-infected BMM which were stereotactically injected i.c. into the basal ganglia of syngeneic C57BL/6J mice. Sham controls were injected i.c. with PBS. Treg or Teff ($1\times10^6$) were adoptively transferred into HIVE mice 1 day postinfection. Serial sections of brain tissue that comprise the injection area were obtained on day 7 postinfection and analyzed by immunohistochemical and Western blot assays for p24, Iba1, Mac-1, GFAP, CD4, and FoxP3 Ags. Brains were collected at day 7 after i.v. injections. Representative brain sections from PBS and the HIV-1/VSV, HIV-1/VSV/Teff, and HIV-1/VSV/Treg groups showing expression of HIV-1 p24, Iba1, Mac-1, GFAP, CD4, and FoxP3. Where indicated, nuclei were stained with DAPI (scale bars, 50 μm; original magnification, ×400). Cellular colocalizations of intracellular HIV-1 p24 and membrane Mac-1 expression are shown in magnified inserts.
Figure 41:
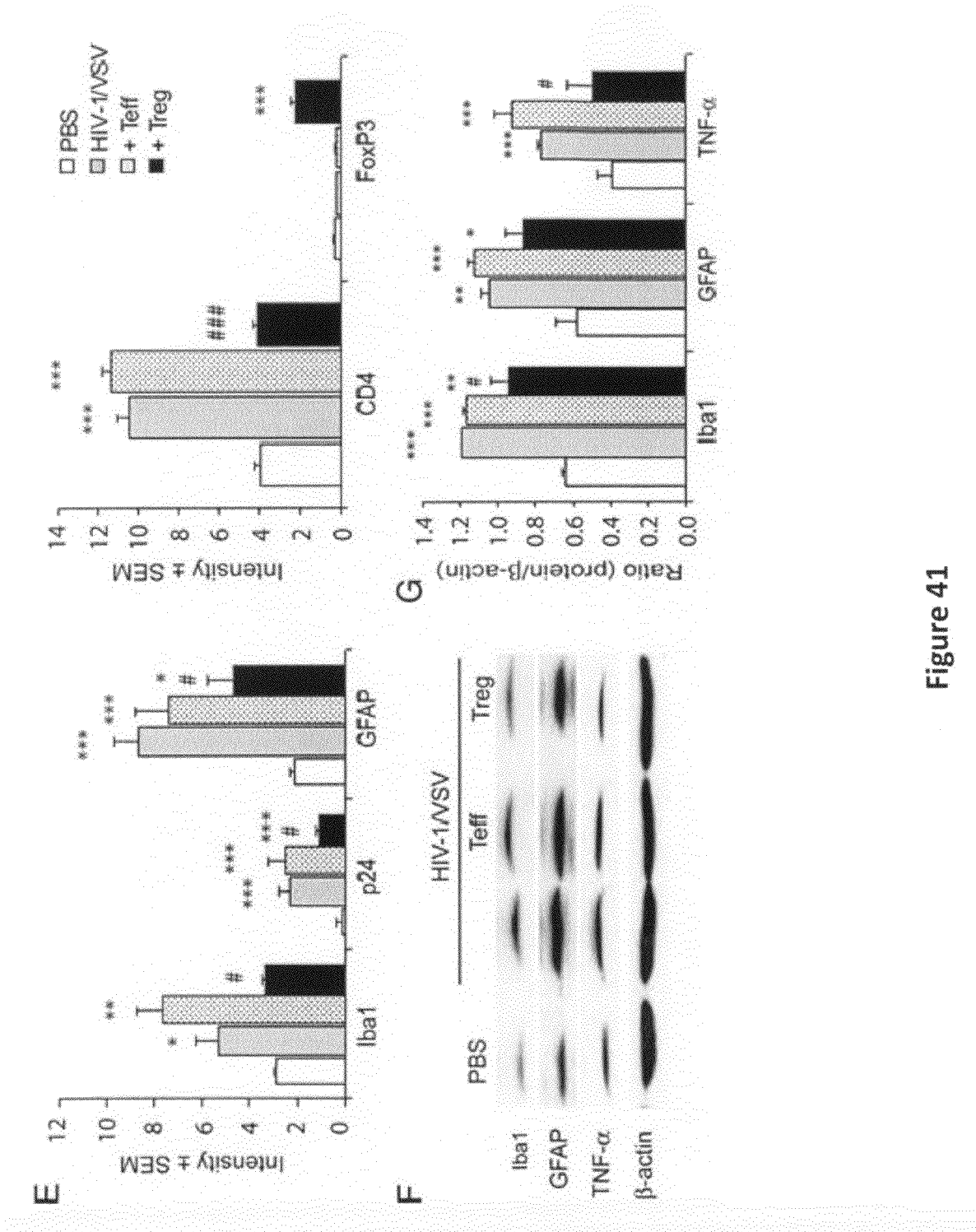

To evaluate the roles of Treg and Teff in regulating neuroinflammatory responses in HIVE mice, $1 \times 10^6$ anti-CD3-activated Treg or Teff were adoptively transferred to HIV-1/VSV-infected recipients 24 hours after induction of HIVE. By 7 days postinfection, immunohistochemistry staining of tissues surrounding the injection tracks indicated that HIV-1/VSV or HIV-1/VSV/Teff-injected mice exhibited dense GFAP and Iba1 expression compared with PBS-sham controls (FIG. 41D). In contrast, both GFAP and Iba1 expression were reduced in HIV-1/VSV/Treg-injected mice. Quantitative measurement of GFAP and Iba1 intensities confirmed significant increases in expression by HIV-1/VSV- and HIV-1/VSV/Teff-treated mice compared with PBS controls and significant reductions in the HIV-1/VSV/Treg group compared with the HIV-1/VSV and HIV-1/VSV/Teff groups (FIG. 41E). Of notable importance was the significant reduction of HIV-1 p24 levels HIVE mice treated with Treg compared with HIV-1/VSV- and HIV-1/VSV/Teff-treated mice (FIGS. 41D and 41E). Based on the observations that Treg attenuate the neuroinflammatory responses following HIV-1 infection, the ingress of CD4+ T cells into the brain was evaluated. The presence of CD4+ cells were observed within the injection site of mice from all treatment groups (FIG. 41D). CD4+ cells were significantly increased in the HIV-1/NSV and HIV-1/VSV/Teff-treated groups (FIG. 41E); however, in contrast, the ingress of CD4+ cells was diminished to the levels of sham control in infected mice treated with Treg (FIGS. 41D and 41E). Interestingly, CD4+ FoxP3+ double-positive cells were present in only the HIV-1/VSV/Treg-treated group.

Of the microglial secretory factors known to influence secondary neuronal degeneration, TNF-α is implicated in affecting neuronal cell loss (Hult et al. (2008) Int. Rev. Psychiatry., 20:3-13; Rostasy et al. (2005) J. Neurol. Neurosurg. Psychiatry 76:960-964; Rostasy, K. M. (2005) Neuropediatrics 36:230-239; Kitaoka et al. (2006) Invest. Opthalmol. Vis. Sci. 47:1448-1457; Nakazawa et al. (2006) J. Neurosci. 26:12633-12641). Western blot analysis of brain lysates revealed that the expression of TNF-α was increased in HIV-1/VSV and HIV-1/VSV/Teff mice compared with sham control, whereas in HIV-1/VSV/Treg mice, TNF-α levels were decreased to PBS sham control levels (FIGS. 41F and 41G). Similarly, levels of Iba1 and GFAP in HIV-1/VSV and HIV-1/VSV/Teff mice were increased above sham control levels, whereas in HIV-1/VSV/Treg mice Iba1 and GFAP levels were diminished. These data indicate that Treg, but not Teff, are capable of attenuating HIV-1/VSV-induced glia activation to a neuroinflammatory phenotype.

Treg-Mediated Neuroprotection in HIVE Mice

Figure 42:
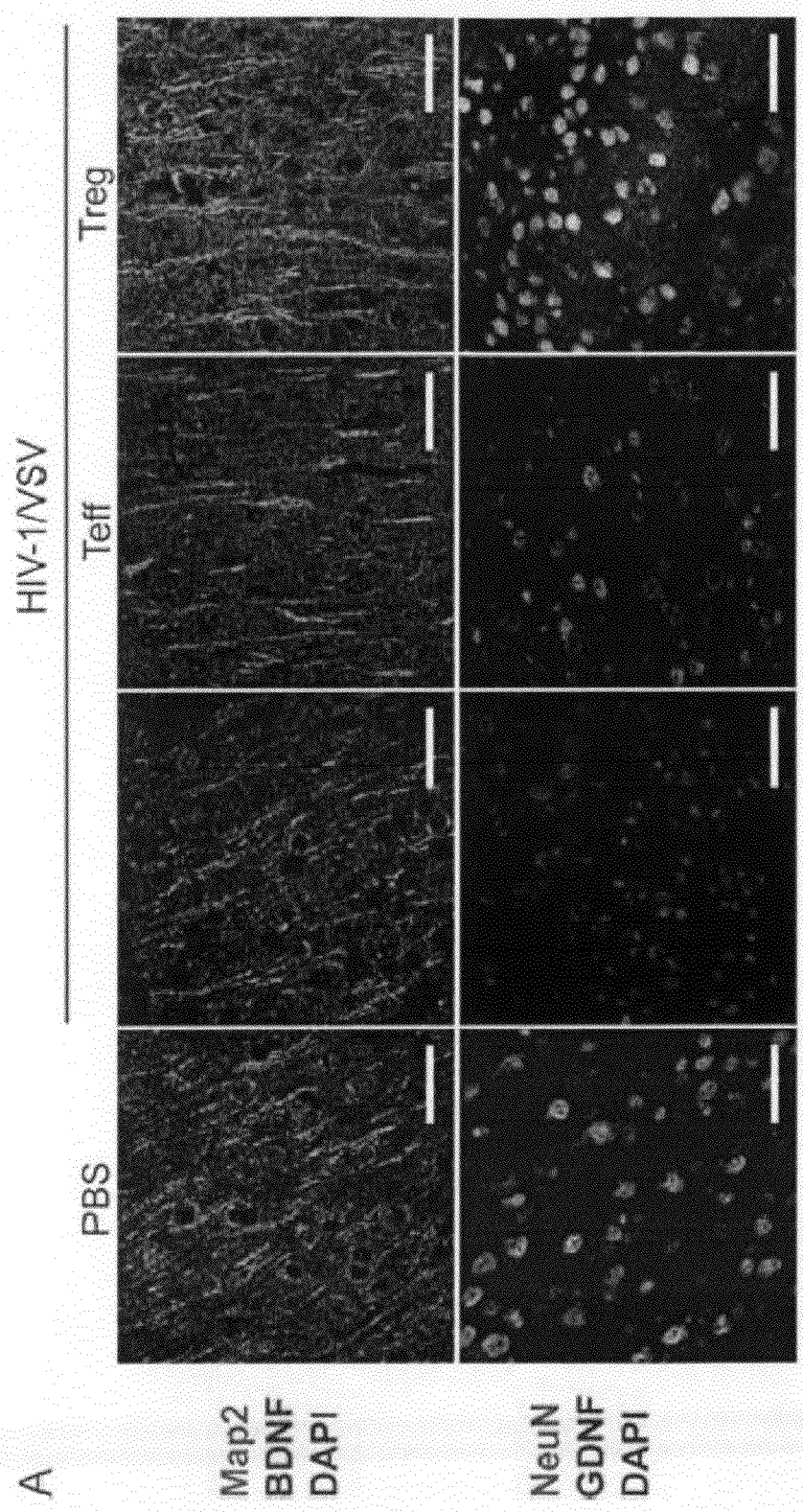
FIG. 42 shows Treg are neuroprotective in HIVE mice. Mice were stereotactically injected into the basal ganglia with HIV-1/VSV-infected syngeneic BMM or with PBS alone as sham controls. After 1 day, Treg or Teff ($1\times10^6$) were adoptively transferred into HIVE mice. Serial sections of brain tissue that encompassed the injection area were obtained on day 7 postinfection and analyzed by immunohistochemistry.
Figure 42:
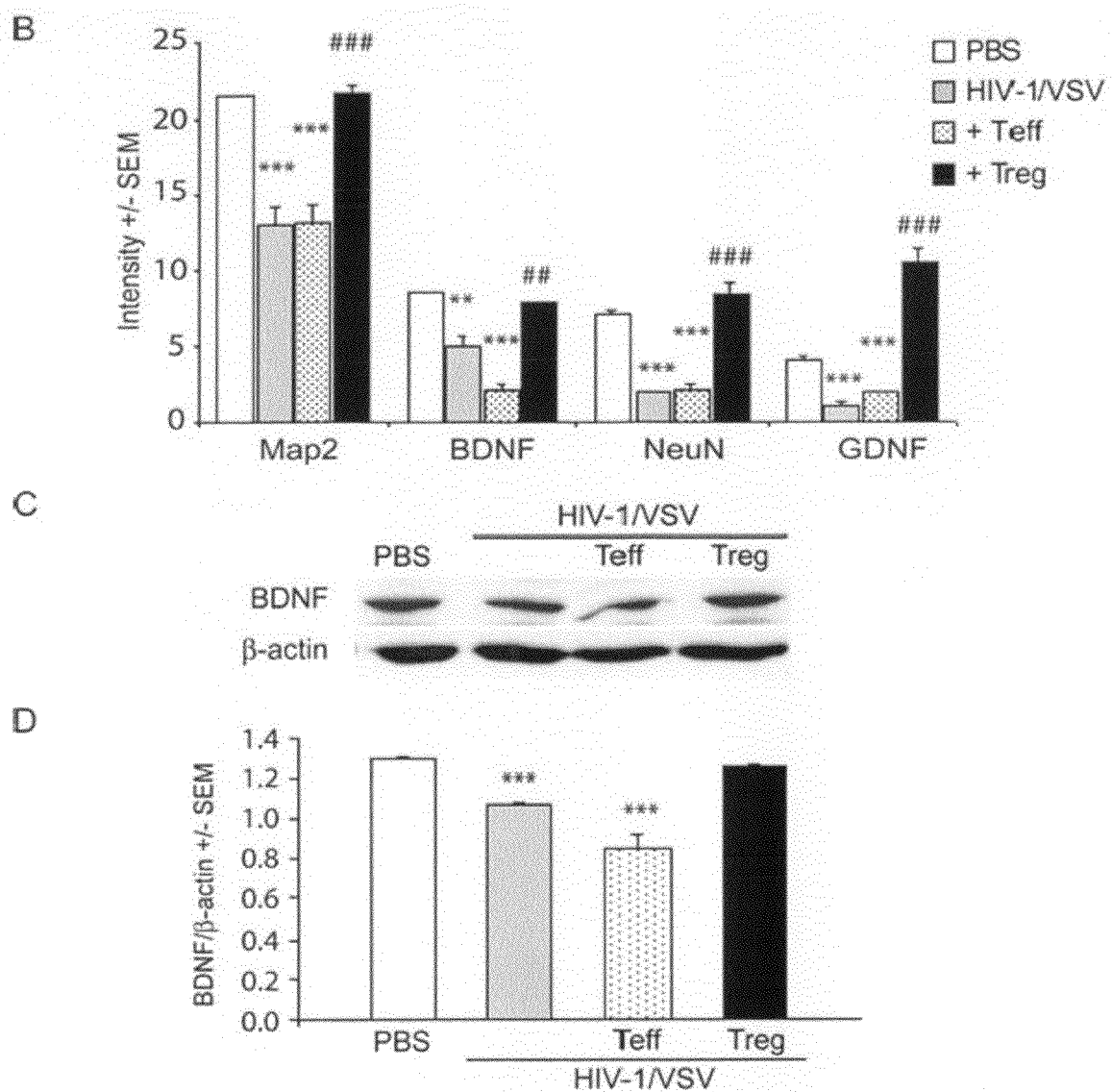

To evaluate the neuroprotective abilities of T cells for HIVE, neuronal density was measured in diseased animals where Treg were adoptively transferred. To determine a mechanism for these effects, expressions of BDNF, GDNF, MAP2, and NeuN were measured with or without T cell transfers. Evidence of neuronal dropout was observed by NeuN/MAP-2 immunostaining (FIG. 42A). Densitometric analysis of neurons revealed that HIV-1/VSV-infected mice showed 40 and 75% reductions in MAP2 and NeuN staining, respectively, and Teff-treated HIVE mice showed MAP2 and NeuN staining reductions comparable to those of HIVE mice (FIG. 42B). In contrast, infected mice treated with Treg exhibited no significant reduction in neuronal expression of MAP2 or NeuN with neuron levels comparable to those of sham control mice. Densitometric analysis of cellular expression of growth factors revealed that BDNF and GDNF expression was diminished by >40% in mice treated with HIV-1/VSV-infected BMM or those mice treated with Teff, whereas levels of growth factor expression in infected mice treated with Treg were comparable to or exceeded that of sham-treated controls. Enhanced expression of BDNF in HIV-1/VSV/Treg-treated mice was confirmed by Western blot analysis (FIGS. 42C and 42D). These data, taken together, indicate that Treg enhance neurotrophin secretion and protect neurons in HIVE mice.

Treg Induces Cytotoxicity in HIV-1/VSV-Infected BMM

Figure 43:
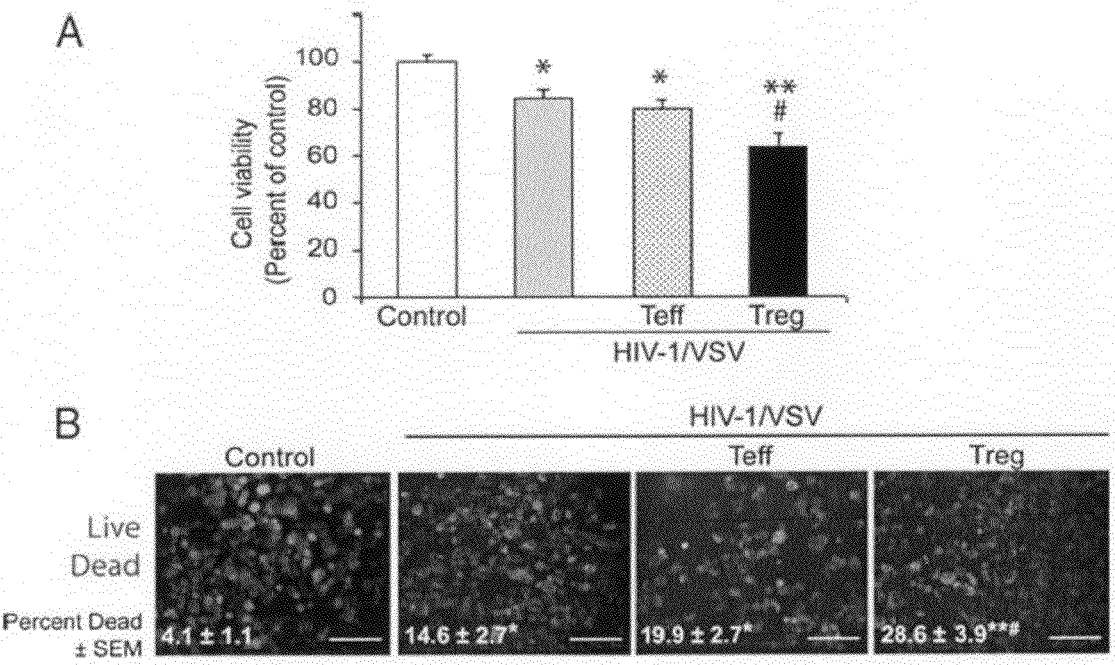
FIG. 43 shows Treg induce apoptosis in HIV-1/VSV-infected BMM. HIV-1/VSV-infected BMM were exposed to Teff or Treg for 3 days in the absence of M-CSF at a ratio of 3:1 (BMM:Treg or BMM:Teff). Uninfected BMM and HIV-1/VSV-infected BMM served as negative and infection controls.
Figure 43:
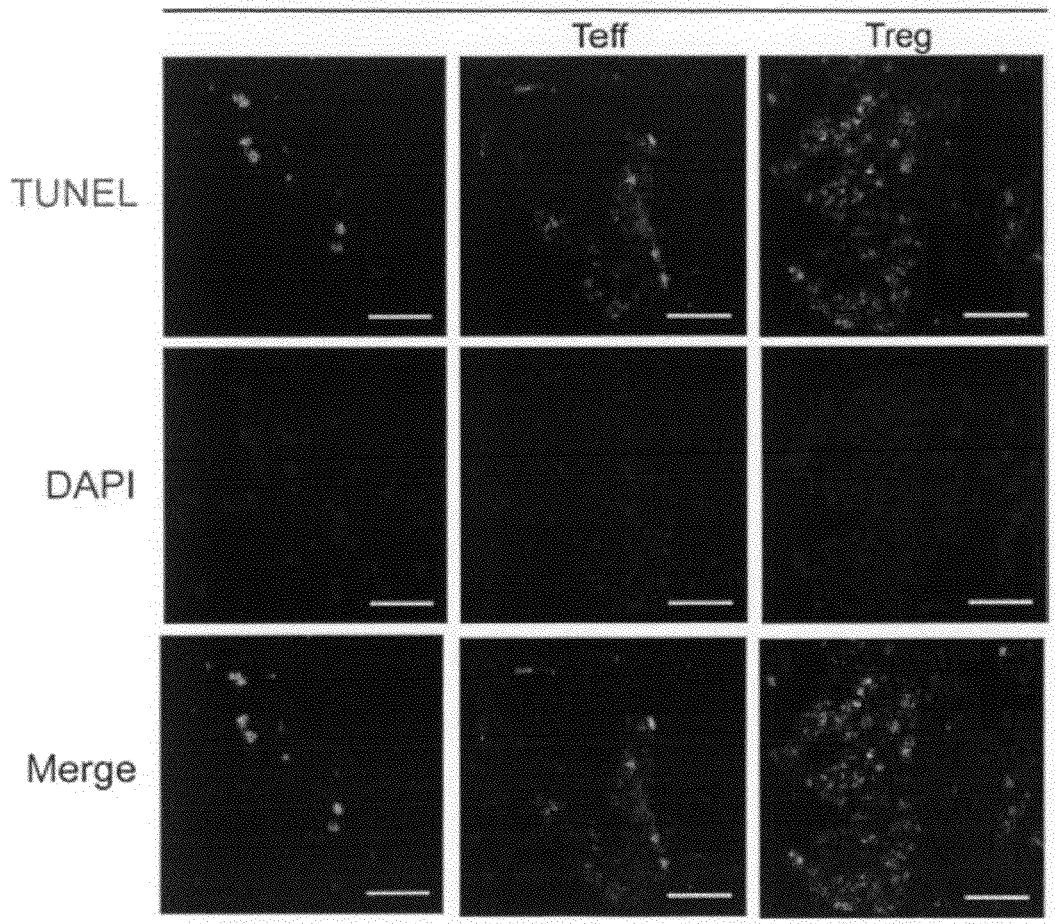

To elucidate mechanisms for Treg-induced neuroprotection, the effects of Treg on HIV-1/VSV-infected BMM was investigated. It was initially evaluated whether Treg affected cell death of infected BMM. In these experiments, BMM were infected with HIV-1/VSV for 24 hours and Teff or Treg were added at a BMM:T cell ratio of 3:1. Cell viability was determined by the MTT assay after 72 hours of treatment with T cell subsets and was normalized as the percentage of uninfected BMM control cultures. Compared with uninfected BMM, viabilities of infected BMM in the absence of T cells or presence of Teff were diminished by 15 and 20%, respectively (FIG. 43A). Most interestingly, the viability of infected BMM treated with Treg was reduced by 37% of uninfected BMM controls and diminished by >20% compared with either of the other infected BMM groups. These results were confirmed by LIVE/DEAD (Invitrogen) cytotoxicity staining, which demonstrated that infected BMM cultured in the absence or presence of Teff increased cytotoxicity to 14.6%±2.7 and 19.9%±2.7%, respectively, compared with the cytotoxicity of uninfected BMM (FIG. 43B). In contrast, coculture of infected BMM with Treg increased BMM cytotoxicity to 28.6%±3.9%, thus confirming that the previously recorded diminution of viable BMM was due to increased cytotoxicity.

Next, it was assessed whether HIV-1-infected BMM cytotoxicity requires cell-cell contact between the infected cells and Treg. BMM were isolated and infected with the HIV-1/VSV pseudotype virus. Treg and HIV-1-infected BMM were cocultured either by Transwell™ inserts or by direct physical contact for 1-3 days without M-CSF. After 3 days, BMM were depleted of Tregs by removing the inserts and by serial washing (3×) and were assessed for viability by MTT assay. Compared with uninfected BMM, percentage of viabilities (±SEM) for HIV-1 infected BMM cultured alone, cocultured directly with Treg, or cocultured with Treg using Transwell™ inserts, were 117±7.6, 75.3±6.2, and 159±8.6, respectively. Compared with HIV-1-infected BMM alone, BMM viability was significantly (p<0.05) lower when cocultured directly with Treg than with Treg separated by Transwell™ inserts. Thus, the lower levels of viability exhibited by infected BMM cocultured in direct contact with Treg compared with the viability levels of those cocultured with barrier-separated Treg support the notion that Treg-induced apoptosis of infected macrophage is mediated by cell-cell contact.

Additionally, to assess the effects of Treg on HIV-1/VSV infected cell apoptosis in vivo, TUNEL staining in brain sections was assessed that encompass the i.c. injection sites from HIVE mice treated without or with Teff or Treg. Surprisingly, TUNEL labeling was concentrated around the injection tracks (FIG. 43C). Treg-treated HIVE mice exhibited a greater density of TUNEL+BMM compared with mice HIV-1/VSV and HIV-1/VSV/Teff groups. This observation suggested that Treg-induced apoptosis of HIV-1/VSV-infected BMM confers neuronal protection in HIVE mice.

Figure 44:
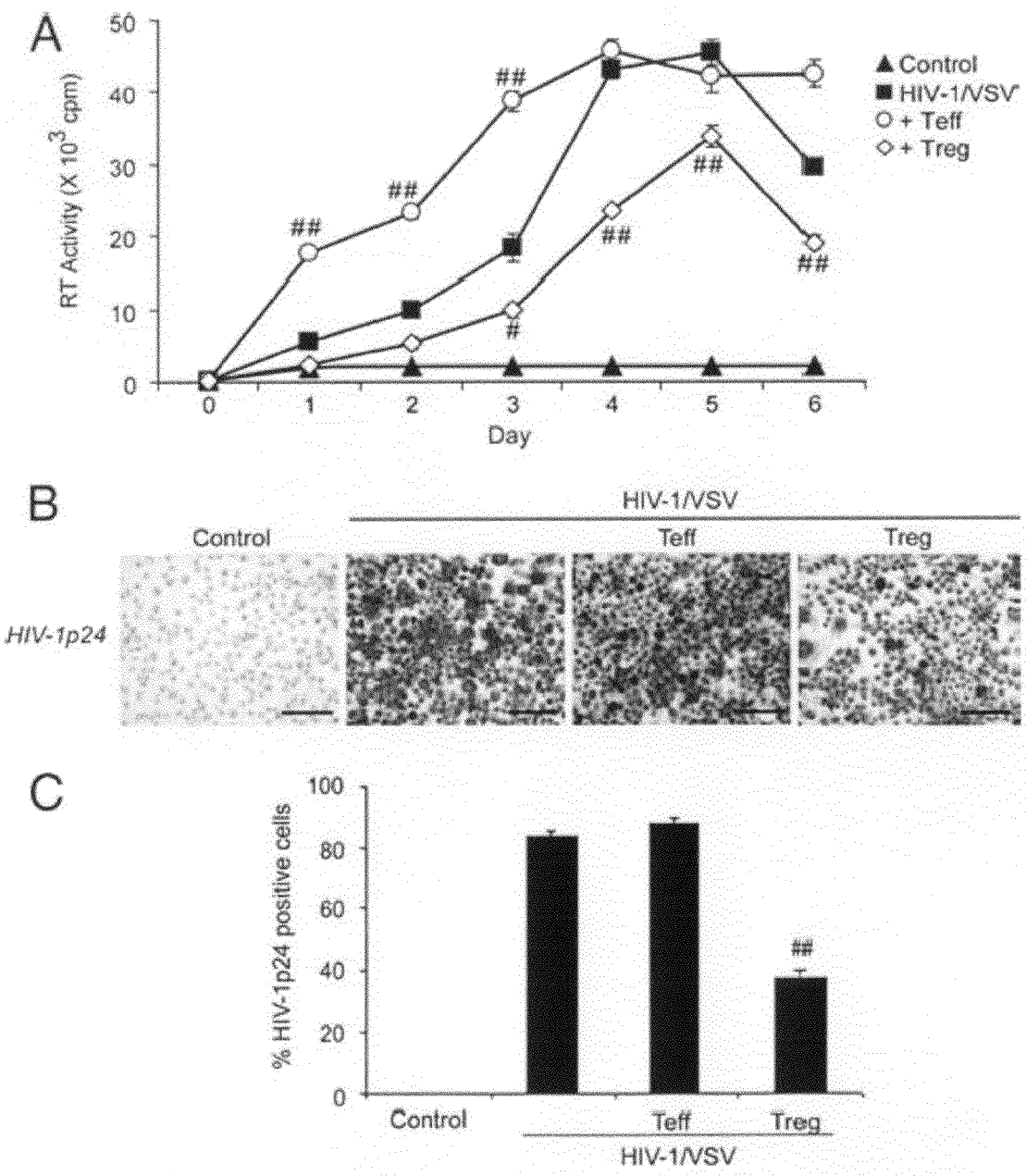
FIG. 44 shows Treg reduce HIV-1 viral replication in BMM. HIV-1/VSV infected BMM were cocultured with Teff or Treg at a ratio of 3:1 (BMM vs Treg or BBB vs Teff).

Treg Reduce HIV-1 Replication, Reactive Oxygen Species (ROS), and Cytotoxicity in BMM To test whether Treg mediated the inhibition of HIV-1 replication in HIV-1/VSV-infected BMM, BMM were infected with HIV-1/VSV for 24 hours. After viral washout, Treg or Teff were applied and cocultured for 6 days. Supernatants, collected at different time points, were used for an HIV-1 reverse-transcriptase activity assay. Compared with reverse transcriptase activities in HIV-1/VSV-infected BMM, levels of progeny virion production were significantly increased by day 1 in the HIV-1/VSV/Teff group and continued to remain higher until both levels reached a plateau at day 4 (FIG. 44A). In contrast, levels of progeny virion in infected BMM cultures treated with Treg (HIV-1/VSV/Treg) never approached those of the other two infected groups and were significantly below those of HIV-1/VSV infected BMM by day 3 and at times thereafter. Furthermore, the numbers of multinucleated giant cells, a hallmark of HIV-1 infection, were significantly reduced in the HIV-1 NSV/Treg group. Also, immunostaining suggested that Treg inhibited HIV-1 p24 protein expression in virally infected BMM (FIG. 44B). Percentages of HIV-1 p24-positive BMM indicated that coculture with Treg, but not Teff, significantly reduced the number of HIV-1-infected BMM compared with HIV-1/VSV-infected BMM controls (FIG. 44C).

Figure 45:
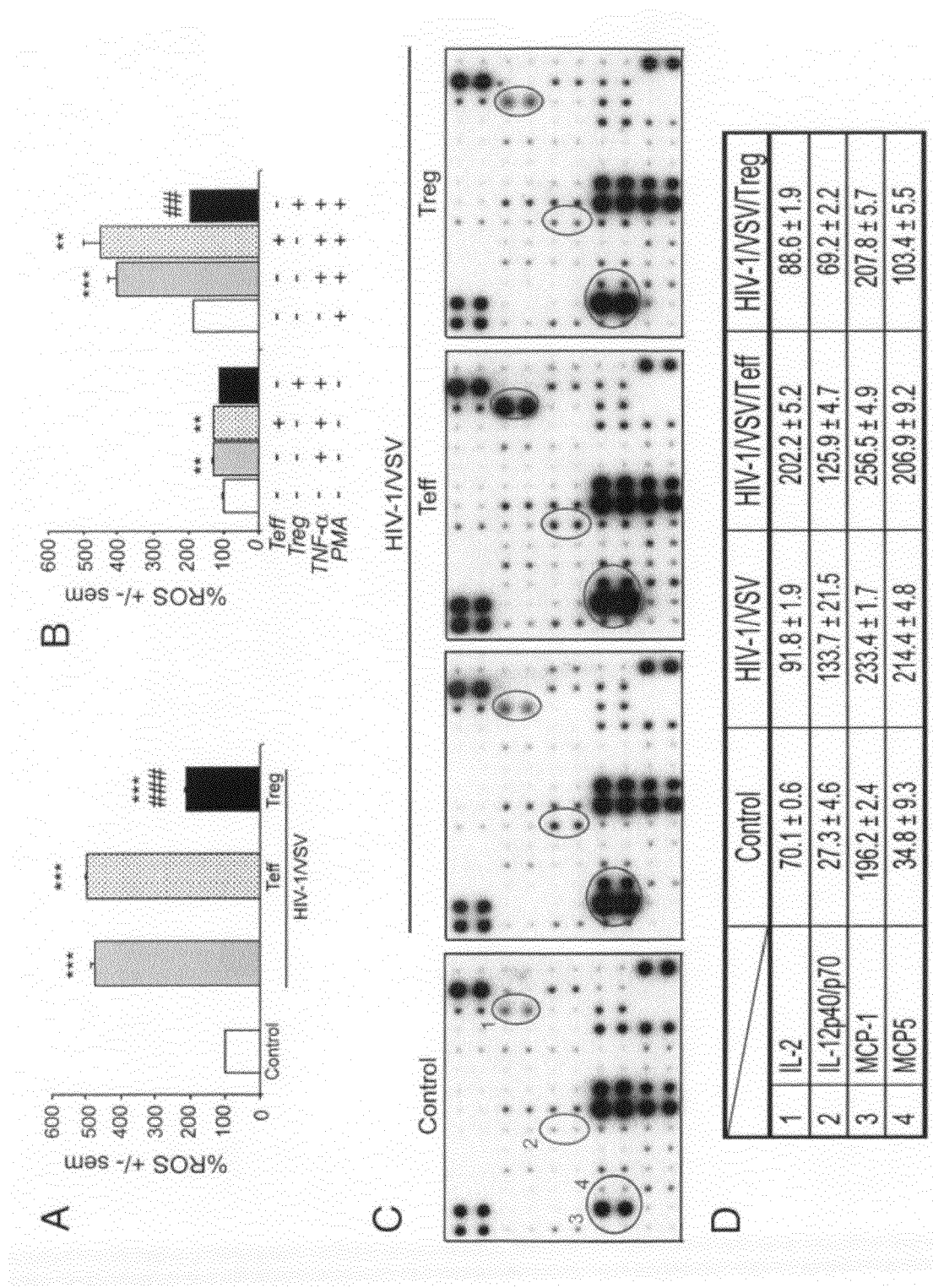
FIG. 45 shows Treg inhibit ROS production and cytotoxicity in BMM. Anti-CD3-activated Treg or Teff were cocultured in the absence or presence of HIV-1/VSV-infected BMM for 24 hours. After removal of T cells, ROS production was measured as a function of $H_2O_2$ accumulation using an Amplex Red assay. Uninfected BMM cultured alone served as ROS baseline controls. For FIG. 45A, compared with uninfected BMM controls (open bar), percentage increases of ROS as a function of $H_2O_2$ levels were determined for HIV-1/VSV-infected BMM cultured alone (gray bar) or cocultured in the presence of Teff (HIV-1 VSV/Teff, speckled bar), or Treg (HIV-1/VSV/Treg, black bar). For FIG. 45B, uninfected BMM cultured in the absence (left set) or presence of PMA (right set) were cocultured without TNF-α or T cells (open bars) in the presence of TNF-α (gray bars), with TNF-α and Teff (speckled bars), or with TNF-α and Treg (black bars). For FIGS. 45A and 45B, mean±SEM were determined for three experimental determinations and significant differences were determined by Student's t test; compared with control group: , p<0.01; *, p<0.001; compared with HIV-1/VSV group: ##, p<0.01; ###, p<0.001. For FIG. 45C, uninfected BMM (Control) and HIV-1/VSV-infected BMM were cultured in the absence or presence of Teff or Treg for 24 hours and supernatants were harvested. Collected supernatants were then subjected to cytokine array blots (RayBiotech). Ovals encompass replicate blots to detect expression of IL-2 (oval 1), IL-12p40/p70 (oval 2), MCP-1 (oval 3), and MCP-5 (oval 4). For FIG. 45D, densitometric analysis of cytokine array blots were achieved by digital image analysis with NIH Image J software, and mean densities±SD were determined for replicate determinations. Mean densities±SD of positive controls for each array of control BMM and HIV-1/VSV-infected BMM cultured in the absence or presence of Teff or Treg were 204.4±9.6, 206.3±6.0, 201.7±14.8, and 202.5±11.9, respectively.

Because oxidative stress is known to enhance neurotoxicity by increased levels of superoxide radicals and NO (Reynolds et al. (2007) J. Leukocyte Biol., 82:1083-1094; Reynolds et al. (2007) Int. Rev. Neurobiol. 82:297-325), it was evaluated whether the extent that Treg may affect ROS production as a mechanism of neuroprotective activity. It was hypothesized that Treg also suppress virally infected BMM-induced toxicity through suppression of ROS production. To test this, ROS production was assessed in HIV-1/VSV-infected BMM cocultured for 24 hours in the absence or presence of anti-CD3-activated Teff or Treg. Compared with uninfected BMM controls, HIV-1NSV-infected BMM resulted in a 4.7-fold increase in H2O2 production; however, Treg treatment of HIV-1/VSV-infected BMM significantly decreased $H_2O_2$ production (p<0.001), although not to baseline control levels (FIG. 45A). In contrast, Teff treatment of HIV-1/VSV-infected BMM failed to significantly affect $H_2O_2$ production. To test the effect of Treg on the ROS responses, uninfected BMM were activated for 24 hours with PMA and TNF-α and cocultured in the absence or presence of Teff or Treg. Similarly as in infected BMM, coculture with Treg significantly suppressed the ROS response of activated uninfected BMM, whereas Teff yielded no significant effects on ROS responses (FIG. 45B). Additionally, cytokine secretion was analyzed by a membrane-based cytokine array. Array analysis showed increased expression of IL-2, IL-12, MCP-1, and MCP5, by HIV/VSV-infected BMM or infected BMM treated with Teff compared with uninfected BMM (FIGS. 45C and 45D). In contrast, treatment of infected BMM with Treg diminished IL-2, IL-12, MCP-1, and MCP5 to levels below those attained either after infection or after infection and culture in the presence of Teff.

Treg Induce Neuroprotective Responses from HIV/VSV-Infected BMM CM

Figure 46:
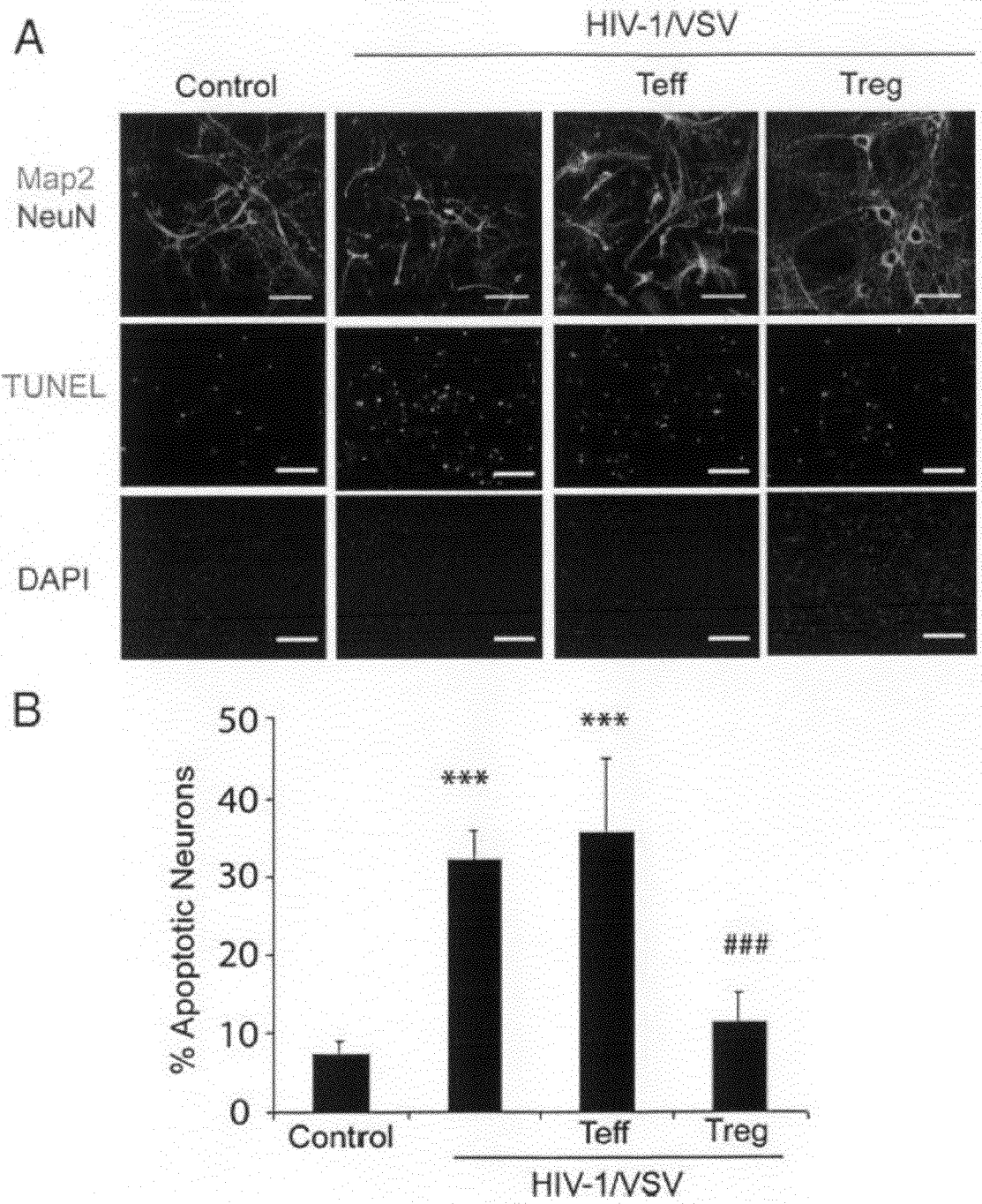
FIG. 46 shows Treg induce neuroprotective responses from HIV-1/VSV infected BMM. Mouse primary neurons were exposed for 24 hours to 10% of CM collected from uninfected BMM (Control), HIV-1/VSV-infected BMM, or HIV-1/VSV-infected BMM cocultured with Treg or Teff. For FIG. 46A, treated primary neuronal isolates were immunostained for expression of MAP-2 and NeuN. Images are at ×400 original magnification and the scale bars equal 50 μm (top row). Apoptotic neurons were determined by TUNEL staining showing apoptotic cells and DAPI nuclear staining. Micrographs are shown at ×200 magnification and scale bars equal 100 μm (middle and lower rows). For FIG. 46B, percentages of apoptotic neurons treated with CM from control BMM, HIV-1/VSV-infected BMM, HIV-1/VSV-infected BMM treated with Teff, or HIV-1/VSV infected BMM treated with Treg. Mean percentages±SEM were determined from three experiments; compared with control group: ***, p<0.001; and compared with HIV-1/VS infected BMM group: ###, p<0.001.

To substantiate the protective capacity of Treg to attenuate neuronal toxicity, neuronal cell death was measutred in primary neuronal cultures cultured for 24 hours in the presence or absence of CM from uninfected BMM (control) or HIV-1/VSV-infected BMM cultured in the absence or presence of Teff or Treg. Expression of MAP-2 and NeuN by primary neurons confirmed the neuronal integrity of control CM-treated neurons. TUNEL staining showed more apoptotic neurons in cultures after treatment with CM from HIV-1/VSV BMM and HIV-1 VSV/Teff BMM compared with control CM, whereas treatment with CM from HIV-1/VSV/Treg BMM showed fewer TUNEL-positive neurons (FIG. 46A). Quantitation of apoptotic neurons confirmed that the percentages of apoptotic neurons were significantly increased after treatment of primary neurons with CM from HIV-1/VSV BMM and HIV-1/VSV/Teff BMM compared with control CM (FIG. 46B). In contrast, treatment of neurons with CM from HIV-1/VSV/Treg BMM significantly diminished percentages of apoptotic neurons to levels attained with control CM.

EXAMPLE 8

Innate immune dysfunction is a pathogenic feature of amyotrophic lateral sclerosis (ALS) (Boillee et al. (2006) Neuron 52: 39-59; Lobsiger et al. (2007) Nat. Neurosci., 10:1355-1360). Transgenic (Tg) mice overexpressing mutated human G93A superoxide dismutase 1 (SOD 1) (Rosen et al. (1993) Nature 362:59-62) recapitulate ALS pathobiology including neuroinflammatory responses and motor neuron degeneration (Gurney et al. (1994) Science 264:1772-1775; Hall et al. (1998) Glia 23:249-256; McGeer et al. (2002) Muscle Nerve 26:459-470; Turner et al. (2004) Neurobiol. Dis., 15:601-609). Microglial inflammatory responses contribute to progressive neuronal loss in SOD1 mutant Tg mice and in human ALS (Beers et al. (2006) Proc. Natl. Acad. Sci., 103:16021-16026; Boillee et al. (2006) Science 312:1389-1392; Clement et al. (2003) Science 302:113-117; Marden et al. (2007) J. Clin. Invest., 117:2913-2919; Wu et al. (2006) Proc Natl Acad. Sci., 103:12132-12137). Functional ties between adaptive immunity and neurodegenerative disease are known for Parkinson's disease (Baba et al. (2005)

Parkinsonism Relat Disord., 11:493-498; Bas et al. (2001) J. Neuroimmunol., 113:146-152), Alzheimer's disease (AD) (Casal et al. (2003) Clin Biochem., 36:553-556; Scali et al. (2002) Neurobiol Aging 23:523-530; Shalit et al. (1995) Clin Immunol Immunopathol., 75:246-250), and multiple sclerosis (MS) (Bar-Or et al. (2003) Brain 126:2738-2749; Filion et al. (2003) Clin Exp Immunol., 131:324-334). Moreover, neuroprotective responses by Copolymer-1 (COP-1) immunization were observed in animal models of these and other neurodegenerative disorders (Aharoni et al. (2005) Proc Natl Acad. Sci., 102:19045-19050; Avidan et al. (2004) Eur J. Immunol., 34:3434-3445; Bakalash et al. (2005) J Mol. Med., 83:904-916; Benner et al. (2004) Proc Natl Acad. Sci., 101:9435-9440; Butovsky et al. (2006) Proc Natl Acad. Sci., 103:11784-11789; Gorantla et al. (2007) J. Immunol., 179:4345-4356; Gorantla et al. (2008) Glia 56:223-232; Kipnis et al. (2000) Proc Natl Acad. Sci., 97:7446-7451; Laurie et al. (2007) J. Neuroimmunol., 183:60-68; Liu et al. (2007) Eur. J. Immunol., 37:3143-3154; Schori et al. (2001) J. Neuroimmunol., 119:199-204). However, links between adaptive immunity and ALS remains obscure. Changes in T cell numbers and adaptive immune molecules in postmortem ALS and SOD1Tg mouse nervous system tissues were reported (Mc-Geer et al. (2002) Muscle Nerve 26:459-470; Alexianu et al. (2001) Neurology 57:1282-1289; Graves et al. (2004) Neuron Disord., 5:213-219; Henkel et al. (2006) Mol Cell Neurosci., 31:427-437; Henkel et al. (2004) Ann Neurol., 55:221-235; Kawamata et al. (1992) Am J. Pathol., 140:691-707; Troost et al. (1990) Neuropathol Appl Neurobiol 16:401-410). Interestingly, such COP-1 immunization strategies yielded mixed results in G93A-SOD1 mice (Angelov et al. (2003) Proc Natl Acad. Sci., 100:4790-4795; Habisch et al. (2007) Exp Neurol., 206:288-295; Haenggeli et al. (2007) Neurobiol Dis., 26:146-152). Taken together, these findings suggest a progressive immune dysfunction in G93A-SOD1 mice.

Mutant SOD1 may play a role in progression of ALS as microglia recovered from G93A-SOD1 mice induce increased motoneuron injury than microglia from over-expressing wild-type (Wt) human SOD1 (Beers et al. (2006) Proc. Natl. Acad. Sci., 103:16021-16026; Xiao et al. (2007) J. Neurochem., 102:2008-2019). Human ALS immunocytes show that both activated monocytes and T cell numbers are linked to disease progression (Zhang et al. (2005) J. Neuroimmunol., 159:215-224; Zhang et al. (2006) J. Neuroimmunol., 179:87-93). These data are consistent with a disease model where systemic immunologic activation plays an active role in ALS progression (Alexianu et al. (2001) Neurology 57:1282-1289; Zhang et al. (2005) J. Neuroimmunol., 159:215-224; Xiao et al. (2007) J. Neurochem., 102:2008-2019; Zhao et al. (2006) J. Neurochem., 99:1176-1187).

Based on these observations, T cell phenotype and function in G93A-SOD1 Tg mice and in ALS patients was investigated. COP-1 immunization provided clinical benefit to only female G93A-SOD1 Tg mice. Profound T cell functional deficits were observed in pre-symptomatic male G93A-SOD 1 Tg mice spleen as well as acute lymphopenia in end stage animals. Transfer of naive lymphoid cells from Wt donor mice to SOD1 Tg recipient mice failed to affect survival or overcome the observed lymphopenia. As COP-1 is linked to neuroprotective T regulatory cells (Treg) and the modulation of neuroinflammatory responses (Benner et al. (2004) Proc Natl Acad. Sci., 101:9435-9440; Laurie et al. (2007) J. Neuroimmunol., 183:60-68), it was then investigated whether CD4+ CD25+Treg or CD4+ CD25− T effector cells (Teff) could affect neurological deficits and survival. Importantly, for SOD1 Tg mice, polyclonal-activated Wt Treg or Teff administered by adoptive transfer extended longevity and attenuated motor deficits. Treg delayed clinical symptom onset, while Teff increased latency from onset to late stage disease. These results together with supportive data in human ALS indicate the presence of aberrant T cell subsets in disease.

Materials and Methods

Animals

Mice from two SOD1 Tg mouse strains expressing the G93A mutation, B6SJL-TgN(SOD1*G93A)1Gur (stock number, 002726; hereafter designated B6SJL SOD1 Tg) and B6.Cg-Tg (SOD1*G93A)1Gur/J (stock number, 004435; hereafter designated B6 SOD1 Tg), and age- and sex-matched Wt littermates were obtained from Jackson Laboratory (Bar Harbor, Me.). B6SJL SOD1 Tg mice survive from 16-20 weeks, while B6 SOD1 Tg mice have a delayed survival phenotype of 19-22 weeks. Mice were randomly separated to control and treatment groups upon receipt. All animal procedures met with National Institutes of Health guidelines and were approved by the Institutional Animal Care and Use Committee (IACUC) of the University of Nebraska Medical Center.

Human Subjects

Experimental procedures involving human subjects were conducted in conformance with the policies and principles contained in the Federal Policy for the Protection of Human Subjects (U.S. Office of Science and Technology Policy) and in the Declaration of Helsinki.

COP-1 Immunization

B6 SOD1 Tg mice (7 weeks old) were immunized with 75 μg of COP-1 in 0.1 ml PBS weekly (q1wk) or every 2 weeks (q2wk), or treated with PBS alone. Subcutaneous injections were administered in the flanks with a 50 μl bolus given to each side.

Spleen Morphology, Weight, Viable Cell Counts

Spleens from Wt and Tg mice were measured and weighed. Single cell suspensions were prepared by pressing spleens through 60 μm sterile wire mesh screens in Hanks' balanced salt solution (HBSS, Mediatech Inc., Herndon, Va.). Erythrocytes were lysed with ammonium chloride potassium buffer and leukocytes washed by centrifugation. Numbers of viable splenic leukocytes were determined by trypan blue exclusion of hemocytometer counts.

Lymphocyte Proliferation

Splenocytes from individual animals were plated in 96-well round-bottom plates at 16106 cell/ml in RPMI medium 1640 (Gibco, Carlsbad, Calif.) supplemented with 10% fetal bovine serum, 2 mM L-glutamine, 25 mM HEPES, 1 mM sodium pyruvate, 1× nonessential amino acids, 55 mM 2-mercaptoethanol, 100 units/ml penicillin, and 100 μg/ml streptomycin (complete RPMI 1640) (Mediatech Inc.). Quadruplicate replicates were stimulated with anti-CD3 (1 μg/ml) (clone 145-2C11, BD Pharmingen), goat anti-IgM (20 μg/ml) (Jackson Immuno Research, West Grove, Pa.) or cultured in media alone at 37° C. in 5% $CO_2$ for 3 days. From Tg mice immunized with COP-1 (Sigma-Aldrich, St. Louis, Mo.), spleen cells were cultured in the presence of COP-1 (5 μg/ml), concanavalin A (Con A, 2 μg/ml, Sigma-Aldrich), or media for 5 days. Cells were pulsed for the final 18 hours of incubation with 1 μCi [$^3$H] methylated thymidine ([$^3$H]-TdR) (MP Biomedicals ICN, Solon, Ohio), harvested onto glass-fiber filters, and counted by β-scintillation spectrometry (Top Count, Packard Instrument Co., Meriden, Conn.). Levels of spleen cell proliferation for each animal were normalized to levels of proliferation obtained from cells cultured in media alone and were reported as a stimulation index.

Immunohistochemical Assays

Fresh frozen spleens of Tg mice and Wt littermates were embedded in OCT media (Sakura Fintek, Torrance, Calif.) and sectioned at 10 μm using a cryostat (CM1900, Leica, Bannockburn, Ill.). Sections were collected on slides and fixed in ice-cold acetone-methanol (1:1) for 30 minutes. Slides were washed in phosphate-buffered saline (PBS) at room temperature (RT) and quenched for endogenous peroxidase activity in 3% hydrogen peroxide in methanol for 15 minutes. Nonspecific staining was blocked with 5% normal rabbit serum (NRS) (Vector Laboratories, Burlingame, Calif.) in PBS for 1 hour. For immunostaining, primary antibodies (clone designations and dilutions) included anti-CD3 (clone 17A2, 1:100), anti-CD19 (clone 1D3, 1:100), anti-F4/80 (clone BM8, 1:500) and anti-Gr-1 (clone RB6-8C5, 1:100) (all obtained from eBioscience, San Diego, Calif.). Sections were incubated with primary antibody diluted in PBS/5% NRS for 90 minutes at room temperature, washed in PBS and incubated with polyclonal rabbit anti-rat:immunoglobulin (1:400) (Dako, Capinteria, Calif.) for 30 minutes followed by streptavidin-horseradish peroxidase solution (ABC Elite vector kit, Vector Laboratories) for 30 minutes. Staining was visualized by addition of hydrogen peroxide substrate and diaminobenzidine chromogen (DAB substrate kit for peroxidase, Vector Laboratories) solution. Sections were counterstained with hematoxylin (Surgipath Medical Industries, Inc., Richmond, Ill.), dehydrated, covered with mounting media (Cytoseal 60, Kalamazoo, Mich.) and mounted with a glass coverslip. Slides were examined under a light microscope (Eclipse E800, Nikon, Inc., Melville, N.Y.) and representative images captured at 100× magnification. Follicle counts, area per follicle, and densities of CD3, CD19, F4/80 and Gr-1 expression were evaluated from 4 fields/animal by digital image analysis using Image-Pro Plus version 4 software (Media Cybernetics, Silver Spring, Md.).

Flow Cytometric (FCM) Analysis of Mouse and Human Leukocytes

Single cell suspensions of spleens from Wt and Tg mice were stained with fluorescein isothiocyanate (FITC)-conjugated (clone designate) anti-CD19 (1D3), anti-CD4 (RM4-4), anti-CD62L (MeI-14), and anti-Gr-1 (RB6-8C5); phycoerythrin (PE)-conjugated (clone) anti-CD4 (GK1.5), anti-CD8b (53-5.8), and F4/80 (BM8, eBioscience); and allophycocyanin (APC)-conjugated (clone) anti-CD3 (145-2C11) and anti-CD44 (1M7). All antibodies except where indicated were obtained from BD Pharmingen (San Diego, Calif.).

Peripheral blood from 10 ALS patients and their age-matched caregivers were collected in ethylenediaminetetraacetic acid (EDTA) containing glass tubes at Columbia University, shipped overnight, and processed upon arrival at the University Nebraska Medical Center. Complete blood count (CBC) and differential analysis for each donor and patient were determined from samples obtained prior to shipping. For FCM analysis, 20 μl of appropriate fluorochrome-conjugated antibodies were added to 100 μl of whole blood and incubated in the dark for 30 minutes at room temperature. Erythrocytes were lysed and leukocytes fixed with FACS Lysing solution (BD Biosciences). Antibodies (clone) utilized in these studies included FITC-conjugated anti-CD8a (RPA-T8), anti-CD16 (55661), anti-CD45RA (HI1100), and anti-CD19 (H1B19); PE-conjugated anti-CD14 (55715) and anti-CD4 (OKT4); and APC-conjugated anti-CD3 (UCHT1), anti-HLA-DR (LN3), and anti-CD45R0 (UCHL1).

Stained mouse and human leukocytes were evaluated by FCM analysis using a FACSCalibur flow cytometer interfaced with CellQuest software (BD-Biosciences, Immunocytometry Systems). Electronic bit maps were utilized to encompass and gate lymphocyte and monocyte subsets during FCM analysis.

Measures of Lymphocyte Apoptosis and Necrosis

Spleen cells from 14 weeks old Wt and Tg mice were evaluated as fresh isolates or were stimulated for 24 or 48 hours as for lymphocyte proliferation. Harvested spleen cells were stained with annexin-V-FITC (ApoptosisDetection kit, Calbiochem/EMD Biosciences, Inc., San Diego, Calif.), PE-anti-Thy-1 (clone 53-2.1) to detect T cells, and APC anti-CD45R/B220 (clone RA3-6B2) to detect B cells (eBioscience). Actinomycin D (7-ADD; BD Pharmingen) was used as a viable exclusion indicator for membrane permeability to distinguish apoptotic (annexin-V+7-ADD-) from necrotic cells (annexin-V+7-ADD+), the latter having lost membrane integrity.

Isolation and Purification of CD4+ CD25+(Treg) and CD4+ CD25-(Teff) Cells

Treg and Teff cells were isolated as previously described. Lymph nodes (cervical, mandibular, axillary, brachial, inguinal and mesenteric) and spleens were harvested from male Wt B6 mice (9 weeks old). After lysis of red blood cells, T cell populations were enriched by negative selection on CD3+ T cell columns (R&D Systems, Minneapolis, Minn.). CD3+ T cells were further passed through CD4+ T cell subset enrichment column (R&D Systems) to obtain a highly pure CD4+ T cell population in the eluted fraction. The CD4+ T cell fraction was incubated with PE-labeled anti-CD25 antibody (BD Pharmingen) followed by anti-PE microbeads (Miltenyi Biotec, Auburn, Calif.) and subjected to magnetic separation (Auto MACS, Miltenyi Biotec). Nonadherent cells were eluted from the magnetic column and were enriched for CD4+CD25- Teff cells, while adherent cells eluted from the column were enriched as CD4+CD25+Treg cells. Purity of nonadherent and adherent cell fractions were determined by FCM analysis (FACSCalibur flow cytometer, BD Biosciences) using antibodies that recognize disparate epitopes to CD3, CD19, CD4, CD8, CD25, and Foxp3 (eBioscience). Prior to activation, fresh isolates of Tregs were >95% CD4+CD25+Foxp3+ while Teff were >95% CD4+ CD25-Foxp3-. To activate and expand enriched T cell populations, purified cells were cultured for 4 days in 24-well plates at $1 \times 10^6$ cells per ml of complete RPMI 1640 with 0.5 μg/ml anti-CD3 (145-2C11; BD Pharmingen) and $3 \times 10^6$ irradiated splenocytes (3,300 rads). CD4+CD25+T cells required the addition of 100 U/ml of mouse recombinant interleukin (IL)-2 (R&D Systems). Furthermore, CD4+CD25+Tregs exhibited increased expression of mRNA for Foxp3, TGF-β and IL-10, whereas Teff showed increased expression of IFN-α mRNA. Tregs also inhibited anti-CD3 induced mitogenesis in a dose-dependent manner.

Adoptive Cell Transfers

Freshly isolated lymphocytes obtained from spleens of naive Wt B6 donor mice and anti-CD3 activated Treg or Teff cells after 4 days of stimulation in vitro were harvested, washed, and resuspended in HBSS. To B6 SOD1 Tg recipient mice, $50 \times 10^6$ lymphocytes or $1 \times 10^6$ Treg or Teff cells in 0.25 ml of HBSS or PBS alone were administered intravenous every 6 weeks at 7, 13, and 19 weeks of age.

Body Weight and Clinical Signs

The initial sign of the disease is a high frequency resting tremor that progresses to gait impairment, asymmetrical or symmetrical paralysis of the hind limbs, followed by complete paralysis at end stage. Beginning at 7 weeks of age, all animals were assessed weekly for body weight and for signs of motor deficit with the following 4 point-scoring system: 4 points if normal (no sign of motor dysfunction), 3 points if hind limb tremors were evident when suspended by the tail, 2 points if gait abnormalities were present, 1 point for dragging of at least one hind limb, and 0 point for symmetrical paralysis (Weydt et al. (2003) Neuroreport., 14:1051-1054). Disease onset was determined at the earliest presentation of symptoms (i.e. score=3). Mice that reached a clinical score of 0 or lost 20% of maximum body weight were deemed unable to survive, removed from the study, immediately euthanized, and scored as a terminal event.

Paw Grip Endurance (PaGE) Test

Grip strength of hind limbs of mice were assessed each week as previously described (Weydt et al. (2003) Neuroreport., 14:1051-1054). Each mouse was placed on the wire-lid of a conventional housing cage and gently shaken to prompt the mouse to hold on to the grid. The lid was turned upside down and the duration determined until the mouse released both hind limbs. Each mouse was given three attempts with a maximum duration of 90 seconds and the longest latency was recorded.

Rotarod Performance

Mice were pre-conditioned for 3 days prior to testing then monitored for rotarod performance once every week starting at 7 weeks of age (Haenggeli et al. (2007) Neurobiol Dis 26:146-152). In brief, mice were placed on a partitioned rotating rod (Rotamex Rota-rod apparatus, Columbus Instruments, Columbus, Ohio) and tested at a 5, 10, and 15 rpm for a maximum of 90 sec at each speed with a minimum of 5 minutes rest between attempts. The overall rotarod performance (ORP) was calculated as the area under the curve using Prism (version 4, Graphpad Graphpad Software, San Diego, Calif.) from the plot of the time that the animal remained on the rod as a function of the rotation speed.

Statistical Analyses

All values are expressed as mean±SEM. Differences among normally distributed means were evaluated by Student's t test for two group comparisons or one-way ANOVA followed by Bonferroni or Fisher's LSD post-hoc tests for pairwise comparisons amongst multiple data sets exhibiting equal variances or by Dunnett's post-hoc tests for data exhibiting unequal variances (Statistica v7, StatSoft, Tulsa, Okla., and SPSS v13, SPSS, Inc., Chicago, Ill.). Cox's F-test comparison was performed for comparison between treatment groups for Kaplan-Meier analyses.

Results

COP-1 Immunization of B6 SOD1 Tg Mice

Figure 47:
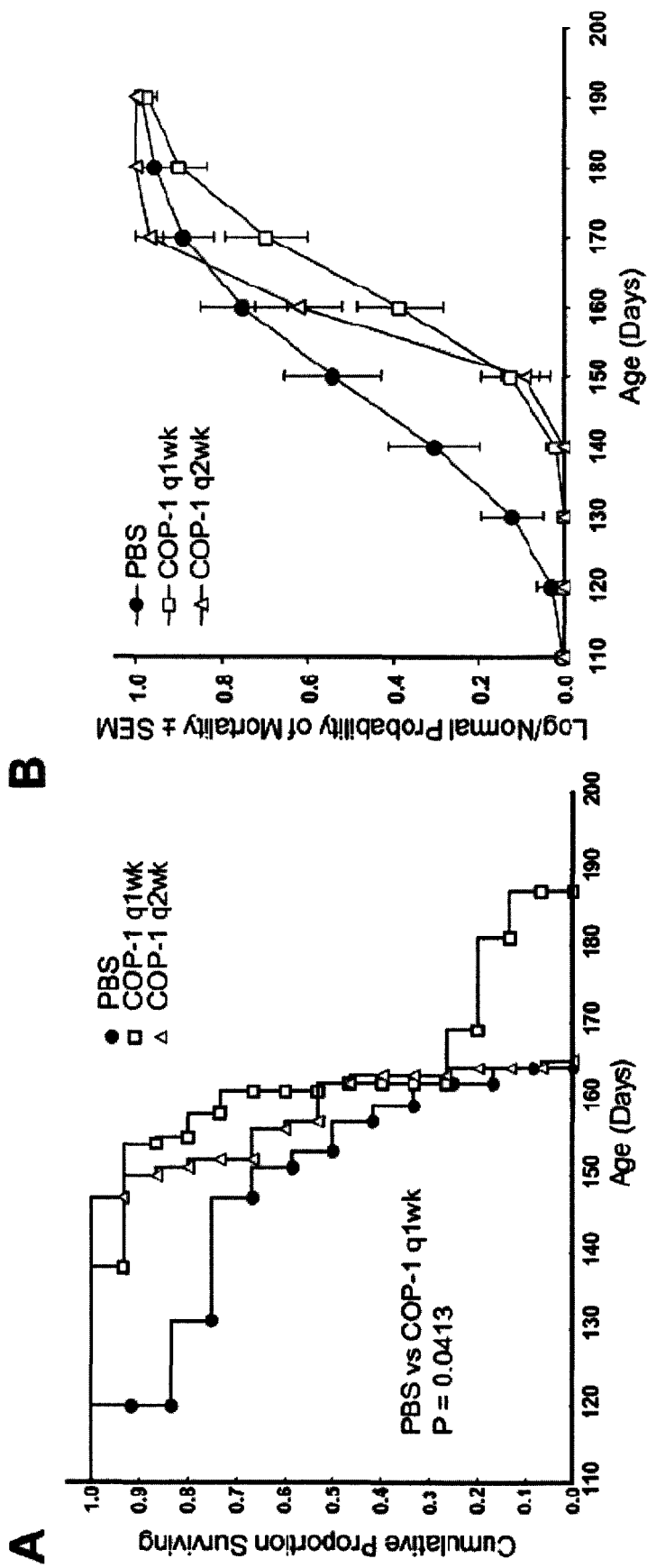
FIG. 47 shows the effect of COP-1 immunization in B6 SOD1 mice. Mice were treated with PBS (closed circles and black bars), COP-1 weekly (q1wk) (open boxes and gray bars), or COP-1 every 2 weeks (q2wk) (open triangles and white bars).
Figure 47:
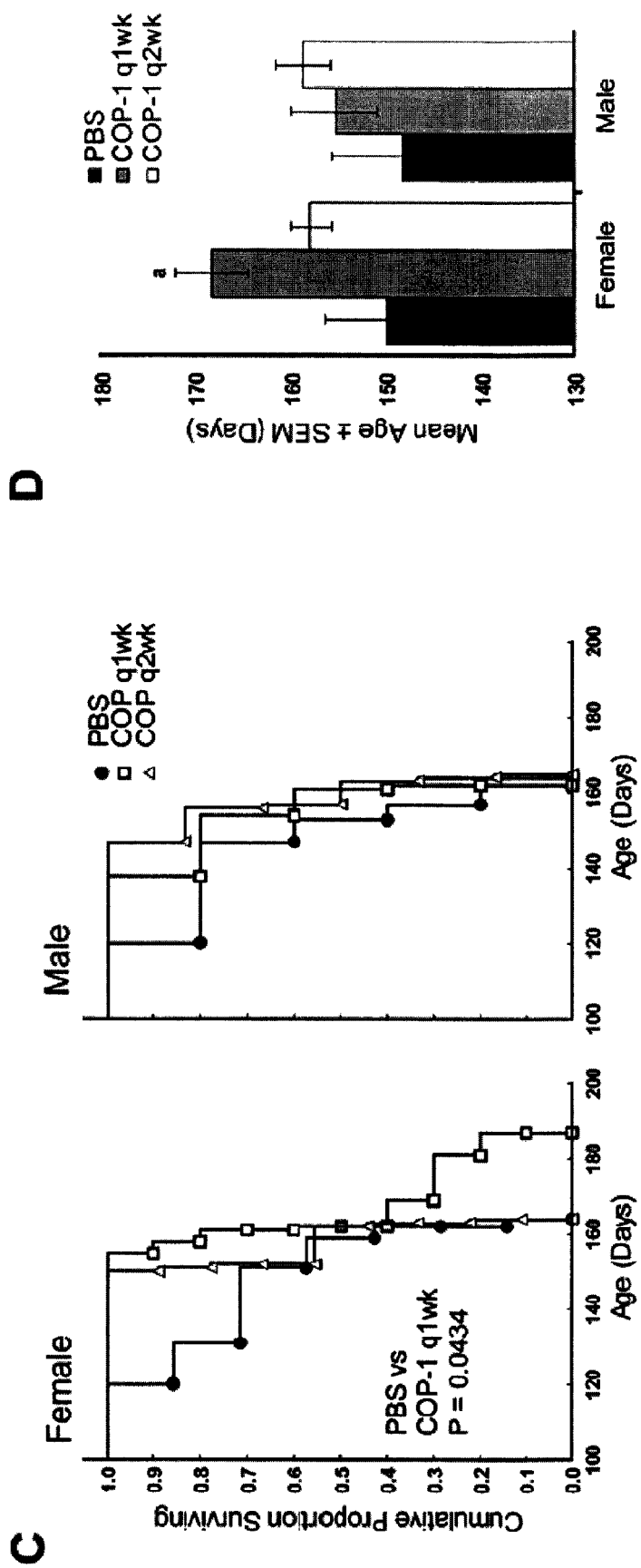
Figure 47:
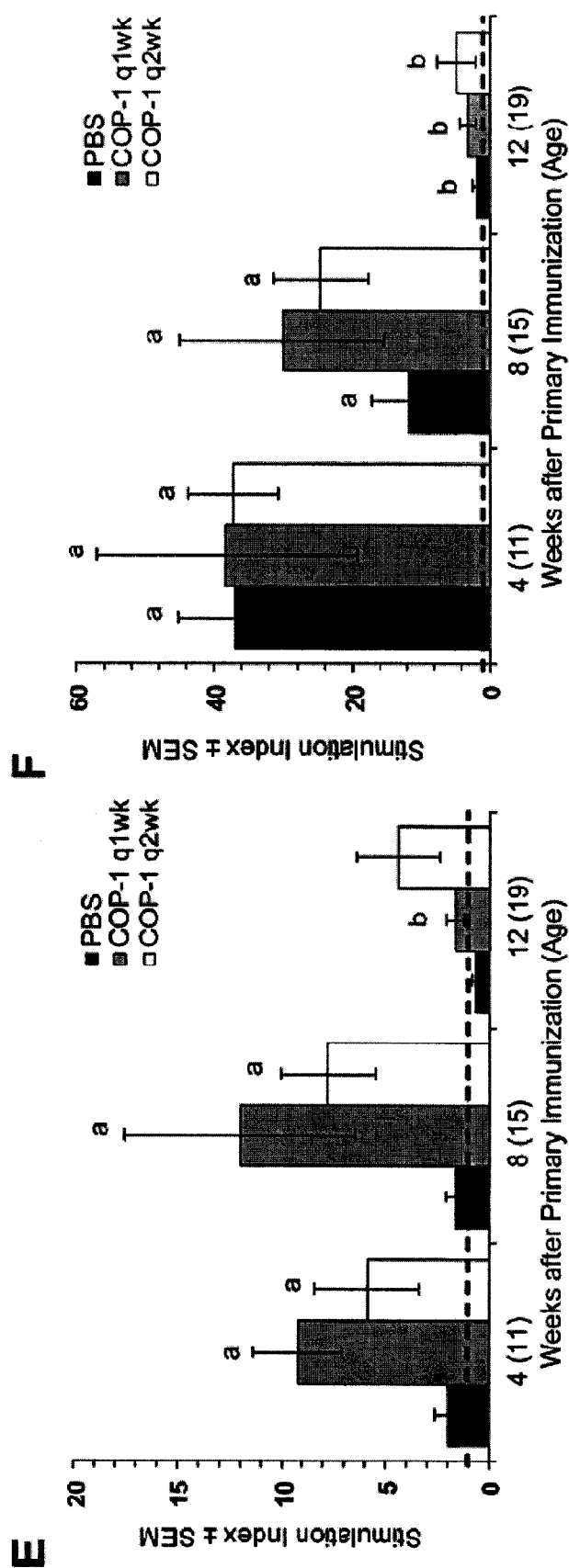

The initial works investigated whether COP-1 immunization of B6 SOD1 Tg mice affect disease progression. In these experiments male and female B6 SOD1 Tg mice were immunized with 75 µg COP-1 s.c. in 0.1 ml PBS either every week (q1wk) or every other week (q2wk), or animals were treated every week with PBS as excipient controls. Kaplan-Meier analysis indicated that weekly COP-1 immunization had an affect on the lifespan of SOD1 Tg mice compared to PBS controls (p=0.0413), however immunization every other week did not increase survival (p=0.1673) (FIG. 47A). For mice immunized weekly with COP-1, the mean age of survival increased by 9.9% compared to PBS controls (p=0.006), while COP-1 immunization every other week increased the mean age of survival by 6.1%, however this did not reach significance. Log-normal analysis of mortality probability at 10 day intervals showed that COP-1 immunization every week and every other week initially provided protective benefits compared to PBS controls; however, by 160 days of age, the probability of mortality for mice immunized every other week evolved to that afforded by PBS controls (FIG. 47B). Kaplan-Meier analysis of treated mice stratified for gender indicated that increased survival by weekly immunization was associated with female mice (p=0.0434), but had no effect on survival of male Tg mice (FIG. 47C). Similarly, compared to PBS treated controls, immunization with COP-1 every week increased the mean age of survival for female, but not male Tg mice, and immunization every other week produced no difference in mean age of survival for either male or female Tg mice (FIG. 47D). These results posed the question as to whether adaptive immunity was fully functional in pre-symptomatic SOD1 Tg mice.

Impaired T Cell Immune Responses in SOD1 Tg Mice

Based on the failure of the COP-1 immunization strategies to increase longevity in male SOD1 Tg mice, and preliminary data showing diminished spleen size and immune responses with age, it was tested whether T cell responses were functional. These studies revealed that T cell immune function elicited in B6 SOD1 Tg male mice was significantly impaired by 19 weeks of age. Spleen cells from 4 and 8 week-immune SOD1 Tg mice, stimulated in vitro with COP-1 exhibited increased stimulation indices compared to those cultured in media alone (dashed line), whereas cells from PBS treated mice were unable to respond to COP-1 (FIG. 47E) indicating that immunization strategies elicited functional COP-1 responsive T cells in early stage of the disease. However, after 12 weeks of weekly or bi-weekly immunizations, stimulation indices of COP-1 stimulated spleen cells diminished to levels statistically indiscernible from those of cells cultured in media alone indicating that the T cell immune responses in those mice had waned. In concomitant assays to test the overall functionality of all T cell populations, spleen cell cultures were stimulated with Con A, a T cell mitogen. Stimulation indices of Con A induced T cells from B6 SOD1Tg mice in all treatment groups after 4 and 8 weeks (at 11 and 15 weeks of age) were significantly above those of media control cells (dashed line) (FIG. 47F), demonstrating the presence of functional T cells in those mice. However in Tg mice at 19 weeks of age, after 12 weeks of treatment, stimulation indices of Con A stimulated T cells were indistinguishable from those cultured in media alone. Regression analysis of stimulation indices of Con A stimulated T cells from PBS controls indicated a progressively diminished proliferative capacity of T cells that was strongly associated with increasing age of B6 SOD1Tg mice ($r^2$=0.6308, p=0.002). Taken together these results suggest a global dysregulation of T cell function with age in SOD1 Tg mice.

Spleen Size, Weight and Cell Counts in SOD1 Tg Mice

Figure 48:
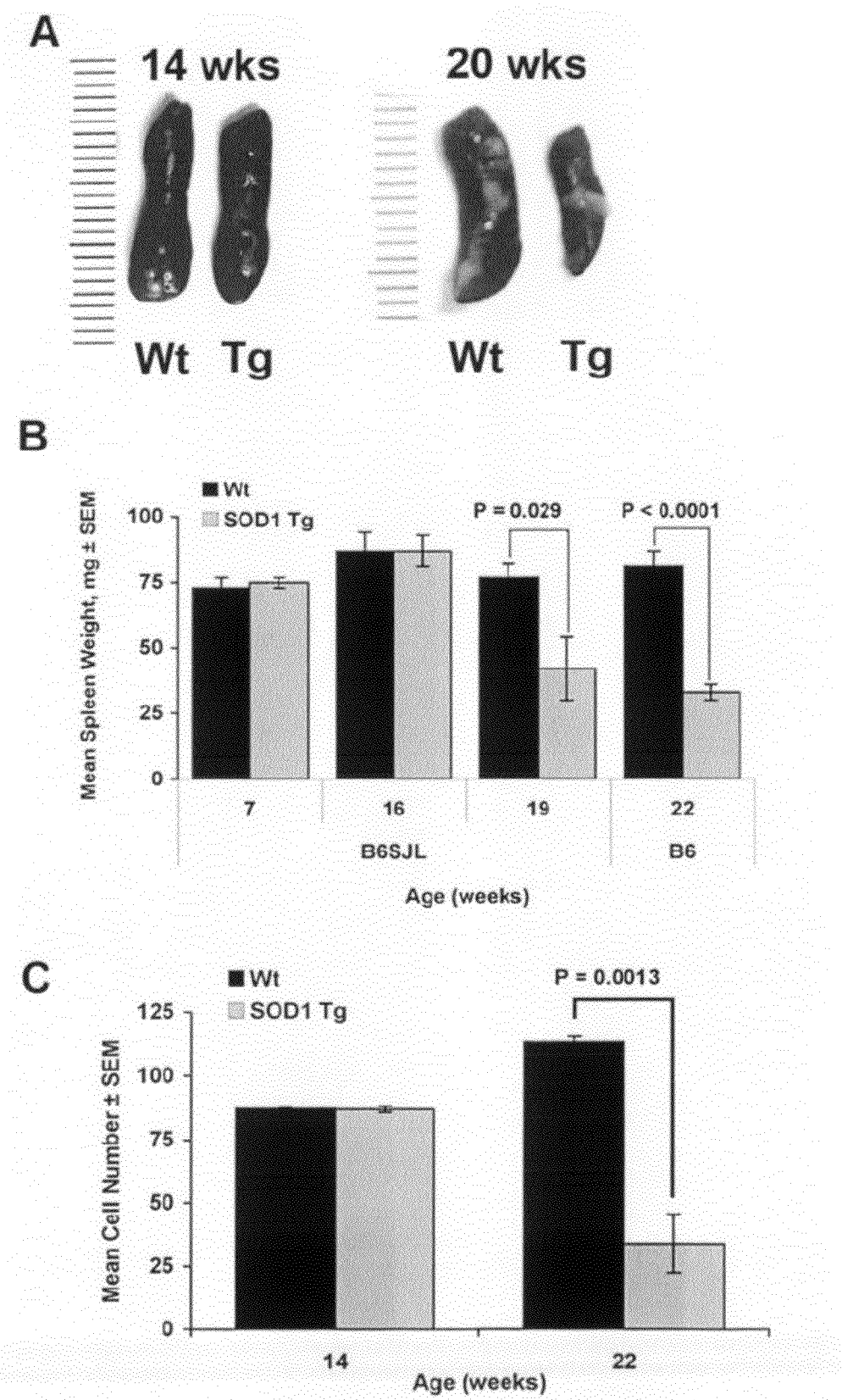
FIG. 48 shows spleen changes in G93A-SOD1 Tg mice.

Based on marginal protection achieved by COP-1 immunization and progressively diminished T cell function with age, the adaptive immune system was investigated in disease whereby spleens from B6SJL G93A-SOD1 Tg mice were compared at early symptomatic stage (14 weeks of age) and end stage (20-22 weeks of age) with those of age and sex-matched Wt littermate controls. All Tg mice at 14 weeks of age exhibited hind limb tremors. Morphologically, spleens from 14 weeks old B6SJL Tg mice were identical to those of Wt controls (FIG. 48A, left panel), whereas, spleens from end stage mice showed marked reduction in size compared to controls (FIG. 48A, right panel). Similarly, no differences in spleen weights from pre-symptomatic and symptomatic B6SJL mice compared to Wt were discerned, whereas at end stage, spleen weights were diminished by 45% in B6SJL Tg mice (19 weeks old) and by 59% in B6 Tg mice (22 weeks old) (FIG. 48B). No differences in gross morphology or weights for non-lymphoid kidneys or livers were discernible between Tg and Wt mice at any age. For end stage B6 Tg mice, total viable spleen cell numbers were diminished by 70% compared to Wt controls, whereas no differences in spleen cell numbers were observed between Tg and Wt mice in early symptomatic stage (FIG. 47C).

Immune Tissue Analyses of SOD1 Tg Mice

Figure 49:
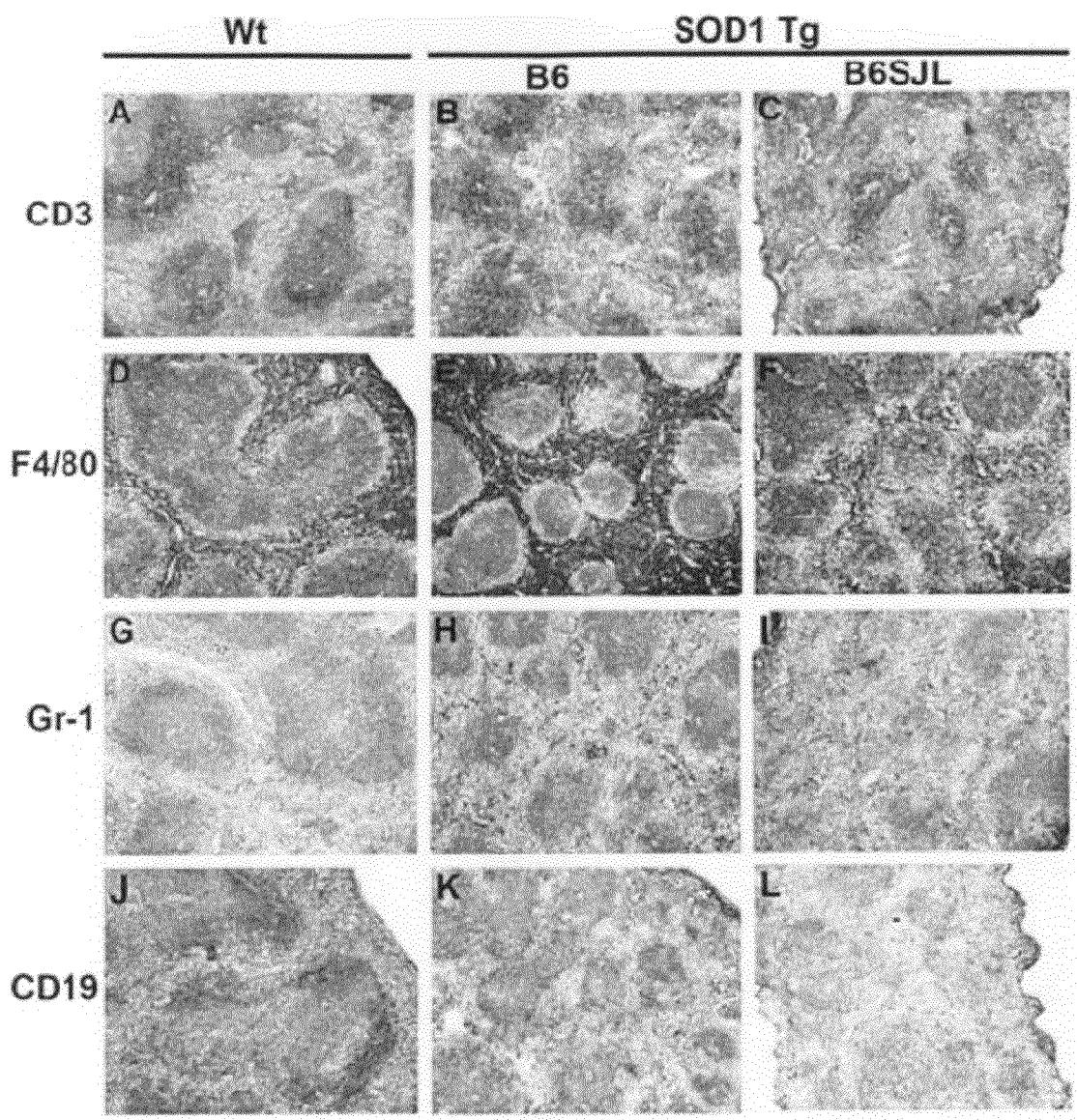
FIG. 49 shows altered spleen architecture from end stage G93A-SOD1 Tg mice. Representative photomicrographs of immunohistochemistry are shown for expression of CD3, F4/80, Gr-1, CD19 of fresh frozen spleen sections from end stage SOD1 Tg mice and age-matched Wt controls. Photomicrographs in the left panels are from B6 Wt mice, while middle and right panels show sections from B6 SOD1 Tg and B6SJL SOD1 Tg mice, respectively. Sections are stained by immunoperoxidase for expression of (A, B, C) CD3 by T cells; (D, E, F) F4/80 by perifollicular macrophages; (G, H, I) Gr-1 immunoreactivity on myeloid cells; and (J, K, L) CD19+ on B cells. Sections are counterstained with hematoxylin.
Figure 50:
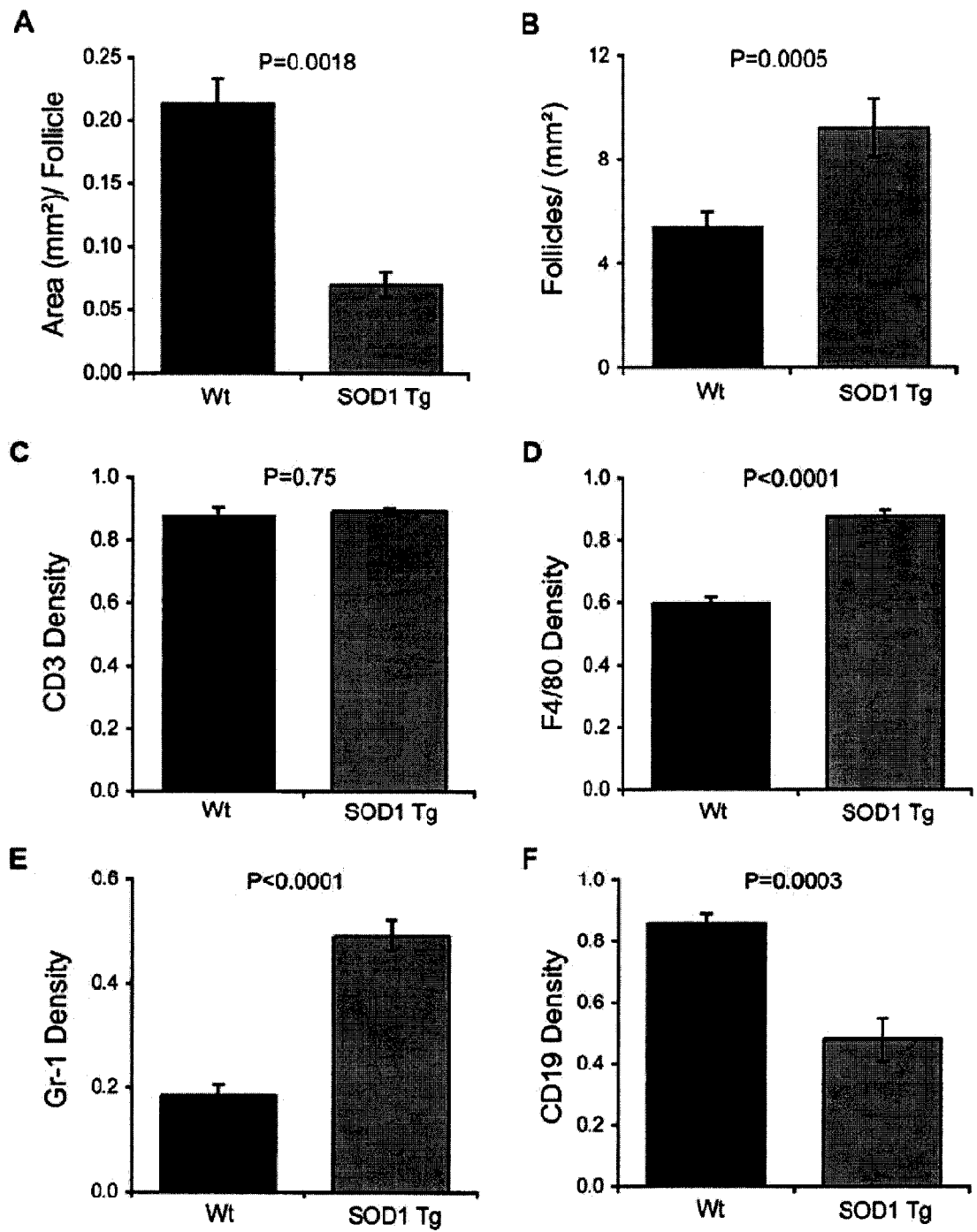
FIG. 50 shows the comparison of spleen architecture between Wt and SOD1 B6 Tg mice (22 weeks old). Mean area/follicle (FIG. 49A) and mean numbers of follicles/mm$^2$ (FIG. 50B) were determined for B6 Wt and B6 SOD1 Tg mice from digital images taken at 100× magnification (4 random fields/mouse). Densities of CD3+ T cells (FIG. 50C), F4/80+ macrophages (FIG. 49D), Gr-1+ cells (FIG. 50E), and CD19+B cells (FIG. 50F) from concomitantly stained sections were determined by digital image analysis from 100× magnifications using Image-Pro Plus software. Values are means6SEM for 3-6 mice per group.

To assess splenic architecture in end stage mice, the expression of CD3, CD19, F4/80, and Gr-1 in fresh frozen sections was assessed from end stage B6 Tg mice (22 weeks old), B6SJL Tg mice (19 weeks old), and age-matched Wt controls. Splenic architecture in end stage B6 Tg and B6SJL Tg mice revealed remarkable alterations in follicle number, size, and expression of hematopoietic lineage markers compared to Wt B6 littermates. Splenic follicular architecture appeared diminished with a greater number of follicles in each field for B6 SOD1 Tg (FIGS. 49B, 49E, 49H, and 49K) and B6SJL SOD1 Tg (FIGS. 49C, 49F, 49I, and 49L) mice compared to Wt controls (FIGS. 49A, 49D, 49G, and 49J). The density of CD3+ T cells in the spleen appeared unaltered in B6 Tg (FIG. 49B) or B6SJL Tg (FIG. 49C) mice compared to Wt mice (FIG. 49A), while expression of F/480 (FIGS. 49D, 49E, and 49F) and Gr-1 (FIGS. 49G, 49H, and 49I) in the perifollicular area of spleen appeared increased in SOD1Tg mice and the density of CD19 expression by B cells within the follicles of SOD1 Tg mice (FIGS. 49K and 49L) appeared diminished compared to Wt controls (FIG. 49J). These observations were validated by digital image analysis in B6 Wt and B6 SOD1 Tg mice. In Tg mice, splenic follicular area was diminished by 67% (FIG. 50A) and numbers of follicles/mm$^2$ were increased by 41% (FIG. 50B) compared to Wt controls. No difference in the densities of splenic CD3 expression could be ascertained between Tg and Wt control mice (FIG. 50C). In the splenic perifollicular area of Tg mice compared to Wt controls, the mean density of F4/80 was increased by 47% (FIG. 50D), density of Gr-1 expressing cells was increased by 165% (FIG. 50E), while the intrafollicular density of CD19 expression was diminished by 88% (FIG. 50F).

Impaired Lymphocyte Proliferation and Necrosis in Spleens of SOD1 Tg Mice

Figure 51:
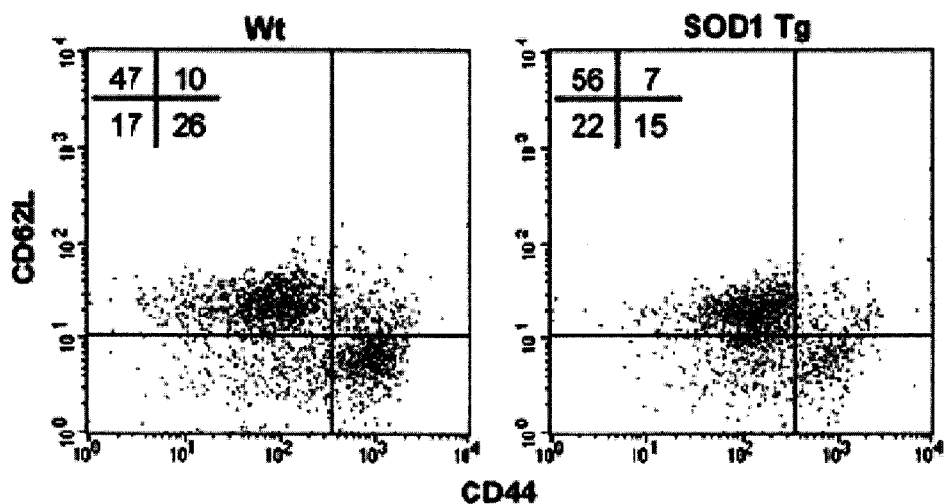
FIG. 51 shows lymphocyte phenotype and function in G93A-SOD1 Tg mice. The phenotype and function of splenic lymphocytes from B6SJL SOD1 Tg and Wt littermates were assessed by flow cytometric analysis (FCM) and proliferation assays.
Figure 51:
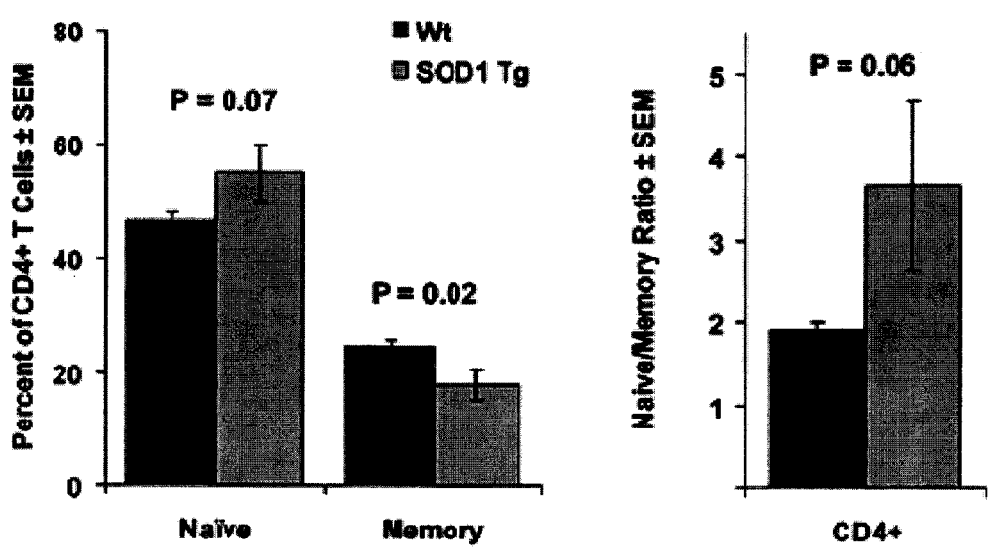
Figure 51:
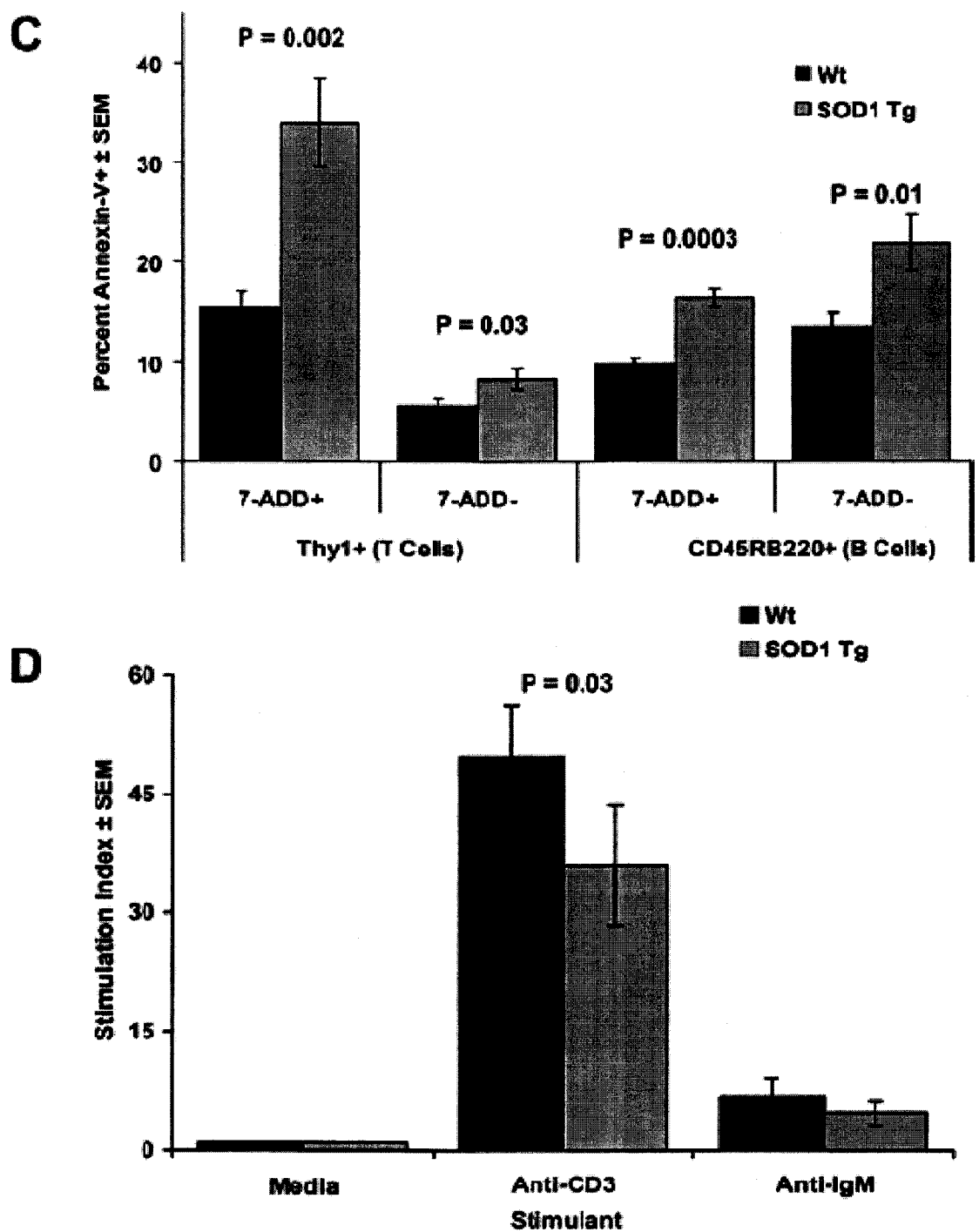

Based on diminished T cell responses and observations of profound lymphopenia in G93A-SOD1 Tg mice at end stage, splenic lymphocyte phenotype and function was assessed in early symptomatic (14 weeks old) B6SJL SOD1 Tg mice to detect early immune cell aberrations in spleen. Flow cytometric analysis of CD62L and CD44 expression on CD4+ gated splenic lymphocytes (FIG. 51A) demonstrated a diminished percentage of CD4+CD44$^{hi}$CD62L$^{lo}$ memory T cells and an increased percentage of CD4+CD44$^{lo}$CD62L$^{hi}$ naive T cells compared to Wt mice which resulted in an increased ratio of naive/memory CD4+ T cells in Tg mice compared to Wt controls (FIG. 51B). To assess lymphocytic demise, apoptotic (annexin-V+7-ADD2) and necrotic (annexin-V+7-ADD+) lymphocytes was evaluated among viable T cells (Thy-1+) and B cells (CD45R/B220+) from spleen cell isolates of early symptomatic (14 weeks old) B6SJL SOD1 Tg mice and Wt controls. Flow cytometric analysis revealed that Tg mice had a greater than 2-fold increase in the percentage of annexin-V+7-ADD+ necrotic splenic T cells and a 30% increase in the percentage of annexin-V+7-ADD− apoptotic T cells compared to Wt littermates (FIG. 51C). Similarly, percentages of necrotic (41%) and apoptotic (38%) B cells were increased in Tg mice compared to control mice.

To assess lymphoid cell function of early symptomatic B6SJL SOD1 Tg mice at 14 weeks of age, T cells were stimulated with anti-CD3 and B cells with anti-IgM and evaluated their proliferative capacity of each lineage. T cell proliferation in B6SJL Tg mice was significantly diminished compared to Wt littermates; however no diminution of B cell function could be ascertained (FIG. 51D). The diminished T cell proliferative responses thus confirmed previous findings (FIG. 47F). It was also assessed whether lymphoid cells from Tg and Wt mice were differentially susceptible to activation-induced cell death at either 24 or 48 hours post-activation, however no differences in induction of apoptotic or necrotic T or B cells at any time point after activation were observed.

Figure 52:
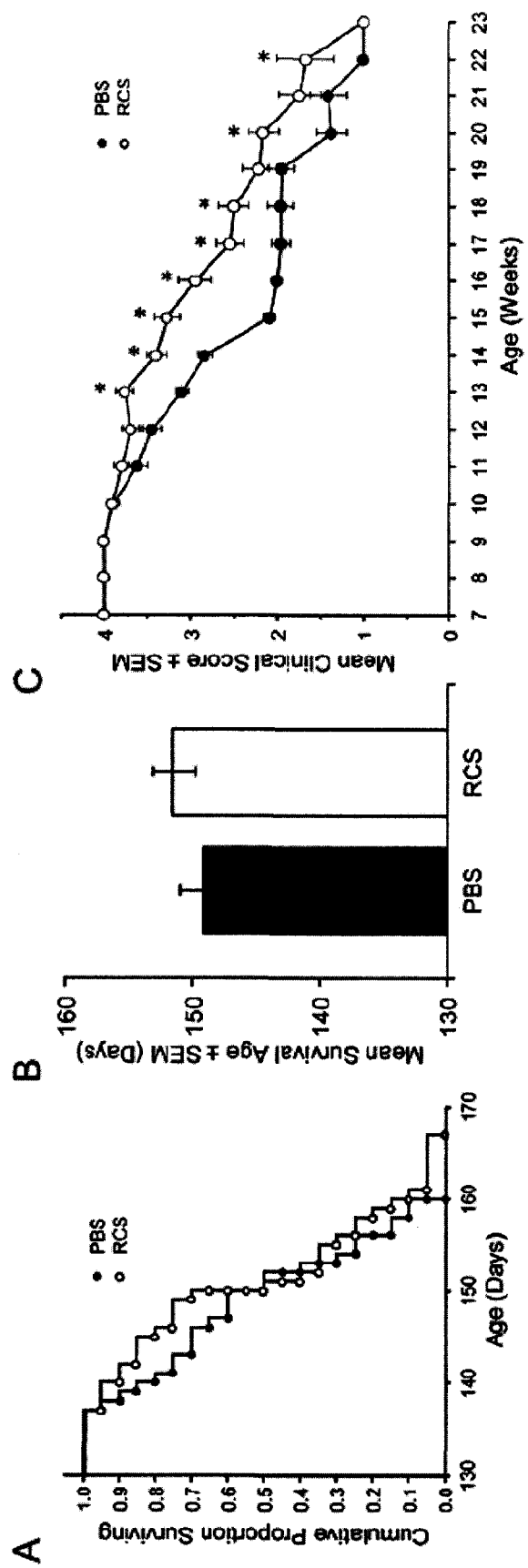
FIG. 52 shows the effect of total lymphocyte reconstitution on survival and clinical scores in B6 SOD1 Tg mice. B6 SOD1 mice (20 mice/group) were treated with PBS (closed circles) or RCS (open circles) with 50×10$^6$ naive splenic lymphocytes.
Figure 52:
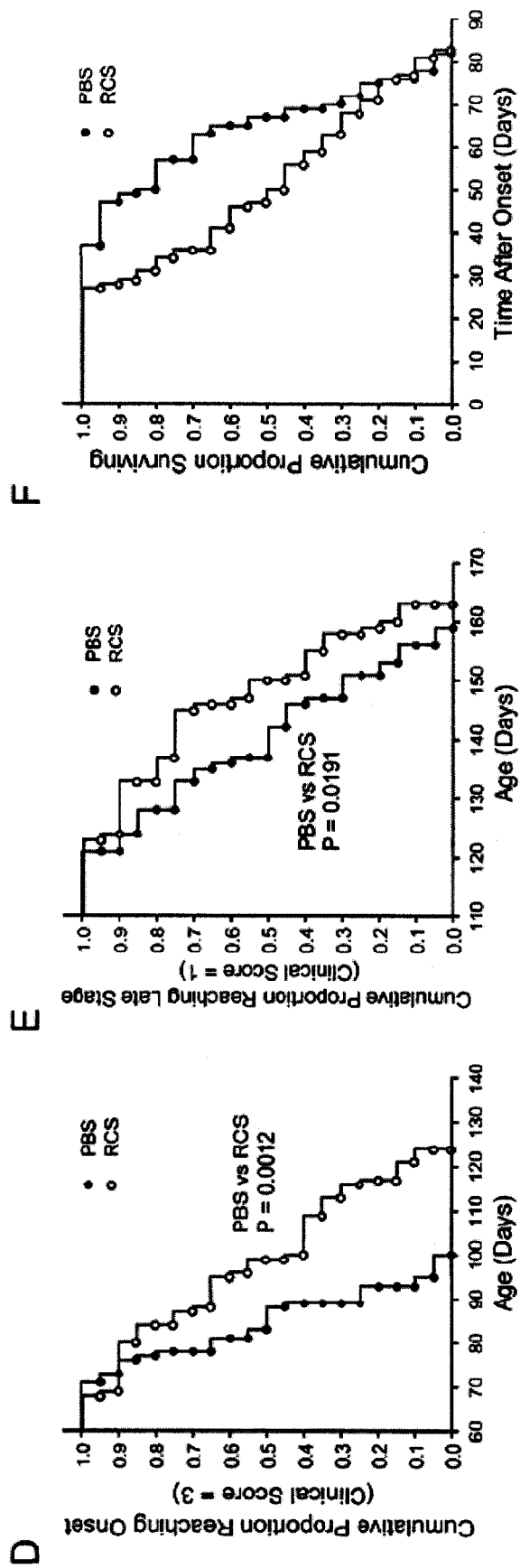

Survival of B6 SOD1 Tg Mice after Adoptive Transfer of Naive Lymphoid Cells, or Activated Treg or Teff Subsets Based on the above findings in SOD1 Tg mice demonstrating a lack of protective response by COP-1 immunization in male mice, diminished T cell functional capacity in early symptomatic and late stage mice, and end stage lymphopenia, a strategy was tested to rectify the lymphoid dysregulation and extend survival by adoptive transfer of B6 Wt naive lymphoid cells to recipient B6 SOD1 Tg mice. B6 SOD1 Tg mice treated with 50×10$^6$ naive spleen cells at 7, 13, and 19 weeks of age yielded no significant differences in the cumulative proportion of survival (FIG. 52A, p=0.2035) or mean age of survival (FIG. 52B, p=0.315) compared to PBS-treated mice. However, mean clinical scores analyzed by factorial ANOVA revealed significant improvement of reconstituted mice compared to PBS-treated controls (FIG. 52C, p=0.000001). Additionally, Kaplan-Meier analysis showed immune reconstituted (RCS) Tg mice exhibited delayed symptom onset (clinical score=3) (FIG. 52D, p=0.0012) as well as delayed entry into late stage (clinical score=1) (FIG. 52E, p=0.0191). However, after onset of symptoms, survival of reconstituted Tg mice trended to be diminished compared to the PBS controls as determined by Kaplan-Meier analysis (FIG. 52F, p=0.2021) and by mean latency after onset to death for PBS-treated (64.5±2.6) and RCS (52.0±4.3) mice (p=0.0167).

No significant differences in body weight were discerned between RCS- and PBS-treated groups as a function of age by factorial ANOVA (p=0.5824). Additionally, no differences in PBS-treated or RCS groups were found in the cumulative proportion (p=0.2744) and the mean age (p=0.2921) of Tg mice that reach 10% loss of maximum body weight. Although an early effect in hind grip strength was observed between 10-13 weeks of age as determined by PaGE, no effects were discernible thereafter. Factorial ANOVA indicated no differences in motor function as determined by ORP in PBS-treated or RCS groups over their lifetime (p=0.8862).

Figure 53:
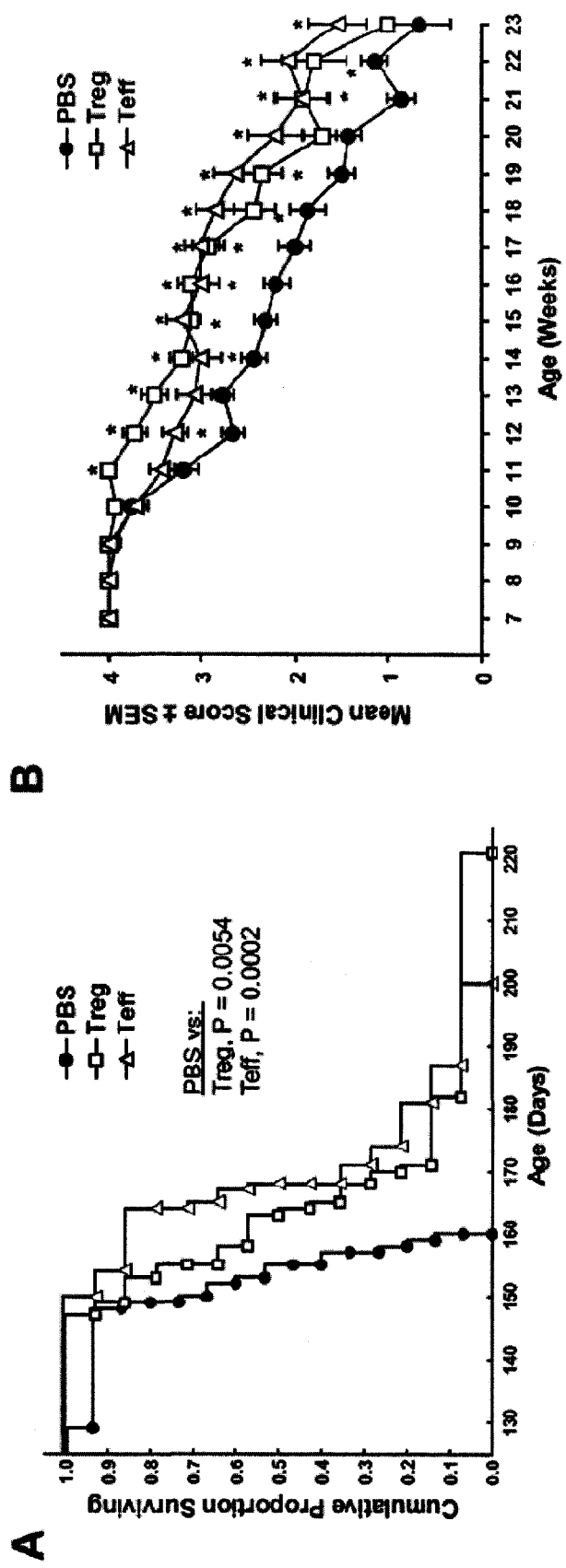
FIG. 53 shows the effect of Treg and Teff on survival, clinical scores and weight loss in B6 SOD1 Tg mice. B6 G93A-SOD1 mice (14-15 mice/group) were treated with PBS (closed circles), 1×10$^6$ activated Treg (open boxes), or 1×10$^6$ activated Teff (open triangles) at 7, 13, and 19 weeks of age.
Figure 53:
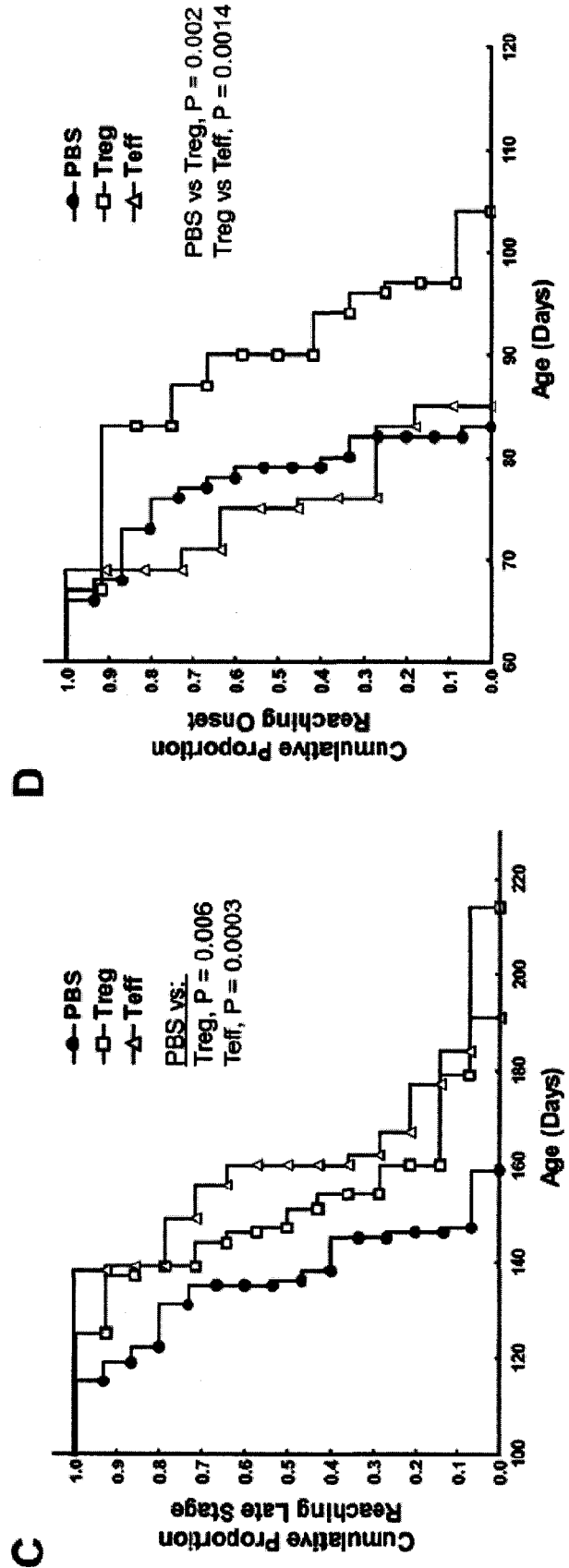
Figure 53:
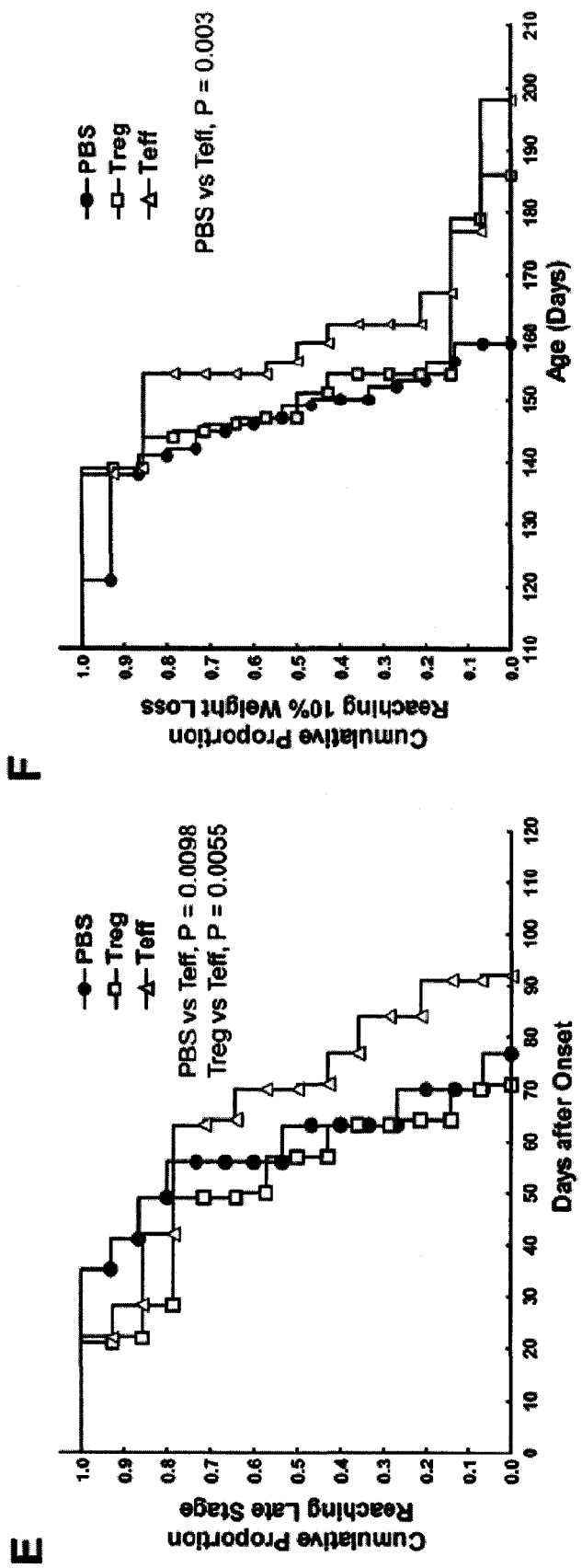
Figure 54:
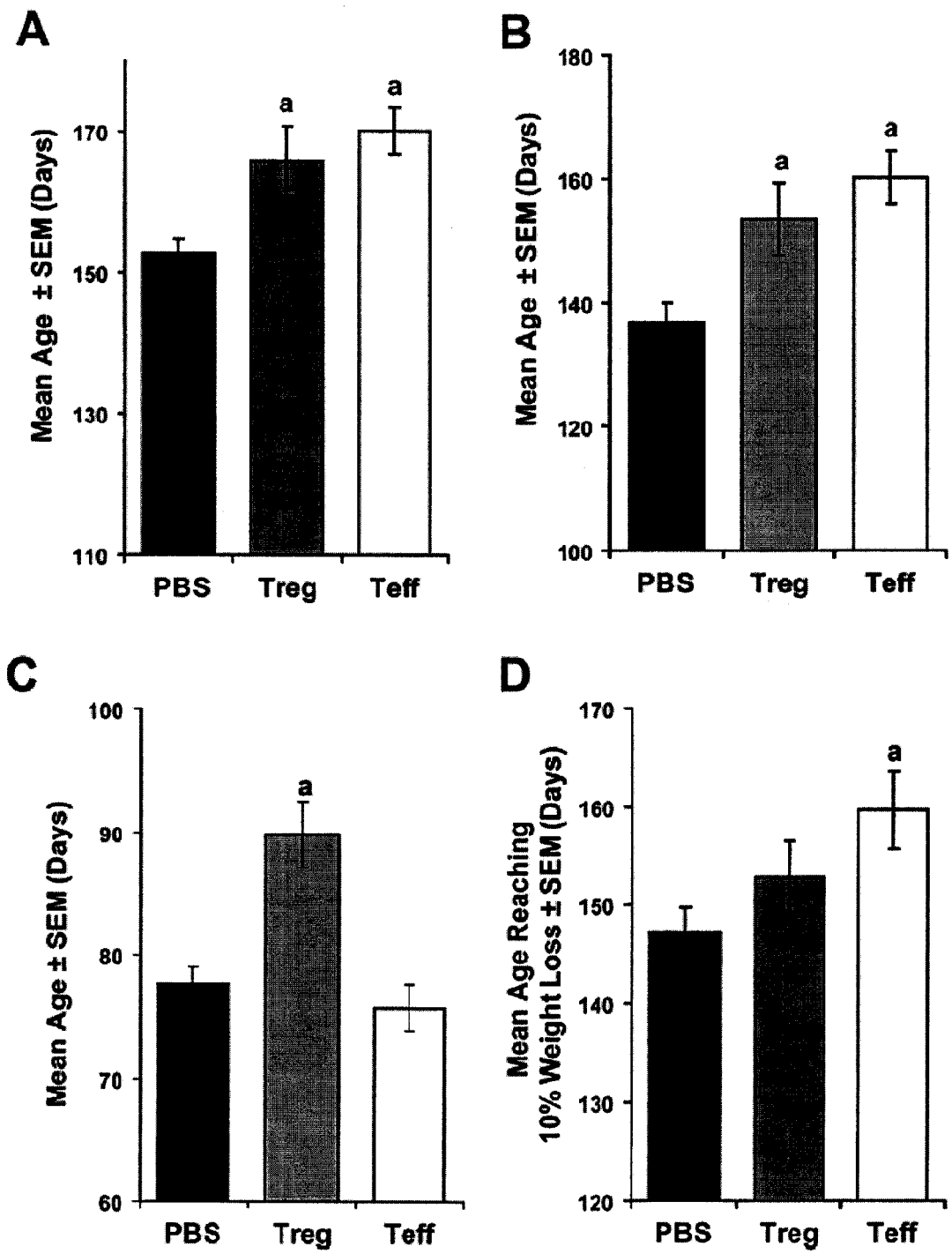
FIG. 54 shoes the effect of Treg and Teff on mean age of survival, clinical scores and weight loss in B6 G93A-SOD1 Tg mice. B6 G93A-SOD1 mice were treated with PBS (black bars), 1×10$^6$ activated Treg (gray bars), or 1×10$^6$ activated Teff (white bars) at 7, 13, and 19 weeks of age.

Based on the previous results which demonstrated that regulatory T cells were neuroprotective in a mouse model of Parkinson's disease, it was evaluated whether activated T cell subsets also provide analogous protection in SOD1 Tg mice. Adoptive transfer of 1×10$^6$ enriched polyclonal-activated Wt Treg (CD4+CD25+) or Teff (CD4+CD25−) to B6 SOD1 Tg mice at 7, 13, and 19 weeks of age led to significant increases in longevity as determined by Kaplan-Meier analysis (FIG. 53A) and mean age of survival (FIG. 54A) compared to PBS-treated controls. Factorial ANOVA of treatment and age showed that by 11-12 weeks of age, clinical scores were increased by reconstitution of B6 Tg recipients with activated Wt Treg or Teff compared to PBS controls (FIG. 53B, p=0.00004). Moreover, entry into late stage disease (clinical score=1) was delayed by reconstitution with Treg or Teff as determined by Kaplan-Meier analysis (FIG. 54C) and mean age of entry into late stage (FIG. 54B). Of interest, transfer of activated Wt Treg, but not Teff to B6 Tg recipient mice delayed disease onset as evaluated by clinical signs (clinical score=3) and as determined by Kaplan-Meier analysis (FIG. 54D, p=0.002) and mean age of disease onset (FIG. 54C, p, 0.0003). On the other hand, transfer of activated Wt Teff, but not Treg to B6 Tg recipients, increased the latency from onset (clinical score=3) to entry into late stage (clinical score=1) as determined by Kaplan-Meier analysis (FIG. 53E, p=0.0098).

Adoptive transfer of Treg or Teff affected weight gain and loss as determined by factorial ANOVA for effects of treatment as a function of age (p=0.0356). Transfer of activated Teff, but not Treg delayed the age at which recipients lost ≧10% of maximum body weight compared to PBS treatment as determined by Kaplan-Meier analysis of proportion (FIG. 53F, p=0.003) and mean age (FIG. 54D) of mice reaching ≧10% weight loss.

Figure 55:
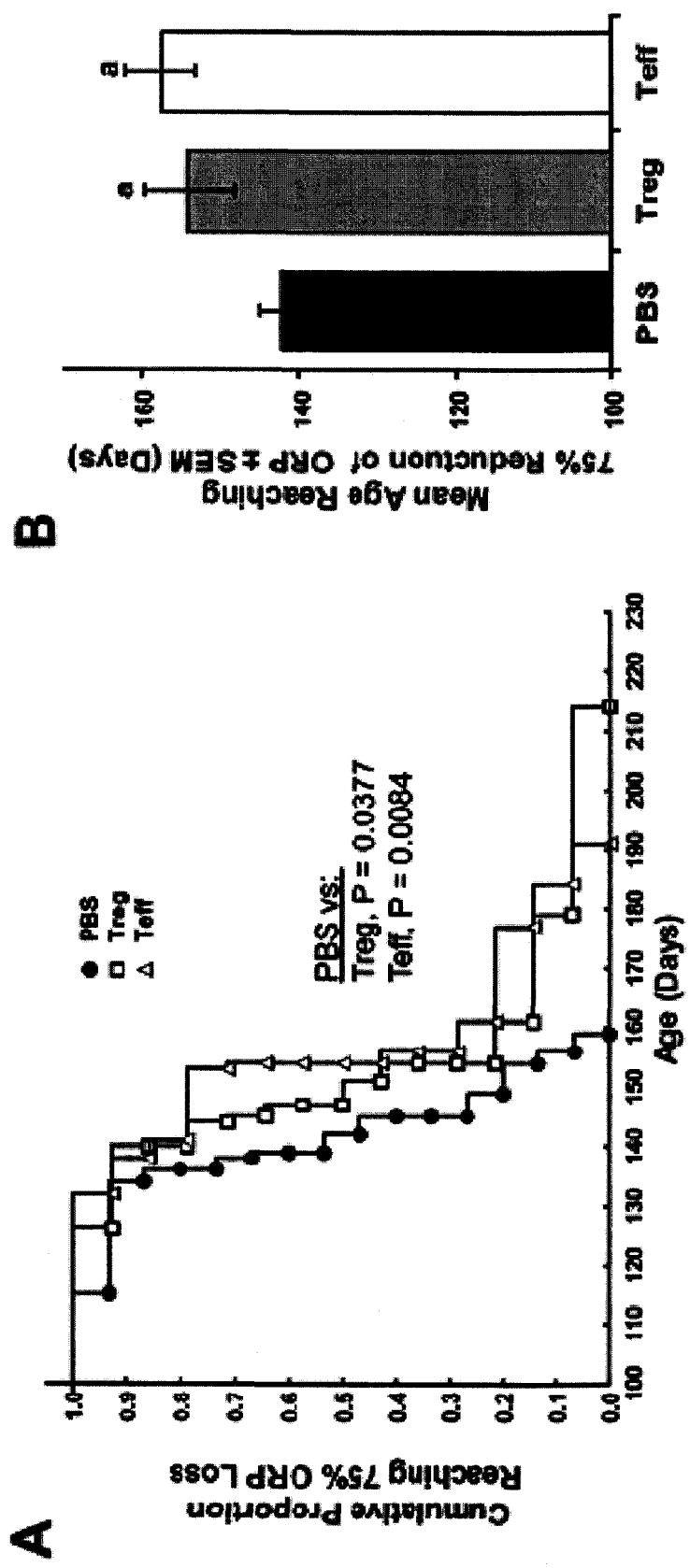
FIG. 55 shows the effect of Treg and Teff on motor function in B6 G93A-SOD1 Tg mice. B6 G93A-SOD1 mice (14-15 mice/group) were treated at 7, 13, and 19 weeks of age with PBS (closed circles and black bars), 1×10$^6$ activated Treg (open boxes and gray bars), or 1×10$^6$ activated Teff (open triangles and white bars).
Figure 55:
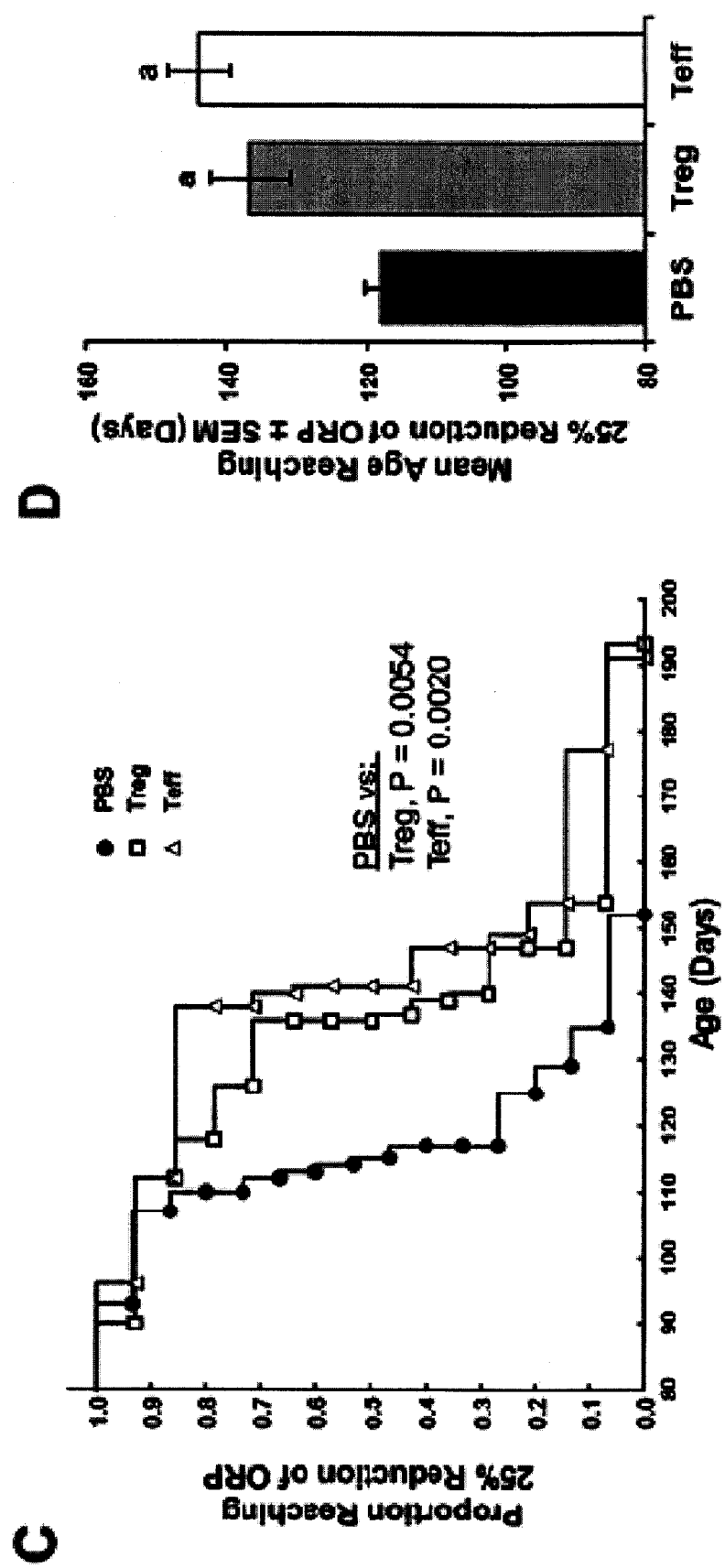
Figure 55:
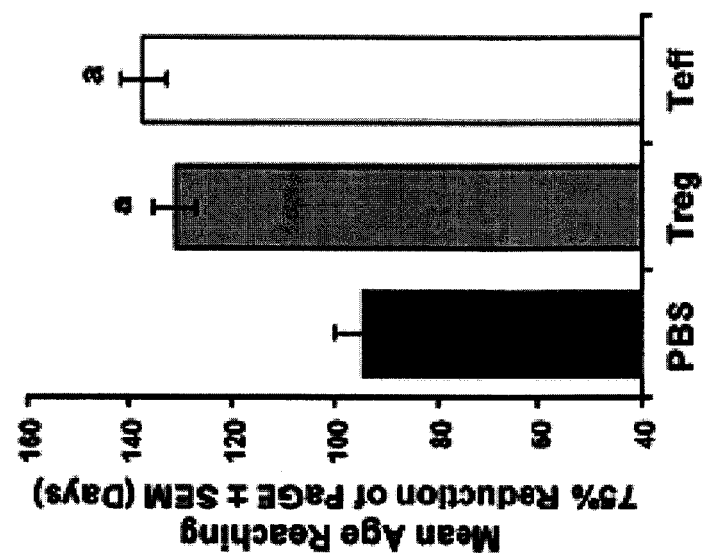
Figure 55:
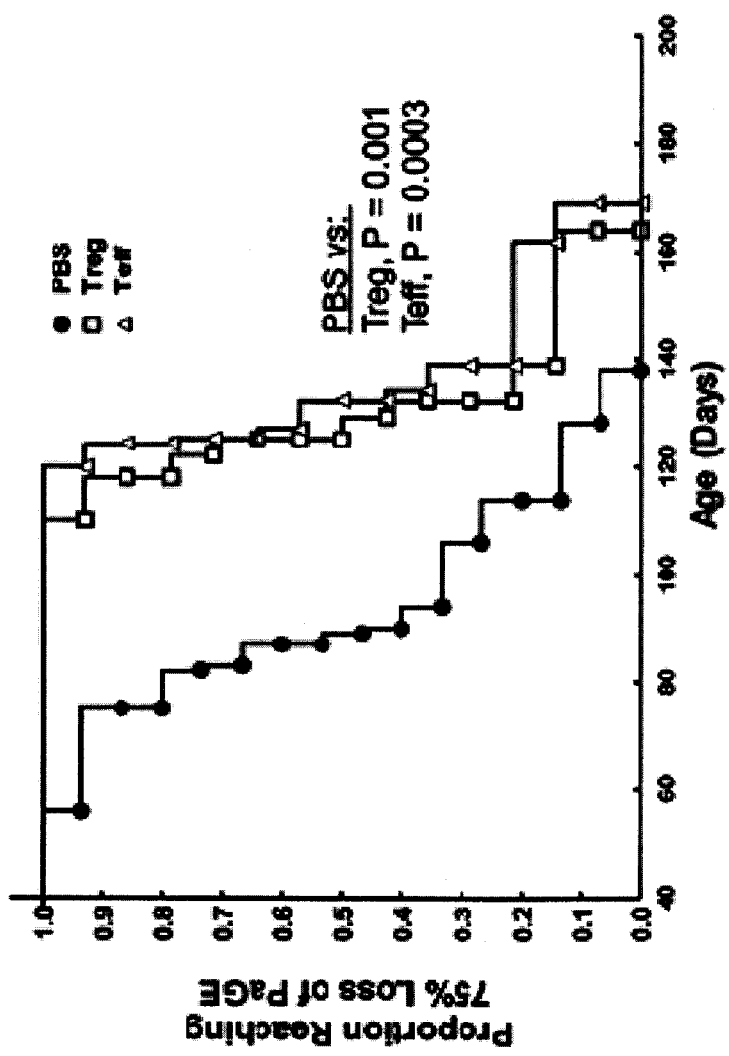
Figure 55:
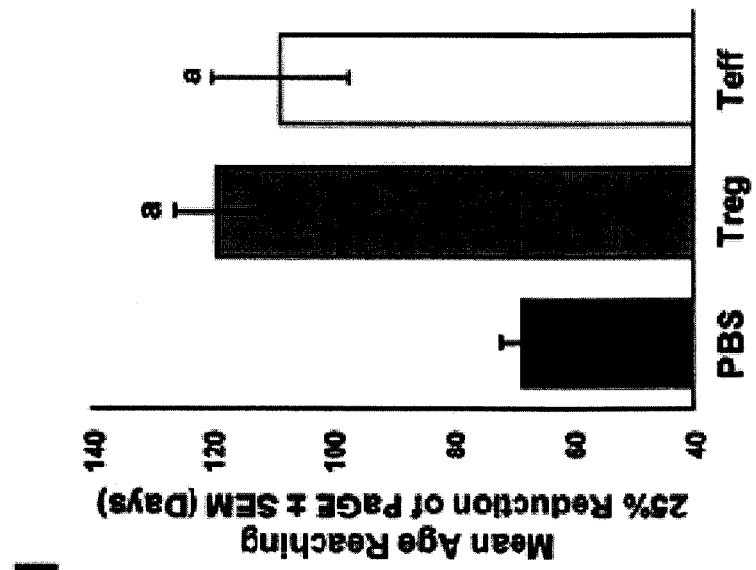
Figure 55:
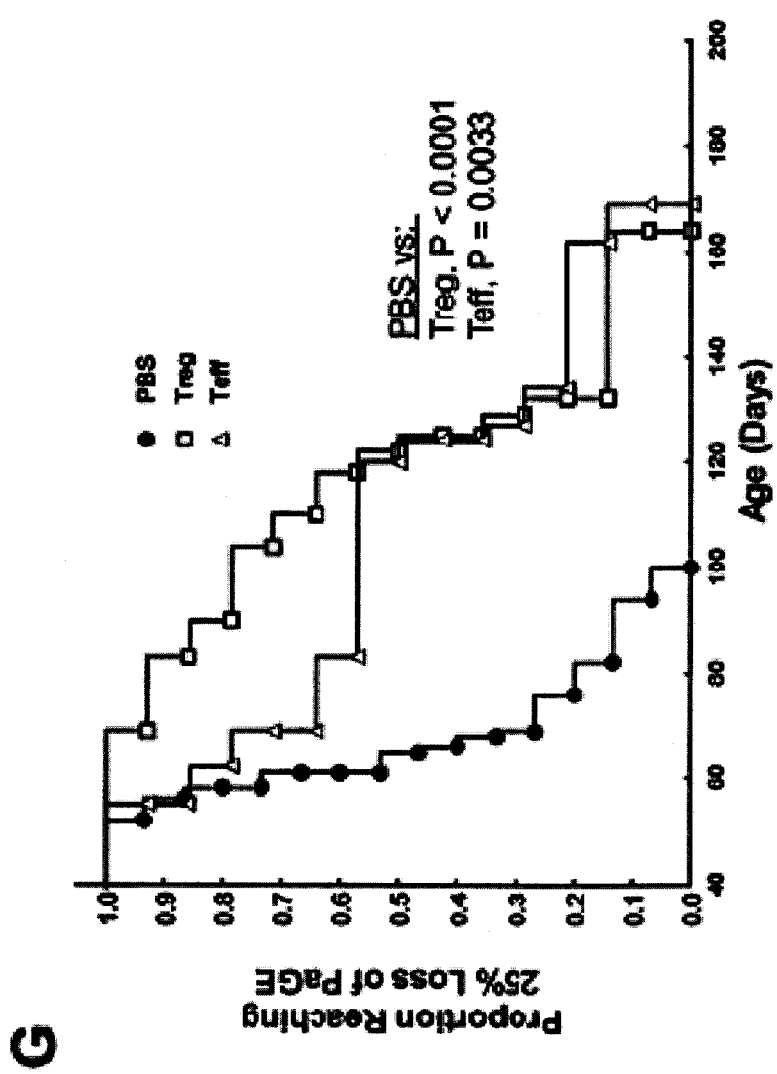

Adoptive transfer of either Treg or Teff to B6 SOD1 Tg mice also improved motor function compared to PBS treated controls as determined by factorial ANOVA for effect of treatment with age on ORP (p=3.361028) and PaGE (p=6.7610211). Activated Wt Treg or Teff delayed loss of rotarod performance as determined by Kaplan-Meier analysis of the proportion (FIG. 55A) and mean age (FIG. 55B) of mice at which ≧75% of ORP was reduced. Also transfer of activated Treg or Teff delayed the initial loss of ORP compared to PBS controls as determined by the cumulative percentage (FIG. 55C) and the mean age (FIG. 55D) of mice that reach ≧25% loss of ORP. Hind limb strength was also assessed by PaGE. Compared to PBS controls, adoptive transfer of activated Treg or Teff delayed the loss of hind limb strength as determined by Kaplan-Meier analysis of the cumulative percentage (FIG. 55E) and increased mean age (FIG. 55F) of SOD1 Tg mice exhibiting ≧75% reduction of PaGE. In addition, transfer of activated Wt Treg or Teff to Tg mice delayed early loss of hind limb grip strength compared to controls as determined by Kaplan-Meier analysis of the cumulative percentage (FIG. 55G) and mean age (FIG. 55H) of mice that exhibit ≧25% reduction of PaGE. Of interest, after one round of Treg and Teff adoptive transfer at 49 days of age, Teff appear less efficient than Treg to attenuate early grip loss in Tg mice, however after a second round (at 91 days of age), the capacities to attenuate loss of grip strength by Teff and Treg were comparable (FIG. 55G).

Preliminary Studies of Altered Adaptive Immunity in ALS Patients

To assess immune alterations in ALS patients, peripheral blood mononuclear cells (PBMC) from 10 ALS patients and 10 age-matched caregivers were characterized. Peripheral blood counts indicated a small, though insignificant increase in the number of leukocytes in patients compared to caregivers. ALS patients exhibited an increase in the mean percentage of polymorphonuclear neutrophils (PMNs) ($8.0 \pm 0.07 \times 10^9$/L compared with $6.6 \pm 0.06 \times 10^9$/L, p=0.022), with slightly reduced levels of lymphocytes (20.7%±2.4% compared with 25.9%±1.8, p=0.054), and no discernible differences in monocyte levels (p=0.35). Flow cytometric analysis showed no differences in levels of peripheral blood CD19+B cells or CD3+ T cells among patients and caregivers. However compared to caregivers, ALS patients exhibited an 11.8% decrease in the percentage of CD4+ CD8− T cells (p=0.032) and a 22.9% increase in the frequency of CD4-CD8+ T cells (p=0.043) compared to age-matched controls. Additionally, the CD45RA/CD45R0 (naive/memory) ratio among CD4+ T cells of ALS patients (0.6±0.1) was diminished by 45% compared to caregivers (1.1±0.2, p=0.028), which was due to the diminution in levels of CD45RA+ naive T cell among CD4+ cells (37.2%+2.5% compared with 47.6%+5.1% for caregivers, p=0.0435) and a concomitant increase in levels of CD45R0+ memory cells among CD4+ T cells (62.1%±2.6% compared with 51.7%±5.2% for caregivers, p=0.0465).

EXAMPLE 9

A randomized, double-blind, sham-controlled trial will be performed. A total of 40 study participants are enrolled in the trial. These will be matched in age and sex and tempo of disease progression. Neurological status will be mild to moderate impairment with all participants physically independent and the ability to ambulate without assistance. Twenty participants will receive an injection of 2 µg of the C-terminal tail peptide of soluble oxidized alpha synuclein given by intradermal injection with and without 2 µg of nanoformulated vasoactive intestinal peptide to maximize dendritic cell responses. The other 20 participants will receive sterile saline solution. Repeat boosting injections will be administered every two weeks for six weeks. Study participants will be assessed for treatment effects by standardized Parkinson's disease ratings including clinical and neurological parameters for movement, gain, and coordination. The primary endpoint for the study will be a clinical assessment of motor function at 6 months using the Unified Parkinson's Disease Rating Scale (UPDRS). All participants in the study will also be monitored for safety for 12 months following the immunization procedure. If the primary endpoint is met following the analysis of 6 month data, then the sham control participants will be offered the opportunity to crossover into an open label study of the Neuropel immunization therapy, if they continue to meet all entry criteria.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated composition comprising:
   a) an immunogen, wherein said immunogen induces a humoral immune response against at least one abnormal protein of a central nervous system disease or disorder, and
   b) at least one adjuvant that stimulates regulatory T cells, wherein said immunogen consists of nitrated alpha synuclein or a fragment thereof,
   wherein said nitrated alpha synuclein fragment is a carboxy terminal fragment consisting of the carboxy terminal 20 amino acids of alpha synuclein up to the carboxy terminal 70 amino acids of alpha synuclein.

2. The composition of claim 1, further comprising at least one pharmaceutically acceptable carrier.

3. The composition of claim 1, wherein said adjuvant is selected from the group consisting of vasoactive intestinal peptide, vitamin D, granulocyte macrophage colony stimulating factor, and transforming growth factor beta.

4. The composition of claim 1, wherein said adjuvant is vasoactive intestinal peptide.

5. The composition of claim 1, wherein said adjuvant is vasoactive intestinal peptide and said immunogen is nitrated alpha synuclein.

6. The composition of claim 1, wherein said nitrated alpha synuclein is human nitrated alpha synuclein.

7. The composition of claim 1, wherein said nitrated alpha synuclein comprises an amino acid sequence having at least 90% identity with SEQ ID NO: 13.

8. The composition of claim 1, wherein said nitrated alpha synuclein fragment comprises at least 90% identity with amino acids 101-140 of SEQ ID NO: 13.

9. The composition of claim 1, wherein said nitrated alpha synuclein or fragment thereof comprises at least one nitrotyrosine.

10. The composition of claim 3, wherein said adjuvant is vasoactive intestinal peptide.

11. The composition of claim 3, wherein said adjuvant is granulocyte macrophage colony stimulating factor.

12. A method for treating a central nervous system disease or disorder in a patient in need thereof, said method comprising administering an effective amount of the composition according to claim 1 to said patient, wherein said central nervous system disease or disorder is characterized by the presence of at least one abnormal protein and is selected from the group consisting of Parkinson's Disease, Alzheimer's Disease, amyotrophic lateral sclerosis, neuroAIDS, Crohn's Disease, and Huntington's Disease.

13. The method of claim 12, wherein said adjuvant is selected from the group consisting of vasoactive intestinal peptide, vitamin D, granulocyte macrophages colony stimulating factor, and transforming growth factor beta.

14. The method of claim 13, wherein said adjuvant is vasoactive intestinal peptide.

15. The method of claim 12, wherein said central nervous disease or disorder is Parkinson's Disease and said immunogen is nitrated alpha synuclein.

16. The method of claim 12, wherein said central nervous disease or disorder is Parkinson's Disease and said immunogen is a fragment of nitrated alpha synuclein.

17. The method of claim 12, wherein said central nervous disease or disorder is Alzheimer's Disease and said immunogen is amyloid beta.

18. The method of claim 12 wherein said central nervous system disease or disorder is amyotrophic lateral sclerosis and said immunogen is superoxide dismutase.

19. The method of claim 12, wherein said composition further comprises at least one pharmaceutically acceptable carrier.

* * * * *